US012435090B2

(12) United States Patent
Szychowski et al.

(10) Patent No.: US 12,435,090 B2
(45) Date of Patent: Oct. 7, 2025

(54) COMPOUNDS, PHARMACEUTICAL COMPOSITIONS, AND METHODS OF PREPARING COMPOUNDS AND OF THEIR USE

(71) Applicant: Repare Therapeutics Inc., St-Laurent (CA)

(72) Inventors: Janek Szychowski, Montreal (CA); Bingcan Liu, Montreal (CA); Evelyne Dietrich, Laval (CA); Frédéric Vallée, Montreal (CA); Alexander Perryman, Pointe-Claire (CA); Jean-François Truchon, Saint-Laurent (CA); Robert Papp, St-Laurent (CA); Patrick Beaulieu, Saint-Romuald (CA); Vouy Linh Truong, Pierrefonds (CA); Kaveh Matinkhoo, Montreal (CA); Sheldon N. Crane, Notre Dame de l'Ile Perrot (CA)

(73) Assignee: Repare Therapeutics Inc., St-Laurent (CA)

( * ) Notice: Subject to any disclaimer, the term of this patent is extended or adjusted under 35 U.S.C. 154(b) by 0 days.

(21) Appl. No.: 17/937,977

(22) Filed: Oct. 4, 2022

(65) Prior Publication Data

US 2023/0122909 A1 Apr. 20, 2023

Related U.S. Application Data

(60) Provisional application No. 63/252,961, filed on Oct. 6, 2021, provisional application No. 63/251,942, filed on Oct. 4, 2021.

(51) Int. Cl.
*C07D 487/04* (2006.01)
*C07D 209/12* (2006.01)
*C07D 471/04* (2006.01)

(52) U.S. Cl.
CPC ......... *C07D 487/04* (2013.01); *C07D 209/12* (2013.01); *C07D 471/04* (2013.01)

(58) Field of Classification Search
CPC ... C07D 487/04; C07D 209/12; C07D 471/04
See application file for complete search history.

(56) References Cited

U.S. PATENT DOCUMENTS

2023/0142913 A1 5/2023 Szychowski et al.
2023/0151014 A1 5/2023 Szychowski et al.
(Continued)

FOREIGN PATENT DOCUMENTS

WO WO-00/33837 A2 6/2000
WO WO-00/33842 A1 6/2000
(Continued)

OTHER PUBLICATIONS

Bos, P. H.; Lowry, E. R.; Costa, J.; et al. "Development of MAP4 Kinase Inhibitors as Motor Neuron-Protecting Agents" Cell Chemical Biology 2019, 26, 1703-1715. (Year: 2019).*
(Continued)

*Primary Examiner* — Andrew D Kosar
*Assistant Examiner* — John D McAnany
(74) *Attorney, Agent, or Firm* — Wolf, Greenfield & Sacks, P.C.

(57) ABSTRACT

Disclosed are compounds and pharmaceutically acceptable salts thereof that may be used in the treatment of subjects in need thereof. The compounds disclosed herein may be inhibitors of tyrosine and threonine-specific cdc2-inhibitory kinase (Myt1). Also disclosed are pharmaceutical compositions containing the compounds or pharmaceutically acceptable salts thereof and methods of their preparation and use.

10 Claims, 12 Drawing Sheets

(56) References Cited

U.S. PATENT DOCUMENTS

| | | | |
|---|---|---|---|
| 2023/0158022 | A1 | 5/2023 | Durocher et al. |
| 2023/0348456 | A1 | 11/2023 | Szychowski et al. |

FOREIGN PATENT DOCUMENTS

| | | | | |
|---|---|---|---|---|
| WO | WO-01/64680 A1 | 9/2001 | | |
| WO | WO-2009005672 A1 * | 1/2009 | | ........... C07D 471/04 |
| WO | WO-2015/144923 A9 | 10/2015 | | |
| WO | WO-2021/195781 A1 | 10/2021 | | |
| WO | WO-2021/195782 A1 | 10/2021 | | |
| WO | WO-2022/213204 A1 | 10/2022 | | |
| WO | WO-2023/155870 A1 | 8/2023 | | |
| WO | WO-2023/155871 A1 | 8/2023 | | |
| WO | WO-2023/155892 A1 | 8/2023 | | |
| WO | WO-2023/174329 A1 | 9/2023 | | |
| WO | WO-2023/174397 A1 | 9/2023 | | |
| WO | WO-2023/198199 A1 | 10/2023 | | |
| WO | WO-2023/220831 A1 | 11/2023 | | |
| WO | WO-2023/226964 A1 | 11/2023 | | |
| WO | WO-2023/241322 A1 | 12/2023 | | |
| WO | WO-2023/249563 A1 | 12/2023 | | |
| WO | WO-2024/012409 A1 | 1/2024 | | |
| WO | WO-2024/041440 A1 | 2/2024 | | |
| WO | WO-2024/048687 A1 | 3/2024 | | |

OTHER PUBLICATIONS

Kim, H,; Lee, S.; Min, J.S.; et al. "Fluorescent sensor array for high-precision pH classification with machine learning-supported mobile devices" Dyes and Pigments 193 (2021) 109492. (Year: 2021).*

Patani, G. A.; LaVoie, E. J. "Bioisosterism: A Rational Approach in Drug Design" Chem. Rev. 1996, 96, 3147-3176. (Year: 1996).*

Chen, P.; Chaikuad, A.; Bamborough, P.; et al. "Discovery and Characterization of GSK2801, a Selective Chemical Probe for the Bromodomains BAZ2A and BAZ2B" J. Med. Chem. 2016, 59, 1410-1424 (Year: 2016).*

U.S. Appl. No. 18/284,614, Repare Therapeutics Inc.

Aamodt et al., "Differences in Protein Expression and Gene Amplification of Cyclins between Colon and Rectal Adenocarcinomas." Gastroenterology Research and Practice. 2009, 285830 (2009) (10 pages).

Agarwal et al., "Gene expression profiling, pathway analysis and subtype classification reveal molecular heterogeneity in hepatocellular carcinoma and suggest subtype specific therapeutic targets." Cancer Genetics. 216-217: 37-51 (Jul. 7, 2017) (15 pages).

Ayeni et al., "Dual Phosphorylation of Cdk1 Coordinates Cell Proliferation with Key Developmental Processes in *Drosophila*." Genetics. 196(1): 197-210 (Jan. 2014) (19 pages).

Aziz et al., "19q12 amplified and non-amplified subsets of high grade serous ovarian cancer with overexpression of cyclin E1 differ in their molecular drivers and clinical outcomes." Gynecol Oncol. 151(2): 327-336 (Sep. 9, 2018) (10 pages).

Barnum et al., "Cell Cycle Regulation by Checkpoints." Methods Mol. Biol. 1170: 29-40 (2014) (11 pages).

Bonelli et al., "CDK/CCN and CDKI Alterations for Cancer Prognosis and Therapeutic Predictivity." BioMed Research International. vol. 2014, Article ID 361020 (Jan. 29, 2014) (16 pages).

Booher et al. "Human Myt1 Is a Cell Cycle-regulated Kinase That Inhibits Cdc2 but Not Cdk2 Activity." Journal of Biological Chemistry. 272(35): 22300-22306 (Aug. 29, 1997) (8 pages).

Carrassa et al., "DNA damage response inhibitors: Mechanisms and potential applications in cancer therapy." Cancer Treatment Reviews. 60:139-151 (Nov. 2017) (13 pages).

Chow et al., "The CDK1 inhibitory kinase MYT1 in DNA damage checkpoint recovery." Oncogene. 32: 4778-4788 (Nov. 12, 2012) (11 pages).

Friedman et al., "Inhibition of WEE1 kinase and cell cycle checkpoint activation sensitizes head and neck cancers to natural killer cell therapies." Journal for Immunotherapy of Cancer. 6(1): 59 (Jun. 21, 2018) (12 pages).

Gavet et al., "Activation of cyclin B1-Cdk1 synchronizes events in the nucleus and the cytoplasm at mitosis." J. Cell. Biol. 189(2): 247-259 (Apr. 19, 2010) (23 pages).

Koh et al., "Mechanistic distinctions between CHK1 and WEE1 inhibition guide the scheduling of triple therapy with gemcitabine." Cancer Res. 78(11): 3054-3066 (Jun. 1, 2018) (44 pages).

Kristjánsdóttir et al., "Autophosphorylation of Ser66 on Xenopus Myt1 is a Prerequisite for Meiotic Inactivation of Myt1." Landes Bioscience Cell Cycle. 5(4): 421-427 (Feb. 16, 2006) (7 pages).

Lafleur, K, Thesis: "Design and synthesis of selective kinase inhibitors," Faculty of Science, University of Zurich, (2012) (165 pages).

Liu et al., "PKMYT1 promoted the growth and motility of hepatocellular carcinoma cells by activating beta-catenin/TCF signaling." Experimental Cell Research. 358(2): 209-216 (Sep. 15, 2017) (8 pages).

Liu et al., "The Human Myt1 Kinase Preferentially Phosphorylates Cdc2 on Threonine 14 and Localizes to the Endoplasmic Reticulum and Golgi Complex." Molecular and Cellular Biology. 17(2): 571-583 (Feb. 1997) (13 pages).

Llobet et al., "Cyclin E expression is associated with high levels of replication stress in triple-negative breast cancer." bioRxiv. (Jan. 28, 2019) (37 pages).

Mueller et al., "Myt1: A Membrane-Associated Inhibitory Kinase that Phosphorylates Cdc2 on Both Threonine-14 and Tyrosine-15." Science, New Series. 270(5233): 86-90 (Oct. 6, 1995) (6 pages).

Otto et al., "Cell cycle proteins as promising targets in cancer therapy." Nature Reviews Cancer. 17(2):93-115 (Jan. 27, 2017) (23 pages).

Platzer et al., "Identification of PKMYT1 inhibitors by screening the GSK published protein kinase inhibitor set I and II." Bioorganic & Medicinal Chemistry. 26(14): 4014-4024 (Aug. 7, 2018) (11 pages).

Rohe et al., "Evaluation of potential Myt1 kinase inhibitors by TR-FRET based binding assay." European Journal of Medicinal Chemistry. 61: 41-48 (Jun. 12, 2012) (8 pages).

Rohe et al., "Identification of peptidic substrates for the human kinase Myt1 using peptide microarrays." Bioorg. Med. Chem. 23(15): 4936-4942 (May 19, 2015) (7 pages).

Sakurikar et al., "Critical reanalysis of the methods that discriminate the activity of CDK2 from CDK1." Cell Cycle 15(9): 1184-1188 (Apr. 25, 2016).

Schmidt et al., "Regulation of G2/M Transition by Inhibition of WEE1 and PKMYT1 Kinases." Molecules. 22(12): 2045 (Nov. 23, 2017) (17 pages).

Szmyd et al., "Premature activation of Cdk1 leads to mitotic events in S phase and embryonic lethality." Oncogene. 38:998-1018 (Sep. 6, 2018) (21 pages).

Unzue et al., "Pyrrolo[3,2-b]quinoxaline Derivatives as Types $I_{1/2}$ and II Eph Tyrosine Kinase Inhibitors: Structure-Based Design, Synthesis, and in Vivo Validation." J. Med. Chem. 57(15):6834-6844 (Jul. 30, 2014) (11pages).

Vigneron et al., "Cyclin A-cdk1-Dependent Phosphorylation of Bora Is the Triggering Factor Promoting Mitotic Entry." Developmental Cell. 45(5): 637-650 (Jun. 4, 2018) (22 pages).

Visconti et al., "Cell cycle checkpoint in cancer: a therapeutically targetable double-edged sword." Journal of Experimental & Clinical Cancer Research 35(153) (Sep. 27, 2016) (8 pages).

Wang et al., "Autophosphorylation kinetics of protein kinases." Biochem. J. 368:947-952 (2002) (6 pages).

Wang et al., "Effects of MCRS1 on proliferation, migration, invasion, and epithelial mesenchymal transition of gastric cancer cells by interacting with Pkmyt1 protein kinase." Cellular Signalling. 59:171-181 (Jul. 2019) (26 pages).

Wichapong et al., "Application of Docking and QM/MM-GBSA Rescoring to Screen for Novel Myt1 Kinase Inhibitors." J. Chem. Inf. Model. 54(3):881-893 (Feb. 3, 2014) (13 pages).

Zhu et al., "Structural basis of Wee kinases functionality and inactivation by diverse small molecule inhibitors." J. Med. Chem. 60(18):7863-7875 (Aug. 9, 2017) (43 pages).

Jeong et al., "Protein kinase, membrane-associated tyrosine/threonine 1 is associated with the progression of colorectal cancer," Oncol Rep. 39(6): 2829-2836 (Jun. 2018).

(56) References Cited

OTHER PUBLICATIONS

Zhang et al., "Overexpressed PKMYT1 promotes tumor progression and associates with poor survival in esophageal squamous cell carcinoma," Cancer Manag Res. 11:7813-7824 (Aug. 2019).

Sun et al., "Overexpression of PKMYT1 indicates the poor prognosis and enhances proliferation and tumorigenesis in non-small cell lung cancer via activation of Notch signal pathway," Eur Rev Med Pharmacol Sci, 23(10): 4210-4219 (May 2019).

Gallo et al., "CCNE1 amplification is synthetic lethal with PKMYT1 kinase inhibition," Nature, 604(7907):749-756 (Apr. 2022) (34 pages).

Repare Therapeutics Inc., "Precision oncology. Corporate Presentation," <https://ir.reparerx.com/static-files/c40cfla9-fc7d-47444-9422-9577lc353b5e>, dated Apr. 2021 (40 pages).

Lewis et al., "Upregulation of Myt1 Promotes Acquired Resistance of Cancer Cells to Wee1 Inhibition," Cancer Res. 79(23):5971-5985 (2019).

Szychowski et al., "Discovery of an Orally Bioavailable and Selective PKMYT1 Inhibitor, RP-6306," Available in PMC Aug. 11, 2023, published in final edited form as J. Med. Chem. 65(15):10251-10284 (Aug. 2022) (Epub Jul. 26, 2022) (34 pages).

Blanton et al., "Clinicopathologic features of breast cancer reclassified as HER2-amplified by fluorescence in situ hybridization with alternative chromosome 17 probes," available in PMC Oct. 1, 2021, published in final edited form as: Ann Diagn Pathol. 48:151576 (Oct. 2020) (Epub Aug. 2020) (15 pages).

CAS RN: 881043-03-4; STN entry date Apr. 19, 2006; amino-N-(furan-2-ylmethyl)-(3-hydroxyphenyl)BLAH carboxamide (2 pages).

Varga et al., "Co-amplification of the HER2 gene and chromosome 17 centromere: a potential diagnostic pitfall in HER2 testing in breast cancer," Breast Cancer Res Treat. 132(3):925-35 (Apr. 2012).

* cited by examiner

COMPOUNDS, PHARMACEUTICAL COMPOSITIONS, AND METHODS OF PREPARING COMPOUNDS AND OF THEIR USE

FIELD OF THE INVENTION

The invention relates to compounds and pharmaceutical compositions, their preparation and their use in the treatment of a disease or condition, e.g., cancer, and, in particular, those diseases or conditions (e.g., cancers that harbor CCNE1 amplification/overexpression or FBXW7-mutated cancers) which depend on the activity of membrane-associated tyrosine and threonine-specific cdc2-inhibitory kinase (Myt1).

BACKGROUND

DNA is continuously subjected to both endogenous insults (e.g., stalled replication forks, reactive oxygen species) and exogenous insults (UV, ionizing radiation, chemical) that can lead to DNA damage. As a result, cells have established sophisticated mechanisms to counteract these deleterious events that would otherwise compromise genomic integrity and lead to genomic instability diseases such as cancer. These mechanisms are collectively referred to as the DNA damage response (DDR). One component of the overall DDR is the activation of various checkpoint pathways that modulate specific DNA-repair mechanisms throughout the various phases of the cell cycle, which includes the G1, S, G2 and Mitosis checkpoints. A majority of cancer cells have lost their G1 checkpoint owing to p53 mutations and as such, rely on the G2 checkpoint to make the necessary DNA damage corrections prior to committing to enter mitosis and divide into 2 daughter cells.

There is a need for new anti-cancer therapeutic approaches, e.g., those utilizing small-molecules, especially therapies allowing for targeted cancer treatment.

SUMMARY OF THE INVENTION

In an aspect, the invention provides a compound of formula (I):

(I)

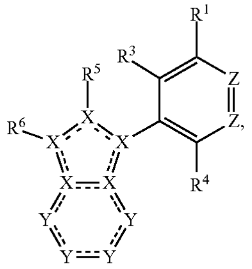

or a pharmaceutically acceptable salt thereof, where each ------ is a single or double bond;

one, two, or three X groups are N, and the remaining X groups are C;

each Y is independently N or $CR^2$;

each Z is independently N or CH;

$R^1$ is OH, and $R^3$ is hydrogen, optionally substituted $C_{1-6}$ alkyl, halogen, or optionally substituted $C_{3-8}$ cycloalkyl; or $R^1$ and $R^3$ combine to form —$CR^9$=N—NH—;

each $R^2$ is independently hydrogen, optionally substituted $C_{1-6}$ alkyl, optionally substituted $C_{2-6}$ alkenyl, optionally substituted $C_{2-6}$ alkynyl, optionally substituted $C_{3-8}$ cycloalkyl, optionally substituted $C_{3-8}$ cycloalkenyl, optionally substituted $C_{2-9}$ heterocyclyl, optionally substituted $C_{2-9}$ heterocyclyl $C_{1-6}$ alkyl, optionally substituted $C_{6-10}$ aryl, optionally substituted $C_{1-9}$ heteroaryl, optionally substituted $C_{1-9}$ heteroaryl $C_{1-6}$ alkyl, halogen, cyano, —$N(R^7)_2$, —$OR^7$, —$C(O)N(R^8)_2$, —$SO_2N(R^8)_2$, —$SO_2R^{7A}$, or -Q-$R^{7B}$;

$R^4$ is independently hydrogen, optionally substituted $C_{1-6}$ alkyl, or halogen;

$R^5$ is hydrogen, halogen, or —$N(R^7)_2$;

$R^6$ is —$C(O)NH(R^8)$, —$C(O)R^{7A}$, or —$SO_2R^{7A}$;

each $R^7$ is independently hydrogen, optionally substituted $C_{1-6}$ alkyl, optionally substituted $C_{6-10}$ aryl $C_{1-6}$ alkyl, optionally substituted $C_{3-8}$ cycloalkyl, optionally substituted $C_{6-10}$ aryl, optionally substituted $C_{2-9}$ heterocyclyl, optionally substituted $C_{1-9}$ heteroaryl, optionally substituted $C_{1-9}$ heteroaryl $C_{1-6}$ alkyl, or —$SO_2R^{7A}$; or two $R^7$ groups, together with the atom to which both are attached, combine to form an optionally substituted $C_{2-9}$ heterocyclyl;

each $R^{7A}$ is independently optionally substituted $C_{1-6}$ alkyl, optionally substituted $C_{3-8}$ cycloalkyl, or optionally substituted $C_{6-10}$ aryl;

each $R^{7B}$ is independently hydroxyl, optionally substituted $C_{1-6}$ alkyl, optionally substituted $C_{6-10}$ aryl, optionally substituted $C_{2-9}$ heterocyclyl, optionally substituted $C_{1-9}$ heteroaryl, —$N(R^7)_2$, —$C(O)N(R^8)_2$, —$SO_2N(R^8)_2$, —$SO_2R^{7A}$, or optionally substituted alkoxy;

each $R^8$ is independently hydrogen, optionally substituted $C_{1-6}$ alkyl, optionally substituted $C_{2-6}$ alkoxyalkyl, optionally substituted $C_{6-10}$ aryl $C_{1-6}$ alkyl, optionally substituted $C_{6-10}$ aryl, optionally substituted $C_{3-8}$ cycloalkyl, or optionally substituted $C_{1-9}$ heteroaryl; or two $R^8$, together with the atom to which they are attached, combine to form an optionally substituted $C_{2-9}$ heterocyclyl;

$R^9$ is hydrogen or halogen; and

Q is optionally substituted $C_{1-6}$ alkylene, optionally substituted $C_{2-6}$ alkenylene, optionally substituted $C_{2-6}$ alkynylene, optionally substituted $C_{3-8}$ cycloalkylene, optionally substituted $C_{3-8}$ cycloalkenylene optionally substituted $C_{6-10}$ arylene, optionally substituted $C_{2-9}$ heterocyclylene, or optionally substituted $C_{1-9}$ heteroarylene.

In some embodiments, one X group is N, and the remaining X groups are C. In some embodiments, all Y groups are $CR^2$. In some embodiments, one Y group is N, and the remaining Y groups are $CR^2$. In some embodiments, two Y group are N, and the remaining Y groups are $CR^2$.

In some embodiments, $R^1$ is OH, and $R^3$ is hydrogen, optionally substituted $C_{1-6}$ alkyl, or halogen. In some embodiments, $R^1$ is OH, and $R^3$ is optionally substituted $C_{1-6}$ alkyl or halogen. In some embodiments, $R^1$ and $R^3$ combine to form —$CR^9$=N—NH— (e.g., $R^9$ is hydrogen).

In some embodiments, the compound is of formula (II):

(II)

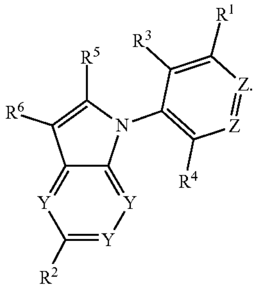

In some embodiments, the compound is:

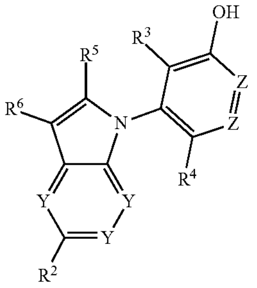

or

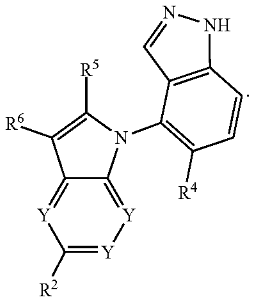

In some embodiments, the compound is enriched for the atropisomer of formula (II-i):

(II-i)

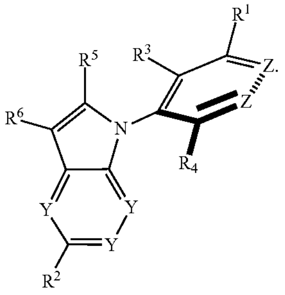

In some embodiments, the compound is enriched for the following atropisomer:

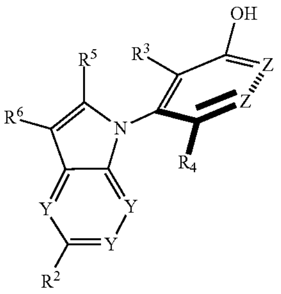

or

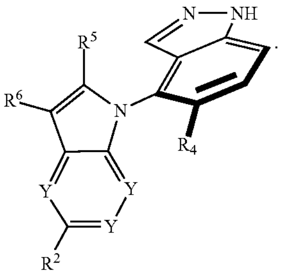

In some embodiments, the compound is of formula (IIA):

(IIA)

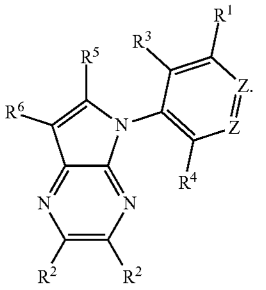

In some embodiments, the compound is:

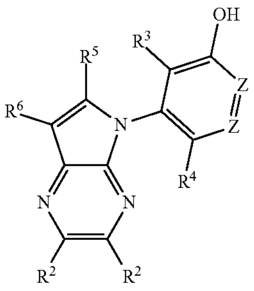

or

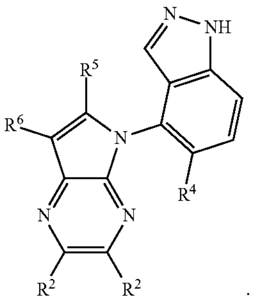

.

In some embodiments, the compound is enriched for the atropisomer of (IIA-i):

(IIA-i)
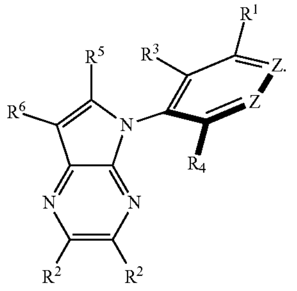
In some embodiments, the compound is enriched for the following atropisomer:
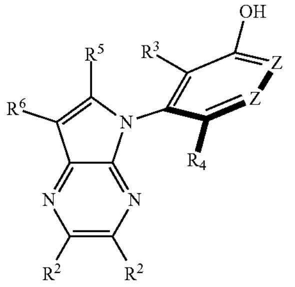
or
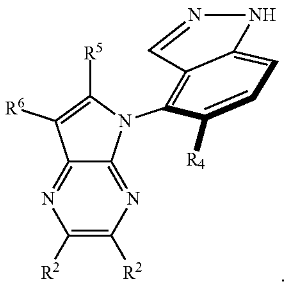
In some embodiments, the compound is of formula (IIB):
(IIB)
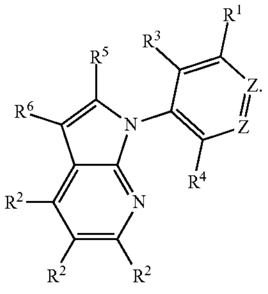
In some embodiments, the compound is:
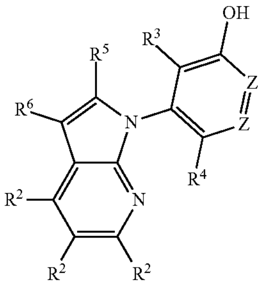
or
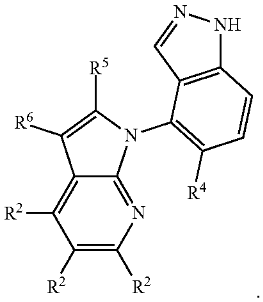
In some embodiments, the compound is enriched for the atropisomer of (IIB-i):
(IIB-i)
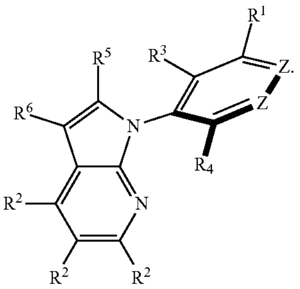
In some embodiments, the compound is enriched for the following atropisomer:
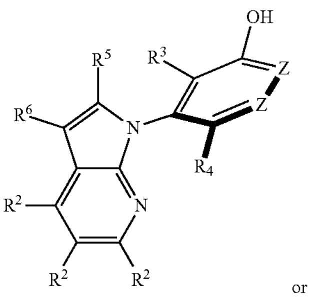
or -continued
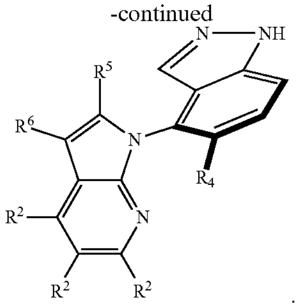
In some embodiments, the compound is of formula (IIC):
(IIC)
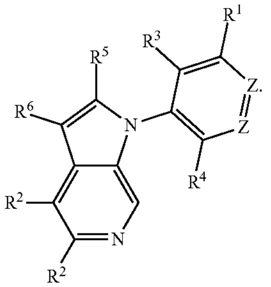
In some embodiments, the compound is:
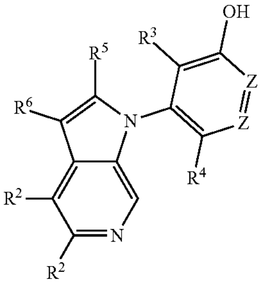
or
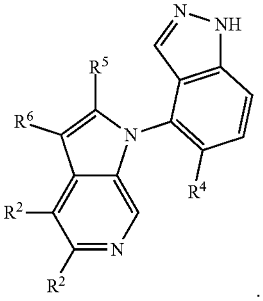
In some embodiments, the compound is enriched for the atropisomer of (IIC-i):
(IIC-i)
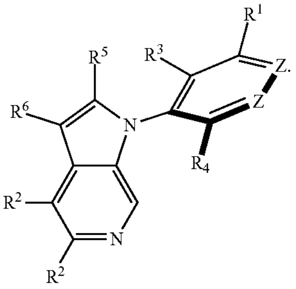
In some embodiments, the compound is enriched for the following atropisomer:
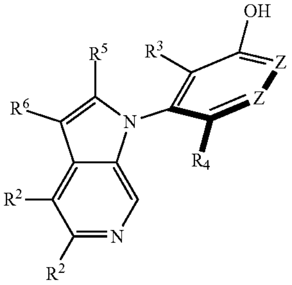
or
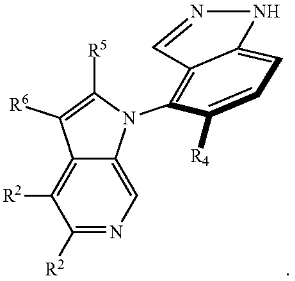
In some embodiments, the compound is of formula (IID):
(IID)
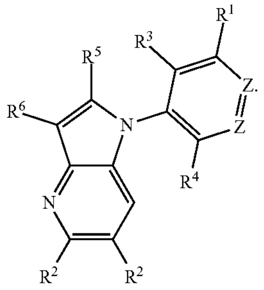

In some embodiments, the compound is:

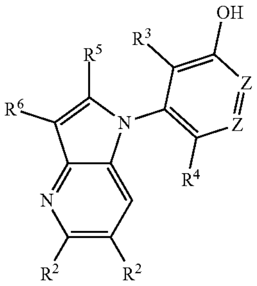

or

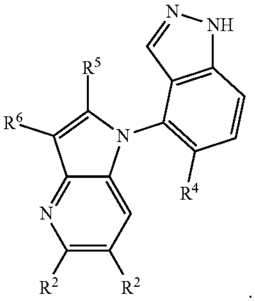

In some embodiments, the compound is enriched for the atropisomer of (IID-i):

(IID-i)

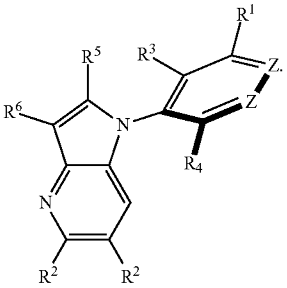

In some embodiments, the compound is enriched for the following atropisomer:

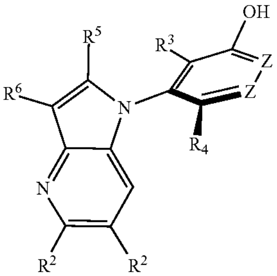

or

-continued

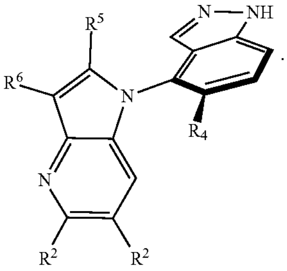

In some embodiments, the compound is of formula (III):

(III)

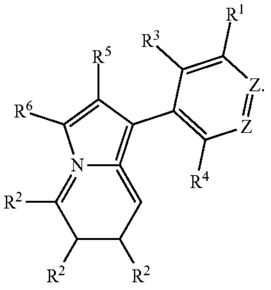

In some embodiments, the compound is:

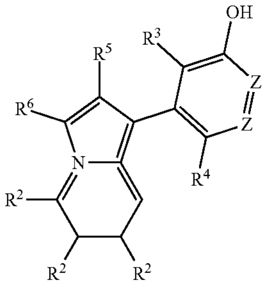

or

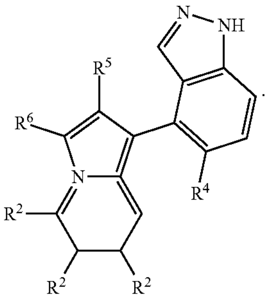

In some embodiments, the compound is enriched for the atropisomer of (III-i):

(III-i)
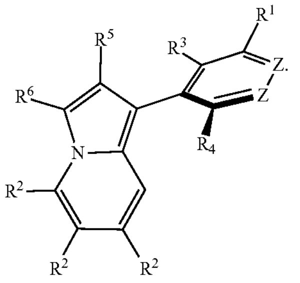
In some embodiments, the compound is enriched for the following atropisomer:
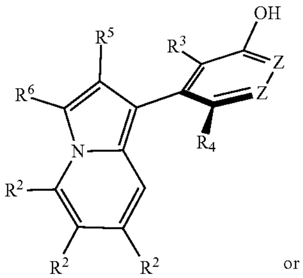
or
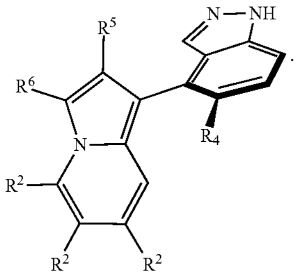
In some embodiments, the compound is of formula (IV):
(IV)
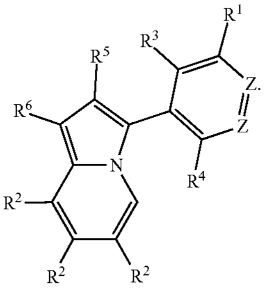
In some embodiments, the compound is:
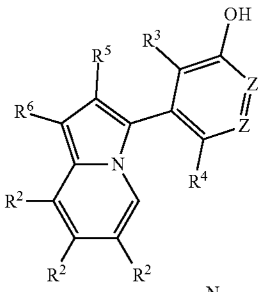
or
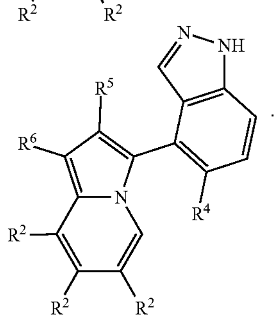
In some embodiments, the compound is enriched for the atropisomer of (IV-i):
(IV-i)
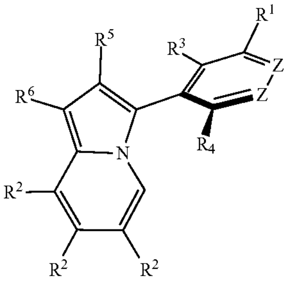
In some embodiments, the compound is enriched for the following atropisomer:
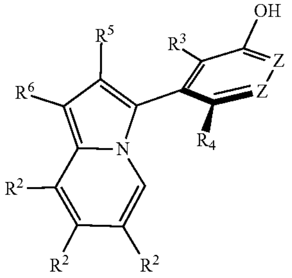
or
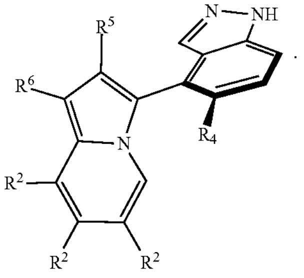

In some embodiments, the compound is of formula (V):

(V)

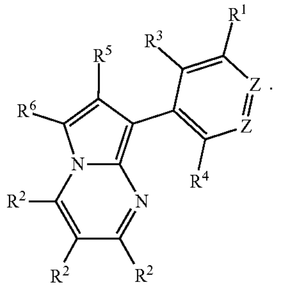

In some embodiments, the compound is:

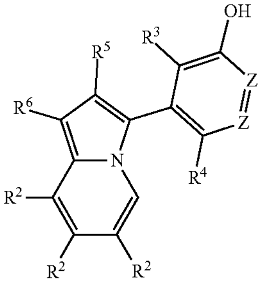

or

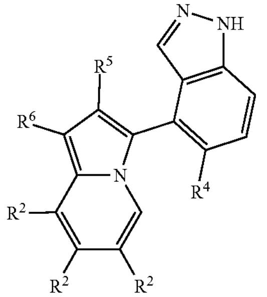

In some embodiments, the compound is enriched for the atropisomer of (V-i):

(V-i)

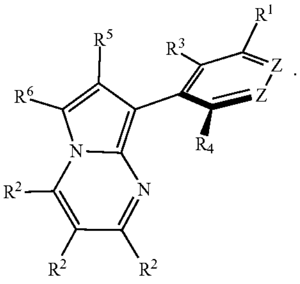

In some embodiments, the compound is enriched for the following atropisomer:

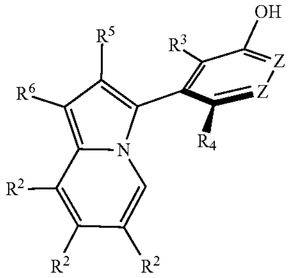

or

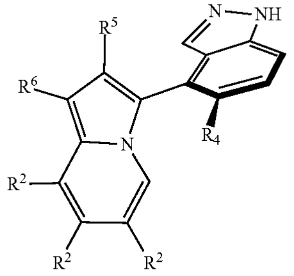

In some embodiments, the compound is of formula (VI)

(VI)

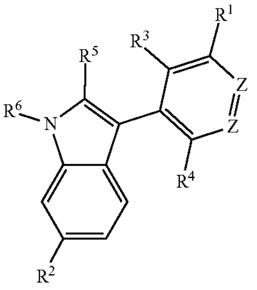

In some embodiments, Z proximal to $R^1$ is N. In some embodiments, Z proximal to $R^1$ is CH. In some embodiments, Z proximal to $R^4$ is N. In some embodiments, Z proximal to $R^4$ is CH.

In some embodiments, $R^3$ is optionally substituted $C_{1-6}$ alkyl. In some embodiments, $R^3$ is halogen. In some embodiments, $R^1$ is OH. In some embodiments, $R^1$ and $R^3$ combine to form —CH═N—NH—.

In some embodiments, $R^4$ is optionally substituted $C_{1-6}$ alkyl. In some embodiments, $R^4$ is halogen (e.g., chlorine or bromine).

In some embodiments, at least one $R^2$ is hydrogen. In some embodiments, one or two $R^2$ is optionally substituted $C_{1-6}$ alkyl. In some embodiments, one or two $R^2$ is optionally substituted $C_{1-6}$ alkyl is methyl or butyl. In some embodiments, one $R^2$ is optionally substituted $C_{1-9}$ heteroaryl or optionally substituted $C_{2-9}$ heterocyclyl. In some embodiments, one $R^2$ is 1,3-thiazol-2-yl or 3,5-difluoropyrid-2-yl. In some embodiments, $R^2$ is optionally substituted $C_{3-8}$ cycloalkyl. In some embodiments, $R^2$ is cyclopropyl. In some embodiments, $R^2$ is halogen (e.g., bromine or chlorine).

In some embodiments, $R^5$ is hydrogen. In some embodiments, $R^5$ is —$N(R^7)_2$. In some embodiments, $R^5$ is —$NH_2$. In some embodiments, $R^5$ is halogen (e.g., chlorine).

In some embodiments, $R^6$ is —C(O)NH($R^8$). In some embodiments, $R^6$ is —C(O)$NH_2$.

In some embodiments, the compound is selected from the group consisting of compounds 1-346 and pharmaceutically acceptable salts thereof. In some embodiments, the compound is selected from the group consisting of compounds 1-344 and pharmaceutically acceptable salts thereof. In some embodiments, the compound is selected from the group consisting of compounds 169, 262, 277, and 329-344 and pharmaceutically acceptable salts thereof.

In another aspect, the invention provides a pharmaceutical composition comprising the compound disclosed herein, or a pharmaceutically acceptable salt thereof, and a pharmaceutically acceptable excipient. In some embodiments, the composition is isotopically enriched in deuterium.

In yet another aspect, the invention provides a method of inhibiting Myt1 in a cell expressing Myt1, the method comprising contacting the cell with the compound disclosed herein.

In some embodiments, the cell is overexpressing CCNE1. In some embodiments, the cell is in a subject.

In still another aspect, the invention provides a method of treating a subject in need thereof comprising administering to the subject the compound disclosed herein, or a pharmaceutically acceptable salt thereof, or the pharmaceutical composition disclosed herein.

In some embodiments, the subject is suffering from, and is in need of a treatment for, a disease or condition having the symptom of cell hyperproliferation. In some embodiments, the disease or condition is a cancer. In some embodiments, the cancer is a cancer overexpressing CCNE1.

In still another aspect, the invention provides a method of treating a cancer in a subject, the method comprising administering to the subject in need thereof a therapeutically effective amount of a Myt1 inhibitor, wherein the cancer has been previously identified as a cancer overexpressing CCNE1.

In another aspect, the invention provides a method of treating a cancer in a subject, the method comprising administering to the subject in need thereof a therapeutically effective amount of a Myt1 inhibitor, wherein the cancer is a cancer overexpressing CCNE1.

In yet another aspect, the invention provides a method of inducing cell death in a cancer cell overexpressing CCNE1, the method comprising contacting the cell with an effective amount of a Myt1 inhibitor.

In some embodiments, the cell is in a subject. In some embodiments, the Myt1 inhibitor is the compound disclosed herein or a pharmaceutically acceptable salt thereof. In some embodiments, the cancer overexpressing CCNE1 is uterine cancer, ovarian cancer, breast cancer, stomach cancer, esophageal cancer, lung cancer, or endometrial cancer.

In still another aspect, the invention provides a method of treating a cancer in a subject, the method comprising administering to the subject in need thereof a therapeutically effective amount of a Myt1 inhibitor, wherein the cancer has been previously identified as a cancer having an inactivating mutation in the FBXW7 gene.

In another aspect, the invention provides a method of treating a cancer in a subject, the method comprising administering to the subject in need thereof a therapeutically effective amount of a Myt1 inhibitor, wherein the cancer has an inactivating mutation in the FBXW7 gene.

In yet another aspect, the invention provides a method of inducing cell death in an FBXW7-mutated cancer cell, the method comprising contacting the cell with an effective amount of a Myt1 inhibitor.

In some embodiments, the cell is in a subject, the cancer is uterine cancer, colorectal cancer, breast cancer, lung cancer, or esophageal cancer. In some embodiments, the Myt1 inhibitor is the compound disclosed herein, or a pharmaceutically acceptable salt thereof.

Abbreviations

Abbreviations and terms that are commonly used in the fields of organic chemistry, medicinal chemistry, pharmacology, and medicine and are well known to practitioners in these fields are used herein. Representative abbreviations and definitions are provided below:

Ac is acetyl [$CH_3C(O)$—];
ACN is acetonitrile;
$Ac_2O$ is acetic anhydride;
AcOH is acetic acid;
APC is antigen-presenting cell;
Ar is aryl;
aq. is aqueous;
9-BBN is 9-borabicyclo[3.3.1]nonane;
BINAP is (2,2'-bis(diphenylphosphino)-1,1'-binaphthyl);
Bn is benzyl;
Boc is tert Butyloxycarbonyl;
n-BuLi is n-butyl lithium;
CDI is carbonyldiimidazole;
cmpd is compound;
conc. is concentrated;
DCM is dichloromethane;
DIAD is diisopropylazodicarboxylate;
DIBAL is diisobutylaluminum hydride;
DIPEA is diisoproplyethyl amine;
DMA is dimethylacetamide;
DMAP is 4-dimethylaminopyridine;
DME is dimethoxyethane;
DMF is N,N-dimethylformamide;
DMSO is dimethyl sulfoxide;
dppf is 1,1'-bis(diphenylphosphino) ferrocene;
EDAC (or EDC) is 1-ethyl-3-[3-(dimethylamino) propyl]-carbodiimide HCl;
ESI is electrospray ionization mass spectrometry;
$Et_2O$ is diethyl ether;
$Et_3N$ is triethylamine;
Et is ethyl;
EtOAc is ethyl acetate;
EtOH is ethanol;
3-F-Ph is 3-fluorophenyl,
h is hour;
HATU is (1-[bis(dimethylamino)methylene]-1H-1,2,3-triazolo[4,5-b]pyridinium 3-oxide hexafluorophosphate;
HCl is hydrochloric acid;
Hex is hexanes;
HOBt is 1-hydroxybenzotriazole;
HPLC is high performance liquid chromatography;
IPA is isopropanol;
LCMS is HPLC with mass spectral detection;
LiHMDS is lithium bis(trimethylsilyl)amide;
LG is leaving group;
M is molar;
mCPBA is metachloroperbenzoic acid;
mmol is millimole;
Me is methyl;
MeCN is acetonitrile;
MeMgBr is methylmagnesium bromide;
MeMgCl is methylmagnesium chloride;
MeOH is methanol;
min is minute;
MOM is methoxymethyl;
Ms is methanesulfonyl;
MS is mass spectrometry;

MW is microwave;
N is normal;
NaHMDS is sodium bis(trimethylsilyl)amide;
NaOAc is sodium acetate;
NaOtBu is sodium tert-butoxide;
NBS is N-bromosuccinimide;
NCS is N-chlorosuccinimide;
NIS is N-iodosuccinimide;
NMO is N-methylmorpholine N-oxide;
NMP is N-methyl pyrrolidinone;
NMR is nuclear magnetic resonance spectroscopy;
$PdCl_2$(dppf) is [1,1'-Bis(diphenylphosphino) ferrocene] dichloropalladium(II);
$PdCl_2(dppf)\cdot CH_2Cl_2$ is [1,1'-Bis(diphenylphosphino) ferrocene]dichloropalladium(II), complex with dichloromethane;
$Pd_2(dba)_3$ is tris(dibenzylideneacetone)dipalladium;
$PdCl_2(PPh_3)_2$ is dichlorobis-(triphenylphosphene)palladium;
Pd-PEPPSI™-SIPr is (1,3-Bis(2,6-diisopropylphenyl) imidazolidene) (3-chloropyridyl) palladium(II) dichloride;
PG Denotes a protecting group;
Ph is phenyl;
PhMe is toluene;
PIV-Cl is pivaloyl chloride, Trimethylacetyl chloride;
$PPh_3$ is triphenylphosphine;
PMB is para-methoxybenzyl;
Rt or RT is room temperature;
RBF is round-bottom flask;
RuPhos Pd G1 is chloro-(2-Dicyclohexylphosphino-2',6'-diisopropoxy-1,1'-biphenyl) [2-(2-aminoethyl)phenyl] palladium(II);
sat. is saturated;
SEM is [2-(trimethylsilyl)ethoxy]methyl;
SFC is supercritical fluid chromatography;
SNAr is nucleophilic aromatic substitution;
TBAB is tetrabutyl ammonium bromide;
TBAF is tetrabutyl ammonium fluoride;
TBS is tert-butyldimethylsilyl;
tBu is tert-butyl;
Tf is trifluoromethanesulfonyl;
TFA is trifluoroacetic acid;
THF is tetrahydrofuran;
THP is tetrahydropyran;
TLC is thin layer chromatography;
TMAD is tetramethylazodicarboxamide;
TMS is trimethylsilyl;
TPAP is tetrapropylammonium perruthenate;
Ts is p-toluenesulfonyl;
UPLC is ultra-performance liquid chromatography;
Xantphos is 4,5-Bis(diphenylphosphino)-9,9-dimethylxanthene.

Definitions

The term "aberrant," as used herein, refers to different from normal. When used to describe activity, aberrant refers to activity that is greater or less than a normal control or the average of normal non-diseased control samples. Aberrant activity may refer to an amount of activity that results in a disease, where returning the aberrant activity to a normal or non-disease-associated amount (e.g. by administering a compound or using a method as described herein), results in reduction of the disease or one or more disease symptoms.

The term "acyl," as used herein, represents a group-C(═O)—R, where R is alkyl, alkenyl, alkynyl, cycloalkyl, cycloalkenyl, cycloalkynyl, aryl, heteroaryl, or heterocyclyl. Acyl may be optionally substituted as described herein for each respective R group.

The term "adenocarcinoma," as used herein, represents a malignancy of the arising from the glandular cells that line organs within an organism. Non-limiting examples of adenocarcinomas include non-small cell lung cancer, prostate cancer, pancreatic cancer, esophageal cancer, and colorectal cancer.

The term "alkanoyl," as used herein, represents a hydrogen or an alkyl group that is attached to the parent molecular group through a carbonyl group and is exemplified by formyl (i.e., a carboxyaldehyde group), acetyl, propionyl, butyryl, and iso-butyryl. Unsubstituted alkanoyl groups contain from 1 to 7 carbons. The alkanoyl group may be unsubstituted of substituted (e.g., optionally substituted $C_{1-7}$ alkanoyl) as described herein for alkyl group. The ending "-oyl" may be added to another group defined herein, e.g., aryl, cycloalkyl, and heterocyclyl, to define "aryloyl," "cycloalkanoyl," and "(heterocyclyl)oyl." These groups represent a carbonyl group substituted by aryl, cycloalkyl, or heterocyclyl, respectively. Each of "aryloyl," "cycloalkanoyl," and "(heterocyclyl)oyl" may be optionally substituted as defined for "aryl," "cycloalkyl," or "heterocyclyl," respectively.

The term "alkenyl," as used herein, represents acyclic monovalent straight or branched chain hydrocarbon groups of containing one, two, or three carbon-carbon double bonds. Non-limiting examples of the alkenyl groups include ethenyl, prop-1-enyl, prop-2-enyl, 1-methylethenyl, but-1-enyl, but-2-enyl, but-3-enyl, 1-methylprop-1-enyl, 2-methylprop-1-enyl, and 1-methylprop-2-enyl. Alkenyl groups may be optionally substituted as defined herein for alkyl.

The term "alkenylene," as used herein, refers to a divalent alkenyl group. An optionally substituted alkenylene is an alkenylene that is optionally substituted as described herein for alkenyl.

The term "alkoxy," as used herein, represents a chemical substituent of formula —OR, where R is a $C_{1-6}$ alkyl group, unless otherwise specified. In some embodiments, the alkyl group can be further substituted as defined herein. The term "alkoxy" can be combined with other terms defined herein, e.g., aryl, cycloalkyl, or heterocyclyl, to define an "aryl alkoxy," "cycloalkyl alkoxy," and "(heterocyclyl)alkoxy" groups. These groups represent an alkoxy that is substituted by aryl, cycloalkyl, or heterocyclyl, respectively. Each of "aryl alkoxy," "cycloalkyl alkoxy," and "(heterocyclyl)alkoxy" may optionally substituted as defined herein for each individual portion.

The term "alkoxyalkyl," as used herein, represents a chemical substituent of formula -L-O—R, where L is $C_{1-6}$ alkylene, and R is $C_{1-6}$ alkyl. An optionally substituted alkoxyalkyl is an alkoxyalkyl that is optionally substituted as described herein for alkyl.

The term "alkyl," as used herein, refers to an acyclic straight or branched chain saturated hydrocarbon group, which, when unsubstituted, has from 1 to 12 carbons, unless otherwise specified. In certain preferred embodiments, unsubstituted alkyl has from 1 to 6 carbons. Alkyl groups are exemplified by methyl; ethyl; n- and iso-propyl; n-, sec-, iso- and tert-butyl; neopentyl, and the like, and may be optionally substituted, valency permitting, with one, two, three, or, in the case of alkyl groups of two carbons or more, four or more substituents independently selected from the group consisting of: amino; alkoxy; aryl; aryloxy; azido; cycloalkyl; cycloalkoxy; cycloalkenyl; cycloalkynyl; halo; heterocyclyl; (heterocyclyl)oxy; heteroaryl; hydroxy; nitro; thiol;

silyl; cyano; alkylsulfonyl; alkylsulfinyl; alkylsulfenyl; =O; =S; —C(O)R or —$SO_2R$, where R is amino; and =NR', where R' is H, alkyl, aryl, or heterocyclyl. Each of the substituents may itself be unsubstituted or, valency permitting, substituted with unsubstituted substituent(s) defined herein for each respective group.

The term "alkylene," as used herein, refers to a divalent alkyl group. An optionally substituted alkylene is an alkylene that is optionally substituted as described herein for alkyl.

The term "alkylamino," as used herein, refers to a group having the formula —$N(R^{N1})_2$ or —$NHR^{N1}$, in which $R^{N1}$ is alkyl, as defined herein. The alkyl portion of alkylamino can be optionally substituted as defined for alkyl. Each optional substituent on the substituted alkylamino may itself be unsubstituted or, valency permitting, substituted with unsubstituted substituent(s) defined herein for each respective group.

The term "alkylsulfenyl," as used herein, represents a group of formula —S-(alkyl). Alkylsulfenyl may be optionally substituted as defined for alkyl.

The term "alkylsulfinyl," as used herein, represents a group of formula —S(O)-(alkyl). Alkylsulfinyl may be optionally substituted as defined for alkyl.

The term "alkylsulfonyl," as used herein, represents a group of formula —S(O)2-(alkyl). Alkylsulfonyl may be optionally substituted as defined for alkyl.

The term "alkynyl," as used herein, represents monovalent straight or branched chain hydrocarbon groups of from two to six carbon atoms containing at least one carbon-carbon triple bond and is exemplified by ethynyl, 1-propynyl, and the like. The alkynyl groups may be unsubstituted or substituted (e.g., optionally substituted alkynyl) as defined for alkyl.

The term "alkynylene," as used herein, refers to a divalent alkynyl group. An optionally substituted alkynylene is an alkynylene that is optionally substituted as described herein for alkynyl.

The term "amino," as used herein, represents-$N(R^{N1})_2$, where, if amino is unsubstituted, both $R^{N1}$ are H; or, if amino is substituted, each $R^{N1}$ is independently H, —OH, —$NO_2$, —$N(R^{N2})_2$, —$SO_2OR^{N2}$, —$SO_2R^{N2}$, —$SOR^{N2}$, —C(O)$OR^{N2}$, an N-protecting group, alkyl, alkenyl, alkynyl, alkoxy, aryl, arylalkyl, aryloxy, cycloalkyl, cycloalkenyl, heteroalkyl, or heterocyclyl, provided that at least one $R^{N1}$ is not H, and where each $R^{N2}$ is independently H, alkyl, or aryl. Each of the substituents may itself be unsubstituted or substituted with unsubstituted substituent(s) defined herein for each respective group. In some embodiments, amino is unsubstituted amino (i.e., —$NH_2$) or substituted amino (e.g., —$NHR^{N1}$), where $R^{N1}$ is independently-OH, $SO_2OR^{N2}$, —$SO_2R^{N2}$, —$SOR^{N2}$, —$COOR^{N2}$, optionally substituted alkyl, or optionally substituted aryl, and each $R^{N2}$ can be optionally substituted alkyl or optionally substituted aryl. In some embodiments, substituted amino may be alkylamino, in which the alkyl groups are optionally substituted as described herein for alkyl. In some embodiments, an amino group is —$NHR^{N1}$, in which $R^{N1}$ is optionally substituted alkyl.

The term "aryl," as used herein, represents a mono-, bicyclic, or multicyclic carbocyclic ring system having one or two aromatic rings. Aryl group may include from 6 to 10 carbon atoms. All atoms within an unsubstituted carbocyclic aryl group are carbon atoms. Non-limiting examples of carbocyclic aryl groups include phenyl, naphthyl, 1,2-dihydronaphthyl, 1,2,3,4-tetrahydronaphthyl, fluorenyl, indanyl, indenyl, etc. The aryl group may be unsubstituted or substituted with one, two, three, four, or five substituents independently selected from the group consisting of: alkyl; alkenyl; alkynyl; alkoxy; alkylsulfinyl; alkylsulfenyl; alkylsulfonyl; amino; aryl; aryloxy; azido; cycloalkyl; cycloalkoxy; cycloalkenyl; cycloalkynyl; halo; heteroalkyl; heterocyclyl; (heterocyclyl)oxy; hydroxy; nitro; thiol; silyl; —$(CH_2)_n$—$C(O)OR^A$; —C(O)R; and —$SO_2R$, where R is amino or alkyl, $R^A$ is H or alkyl, and n is 0 or 1. Each of the substituents may itself be unsubstituted or substituted with unsubstituted substituent(s) defined herein for each respective group.

The term "aryl alkyl," as used herein, represents an alkyl group substituted with an aryl group. The aryl and alkyl portions may be optionally substituted as the individual groups as described herein.

The term "arylene," as used herein, refers to a divalent aryl group. An optionally substituted arylene is an arylene that is optionally substituted as described herein for aryl.

The term "aryloxy," as used herein, represents a chemical substituent of formula —OR, where R is an aryl group, unless otherwise specified. In optionally substituted aryloxy, the aryl group is optionally substituted as described herein for aryl.

The term "azido," as used herein, represents an —$N_3$ group.

The term "cancer," as used herein, refers to all types of cancer, neoplasm or malignant tumors found in mammals (e.g., humans).

The term "carbocyclic," as used herein, represents an optionally substituted $C_{3-16}$ monocyclic, bicyclic, or tricyclic structure in which the rings, which may be aromatic or non-aromatic, are formed by carbon atoms. Carbocyclic structures include cycloalkyl, cycloalkenyl, cycloalkynyl, and certain aryl groups.

The term "carbonyl," as used herein, represents a —C(O)— group.

The term "carcinoma," as used herein, refers to a malignant new growth made up of epithelial cells tending to infiltrate the surrounding tissues and give rise to metastases.

The term "cyano," as used herein, represents-CN group.

The terms "CCNE1" and "cyclin E1," as used interchangeably herein, refer to G1/S specific cyclin E1 (Gene name: CCNE1). A cell overexpressing CCNE1 is one that exhibits a higher activity of CCNE1 than a cell normally expressing CCNE1. For example, a CCNE1-overexpressing cell is a cell that exhibits a copy number of at least 3 compared to a diploid normal cell with 2 copies. Thus, a cell exhibiting a copy number greater than 3 of CCNE1 is a cell overexpressing CCNE1. The CCNE1 overexpression may be measured by identifying the expression level of the gene product in a cell (e.g., CCNE1 mRNA transcript count or CCNE1 protein level).

The term "cycloalkenyl," as used herein, refers to a non-aromatic carbocyclic group having at least one double bond in the ring and from three to ten carbons (e.g., a $C_{3-10}$ cycloalkenyl), unless otherwise specified. Non-limiting examples of cycloalkenyl include cycloprop-1-enyl, cycloprop-2-enyl, cyclobut-1-enyl, cyclobut-1-enyl, cyclobut-2-enyl, cyclopent-1-enyl, cyclopent-2-enyl, cyclopent-3-enyl, norbornen-1-yl, norbornen-2-yl, norbornen-5-yl, and norbornen-7-yl. The cycloalkenyl group may be unsubstituted or substituted (e.g., optionally substituted cycloalkenyl) as described for cycloalkyl.

The term "cycloalkenyl alkyl," as used herein, represents an alkyl group substituted with a cycloalkenyl group, each as defined herein. The cycloalkenyl and alkyl portions may be substituted as the individual groups defined herein.

The term "cycloalkenylene," as used herein, represents a divalent cycloalkenyl group. An optionally substituted cycloalkenylene is a cycloalkenylene that is optionally substituted as described herein for cycloalkyl.

The term "cycloalkoxy," as used herein, represents a chemical substituent of formula —OR, where R is cycloalkyl group, unless otherwise specified. In some embodiments, the cycloalkyl group can be further substituted as defined herein.

The term "cycloalkyl," as used herein, refers to a cyclic alkyl group having from three to ten carbons (e.g., a $C_{3\text{-}c10}$ cycloalkyl), unless otherwise specified. Cycloalkyl groups may be monocyclic or bicyclic. Bicyclic cycloalkyl groups may be of bicyclo[p.q.0]alkyl type, in which each of p and q is, independently, 1, 2, 3, 4, 5, 6, or 7, provided that the sum of p and q is 2, 3, 4, 5, 6, 7, or 8. Alternatively, bicyclic cycloalkyl groups may include bridged cycloalkyl structures, e.g., bicyclo[p.q.r]alkyl, in which r is 1, 2, or 3, each of p and q is, independently, 1, 2, 3, 4, 5, or 6, provided that the sum of p, q, and r is 3, 4, 5, 6, 7, or 8. The cycloalkyl group may be a spirocyclic group, e.g., spiro[p.q]alkyl, in which each of p and q is, independently, 2, 3, 4, 5, 6, or 7, provided that the sum of p and q is 4, 5, 6, 7, 8, or 9. Non-limiting examples of cycloalkyl include cyclopropyl, cyclobutyl, cyclopentyl, cyclohexyl, cycloheptyl, 1-bicyclo [2.2.1.]heptyl, 2-bicyclo[2.2.1.]heptyl, 5-bicyclo[2.2.1.]heptyl, 7-bicyclo[2.2.1.]heptyl, and decalinyl. The cycloalkyl group may be unsubstituted or substituted (e.g., optionally substituted cycloalkyl) with one, two, three, four, or five substituents independently selected from the group consisting of: alkyl; alkenyl; alkynyl; alkoxy; alkylsulfinyl; alkylsulfenyl; alkylsulfonyl; amino; aryl; aryloxy; azido; cycloalkyl; cycloalkoxy; cycloalkenyl; cycloalkynyl; halo; heteroalkyl; heterocyclyl; (heterocyclyl)oxy; heteroaryl; hydroxy; nitro; thiol; silyl; cyano; =O; =S; —$SO_2$R, where R is optionally substituted amino; =NR', where R' is H, alkyl, aryl, or heterocyclyl; and —CON($R^A$)$_2$, where each $R^A$ is independently H or alkyl, or both $R^A$, together with the atom to which they are attached, combine to form heterocyclyl. Each of the substituents may itself be unsubstituted or substituted with unsubstituted substituent(s) defined herein for each respective group.

The term "cycloalkyl alkyl," as used herein, represents an alkyl group substituted with a cycloalkyl group, each as defined herein. The cycloalkyl and alkyl portions may be optionally substituted as the individual groups described herein.

The term "cycloalkylene," as used herein, represents a divalent cycloalkyl group. An optionally substituted cycloalkylene is a cycloalkylene that is optionally substituted as described herein for cycloalkyl.

The term "cycloalkynyl," as used herein, refers to a monovalent carbocyclic group having one or two carbon-carbon triple bonds and having from eight to twelve carbons, unless otherwise specified. Cycloalkynyl may include one transannular bond or bridge. Non-limiting examples of cycloalkynyl include cyclooctynyl, cyclononynyl, cyclodecynyl, and cyclodecadiynyl. The cycloalkynyl group may be unsubstituted or substituted (e.g., optionally substituted cycloalkynyl) as defined for cycloalkyl.

"Disease" or "condition" refer to a state of being or health status of a patient or subject capable of being treated with the compounds or methods provided herein.

The term "FBXW7," as used herein, refers to F-box/WD Repeat-Containing Protein 7 gene, transcript, or protein. An FBXW7-mutated gene, also described herein as an FBXW7 gene having an inactivating mutation, is one that fails to produce a functional FBXW7 protein or produces reduced quantities of FBXW7 protein in a cell.

The term "halo," as used herein, represents a halogen selected from bromine, chlorine, iodine, and fluorine.

The term "heteroalkyl," as used herein refers to an alkyl, alkenyl, or alkynyl group interrupted once by one or two heteroatoms; twice, each time, independently, by one or two heteroatoms; three times, each time, independently, by one or two heteroatoms; or four times, each time, independently, by one or two heteroatoms. Each heteroatom is, independently, O, N, or S. In some embodiments, the heteroatom is O or N. None of the heteroalkyl groups includes two contiguous oxygen or sulfur atoms. The heteroalkyl group may be unsubstituted or substituted (e.g., optionally substituted heteroalkyl). When heteroalkyl is substituted and the substituent is bonded to the heteroatom, the substituent is selected according to the nature and valency of the heteratom. Thus, the substituent bonded to the heteroatom, valency permitting, is selected from the group consisting of =O, —N($R^{N2}$)$_2$, —$SO_2OR^{N3}$, —$SO_2R^{N2}$, —$SOR^{N3}$, —CO$OR^{N3}$, an N protecting group, alkyl, alkenyl, alkynyl, aryl, cycloalkyl, cycloalkenyl, cycloalkynyl, heterocyclyl, or cyano, where each $R^{N2}$ is independently H, alkyl, cycloalkyl, cycloalkenyl, cycloalkynyl, aryl, or heterocyclyl, and each $R^{N3}$ is independently alkyl, cycloalkyl, cycloalkenyl, cycloalkynyl, aryl, or heterocyclyl. Each of these substituents may itself be unsubstituted or substituted with unsubstituted substituent(s) defined herein for each respective group. When heteroalkyl is substituted and the substituent is bonded to carbon, the substituent is selected from those described for alkyl, provided that the substituent on the carbon atom bonded to the heteroatom is not Cl, Br, or I. It is understood that carbon atoms are found at the termini of a heteroalkyl group.

The term "heteroaryl alkyl," as used herein, represents an alkyl group substituted with a heteroaryl group, each as defined herein. The heteroaryl and alkyl portions may be optionally substituted as the individual groups described herein.

The term "heteroarylene," as used herein, represents a divalent heteroaryl. An optionally substituted heteroarylene is a heteroarylene that is optionally substituted as described herein for heteroaryl.

The term "heteroaryloxy," as used herein, refers to a structure —OR, in which R is heteroaryl. Heteroaryloxy can be optionally substituted as defined for heterocyclyl.

The term "heterocyclyl," as used herein, represents a monocyclic, bicyclic, tricyclic, or tetracyclic ring system having fused, bridging, and/or spiro 3-, 4-, 5-, 6-, 7-, or 8-membered rings, unless otherwise specified, containing one, two, three, or four heteroatoms independently selected from the group consisting of nitrogen, oxygen, and sulfur. In some embodiments, "heterocyclyl" is a monocyclic, bicyclic, tricyclic, or tetracyclic ring system having fused or bridging 5-, 6-, 7-, or 8-membered rings, unless otherwise specified, containing one, two, three, or four heteroatoms independently selected from the group consisting of nitrogen, oxygen, and sulfur. Heterocyclyl can be aromatic or non-aromatic. Non-aromatic 5-membered heterocyclyl has zero or one double bonds, non-aromatic 6- and 7-membered heterocyclyl groups have zero to two double bonds, and non-aromatic 8-membered heterocyclyl groups have zero to two double bonds and/or zero or one carbon-carbon triple bond. Heterocyclyl groups include from 1 to 16 carbon atoms unless otherwise specified. Certain heterocyclyl groups may include up to 9 carbon atoms. Non-aromatic heterocyclyl groups include pyrrolinyl, pyrrolidinyl, pyrazolinyl, pyrazolidinyl, imidazolinyl, imidazolidinyl, piperidinyl, homopiperidinyl, piperazinyl, pyridazinyl, oxazolidinyl, isoxazolidiniyl, morpholinyl, thiomorpholinyl, thiazolidinyl, isothiazolidinyl, thiazolidinyl, tetrahydrofuranyl, dihydrofuranyl, tetrahydrothienyl, dihydrothienyl, dihydroindolyl, tetrahydroquinolyl, tetrahydroisoquinolyl, pyranyl, dihydropyranyl, dithiazolyl, etc. If the heterocyclic ring system has at least one aromatic resonance structure or at least one aromatic tautomer, such structure is an aromatic heterocyclyl (i.e., heteroaryl). Non-limiting examples of heteroaryl groups include benzimidazolyl, benzofuryl, benzothiazolyl, benzothienyl, benzoxazolyl, furyl, imidazolyl, indolyl, isoindazolyl, isoquinolinyl, isothiazolyl, isothiazolyl, isoxazolyl, oxadiazolyl, oxazolyl, purinyl, pyrrolyl, pyridinyl, pyrazinyl, pyrimidinyl, qunazolinyl, quinolinyl, thiadiazolyl (e.g., 1,3,4-thiadiazole), thiazolyl, thienyl, triazolyl, tetrazolyl, etc. The term “heterocyclyl” also represents a heterocyclic compound having a bridged multicyclic structure in which one or more carbons and/or heteroatoms bridges two non-adjacent members of a monocyclic ring, e.g., quinuclidine, tropanes, or diaza-bicyclo[2.2.2]octane. The term “heterocyclyl” includes bicyclic, tricyclic, and tetracyclic groups in which any of the above heterocyclic rings is fused to one, two, or three carbocyclic rings, e.g., an aryl ring, a cyclohexane ring, a cyclohexene ring, a cyclopentane ring, a cyclopentene ring, or another monocyclic heterocyclic ring. Examples of fused heterocyclyls include 1,2,3,5,8,8a-hexahydroindolizine; 2,3-dihydrobenzofuran; 2,3-dihydroindole; and 2,3-dihydrobenzothiophene. The heterocyclyl group may be unsubstituted or substituted with one, two, three, four or five substituents independently selected from the group consisting of: alkyl; alkenyl; alkynyl; alkoxy; alkylsulfinyl; alkylsulfenyl; alkylsulfonyl; amino; aryl; aryloxy; azido; cycloalkyl; cycloalkoxy; cycloalkenyl; cycloalkynyl; halo; heteroalkyl; heterocyclyl; (heterocyclyl)oxy; hydroxy; nitro; thiol; silyl; cyano; —C(O)R or —$SO_2$R, where R is amino or alkyl; =O; =S; =NR', where R' is H, alkyl, aryl, or heterocyclyl. Each of the substituents may itself be unsubstituted or substituted with unsubstituted substituent(s) defined herein for each respective group.

The term “heterocyclyl alkyl,” as used herein, represents an alkyl group substituted with a heterocyclyl group, each as defined herein. The heterocyclyl and alkyl portions may be optionally substituted as the individual groups described herein.

The term “heterocyclylene,” as used herein, represents a divalent heterocyclyl. An optionally substituted heterocyclylene is a heterocyclylene that is optionally substituted as described herein for heterocyclyl.

The term “(heterocyclyl)oxy,” as used herein, represents a chemical substituent of formula —OR, where R is a heterocyclyl group, unless otherwise specified. (Heterocyclyl)oxy can be optionally substituted in a manner described for heterocyclyl.

The terms “hydroxyl” and “hydroxy,” as used interchangeably herein, represent an —OH group.

The term “isotopically enriched,” as used herein, refers to the pharmaceutically active agent with the isotopic content for one isotope at a predetermined position within a molecule that is at least 100 times greater than the natural abundance of this isotope. For example, a composition that is isotopically enriched for deuterium includes an active agent with at least one hydrogen atom position having at least 100 times greater abundance of deuterium than the natural abundance of deuterium. Preferably, an isotopic enrichment for deuterium is at least 1000 times greater than the natural abundance of deuterium. More preferably, an isotopic enrichment for deuterium is at least 4000 times greater (e.g., at least 4750 times greater, e.g., up to 5000 times greater) than the natural abundance of deuterium.

The term “leukemia,” as used herein, refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic).

The term “lymphoma,” as used herein, refers to a cancer arising from cells of immune origin.

The term “melanoma,” as used herein, is taken to mean a tumor arising from the melanocytic system of the skin and other organs.

The term “Myt1,” as used herein, refers to membrane-associated tyrosine and threonine-specific cdc2-inhibitory kinase (Myt1) (Gene name PKMYT1).

The term “Myt1 inhibitor,” as used herein, represents a compound that upon contacting the enzyme Myt1, whether in vitro, in cell culture, or in an animal, reduces the activity of Myt1, such that the measured Myt1 $IC_{50}$ is 10 UM or less (e.g., 5 UM or less or 1 UM or less). For certain Myt1 inhibitors, the Myt1 $IC_{50}$ may be 100 nM or less (e.g., 10 nM or less, or 3 nM or less) and could be as low as 100 pM or 10 pM. Preferably, the Myt1 $IC_{50}$ is 1 nM to 1 μM (e.g., 1 nM to 750 nM, 1 nM to 500 nM, or 1 nM to 250 nM). Even more preferably, the Myt1 $IC_{50}$ is less than 20 nm (e.g., 1 nM to 20 nM).

The term “nitro,” as used herein, represents an —$NO_2$ group.

The term “oxo,” as used herein, represents a divalent oxygen atom (e.g., the structure of oxo may be shown as =O).

The term “Ph,” as used herein, represents phenyl.

The term “pharmaceutical composition,” as used herein, represents a composition containing a compound described herein, formulated with a pharmaceutically acceptable excipient, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

The term “pharmaceutically acceptable excipient” or “pharmaceutically acceptable carrier,” as used interchangeably herein, refers to any ingredient other than the compounds described herein (e.g., a vehicle capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The term "pharmaceutically acceptable salt," as use herein, represents those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., J. Pharmaceutical Sciences 66:1-19, 1977 and in Pharmaceutical Salts: Properties, Selection, and Use, (Eds. P. H. Stahl and C. G. Wermuth), Wiley-VCH, 2008. The salts can be prepared in situ during the final isolation and purification of the compounds described herein or separately by reacting the free base group with a suitable organic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

The term "pre-malignant" or "pre-cancerous," as used herein, refers to a condition that is not malignant but is poised to become malignant.

The term "protecting group," as used herein, represents a group intended to protect a hydroxy, an amino, or a carbonyl from participating in one or more undesirable reactions during chemical synthesis. The term "O-protecting group," as used herein, represents a group intended to protect a hydroxy or carbonyl group from participating in one or more undesirable reactions during chemical synthesis. The term "N-protecting group," as used herein, represents a group intended to protect a nitrogen containing (e.g., an amino, amido, heterocyclic N—H, or hydrazine) group from participating in one or more undesirable reactions during chemical synthesis. Commonly used O- and N-protecting groups are disclosed in Greene, "Protective Groups in Organic Synthesis," 3rd Edition (John Wiley & Sons, New York, 1999), which is incorporated herein by reference. Exemplary O- and N-protecting groups include alkanoyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, t-butyldimethylsilyl, tri-iso-propylsilyloxymethyl, 4,4'-dimethoxytrityl, isobutyryl, phenoxyacetyl, 4-isopropylpehenoxyacetyl, dimethylformamidino, and 4-nitrobenzoyl.

Exemplary O-protecting groups for protecting carbonyl containing groups include, but are not limited to: acetals, acylals, 1,3-dithianes, 1,3-dioxanes, 1,3-dioxolanes, and 1,3-dithiolanes.

Other O-protecting groups include, but are not limited to: substituted alkyl, aryl, and aryl-alkyl ethers (e.g., trityl; methylthiomethyl; methoxymethyl; benzyloxymethyl; siloxymethyl; 2,2,2,-trichloroethoxymethyl; tetrahydropyranyl; tetrahydrofuranyl; ethoxyethyl; 1-[2-(trimethylsilyl) ethoxy]ethyl; 2-trimethylsilylethyl; t-butyl ether; p-chlorophenyl, p-methoxyphenyl, p-nitrophenyl, benzyl, p-methoxybenzyl, and nitrobenzyl); silyl ethers (e.g., trimethylsilyl; triethylsilyl; triisopropylsilyl; dimethylisopropylsilyl; t-butyldimethylsilyl; t-butyldiphenylsilyl; tribenzylsilyl; triphenylsilyl; and diphenymethylsilyl); carbonates (e.g., methyl, methoxymethyl, 9-fluorenylmethyl; ethyl; 2,2,2-trichloroethyl; 2-(trimethylsilyl)ethyl; vinyl, allyl, nitrophenyl; benzyl; methoxybenzyl; 3,4-dimethoxybenzyl; and nitrobenzyl).

Other N-protecting groups include, but are not limited to, chiral auxiliaries such as protected or unprotected D, L or D, L-amino acids such as alanine, leucine, phenylalanine, and the like; sulfonyl-containing groups such as benzenesulfonyl, p-toluenesulfonyl, and the like; carbamate forming groups such as benzyloxycarbonyl, p-chlorobenzyloxycarbonyl, p methoxybenzyloxycarbonyl, p-nitrobenzyloxycarbonyl, 2-nitrobenzyloxycarbonyl, p bromobenzyloxycarbonyl, 3,4-dimethoxybenzyloxycarbonyl, 3,5 dimethoxybenzyl oxycarbonyl, 2,4-dimethoxybenzyloxycarbonyl, 4 methoxybenzyloxycarbonyl, 2-nitro-4,5-dimethoxybenzyloxycarbonyl, 3,4,5 trimethoxybenzyloxycarbonyl, 1-(p-biphenylyl)-1-methylethoxycarbonyl, α,α-dimethyl-3,5 dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl, and the like, aryl-alkyl groups such as benzyl, p-methoxybenzyl, 2,4-dimethoxybenzyl, triphenylmethyl, benzyloxymethyl, and the like, silylalkylacetal groups such as [2-(trimethylsilyl) ethoxy]methyl and silyl groups such as trimethylsilyl, and the like. Useful N-protecting groups are formyl, acetyl, benzoyl, pivaloyl, t-butylacetyl, alanyl, phenylsulfonyl, benzyl, dimethoxybenzyl, [2-(trimethylsilyl)ethoxy]methyl (SEM), tetrahydropyranyl (THP), t-butyloxycarbonyl (Boc), and benzyloxycarbonyl (Cbz).

The term "tautomer" refers to structural isomers that readily interconvert, often by relocation of a proton. Tautomers are distinct chemical species that can be identified by differing spectroscopic characteristics, but generally cannot be isolated individually. Non-limiting examples of tautomers include ketone-enol, enamine-imine, amide-imidic acid, nitroso-oxime, ketene-ynol, and amino acid-ammonium carboxylate.

The term "sarcoma" generally refers to a tumor which is made up of a substance like the embryonic connective tissue and is generally composed of closely packed cells embedded in a fibrillar or homogeneous substance.

The term "subject," as used herein, represents a human or non-human animal (e.g., a mammal) that is suffering from, or is at risk of, disease or condition, as determined by a qualified professional (e.g., a doctor or a nurse practitioner) with or without known in the art laboratory test(s) of sample(s) from the subject. Preferably, the subject is a human. Non-limiting examples of diseases and conditions include diseases having the symptom of cell hyperproliferation, e.g., a cancer.

"Treatment" and "treating," as used herein, refer to the medical management of a subject with the intent to improve, ameliorate, stabilize, prevent or cure a disease or condition. This term includes active treatment (treatment directed to improve the disease or condition); causal treatment (treatment directed to the cause of the associated disease or condition); palliative treatment (treatment designed for the relief of symptoms of the disease or condition); preventative treatment (treatment directed to minimizing or partially or completely inhibiting the development of the associated disease or condition); and supportive treatment (treatment employed to supplement another therapy).

DETAILED DESCRIPTION

Figure 1:
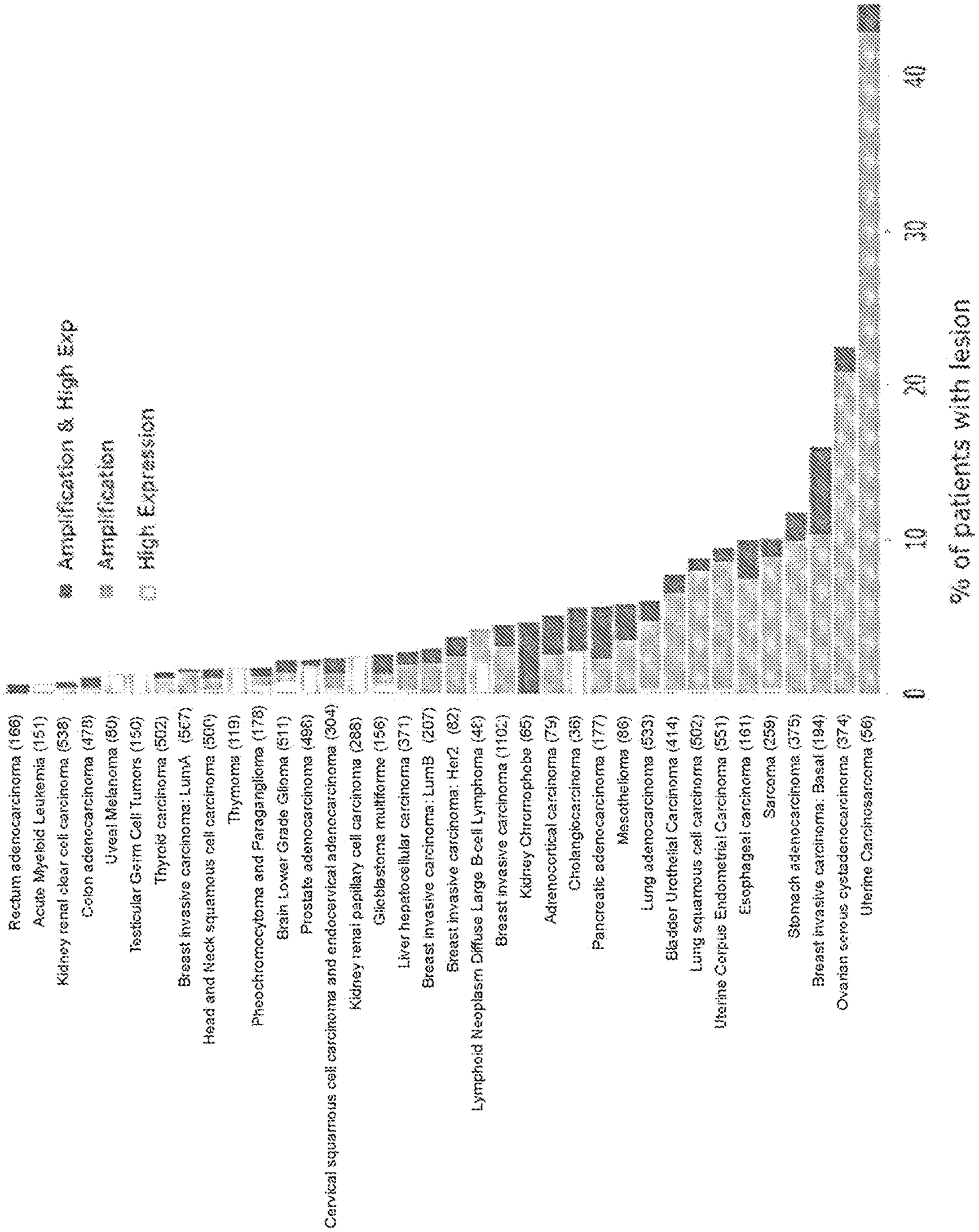
FIG. 1 is a bar graph showing the CCNE1 amplification/overexpression across tumors sequenced from TCGA PanCancer Atlas.

In general, the invention provides compounds, pharmaceutical compositions containing the same, methods of preparing the compounds, and methods of use. Compounds of the invention may be Myt1 inhibitors. These compounds may be used to inhibit Myt1 in a cell, e.g., a cell in a subject (e.g., a cell overexpressing CCNE1 or having an inactivating mutation in the FBXW7 gene). The subject may be in need of a treatment for a disease or condition, e.g., a disease or condition having a symptom of cell hyperproliferation, e.g., a cancer. The Myt1 inhibitory activity of the compounds disclosed herein is useful for treating a subject in need of a treatment for cancer.

Myt1 is a cell cycle regulating kinase localized predominantly in the endoplasmic reticulum and golgi complex. It is part of the Wee family of kinases that includes Wee1 and Wee1b. It is involved in the negative regulation of the CDK1-Cyclin B complex which promotes the progression of cells from G2-phase into the mitotic phase (M-phase) of the cell cycle. During DNA damage, Myt1 drives the phosphorylation on CDK1 (both Tyr15 and Thr14 of CDK1) which maintains the kinase complex in an inactive state in G2 as part of the G2 checkpoint response along with Wee1 (which mediates only Tyr15 phosphorylation) and prevents entry into mitosis until the damage has been repaired. Additionally, it has been proposed that Myt1 directly interacts with CDK1 complexes in the cytoplasm and prevents their nuclear translocation thus inhibiting cell cycle progression.

Myt1 has been implicated as a potentially important cancer target as it is essential in many cancer cells. Overexpression of Myt1 has been observed in various cancers including hepatocellular carcinoma as well as clear-cell renal-cell carcinoma. Myt1 downregulation has a minor role in unperturbed cells but has a more prominent role in cells exposed to DNA damage. Additionally, cells that exhibit high levels of replication stress in addition to defective G1 checkpoint regulation may be particularly sensitive to loss of Myt1 function, as these cells will be prone to entering mitosis prematurely with compromised genomic material leading to mitotic catastrophe.

Inhibitors of Myt1, a regulator of G2-M transition, may be particularly useful in the treatment of tumors harboring CCNE1-amplification or FBXW7 loss-of-function mutations using a synthetic lethal therapeutic strategy.

Cyclin E1 (encoded by the CCNE1 gene) is involved in the G1 to S phase cell cycle transition. In late G1 phase of the cell cycle, it complexes with cyclin-dependent kinase 2 (CDK2) to promote E2F transcription factor activation and entry into S-phase. Cyclin E1 levels are tightly regulated during normal cell cycles, accumulating at the G1/S transition and being completely degraded by the end of S phase. The cell cycle-dependent proteasomal degradation of Cyclin E1 is mediated by the $SCF^{FBW7}$ ubiquitin ligase complex. Once activated in late G1, the Cyclin E1/CDK2 complex promotes the transition into S phase through phosphorylation and inactivation of RB1 and subsequent release of E2F transcription factors. S phase is promoted by E2F-mediated transcription of numerous genes involved in DNA replication including the pre-replication complex subunits ORC1, CDC6, CDT1, and the MCM helicase factors.

CCNE1 is frequently amplified and/or over-expressed in human cancers (FIG. 1). CCNE1 amplification has been reported in several cancer types including endometrial, ovarian, breast and gastric, ranging in frequency from 5-40%. Importantly, numerous studies have confirmed Cyclin E1 as a driver of tumorigenesis in these indications and CCNE1 amplification is observed in the more aggressive subtypes including uterine carcinosarcoma (UCS; ~40%), uterine serous carcinoma (USC; ~25%), high-grade serous ovarian carcinoma (HGSOC; ~25%), and triple-negative breast cancer (TNBC; ~8%). Patients with evidence of Cyclin E1 over-expression in tumor biopsies by immunohistochemistry and/or genomic copy number analysis have a lower overall survival compared to patients with normal Cyclin E1 levels. HGSOC patients with Cyclin E1 over-expression have a lower response rate to cisplatin, the current standard of care.

Figure 2A:
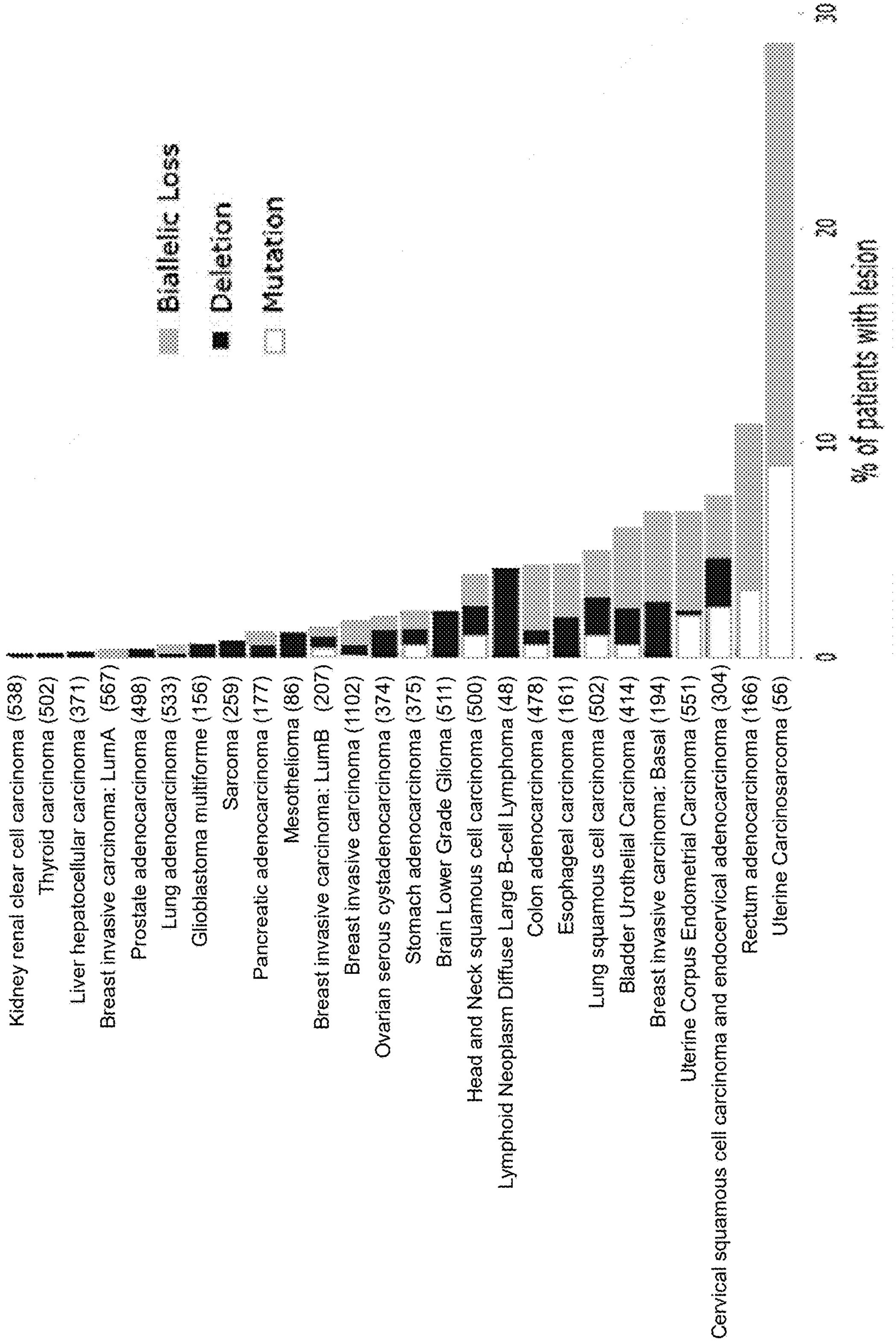
FIG. 2A is a bar graph showing the FBXW7 mutations across tumors sequenced from TCGA PanCancer Atlas.
Figure 2B:
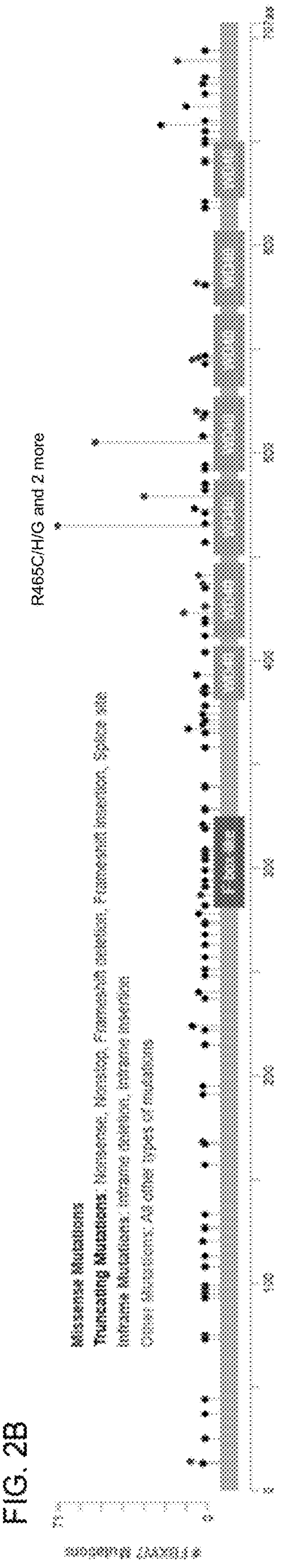
FIG. 2B is a lollipop graph showing the frequency of FBXW7 mutations across the gene. This graph highlights three common arginine hotspot mutations (R465, R479, and R505) within the third and fourth WD40 repeats that disrupt recognition of the Cyclin E1 substrate and are classified as deleterious.

Defective cell cycle-regulated proteolysis of Cyclin E1 by the $SCF^{FBW7}$ ubiquitin ligase complex is another mechanism of CCNE1 over-expression observed in tumors. The F-box protein gene, FBXW7, is frequently mutated in several cancer types including endometrial, colorectal, and gastric, ranging in frequency from 5-35% (FIG. 2). Like CCNE1, FBXW7 driver mutations are observed in the more aggressive subtypes of endometrial cancer including UCS (~35%) and USC (~25%). FBXW7 has a diverse spectrum of loss-of-function mutations in cancer including truncating mutations peppered across the gene and missense mutations within the Cyclin E1 recognizing WD40 repeats. FBW7 functions as a homodimer within the SCF complex and many deleterious missense mutations within the WD40 repeats are mostly heterozygous and dominant negative. Remarkably, several recurring hotspot missense mutations are found in the WD40 repeats including R465, R479, and R505—all of which disrupt Cyclin E1 binding and ubiquitylation.

Cyclin E1 over-expression and/or FBXW7 loss-of-function is thought to drive tumorigenesis by inducing genome instability (e.g., increased origin firing, defective nucleotide pools, transcription-replication conflicts, and/or fork instability). Over-expression of Cyclin E1 has been shown to induce replication stress characterized by slowed or stalled replication forks and loss-of-heterozygosity at fragile sites. The primary mechanism by which Cyclin E1 over-expression causes replication stress is increased origin firing in early S-phase followed by depletion of replication factors including nucleotide pools. The decrease in overall replication proteins and nucleotides decreases fork progression and causes stalling and subsequent collapse or reversal.

The compound of the invention may be, e.g., a compound of formula (I):

(I)

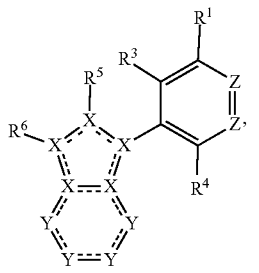

or a pharmaceutically acceptable salt thereof, where each ====== is a single or double bond;

one, two, or three X groups are N, and the remaining X groups are C;

each Y is independently N or $CR^2$;

each Z is independently N or CH;

$R^1$ is OH, and $R^3$ is hydrogen, optionally substituted $C_{1-6}$ alkyl, halogen, or optionally substituted $C_{3-8}$ cycloalkyl; or $R^1$ and $R^3$ combine to form —$CR^9$═N—NH—;

each $R^2$ is independently hydrogen, optionally substituted $C_{1-6}$ alkyl, optionally substituted $C_{2-6}$ alkenyl, optionally substituted $C_{2-6}$ alkynyl, optionally substituted $C_{3-8}$ cycloalkyl, optionally substituted $C_{3-8}$ cycloalkenyl, optionally substituted $C_{2-9}$ heterocyclyl, optionally substituted $C_{2-9}$ heterocyclyl $C_{1-6}$ alkyl, optionally substituted $C_{6-10}$ aryl, optionally substituted $C_{1-9}$ heteroaryl, optionally substituted $C_{1-9}$ heteroaryl $C_{1-6}$ alkyl, halogen, cyano, —$N(R^7)_2$, —$OR^7$, —$C(O)N(R^8)_2$, —$SO_2N(R^8)_2$, —$SO_2R^{7A}$, or -Q-$R^{7B}$;

$R^4$ is independently hydrogen, optionally substituted $C_{1-6}$ alkyl, or halogen;

$R^5$ is hydrogen, halogen, or —$N(R^7)_2$;

$R^6$ is —$C(O)NH(R^8)$, —$C(O)R^{7A}$, or —$SO_2R^{7A}$;

each $R^7$ is independently hydrogen, optionally substituted $C_{1-6}$ alkyl, optionally substituted $C_{6-10}$ aryl $C_{1-6}$ alkyl, optionally substituted $C_{3-8}$ cycloalkyl, optionally substituted $C_{6-10}$ aryl, optionally substituted $C_{2-9}$ heterocyclyl, optionally substituted $C_{1-9}$ heteroaryl, optionally substituted $C_{1-9}$ heteroaryl $C_{1-6}$ alkyl, or —$SO_2R^{7A}$; or two $R^7$ groups, together with the atom to which both are attached, combine to form an optionally substituted $C_{2-9}$ heterocyclyl;

each $R^{7A}$ is independently optionally substituted $C_{1-6}$ alkyl, optionally substituted $C_{3-8}$ cycloalkyl, or optionally substituted $C_{6-10}$ aryl;

each $R^{7B}$ is independently hydroxyl, optionally substituted $C_{1-6}$ alkyl, optionally substituted $C_{6-10}$ aryl, optionally substituted $C_{2-9}$ heterocyclyl, optionally substituted $C_{1-9}$ heteroaryl, —N($R^7$)$_2$, —C(O)N($R^8$)$_2$, —$SO_2$N($R^8$)$_2$, —$SO_2R^{7A}$, or optionally substituted alkoxy;

each $R^8$ is independently hydrogen, optionally substituted $C_{1-6}$ alkyl, optionally substituted $C_{2-6}$ alkoxyalkyl, optionally substituted $C_{6-10}$ aryl $C_{1-6}$ alkyl, optionally substituted $C_{6-10}$ aryl, optionally substituted $C_{3-8}$ cycloalkyl, or optionally substituted $C_{1-9}$ heteroaryl; or two $R^8$, together with the atom to which they are attached, combine to form an optionally substituted $C_{2-9}$ heterocyclyl;

$R^9$ is hydrogen or halogen; and

Q is optionally substituted $C_{1-6}$ alkylene, optionally substituted $C_{2-6}$ alkenylene, optionally substituted $C_{2-6}$ alkynylene, optionally substituted $C_{3-8}$ cycloalkylene, optionally substituted $C_{3-8}$ cycloalkenylene optionally substituted $C_{6-10}$ arylene, optionally substituted $C_{2-9}$ heterocyclylene, or optionally substituted $C_{1-9}$ heteroarylene.

The compound of the invention may be, e.g., a compound listed in Table 1 below or a pharmaceutically acceptable salt thereof.

TABLE 1

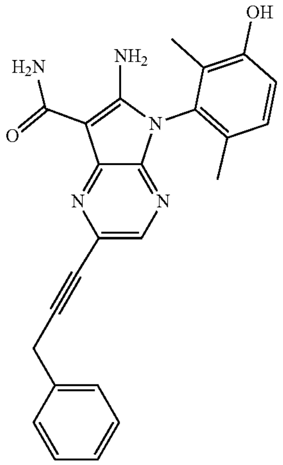 [SMILES: Cc1ccc(O)c(C)c1-n1c(N)c(C(N)=O)c2nc(C#CCc3ccccc3)cnc21]
1

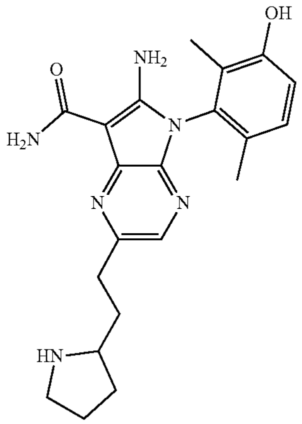 [SMILES: Cc1ccc(O)c(C)c1-n1c(N)c(C(N)=O)c2nc(CCC3CCCN3)cnc21]
2

TABLE 1-continued

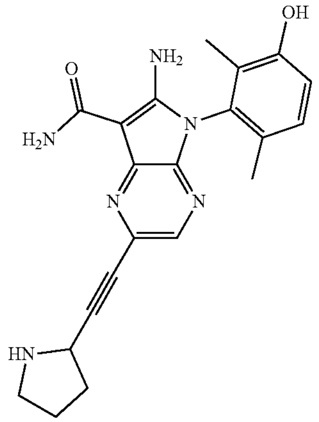 [SMILES: Cc1ccc(O)c(C)c1-n1c(N)c(C(N)=O)c2nc(C#CC3CCCN3)cnc21]
3

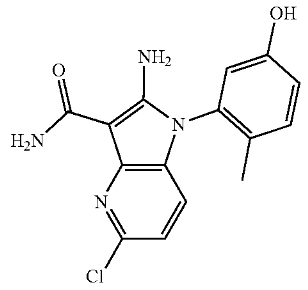 [SMILES: Cc1ccc(O)cc1-n1c(N)c(C(N)=O)c2nc(Cl)ccc21]
4

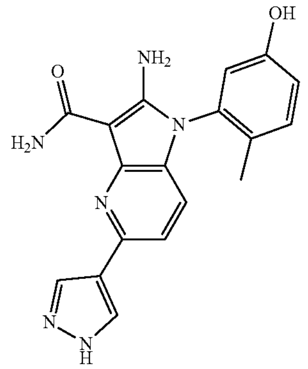 [SMILES: Cc1ccc(O)cc1-n1c(N)c(C(N)=O)c2nc(-c3cn[nH]c3)ccc21]
5

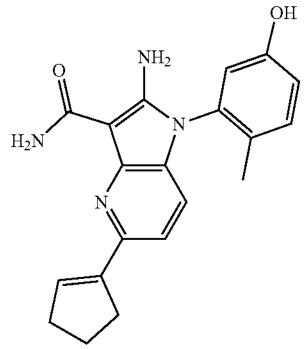 [SMILES: Cc1ccc(O)cc1-n1c(N)c(C(N)=O)c2nc(C3=CCCC3)ccc21]
6

TABLE 1-continued
7
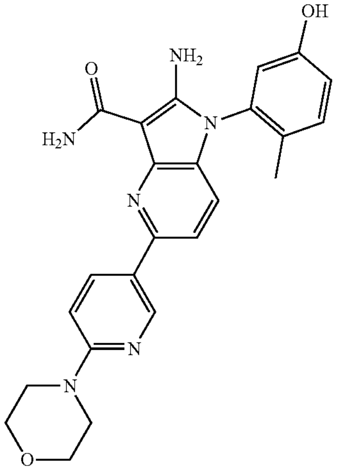 [SMILES: Cc1ccc(O)cc1-n1c(N)c(C(N)=O)c2nc(-c3ccc(N4CCOCC4)nc3)ccc21]
8
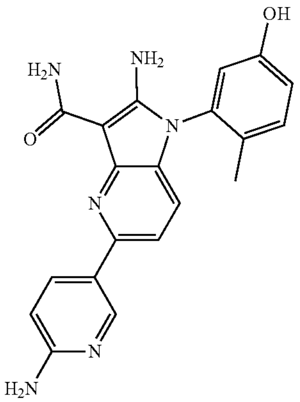 [SMILES: Cc1ccc(O)cc1-n1c(N)c(C(N)=O)c2nc(-c3ccc(N)nc3)ccc21]
9
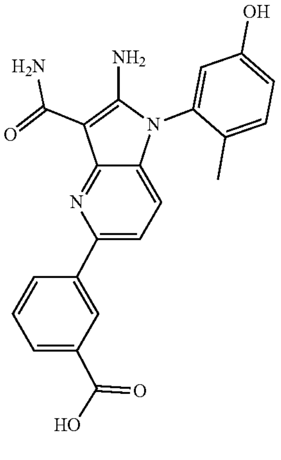 [SMILES: Cc1ccc(O)cc1-n1c(N)c(C(N)=O)c2nc(-c3cccc(C(=O)O)c3)ccc21]
10
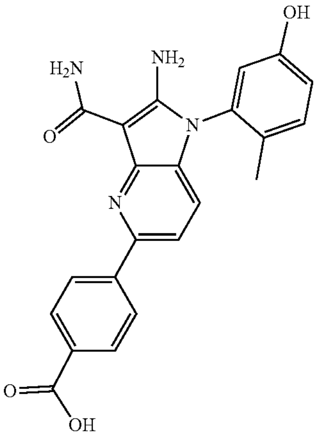 [SMILES: Cc1ccc(O)cc1-n1c(N)c(C(N)=O)c2nc(-c3ccc(C(=O)O)cc3)ccc21]
11
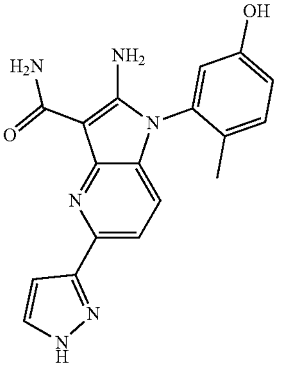 [SMILES: Cc1ccc(O)cc1-n1c(N)c(C(N)=O)c2nc(-c3cc[nH]n3)ccc21]
12
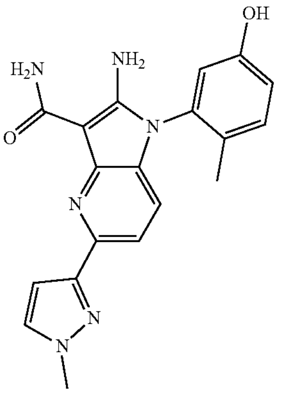 [SMILES: Cc1ccc(O)cc1-n1c(N)c(C(N)=O)c2nc(-c3ccn(C)n3)ccc21]

TABLE 1-continued
13
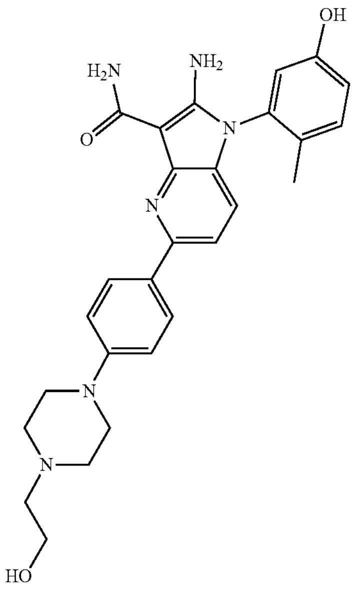 [SMILES: Cc1ccc(O)cc1-n1c(N)c(C(N)=O)c2nc(-c3ccc(N4CCN(CCO)CC4)cc3)ccc21]
14
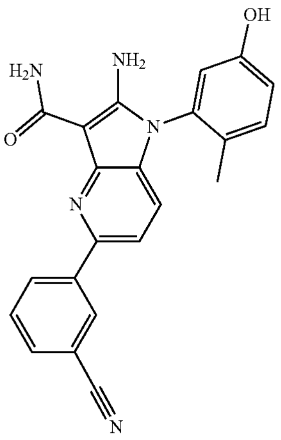 [SMILES: Cc1ccc(O)cc1-n1c(N)c(C(N)=O)c2nc(-c3cccc(C#N)c3)ccc21]
15
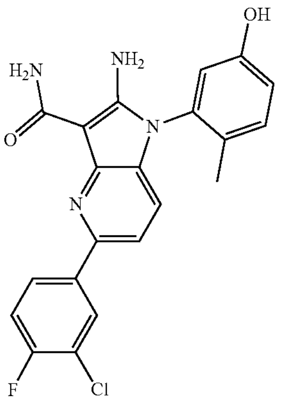 [SMILES: Cc1ccc(O)cc1-n1c(N)c(C(N)=O)c2nc(-c3ccc(F)c(Cl)c3)ccc21]
TABLE 1-continued
16
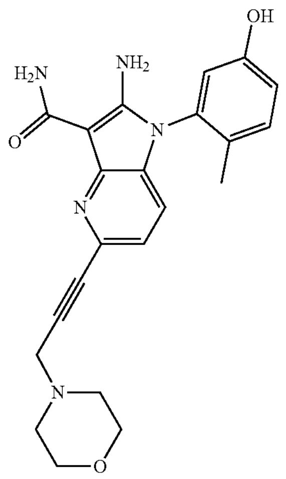 [SMILES: Cc1ccc(O)cc1-n1c(N)c(C(N)=O)c2nc(C#CCN3CCOCC3)ccc21]
17
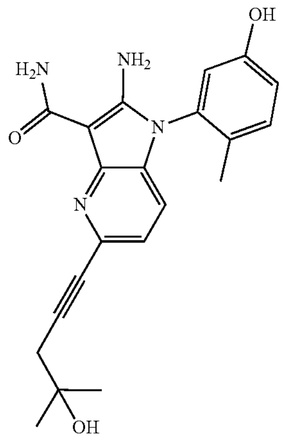 [SMILES: Cc1ccc(O)cc1-n1c(N)c(C(N)=O)c2nc(C#CCC(C)(C)O)ccc21]
18
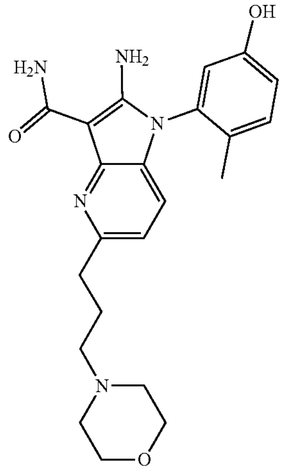 [SMILES: Cc1ccc(O)cc1-n1c(N)c(C(N)=O)c2nc(CCCN3CCOCC3)ccc21]

TABLE 1-continued
19
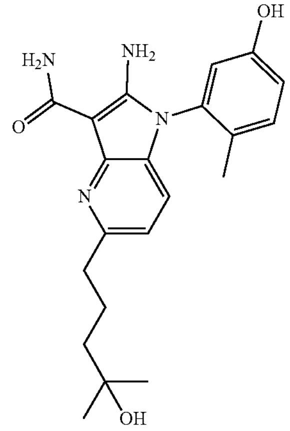 [SMILES: Cc1ccc(O)cc1-n1c(N)c(C(N)=O)c2nc(CCCC(C)(C)O)ccc21]
20
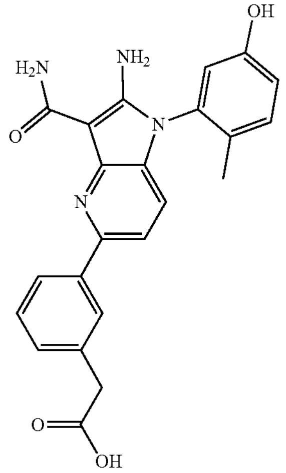 [SMILES: Cc1ccc(O)cc1-n1c(N)c(C(N)=O)c2nc(-c3cccc(CC(=O)O)c3)ccc21]
21
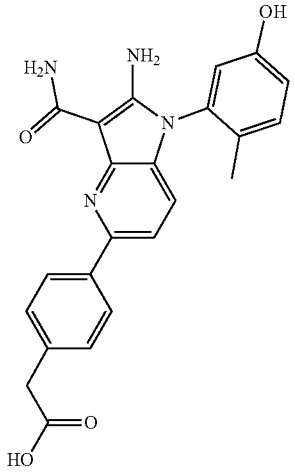 [SMILES: Cc1ccc(O)cc1-n1c(N)c(C(N)=O)c2nc(-c3ccc(CC(=O)O)cc3)ccc21]
TABLE 1-continued
22
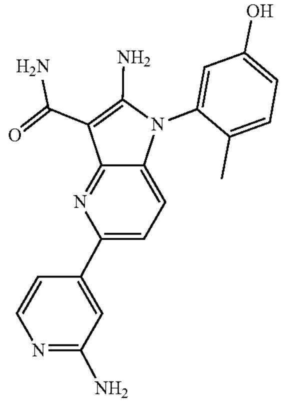 [SMILES: Cc1ccc(O)cc1-n1c(N)c(C(N)=O)c2nc(-c3ccnc(N)c3)ccc21]
23
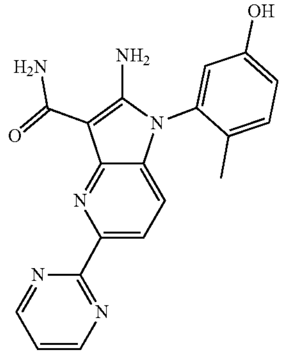 [SMILES: Cc1ccc(O)cc1-n1c(N)c(C(N)=O)c2nc(-c3ncccn3)ccc21]
24
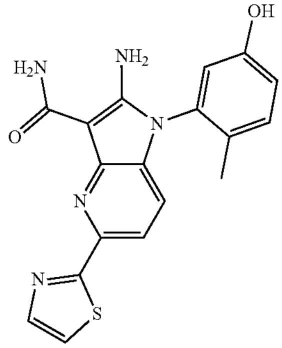 [SMILES: Cc1ccc(O)cc1-n1c(N)c(C(N)=O)c2nc(-c3nccs3)ccc21]
25
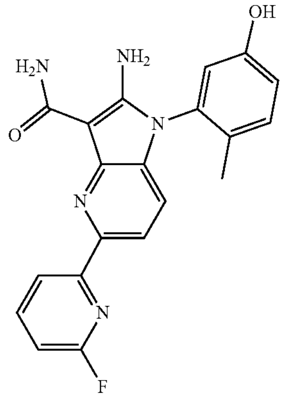 [SMILES: Cc1ccc(O)cc1-n1c(N)c(C(N)=O)c2nc(-c3cccc(F)n3)ccc21]

TABLE 1-continued
| | |
|---|---|
| 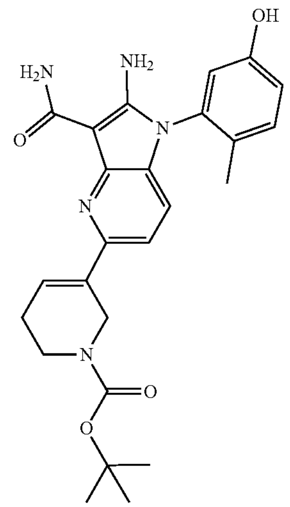 [SMILES: Cc1ccc(O)cc1-n1c(N)c(C(N)=O)c2nc(C3=CCCN(C(=O)OC(C)(C)C)C3)ccc21] | 26 |
| 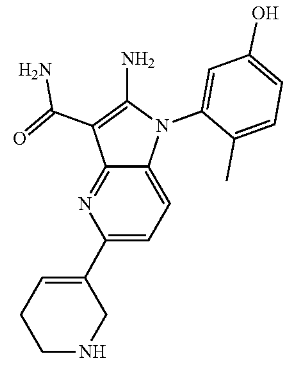 [SMILES: Cc1ccc(O)cc1-n1c(N)c(C(N)=O)c2nc(C3=CCCNC3)ccc21] | 27 |
| 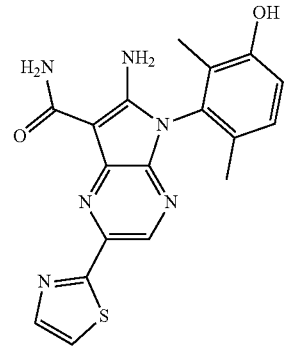 [SMILES: Cc1ccc(O)c(C)c1-n1c(N)c(C(N)=O)c2nc(-c3nccs3)cnc21] | 28 |
| 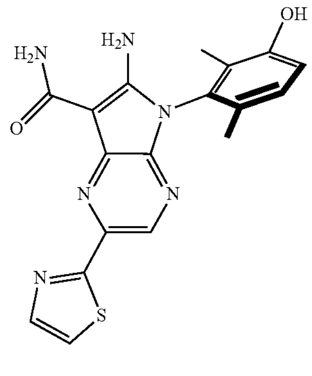 | 29 |
TABLE 1-continued
| | |
|---|---|
| 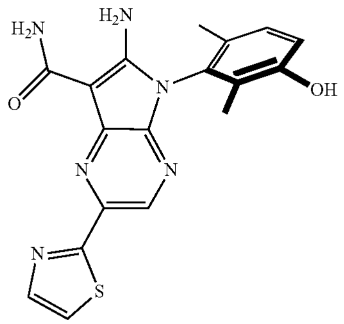 | 30 |
| 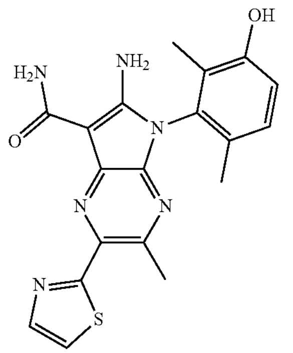 [SMILES: Cc1ccc(O)c(C)c1-n1c(N)c(C(N)=O)c2nc(-c3nccs3)c(C)nc21] | 31 |
| 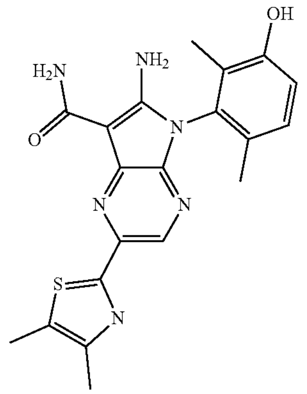 | 32 |
| 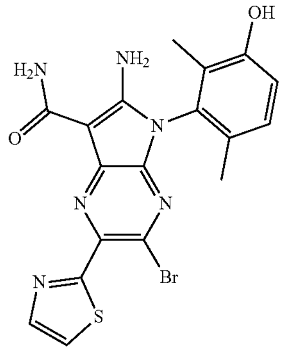 [SMILES: Cc1ccc(O)c(C)c1-n1c(N)c(C(N)=O)c2nc(-c3nccs3)c(Br)nc21] | 33 |

TABLE 1-continued
34
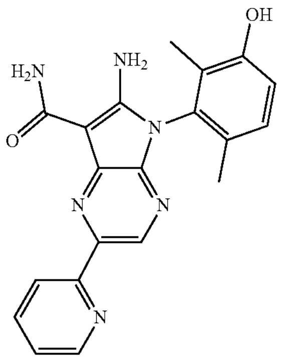 [SMILES: Cc1ccc(O)c(C)c1-n1c(N)c(C(N)=O)c2nc(-c3ccccn3)cnc21]
35
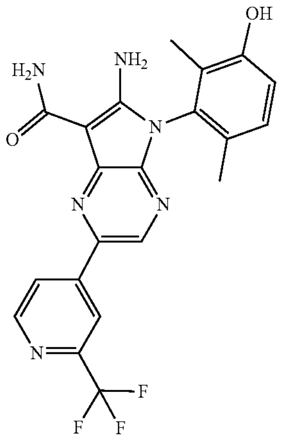 [SMILES: Cc1ccc(O)c(C)c1-n1c(N)c(C(N)=O)c2nc(-c3ccnc(C(F)(F)F)c3)cnc21]
36
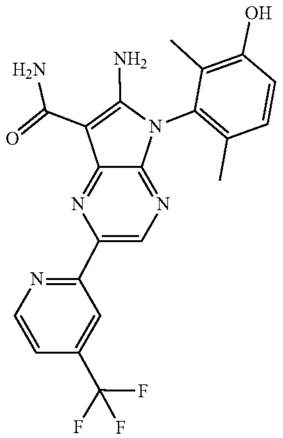 [SMILES: Cc1ccc(O)c(C)c1-n1c(N)c(C(N)=O)c2nc(-c3cc(C(F)(F)F)ccn3)cnc21]
37
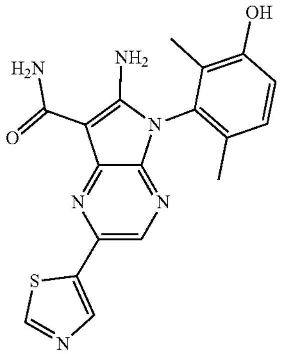 [SMILES: Cc1ccc(O)c(C)c1-n1c(N)c(C(N)=O)c2nc(-c3cncs3)cnc21]
TABLE 1-continued
38
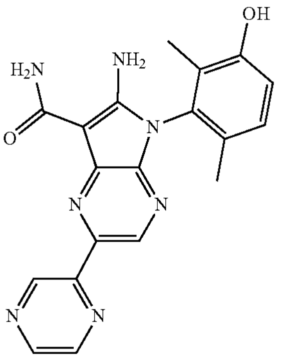 [SMILES: Cc1ccc(O)c(C)c1-n1c(N)c(C(N)=O)c2nc(-c3cnccn3)cnc21]
39
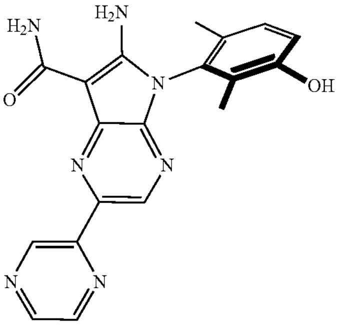
40
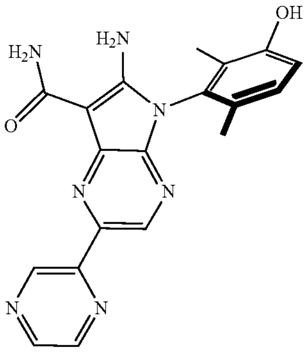
41
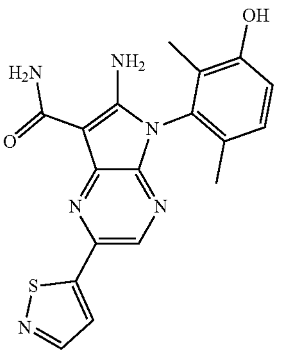 [SMILES: Cc1ccc(O)c(C)c1-n1c(N)c(C(N)=O)c2nc(-c3ccns3)cnc21]

TABLE 1-continued
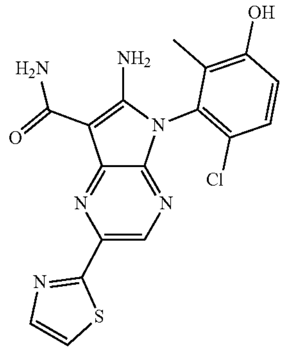 [SMILES: Cc1c(O)ccc(Cl)c1-n1c(N)c(C(N)=O)c2nc(-c3nccs3)cnc21]
42
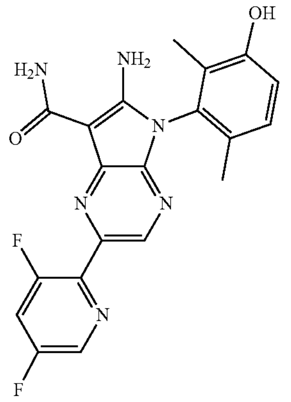 [SMILES: Cc1ccc(O)c(C)c1-n1c(N)c(C(N)=O)c2nc(-c3ncc(F)cc3F)cnc21]
43
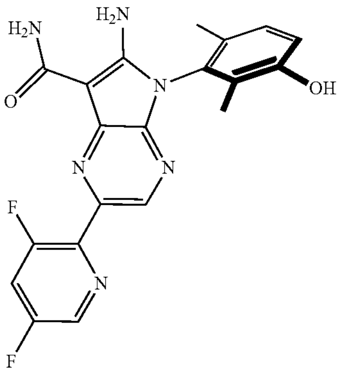
44
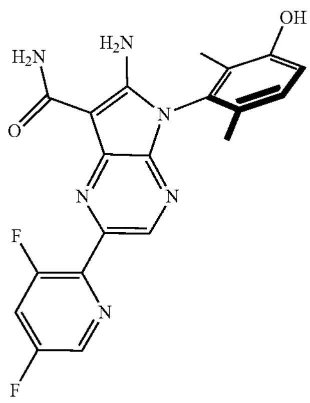
45
TABLE 1-continued
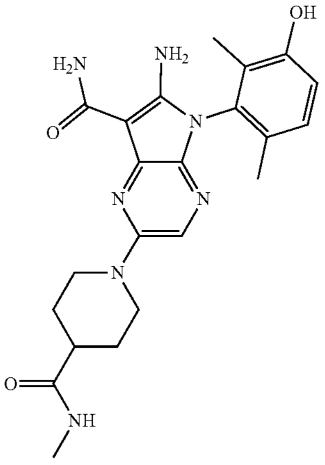 [SMILES: CNC(=O)C1CCN(c2cnc3c(n2)c(C(N)=O)c(N)n3-c2c(C)ccc(O)c2C)CC1]
46
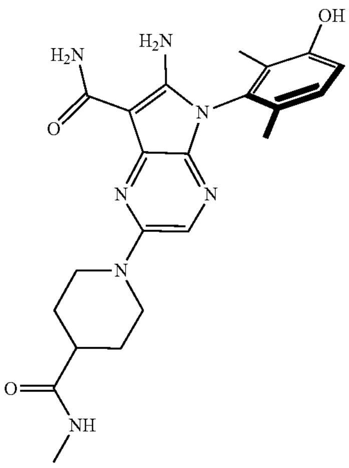
47
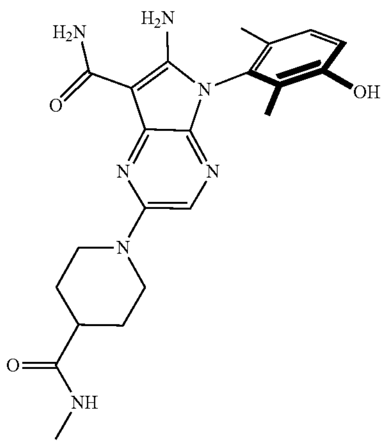
48

TABLE 1-continued
49
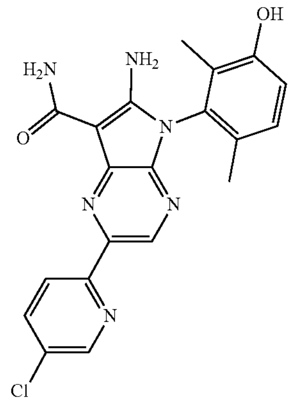 [SMILES: Cc1ccc(O)c(C)c1-n1c(N)c(C(N)=O)c2nc(-c3ccc(Cl)cn3)cnc21]
50
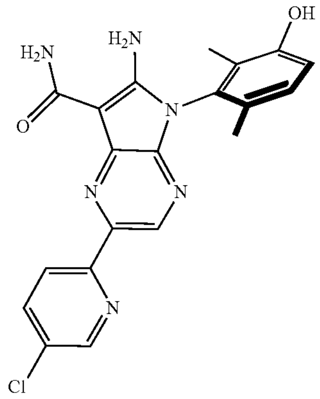
51
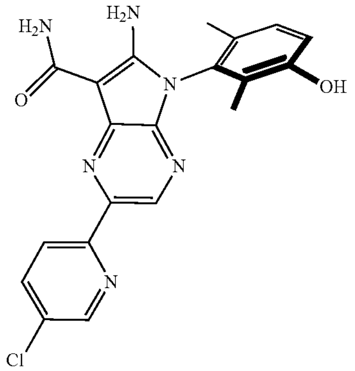
52
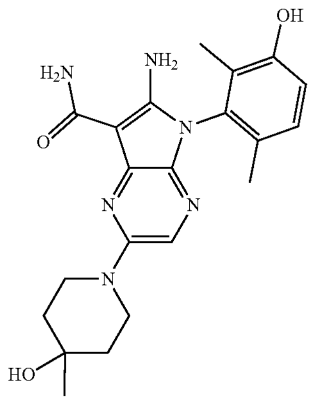 [SMILES: Cc1ccc(O)c(C)c1-n1c(N)c(C(N)=O)c2nc(N3CCC(C)(O)CC3)cnc21]
TABLE 1-continued
53
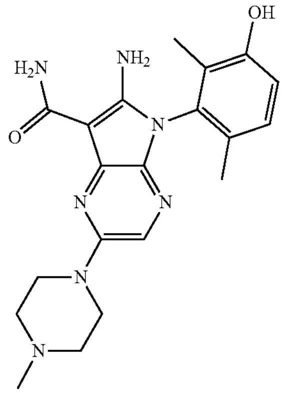 [SMILES: Cc1ccc(O)c(C)c1-n1c(N)c(C(N)=O)c2nc(N3CCN(C)CC3)cnc21]
54
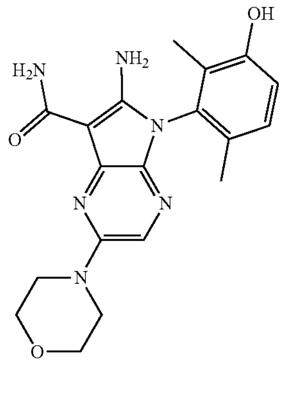 [SMILES: Cc1ccc(O)c(C)c1-n1c(N)c(C(N)=O)c2nc(N3CCOCC3)cnc21]
55
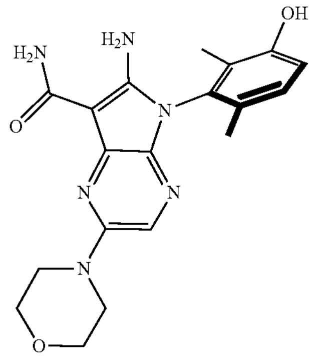
56
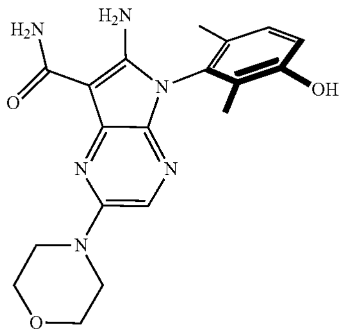

TABLE 1-continued
57
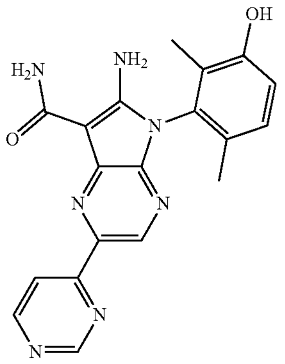 [SMILES: Cc1ccc(O)c(C)c1-n1c(N)c(C(N)=O)c2nc(-c3ccncn3)cnc21]
58
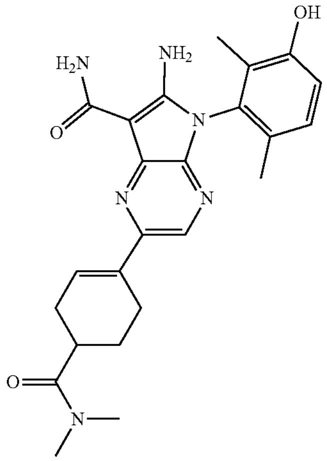 [SMILES: Cc1ccc(O)c(C)c1-n1c(N)c(C(N)=O)c2nc(C3=CCC(C(=O)N(C)C)CC3)cnc21]
59
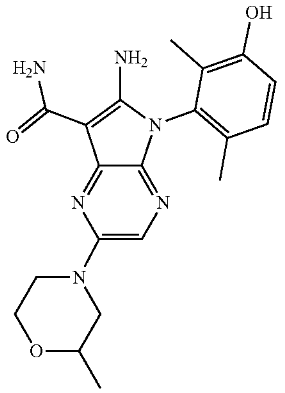 [SMILES: Cc1ccc(O)c(C)c1-n1c(N)c(C(N)=O)c2nc(N3CCOC(C)C3)cnc21]
60
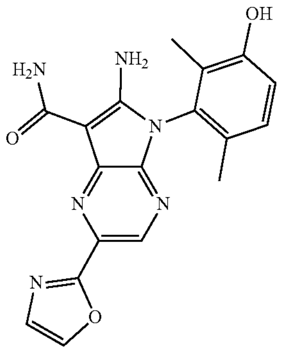 [SMILES: Cc1ccc(O)c(C)c1-n1c(N)c(C(N)=O)c2nc(-c3ncco3)cnc21]
TABLE 1-continued
61
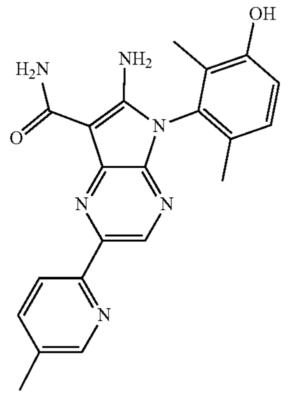 [SMILES: Cc1ccc(-c2cnc3c(n2)c(C(N)=O)c(N)n3-c2c(C)ccc(O)c2C)nc1]
62
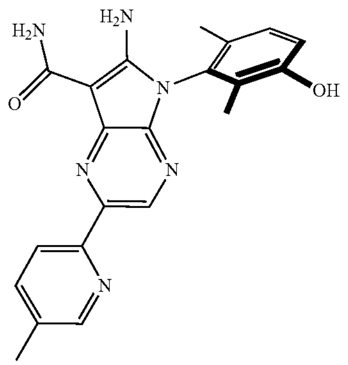
63
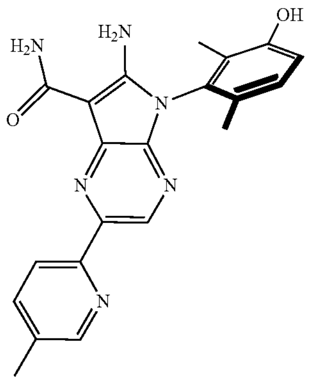
64
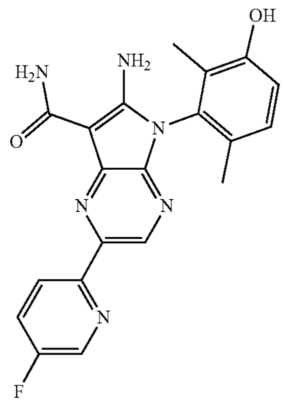 [SMILES: Cc1ccc(O)c(C)c1-n1c(N)c(C(N)=O)c2nc(-c3ccc(F)cn3)cnc21]

TABLE 1-continued
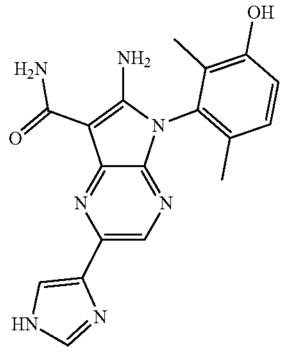 [SMILES: Cc1ccc(O)c(C)c1-n1c(N)c(C(N)=O)c2nc(-c3c[nH]cn3)cnc21]
65
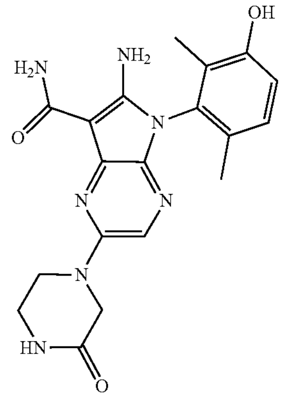 [SMILES: Cc1ccc(O)c(C)c1-n1c(N)c(C(N)=O)c2nc(N3CCNC(=O)C3)cnc21]
66
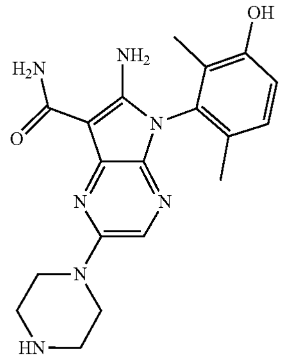 [SMILES: Cc1ccc(O)c(C)c1-n1c(N)c(C(N)=O)c2nc(N3CCNCC3)cnc21]
67
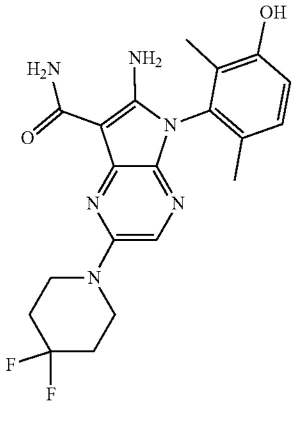 [SMILES: Cc1ccc(O)c(C)c1-n1c(N)c(C(N)=O)c2nc(N3CCC(F)(F)CC3)cnc21]
68
TABLE 1-continued
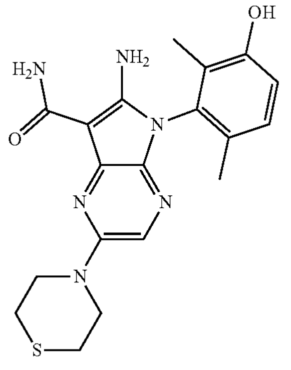 [SMILES: Cc1ccc(O)c(C)c1-n1c(N)c(C(N)=O)c2nc(N3CCSCC3)cnc21]
69
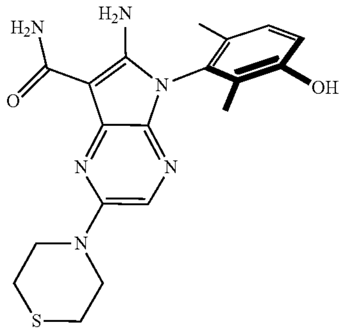
70
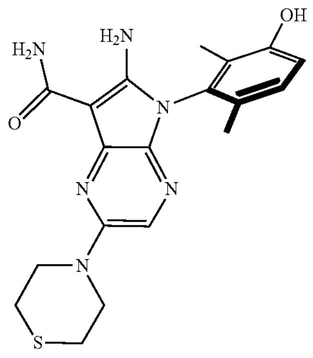
71
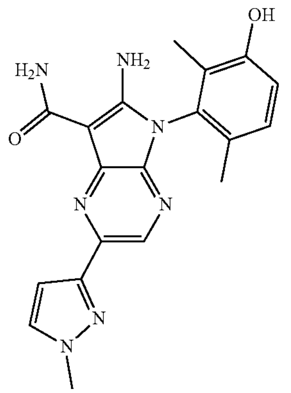 [SMILES: Cc1ccc(O)c(C)c1-n1c(N)c(C(N)=O)c2nc(-c3ccn(C)n3)cnc21]
72

TABLE 1-continued
73
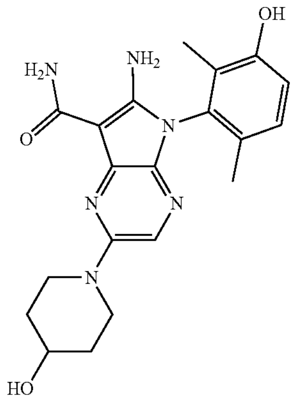 [SMILES: Cc1ccc(O)c(C)c1-n1c(N)c(C(N)=O)c2nc(N3CCC(O)CC3)cnc21]
74
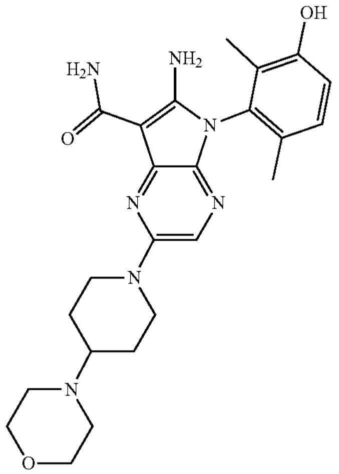 [SMILES: Cc1ccc(O)c(C)c1-n1c(N)c(C(N)=O)c2nc(N3CCC(N4CCOCC4)CC3)cnc21]
75
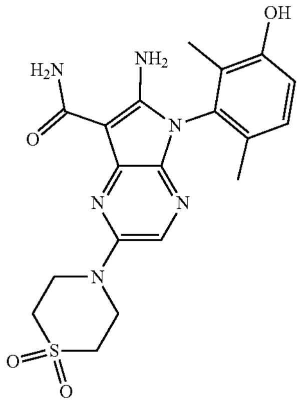 [SMILES: Cc1ccc(O)c(C)c1-n1c(N)c(C(N)=O)c2nc(N3CCS(=O)(=O)CC3)cnc21]
TABLE 1-continued
76
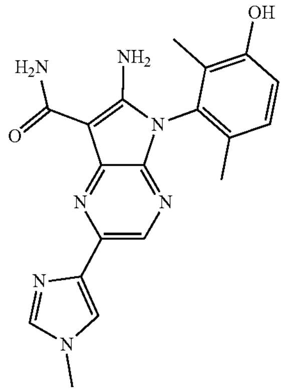 [SMILES: Cc1ccc(O)c(C)c1-n1c(N)c(C(N)=O)c2nc(-c3cn(C)cn3)cnc21]
77
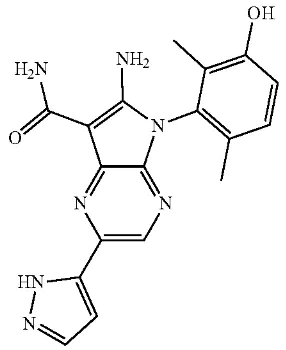 [SMILES: Cc1ccc(O)c(C)c1-n1c(N)c(C(N)=O)c2nc(-c3ccn[nH]3)cnc21]
78
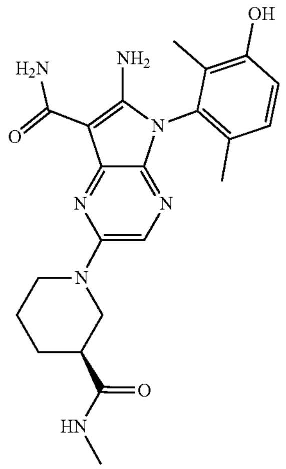 [SMILES: CNC(=O)[C@H]1CCCN(c2cnc3c(n2)c(C(N)=O)c(N)n3-c2c(C)ccc(O)c2C)C1]

TABLE 1-continued
79
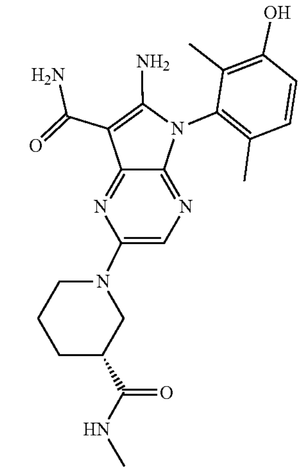 [SMILES: CNC(=O)[C@@H]1CCCN(c2cnc3c(n2)c(C(N)=O)c(N)n3-c2c(C)ccc(O)c2C)C1]
80
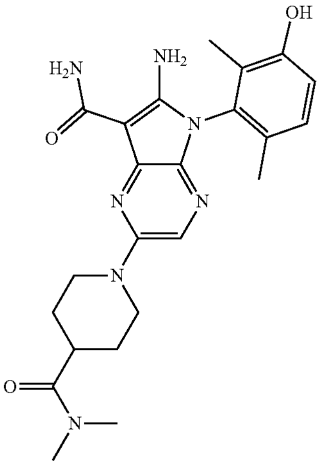 [SMILES: Cc1ccc(O)c(C)c1-n1c(N)c(C(N)=O)c2nc(N3CCC(C(=O)N(C)C)CC3)cnc21]
81
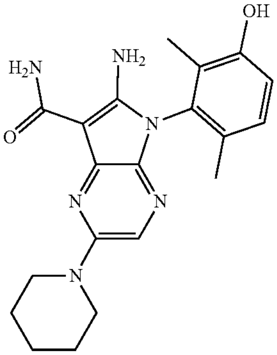 [SMILES: Cc1ccc(O)c(C)c1-n1c(N)c(C(N)=O)c2nc(N3CCCCC3)cnc21]
82
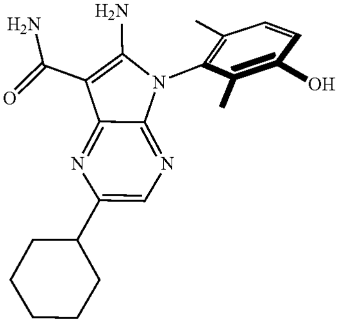
TABLE 1-continued
83
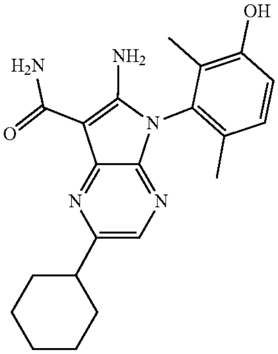 [SMILES: Cc1ccc(O)c(C)c1-n1c(N)c(C(N)=O)c2nc(C3CCCCC3)cnc21]
84
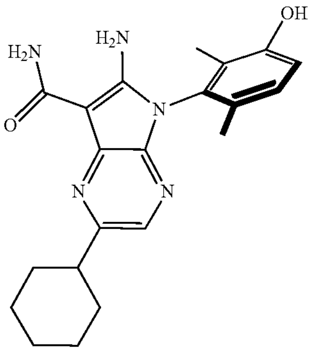
85
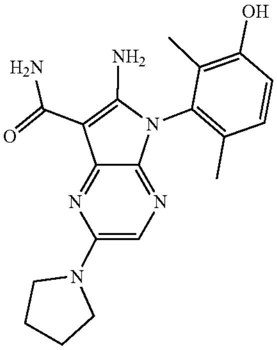 [SMILES: Cc1ccc(O)c(C)c1-n1c(N)c(C(N)=O)c2nc(N3CCCC3)cnc21]
86
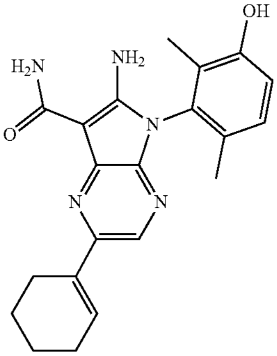 [SMILES: Cc1ccc(O)c(C)c1-n1c(N)c(C(N)=O)c2nc(C3=CCCCC3)cnc21]

TABLE 1-continued
87
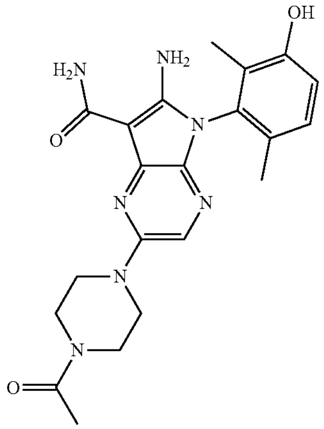 [SMILES: CC(=O)N1CCN(c2cnc3c(n2)c(C(N)=O)c(N)n3-c2c(C)ccc(O)c2C)CC1]
88
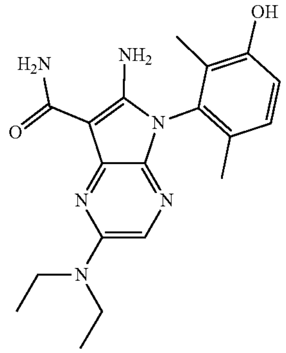 [SMILES: CCN(CC)c1cnc2c(n1)c(C(N)=O)c(N)n2-c1c(C)ccc(O)c1C]
89
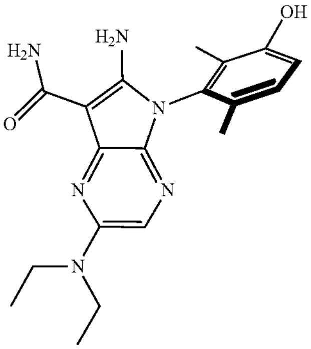
90
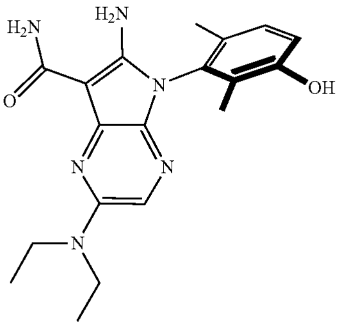
TABLE 1-continued
91
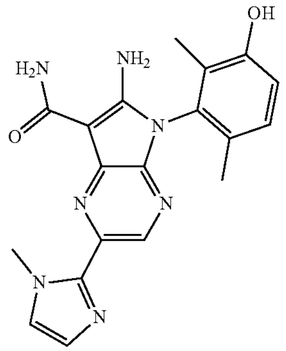 [SMILES: Cc1ccc(O)c(C)c1-n1c(N)c(C(N)=O)c2nc(-c3nccn3C)cnc21]
92
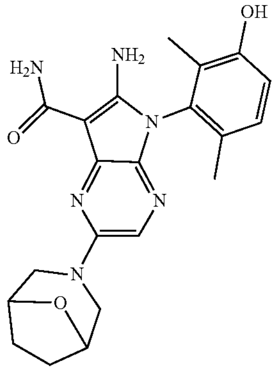 [SMILES: Cc1ccc(O)c(C)c1-n1c(N)c(C(N)=O)c2nc(N3CC4CCC(C3)O4)cnc21]
93
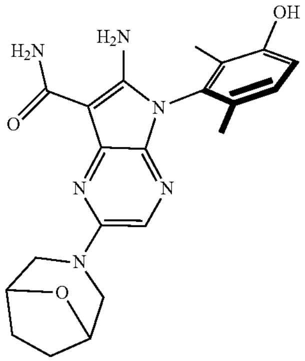
94
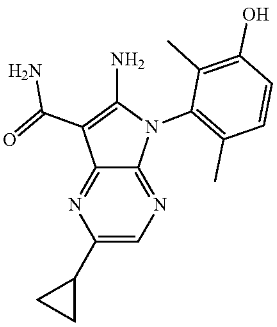 [SMILES: Cc1ccc(O)c(C)c1-n1c(N)c(C(N)=O)c2nc(C3CC3)cnc21]

TABLE 1-continued
95
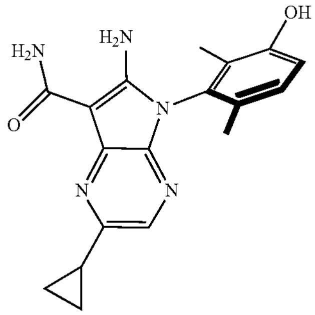
96
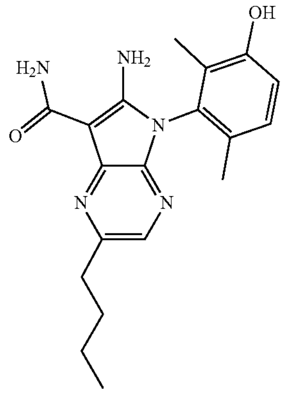 [SMILES: CCCCc1cnc2c(n1)c(C(N)=O)c(N)n2-c1c(C)ccc(O)c1C]
97
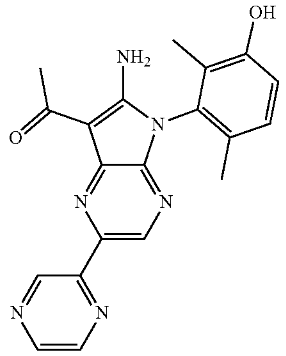 [SMILES: CC(=O)c1c(N)n(-c2c(C)ccc(O)c2C)c2ncc(-c3cnccn3)nc12]
98
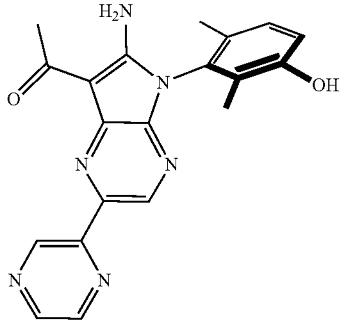
TABLE 1-continued
99
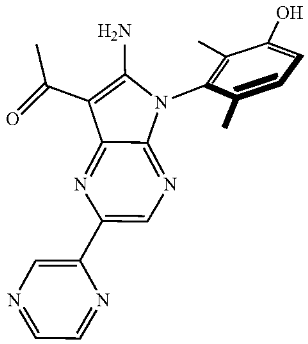
100
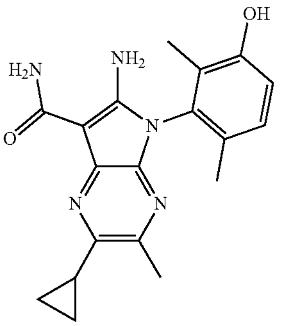 [SMILES: Cc1ccc(O)c(C)c1-n1c(N)c(C(N)=O)c2nc(C3CC3)c(C)nc21]
101
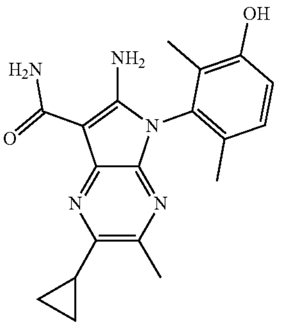 [SMILES: Cc1ccc(O)c(C)c1-n1c(N)c(C(N)=O)c2nc(C3CC3)c(C)nc21]
102
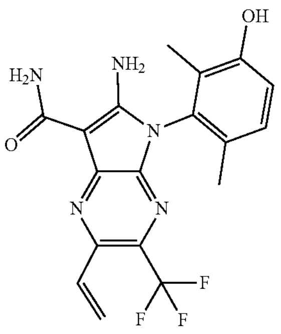 [SMILES: C=Cc1nc2c(C(N)=O)c(N)n(-c3c(C)ccc(O)c3C)c2nc1C(F)(F)F]

TABLE 1-continued
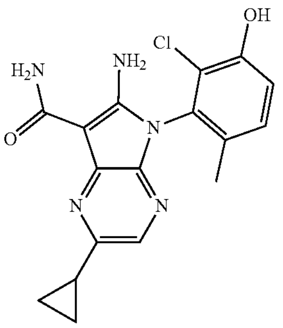 [SMILES: Cc1ccc(O)c(Cl)c1-n1c(N)c(C(N)=O)c2nc(C3CC3)cnc21]
104
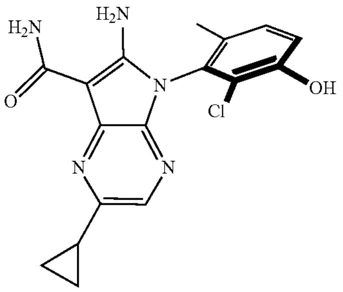
105
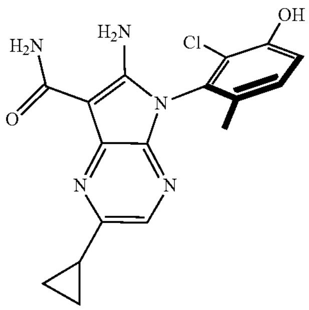
106
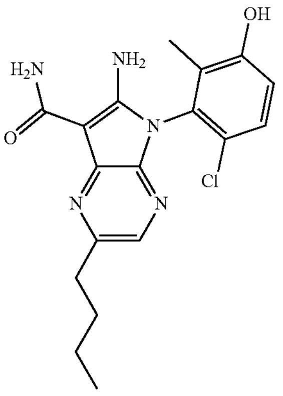 [SMILES: CCCCc1cnc2c(n1)c(C(N)=O)c(N)n2-c1c(Cl)ccc(O)c1C]
107
TABLE 1-continued
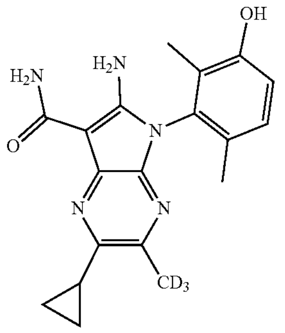 [SMILES: [2H]C([2H])([2H])c1nc2c(nc1C1CC1)c(C(N)=O)c(N)n2-c1c(C)ccc(O)c1C]
110
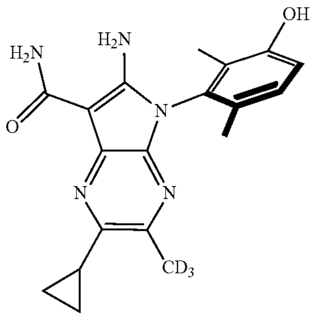
111
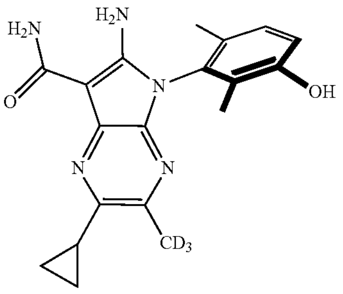
112
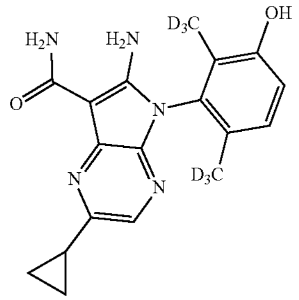 [SMILES: [2H]C([2H])([2H])c1ccc(O)c(C([2H])([2H])[2H])c1-n1c(N)c(C(N)=O)c2nc(C3CC3)cnc21]
113
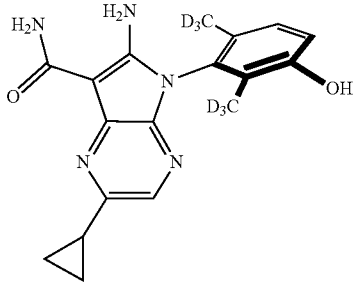
114

TABLE 1-continued
115
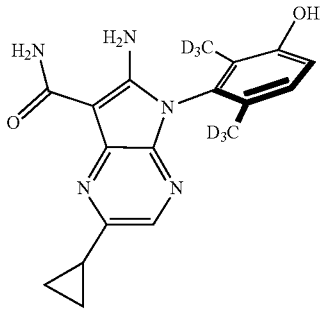
116
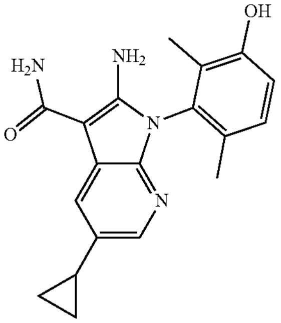 [SMILES: Cc1ccc(O)c(C)c1-n1c(N)c(C(N)=O)c2cc(C3CC3)cnc21]
117
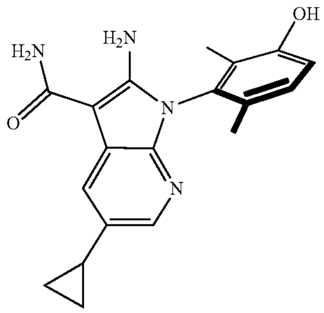
118
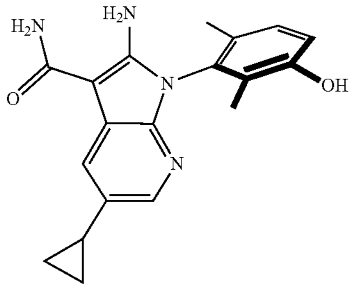
119
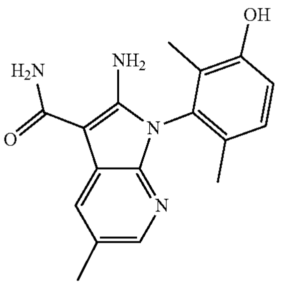 [SMILES: Cc1cnc2c(c1)c(C(N)=O)c(N)n2-c1c(C)ccc(O)c1C]
TABLE 1-continued
120
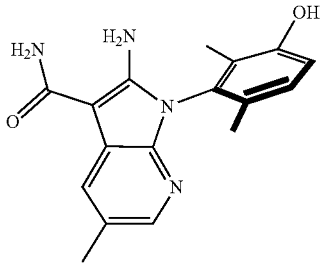
121
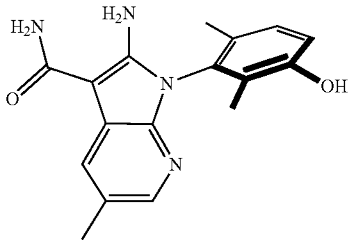
125
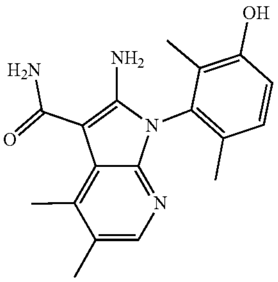 [SMILES: Cc1ccc(O)c(C)c1-n1c(N)c(C(N)=O)c2c(C)c(C)cnc21]
126
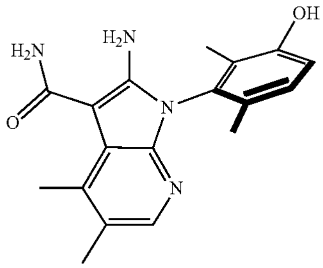
127
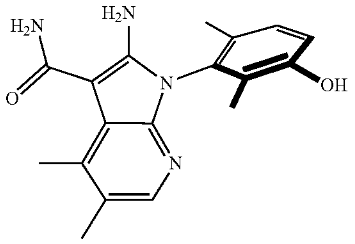

TABLE 1-continued
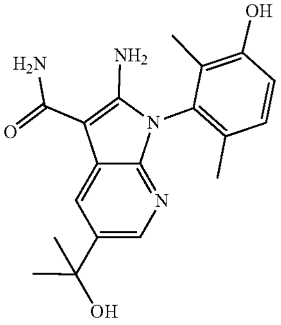 [SMILES: Cc1ccc(O)c(C)c1-n1c(N)c(C(N)=O)c2cc(C(C)(C)O)cnc21]
131
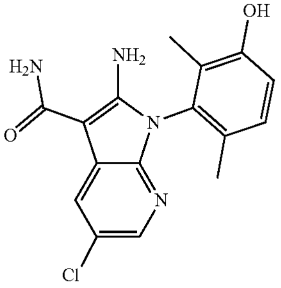 [SMILES: Cc1ccc(O)c(C)c1-n1c(N)c(C(N)=O)c2cc(Cl)cnc21]
132
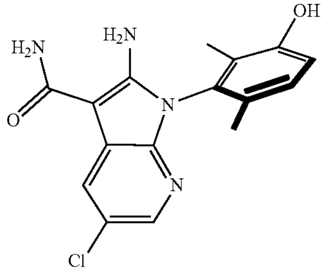
133
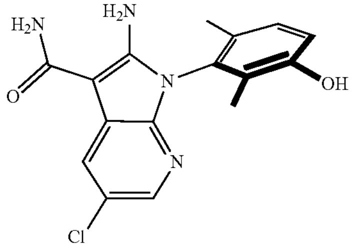
134
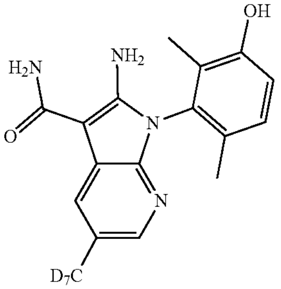
135
TABLE 1-continued
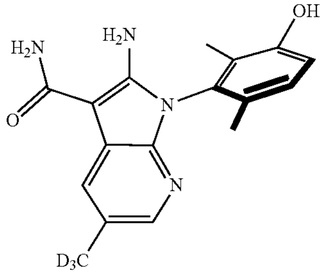
136
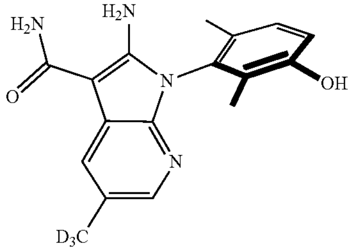
137
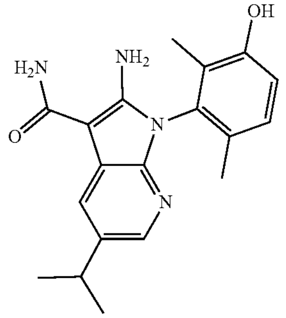 [SMILES: Cc1ccc(O)c(C)c1-n1c(N)c(C(N)=O)c2cc(C(C)C)cnc21]
138
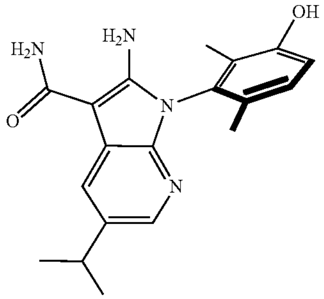
139
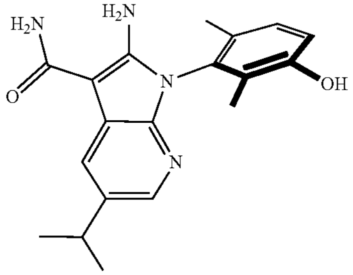
140

141
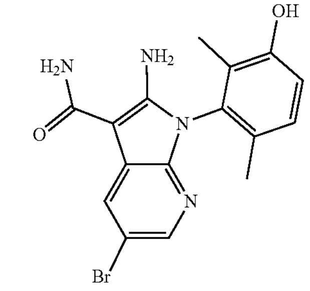 [SMILES: Cc1ccc(O)c(C)c1-n1c(N)c(C(N)=O)c2cc(Br)cnc21]
142
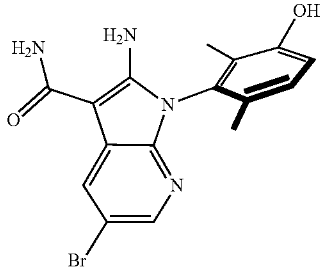
143
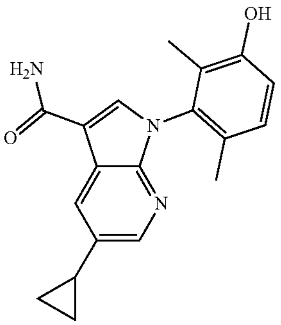 [SMILES: Cc1ccc(O)c(C)c1-n1cc(C(N)=O)c2cc(C3CC3)cnc21]
144
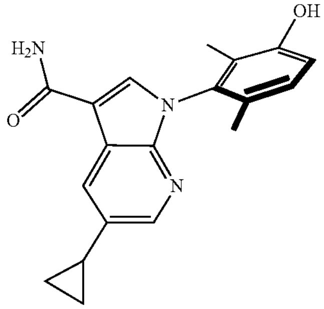
145
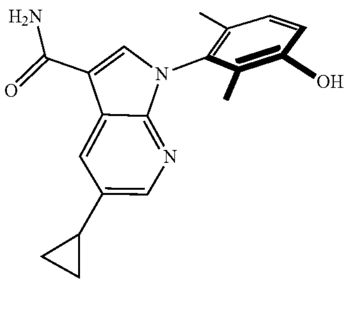
TABLE 1-continued
146
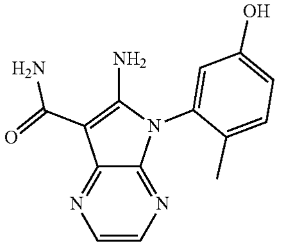 [SMILES: Cc1ccc(O)cc1-n1c(N)c(C(N)=O)c2nccnc21]
147
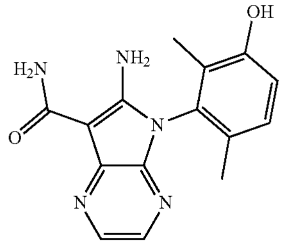 [SMILES: Cc1ccc(O)c(C)c1-n1c(N)c(C(N)=O)c2nccnc21]
148
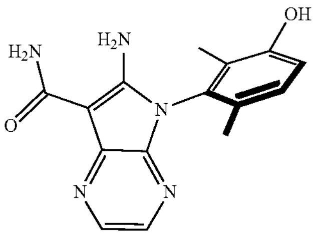
149
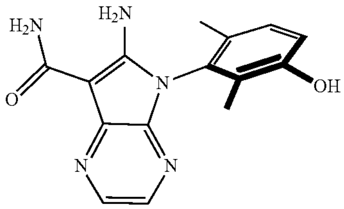
150
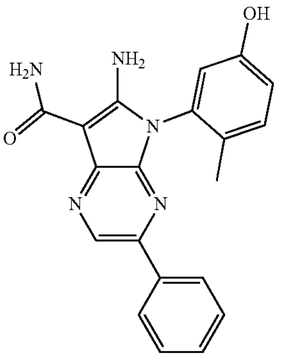 [SMILES: Cc1ccc(O)cc1-n1c(N)c(C(N)=O)c2ncc(-c3ccccc3)nc21]

TABLE 1-continued
151
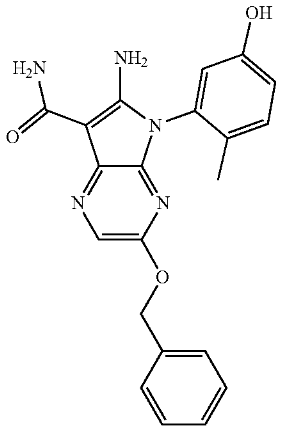 [SMILES: Cc1ccc(O)cc1-n1c(N)c(C(N)=O)c2ncc(OCc3ccccc3)nc21]
152
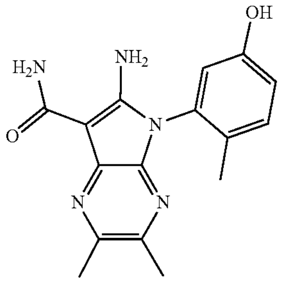 [SMILES: Cc1ccc(O)cc1-n1c(N)c(C(N)=O)c2nc(C)c(C)nc21]
153
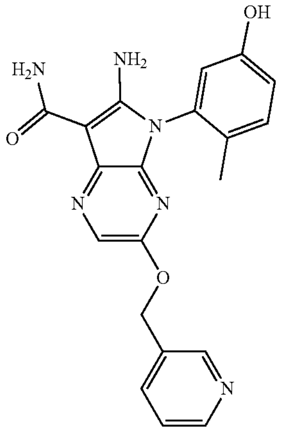 [SMILES: Cc1ccc(O)cc1-n1c(N)c(C(N)=O)c2ncc(OCc3cccnc3)nc21]
154
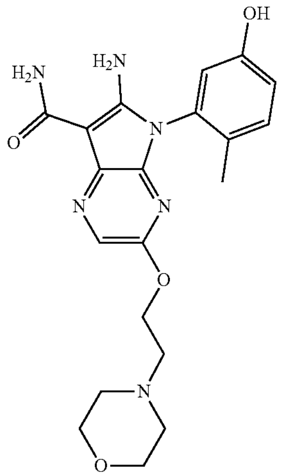 [SMILES: Cc1ccc(O)cc1-n1c(N)c(C(N)=O)c2ncc(OCCN3CCOCC3)nc21]
TABLE 1-continued
155
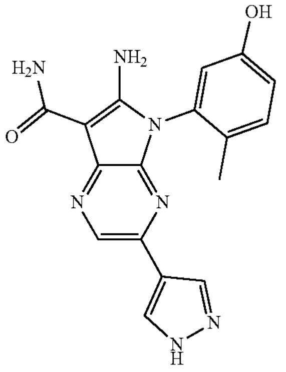 [SMILES: Cc1ccc(O)cc1-n1c(N)c(C(N)=O)c2ncc(-c3cn[nH]c3)nc21]
156
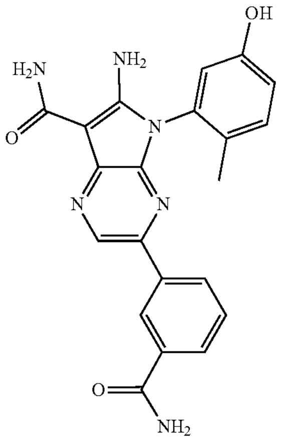 [SMILES: Cc1ccc(O)cc1-n1c(N)c(C(N)=O)c2ncc(-c3cccc(C(N)=O)c3)nc21]
157
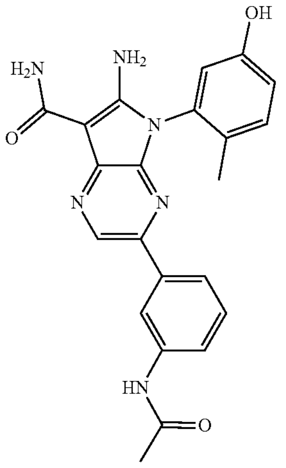 [SMILES: CC(=O)Nc1cccc(-c2cnc3c(C(N)=O)c(N)n(-c4cc(O)ccc4C)c3n2)c1]

TABLE 1-continued
158
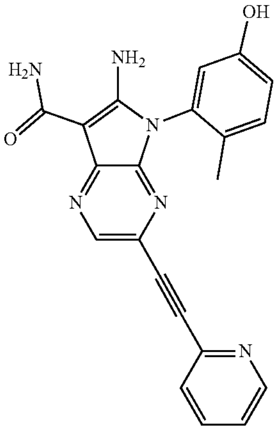 [SMILES: Cc1ccc(O)cc1-n1c(N)c(C(N)=O)c2ncc(C#Cc3ccccn3)nc21]
159
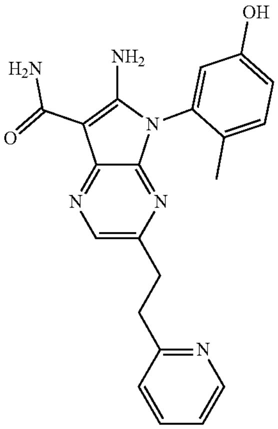 [SMILES: Cc1ccc(O)cc1-n1c(N)c(C(N)=O)c2ncc(CCc3ccccn3)nc21]
160
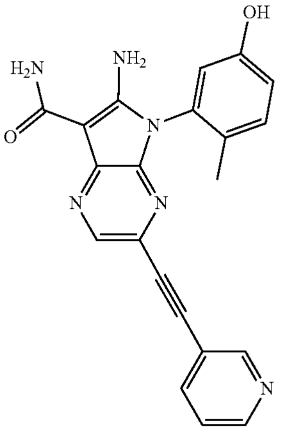 [SMILES: Cc1ccc(O)cc1-n1c(N)c(C(N)=O)c2ncc(C#Cc3cccnc3)nc21]
TABLE 1-continued
161
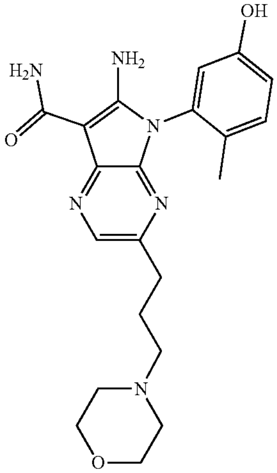 [SMILES: Cc1ccc(O)cc1-n1c(N)c(C(N)=O)c2ncc(CCCN3CCOCC3)nc21]
162
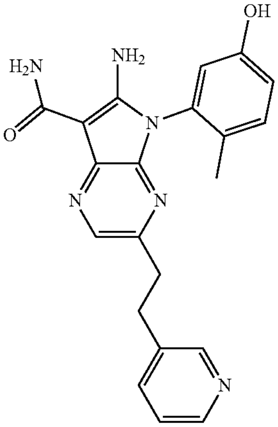 [SMILES: Cc1ccc(O)cc1-n1c(N)c(C(N)=O)c2ncc(CCc3cccnc3)nc21]
163
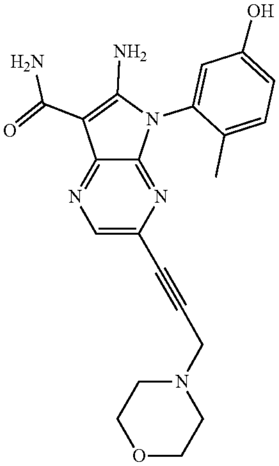 [SMILES: Cc1ccc(O)cc1-n1c(N)c(C(N)=O)c2ncc(C#CCN3CCOCC3)nc21]
164
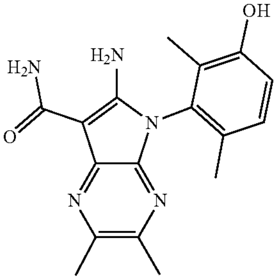 [SMILES: Cc1ccc(O)c(C)c1-n1c(N)c(C(N)=O)c2nc(C)c(C)nc21]

TABLE 1-continued
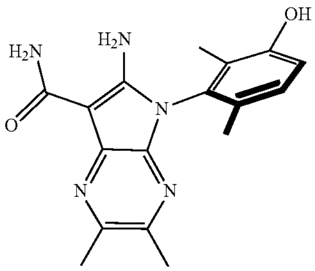
165
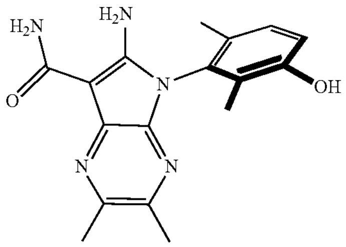
166
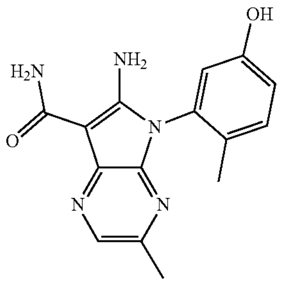 [SMILES: Cc1cnc2c(C(N)=O)c(N)n(-c3cc(O)ccc3C)c2n1]
167
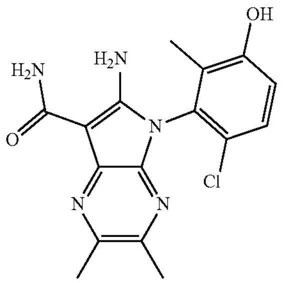 [SMILES: Cc1nc2c(C(N)=O)c(N)n(-c3c(Cl)ccc(O)c3C)c2nc1C]
168
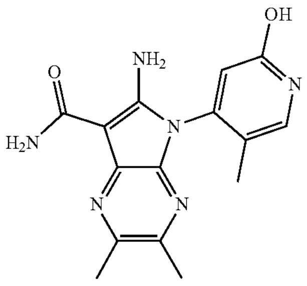 [SMILES: Cc1cnc(O)cc1-n1c(N)c(C(N)=O)c2nc(C)c(C)nc21]
169
TABLE 1-continued
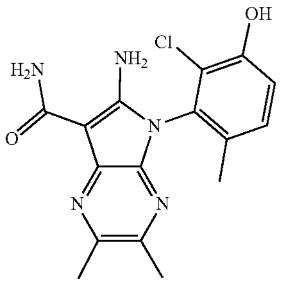 [SMILES: Cc1ccc(O)c(Cl)c1-n1c(N)c(C(N)=O)c2nc(C)c(C)nc21]
170
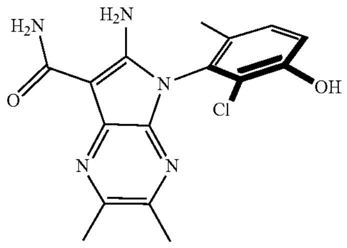
171
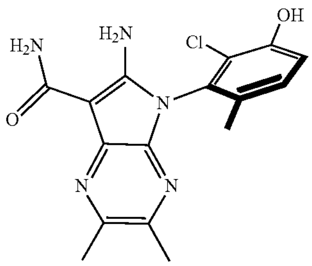
172
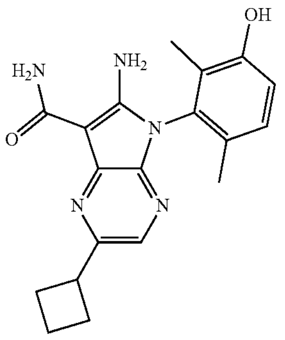 [SMILES: Cc1ccc(O)c(C)c1-n1c(N)c(C(N)=O)c2nc(C3CCC3)cnc21]
173
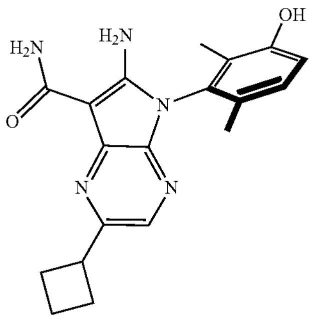
174

TABLE 1-continued
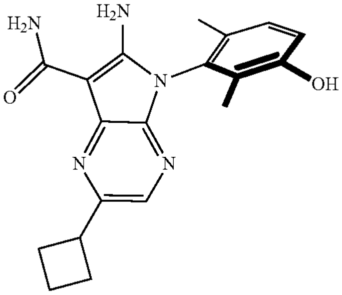
175
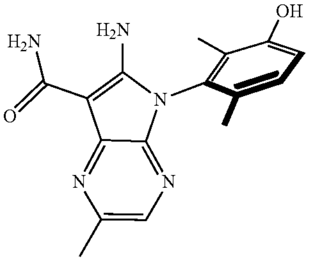
176
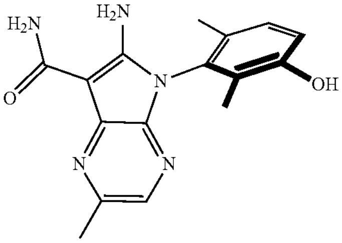
177
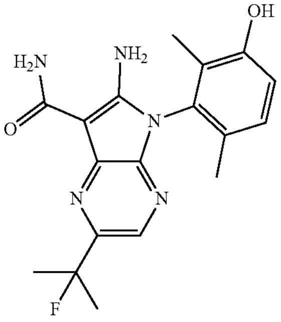 [SMILES: Cc1ccc(O)c(C)c1-n1c(N)c(C(N)=O)c2nc(C(C)(C)F)cnc21]
178
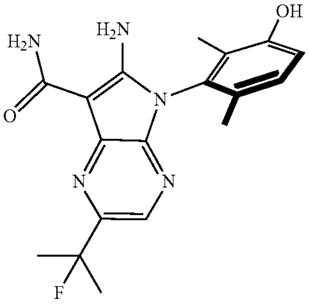
179
TABLE 1-continued
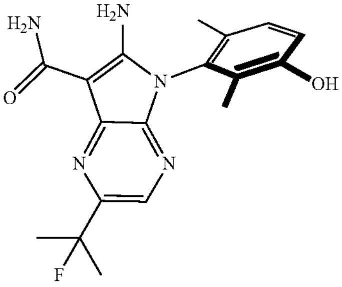
180
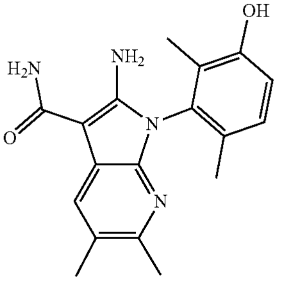 [SMILES: Cc1cc2c(C(N)=O)c(N)n(-c3c(C)ccc(O)c3C)c2nc1C]
181
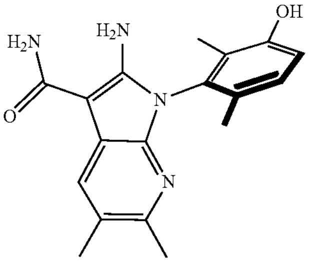
182
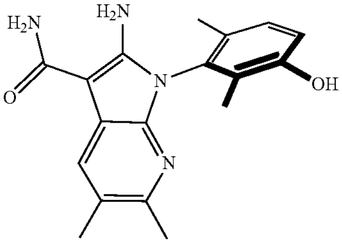
183
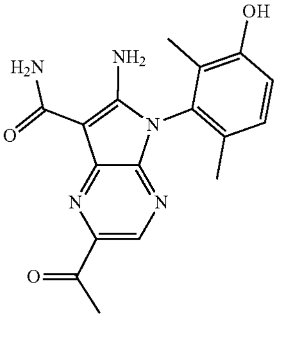 [SMILES: CC(=O)c1cnc2c(n1)c(C(N)=O)c(N)n2-c1c(C)ccc(O)c1C]
184

TABLE 1-continued
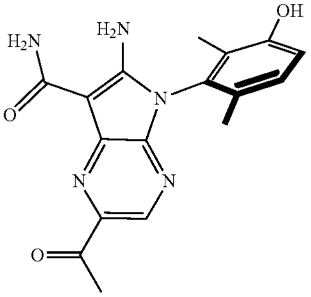
185
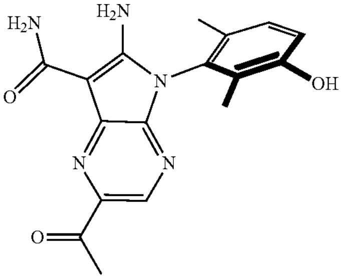
186
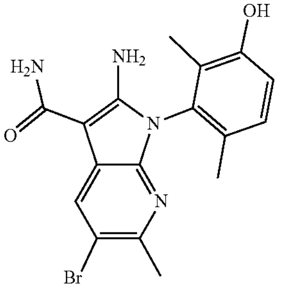 [SMILES: Cc1ccc(O)c(C)c1-n1c(N)c(C(N)=O)c2cc(Br)c(C)nc21]
187
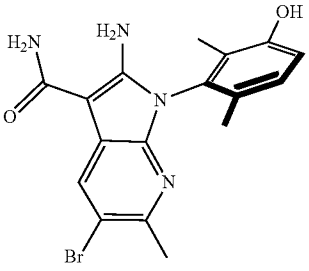
188
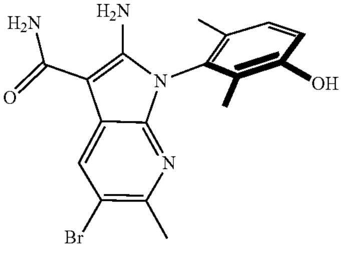
189
TABLE 1-continued
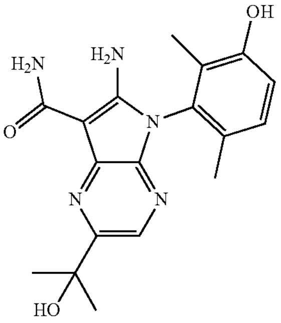 [SMILES: Cc1ccc(O)c(C)c1-n1c(N)c(C(N)=O)c2nc(C(C)(C)O)cnc21]
190
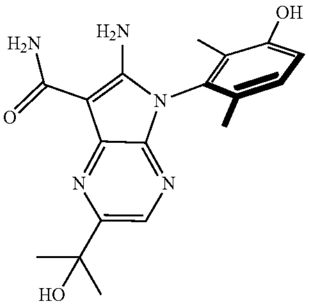
191
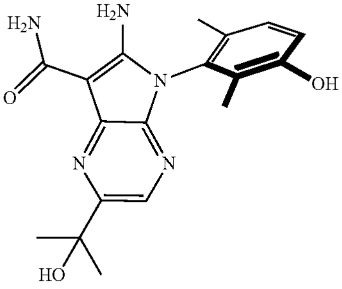
192
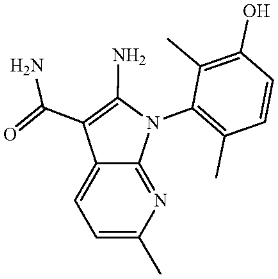 [SMILES: Cc1ccc2c(C(N)=O)c(N)n(-c3c(C)ccc(O)c3C)c2n1]
193
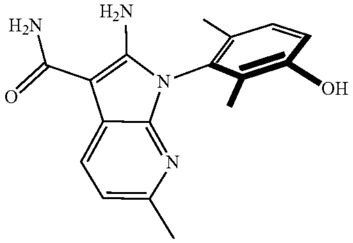
194

TABLE 1-continued
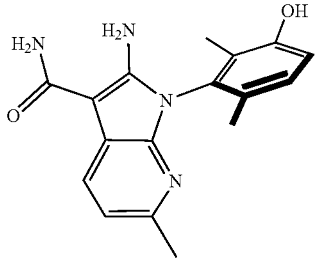
195
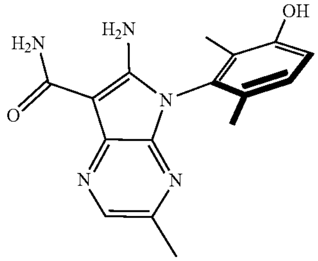
196
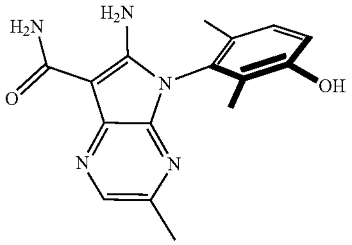
197
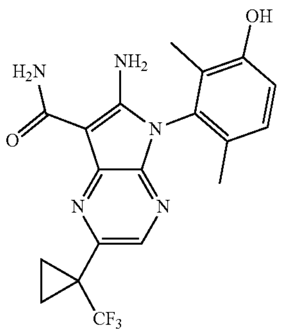 [SMILES: Cc1ccc(O)c(C)c1-n1c(N)c(C(N)=O)c2nc(C3(C(F)(F)F)CC3)cnc21]
198
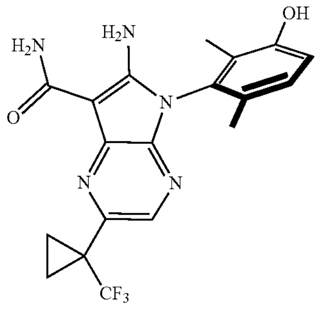
199
TABLE 1-continued
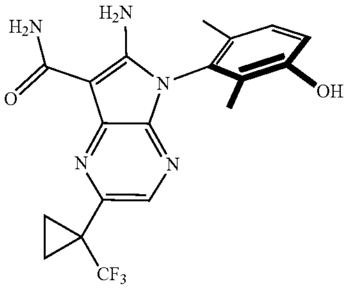
200
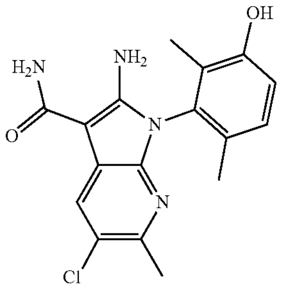 [SMILES: Cc1ccc(O)c(C)c1-n1c(N)c(C(N)=O)c2cc(Cl)c(C)nc21]
201
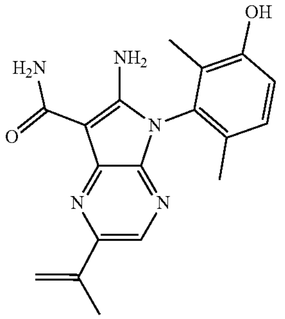 [SMILES: C=C(C)c1cnc2c(n1)c(C(N)=O)c(N)n2-c1c(C)ccc(O)c1C]
202
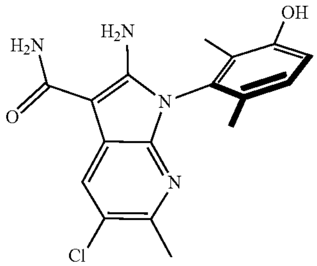
203
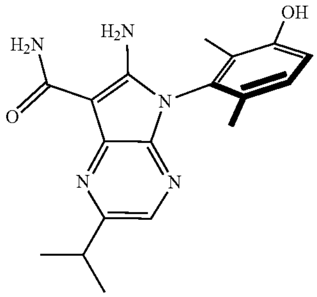
204

TABLE 1-continued
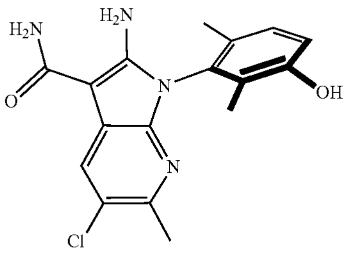
205
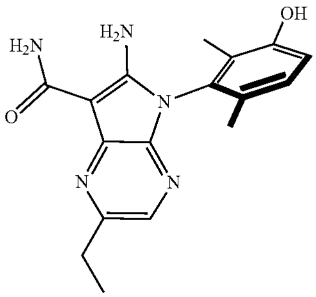
206
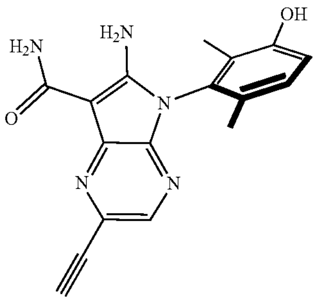
208
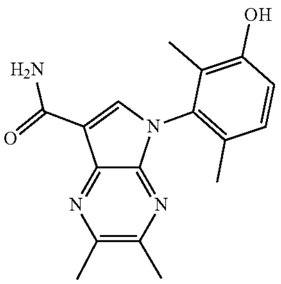 [SMILES: Cc1ccc(O)c(C)c1-n1cc(C(N)=O)c2nc(C)c(C)nc21]
209
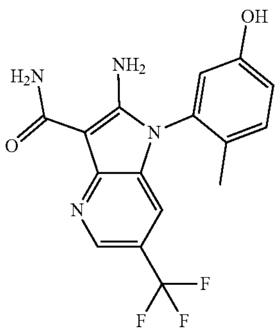 [SMILES: Cc1ccc(O)cc1-n1c(N)c(C(N)=O)c2ncc(C(F)(F)F)cc21]
212
TABLE 1-continued
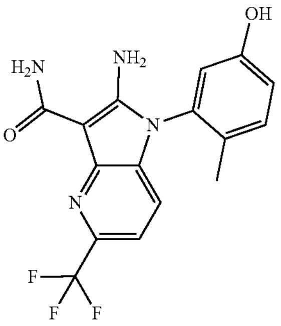 [SMILES: Cc1ccc(O)cc1-n1c(N)c(C(N)=O)c2nc(C(F)(F)F)ccc21]
213
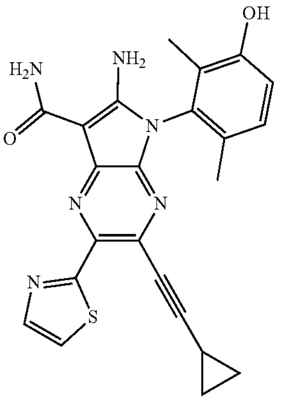 [SMILES: Cc1ccc(O)c(C)c1-n1c(N)c(C(N)=O)c2nc(-c3nccs3)c(C#CC3CC3)nc21]
214
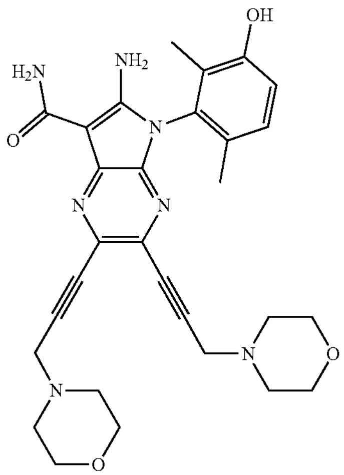 [SMILES: Cc1ccc(O)c(C)c1-n1c(N)c(C(N)=O)c2nc(C#CCN3CCOCC3)c(C#CCN3CCOCC3)nc21]
215

TABLE 1-continued
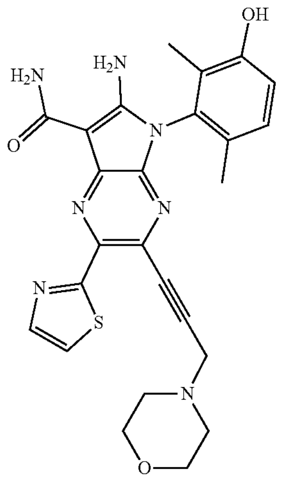 [SMILES: Cc1ccc(O)c(C)c1-n1c(N)c(C(N)=O)c2nc(-c3nccs3)c(C#CCN3CCOCC3)nc21]
216
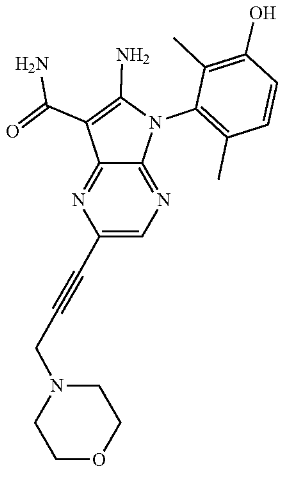 [SMILES: Cc1ccc(O)c(C)c1-n1c(N)c(C(N)=O)c2nc(C#CCN3CCOCC3)cnc21]
217
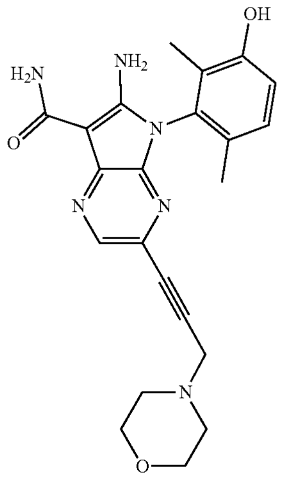 [SMILES: Cc1ccc(O)c(C)c1-n1c(N)c(C(N)=O)c2ncc(C#CCN3CCOCC3)nc21]
218
TABLE 1-continued
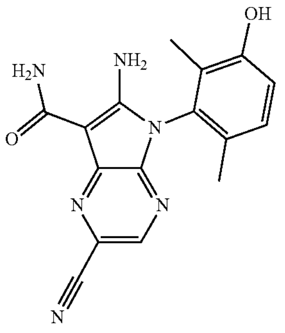 [SMILES: Cc1ccc(O)c(C)c1-n1c(N)c(C(N)=O)c2nc(C#N)cnc21]
219
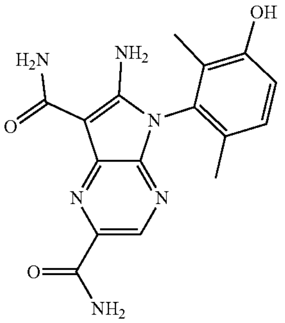 [SMILES: Cc1ccc(O)c(C)c1-n1c(N)c(C(N)=O)c2nc(C(N)=O)cnc21]
220
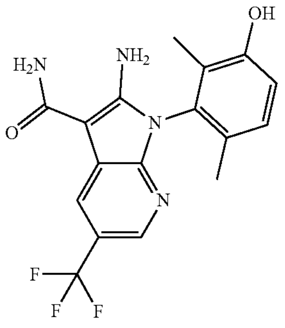 [SMILES: Cc1ccc(O)c(C)c1-n1c(N)c(C(N)=O)c2cc(C(F)(F)F)cnc21]
221
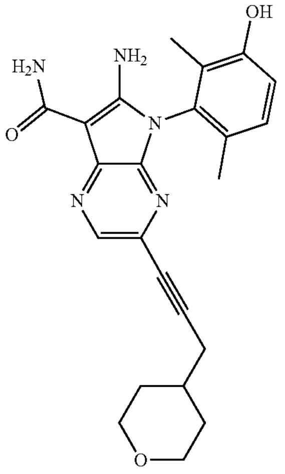 [SMILES: Cc1ccc(O)c(C)c1-n1c(N)c(C(N)=O)c2ncc(C#CCC3CCOCC3)nc21]
222

TABLE 1-continued
223
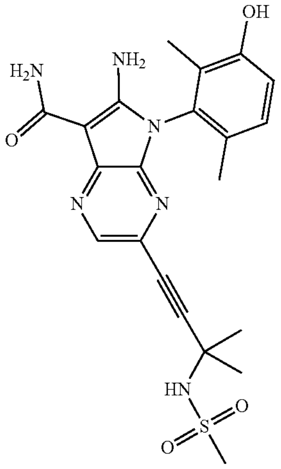 [SMILES: Cc1ccc(O)c(C)c1-n1c(N)c(C(N)=O)c2ncc(C#CC(C)(C)NS(C)(=O)=O)nc21]
224
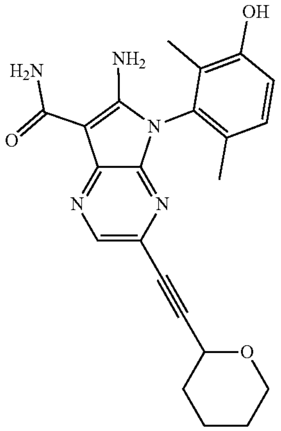 [SMILES: Cc1ccc(O)c(C)c1-n1c(N)c(C(N)=O)c2ncc(C#CC3CCCCO3)nc21]
225
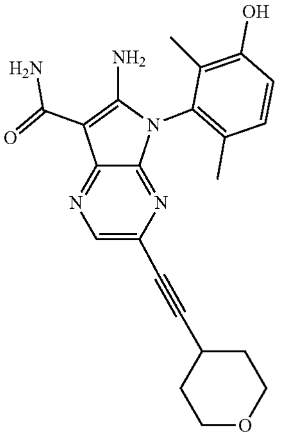 [SMILES: Cc1ccc(O)c(C)c1-n1c(N)c(C(N)=O)c2ncc(C#CC3CCOCC3)nc21]
TABLE 1-continued
226
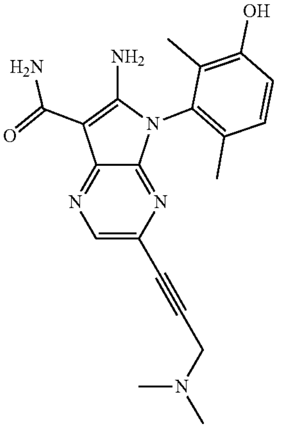 [SMILES: Cc1ccc(O)c(C)c1-n1c(N)c(C(N)=O)c2ncc(C#CCN(C)C)nc21]
227
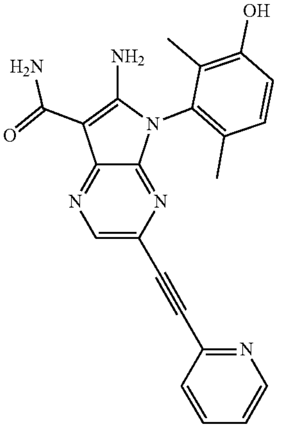 [SMILES: Cc1ccc(O)c(C)c1-n1c(N)c(C(N)=O)c2ncc(C#Cc3ccccn3)nc21]
228
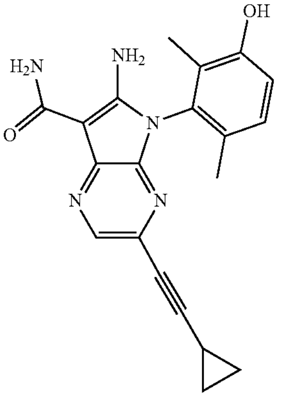 [SMILES: Cc1ccc(O)c(C)c1-n1c(N)c(C(N)=O)c2ncc(C#CC3CC3)nc21]
229
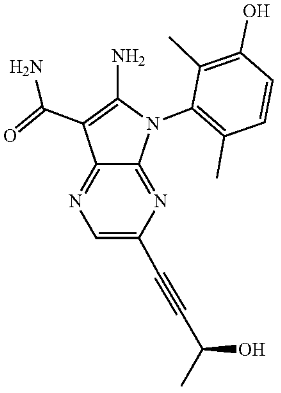 [SMILES: Cc1ccc(O)c(C)c1-n1c(N)c(C(N)=O)c2ncc(C#C[C@H](C)O)nc21]

TABLE 1-continued
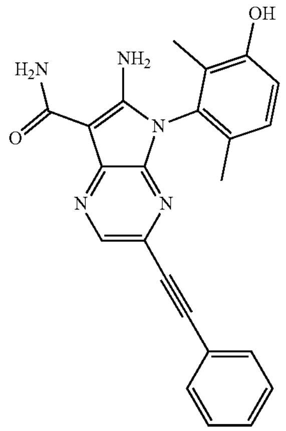 [SMILES: Cc1ccc(O)c(C)c1-n1c(N)c(C(N)=O)c2ncc(C#Cc3ccccc3)nc21]
230
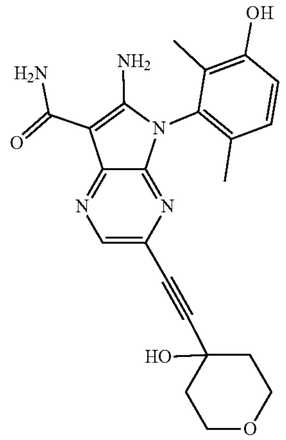 [SMILES: Cc1ccc(O)c(C)c1-n1c(N)c(C(N)=O)c2ncc(C#CC3(O)CCOCC3)nc21]
231
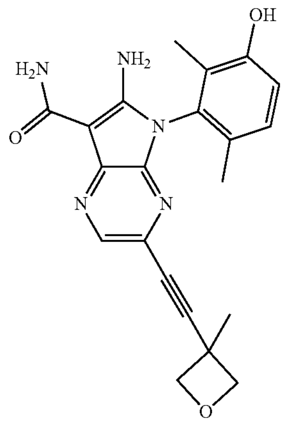 [SMILES: Cc1ccc(O)c(C)c1-n1c(N)c(C(N)=O)c2ncc(C#CC3(C)COC3)nc21]
232
TABLE 1-continued
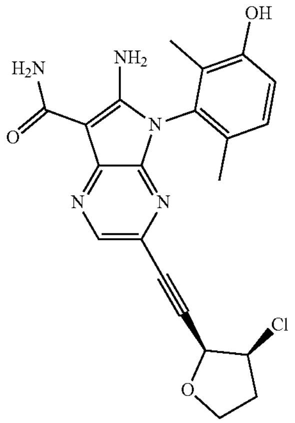 [SMILES: Cc1ccc(O)c(C)c1-n1c(N)c(C(N)=O)c2ncc(C#C[C@@H]3OCC[C@@H]3Cl)nc21]
233
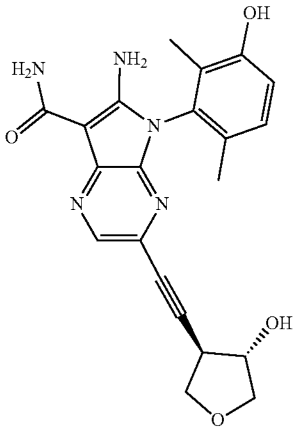 [SMILES: Cc1ccc(O)c(C)c1-n1c(N)c(C(N)=O)c2ncc(C#C[C@@H]3COC[C@H]3O)nc21]
234
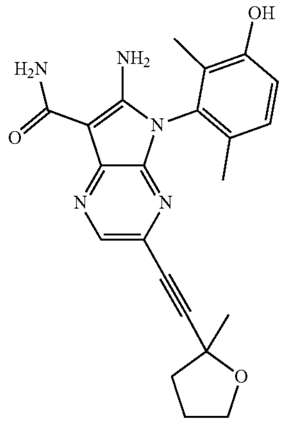 [SMILES: Cc1ccc(O)c(C)c1-n1c(N)c(C(N)=O)c2ncc(C#CC3(C)CCCO3)nc21]
235

TABLE 1-continued
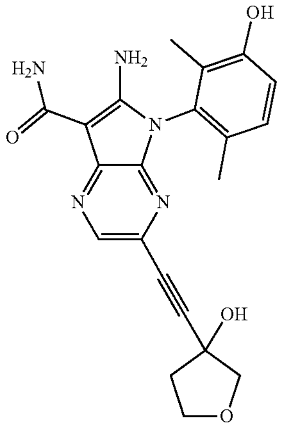 [SMILES: Cc1ccc(O)c(C)c1-n1c(N)c(C(N)=O)c2ncc(C#CC3(O)CCOC3)nc21]
236
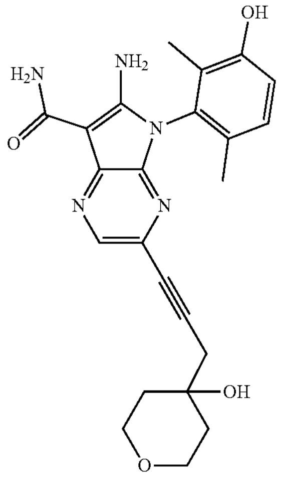 [SMILES: Cc1ccc(O)c(C)c1-n1c(N)c(C(N)=O)c2ncc(C#CCC3(O)CCOCC3)nc21]
237
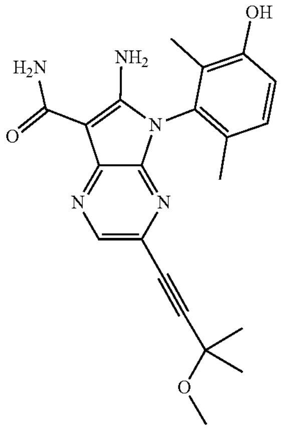 [SMILES: COC(C)(C)C#Cc1cnc2c(C(N)=O)c(N)n(-c3c(C)ccc(O)c3C)c2n1]
238
TABLE 1-continued
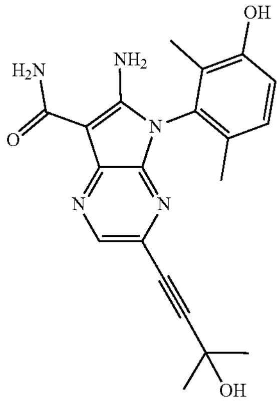 [SMILES: Cc1ccc(O)c(C)c1-n1c(N)c(C(N)=O)c2ncc(C#CC(C)(C)O)nc21]
239
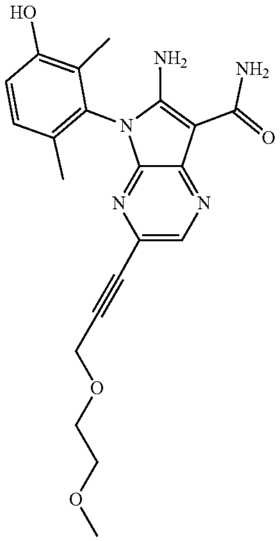 [SMILES: COCCOCC#Cc1cnc2c(C(N)=O)c(N)n(-c3c(C)ccc(O)c3C)c2n1]
240
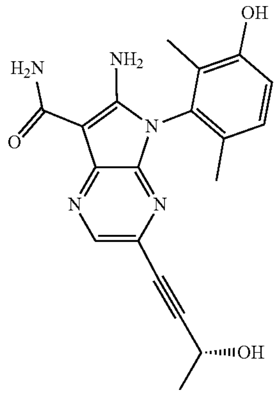 [SMILES: Cc1ccc(O)c(C)c1-n1c(N)c(C(N)=O)c2ncc(C#C[C@@H](C)O)nc21]
241

TABLE 1-continued
242
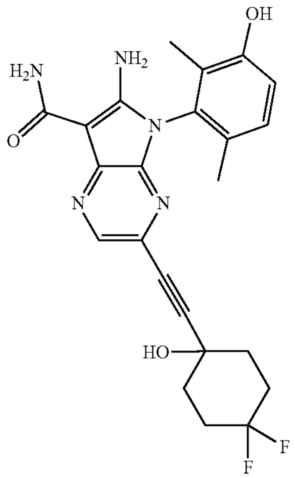 [SMILES: Cc1ccc(O)c(C)c1-n1c(N)c(C(N)=O)c2ncc(C#CC3(O)CCC(F)(F)CC3)nc21]
243
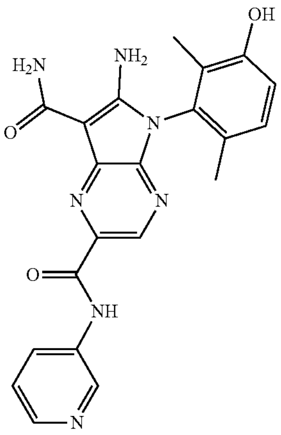 [SMILES: Cc1ccc(O)c(C)c1-n1c(N)c(C(N)=O)c2nc(C(=O)Nc3cccnc3)cnc21]
244
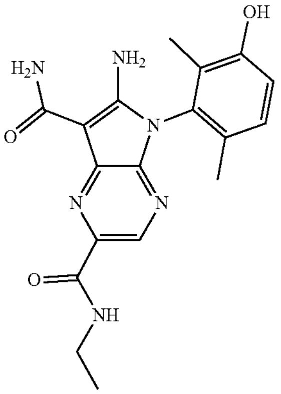 [SMILES: CCNC(=O)c1cnc2c(n1)c(C(N)=O)c(N)n2-c1c(C)ccc(O)c1C]
TABLE 1-continued
245
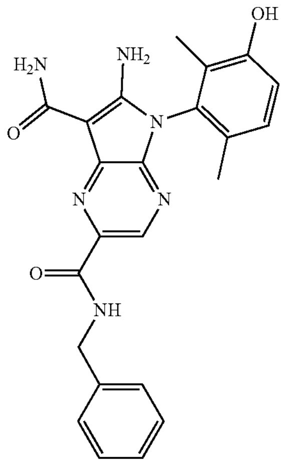 [SMILES: Cc1ccc(O)c(C)c1-n1c(N)c(C(N)=O)c2nc(C(=O)NCc3ccccc3)cnc21]
246
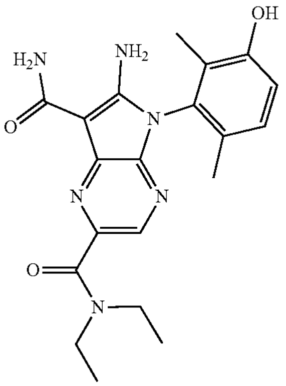 [SMILES: CCN(CC)C(=O)c1cnc2c(n1)c(C(N)=O)c(N)n2-c1c(C)ccc(O)c1C]
247
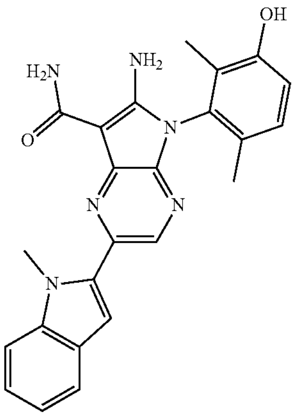 [SMILES: Cc1ccc(O)c(C)c1-n1c(N)c(C(N)=O)c2nc(-c3cc4ccccc4n3C)cnc21]

TABLE 1-continued
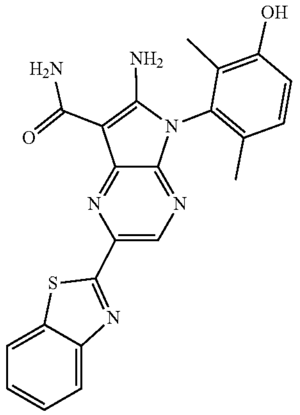 [SMILES: Cc1ccc(O)c(C)c1-n1c(N)c(C(N)=O)c2nc(-c3nc4ccccc4s3)cnc21]
248
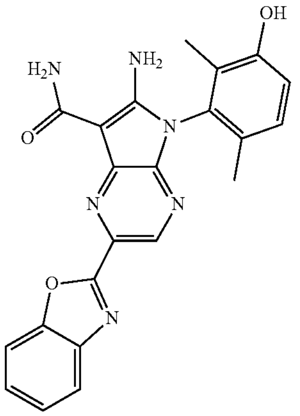 [SMILES: Cc1ccc(O)c(C)c1-n1c(N)c(C(N)=O)c2nc(-c3nc4ccccc4o3)cnc21]
249
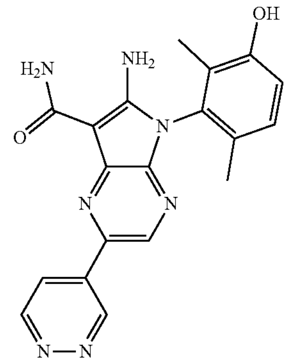 [SMILES: Cc1ccc(O)c(C)c1-n1c(N)c(C(N)=O)c2nc(-c3ccnnc3)cnc21]
250
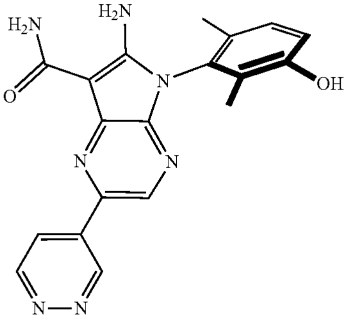
251
TABLE 1-continued
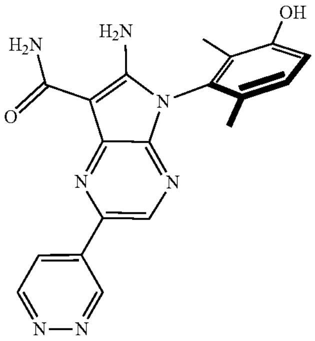
252
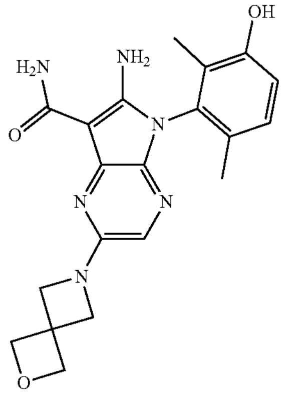 [SMILES: Cc1ccc(O)c(C)c1-n1c(N)c(C(N)=O)c2nc(N3CC4(COC4)C3)cnc21]
253
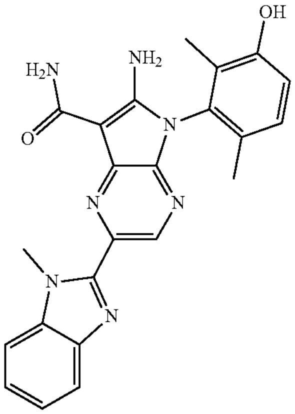 [SMILES: Cc1ccc(O)c(C)c1-n1c(N)c(C(N)=O)c2nc(-c3nc4ccccc4n3C)cnc21]
254
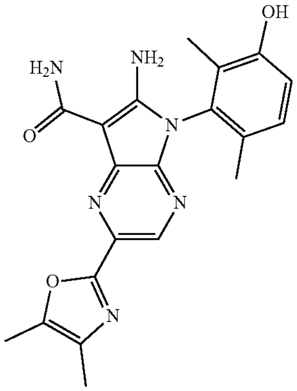 [SMILES: Cc1ccc(O)c(C)c1-n1c(N)c(C(N)=O)c2nc(-c3nc(C)c(C)o3)cnc21]
255

TABLE 1-continued
256
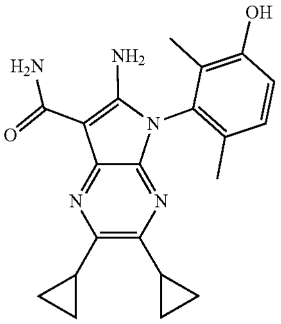 [SMILES: Cc1ccc(O)c(C)c1-n1c(N)c(C(N)=O)c2nc(C3CC3)c(C3CC3)nc21]
257
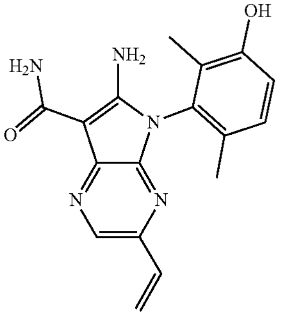 [SMILES: C=Cc1cnc2c(C(N)=O)c(N)n(-c3c(C)ccc(O)c3C)c2n1]
258
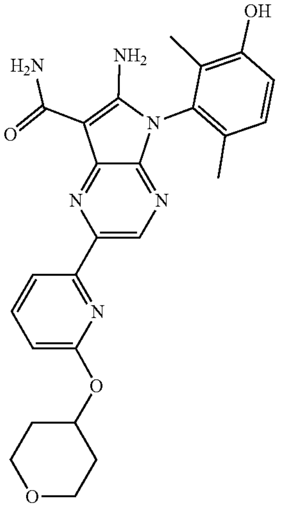 [SMILES: Cc1ccc(O)c(C)c1-n1c(N)c(C(N)=O)c2nc(-c3cccc(OC4CCOCC4)n3)cnc21]
259
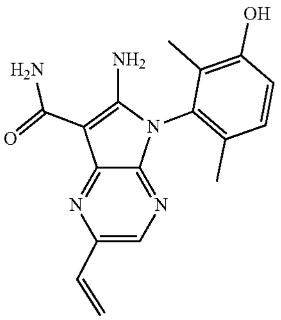 [SMILES: C=Cc1cnc2c(n1)c(C(N)=O)c(N)n2-c1c(C)ccc(O)c1C]
TABLE 1-continued
260
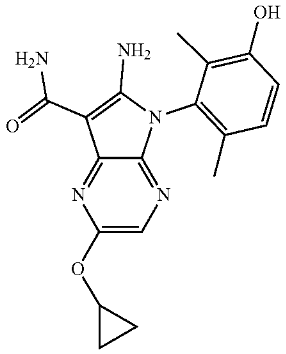 [SMILES: Cc1ccc(O)c(C)c1-n1c(N)c(C(N)=O)c2nc(OC3CC3)cnc21]
261
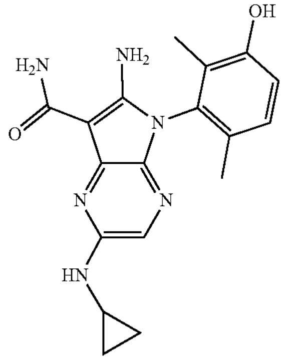 [SMILES: Cc1ccc(O)c(C)c1-n1c(N)c(C(N)=O)c2nc(NC3CC3)cnc21]
262
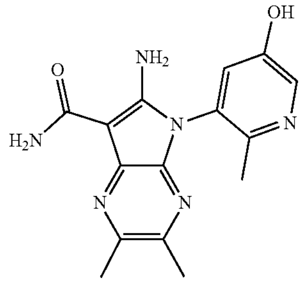 [SMILES: Cc1ncc(O)cc1-n1c(N)c(C(N)=O)c2nc(C)c(C)nc21]
263
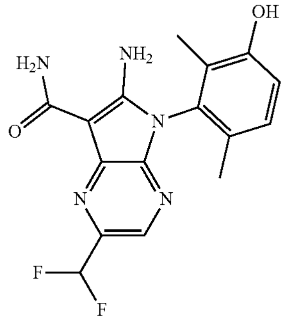 [SMILES: Cc1ccc(O)c(C)c1-n1c(N)c(C(N)=O)c2nc(C(F)F)cnc21]
264
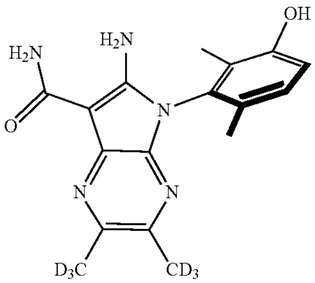

TABLE 1-continued
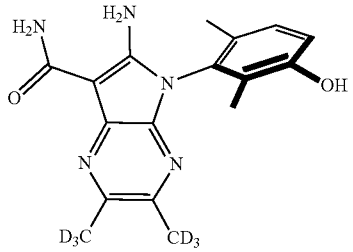
265
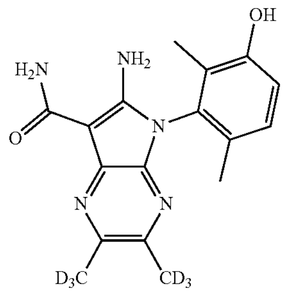 [SMILES: [2H]C([2H])([2H])c1nc2c(C(N)=O)c(N)n(-c3c(C)ccc(O)c3C)c2nc1C([2H])([2H])[2H]]
266
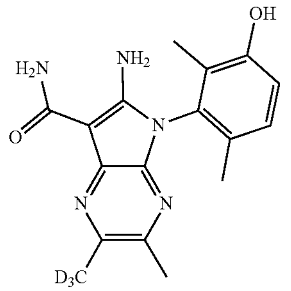 [SMILES: [2H]C([2H])([2H])c1nc2c(C(N)=O)c(N)n(-c3c(C)ccc(O)c3C)c2nc1C]
267
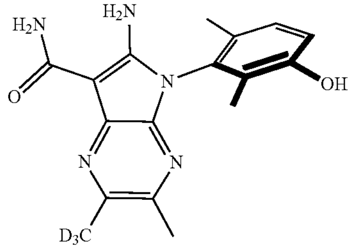
268
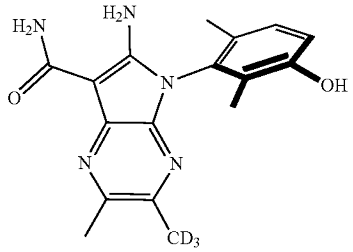
269
TABLE 1-continued
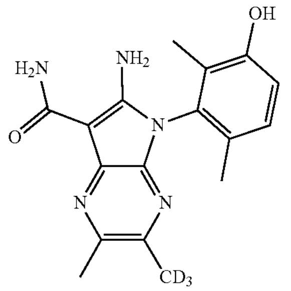 [SMILES: [2H]C([2H])([2H])c1nc2c(nc1C)c(C(N)=O)c(N)n2-c1c(C)ccc(O)c1C]
270
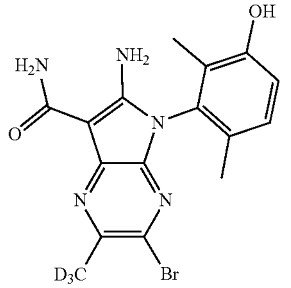
271
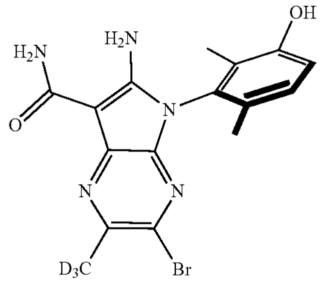
272
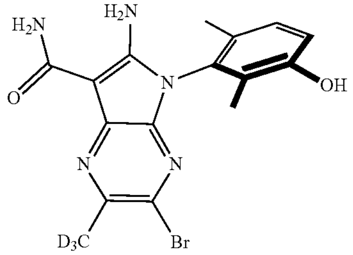
273
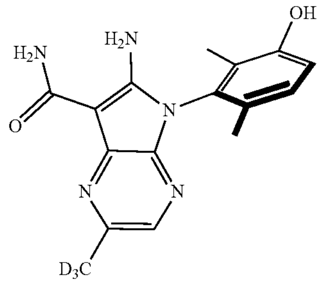
274

TABLE 1-continued
275
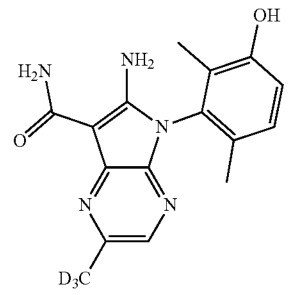
276
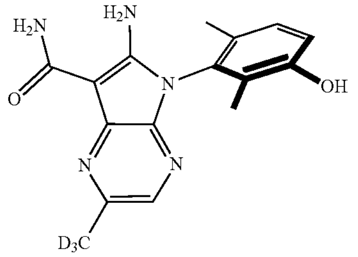
277
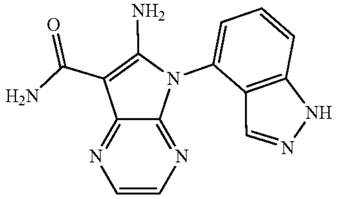 [SMILES: NC(=O)c1c(N)n(-c2cccc3[nH]ncc23)c2nccnc12]
278
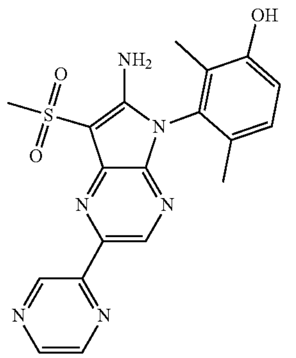 [SMILES: Cc1ccc(O)c(C)c1-n1c(N)c(S(C)(=O)=O)c2nc(-c3cnccn3)cnc21]
279
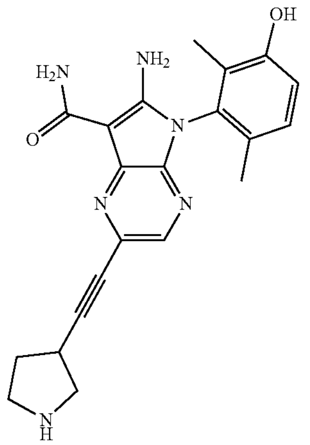 [SMILES: Cc1ccc(O)c(C)c1-n1c(N)c(C(N)=O)c2nc(C#CC3CCNC3)cnc21]
TABLE 1-continued
280
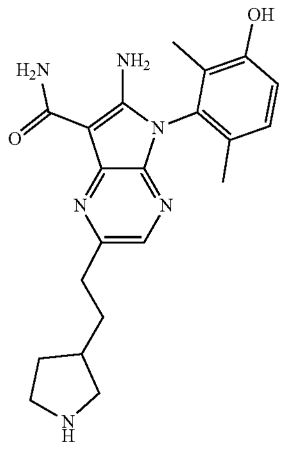 [SMILES: Cc1ccc(O)c(C)c1-n1c(N)c(C(N)=O)c2nc(CCC3CCNC3)cnc21]
281
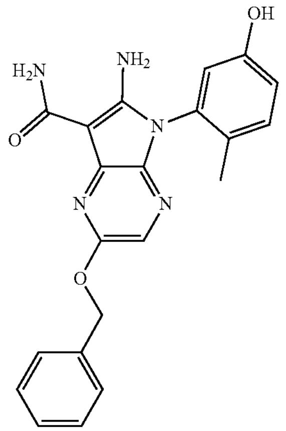 [SMILES: Cc1ccc(O)cc1-n1c(N)c(C(N)=O)c2nc(OCc3ccccc3)cnc21]
282
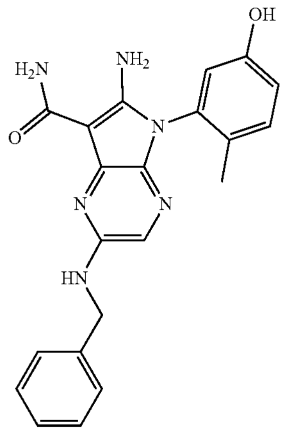 [SMILES: Cc1ccc(O)cc1-n1c(N)c(C(N)=O)c2nc(NCc3ccccc3)cnc21]

TABLE 1-continued
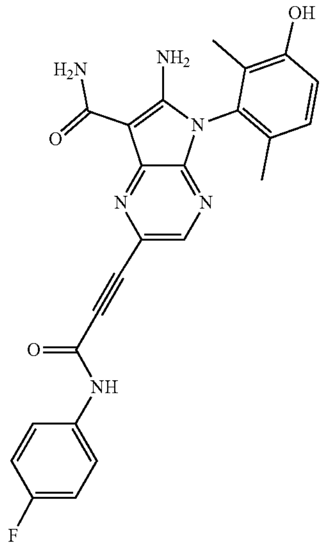 [SMILES: Cc1ccc(O)c(C)c1-n1c(N)c(C(N)=O)c2nc(C#CC(=O)Nc3ccc(F)cc3)cnc21]
283
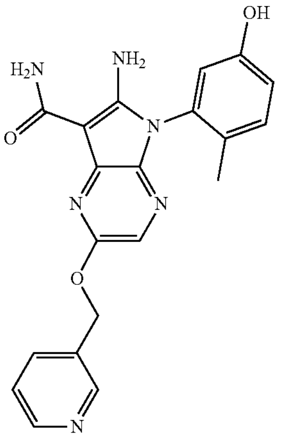 [SMILES: Cc1ccc(O)cc1-n1c(N)c(C(N)=O)c2nc(OCc3cccnc3)cnc21]
284
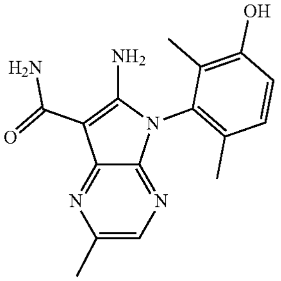 [SMILES: Cc1cnc2c(n1)c(C(N)=O)c(N)n2-c1c(C)ccc(O)c1C]
285
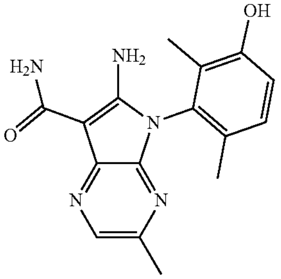
286
TABLE 1-continued
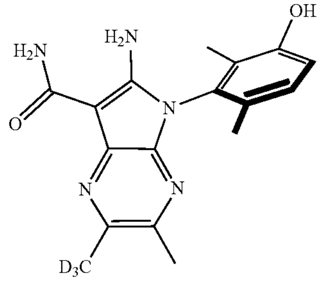
287
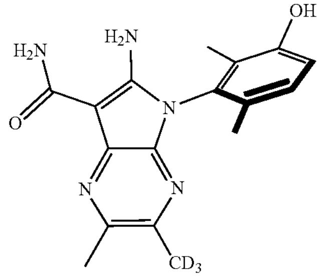
288
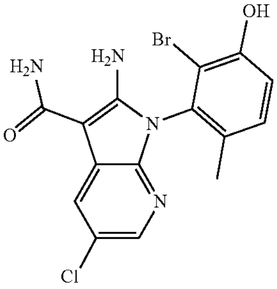 [SMILES: Cc1ccc(O)c(Br)c1-n1c(N)c(C(N)=O)c2cc(Cl)cnc21]
289
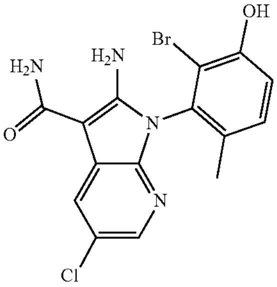 [SMILES: Cc1ccc(O)c(Br)c1-n1c(N)c(C(N)=O)c2cc(Cl)cnc21]
290
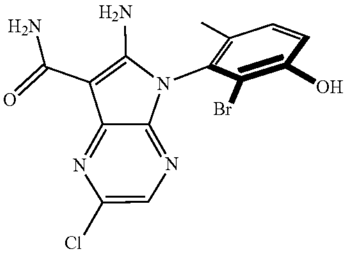
291

TABLE 1-continued
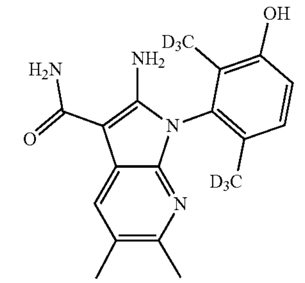 [SMILES: [2H]C([2H])([2H])c1ccc(O)c(C([2H])([2H])[2H])c1-n1c(N)c(C(N)=O)c2cc(C)c(C)nc21]
292
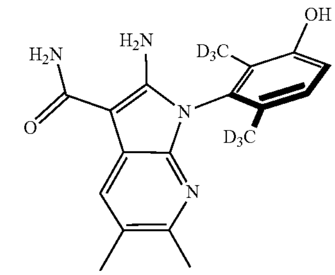
293
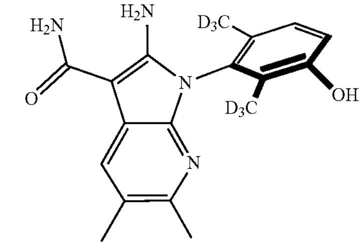
294
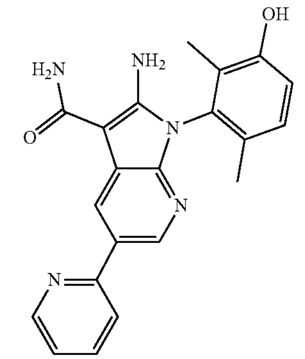 [SMILES: Cc1ccc(O)c(C)c1-n1c(N)c(C(N)=O)c2cc(-c3ccccn3)cnc21]
295
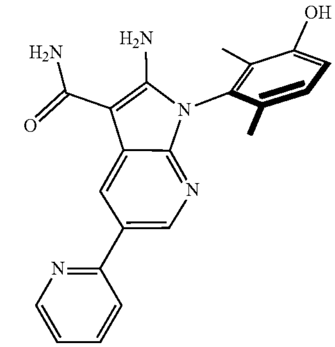
296
TABLE 1-continued
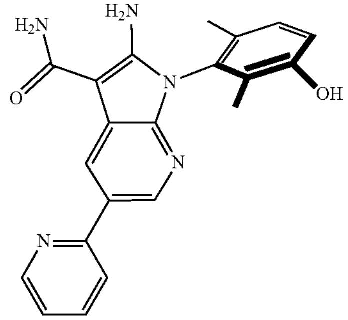
297
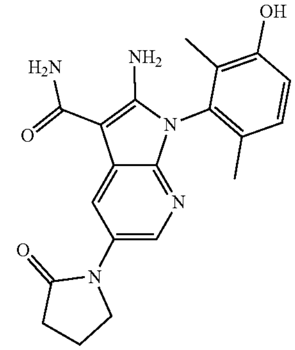 [SMILES: Cc1ccc(O)c(C)c1-n1c(N)c(C(N)=O)c2cc(N3CCCC3=O)cnc21]
298
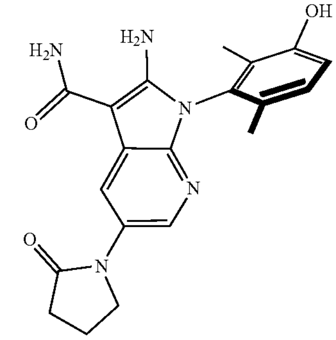
299
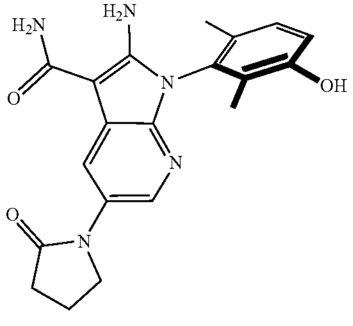
300
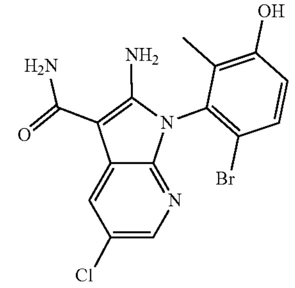 [SMILES: Cc1c(O)ccc(Br)c1-n1c(N)c(C(N)=O)c2cc(Cl)cnc21]
301

TABLE 1-continued
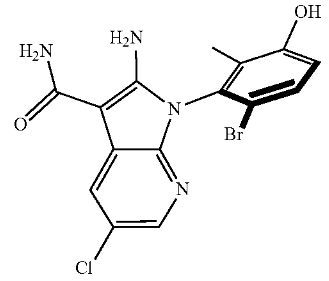
302
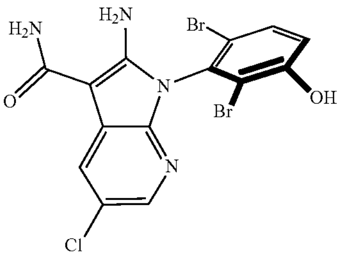
303
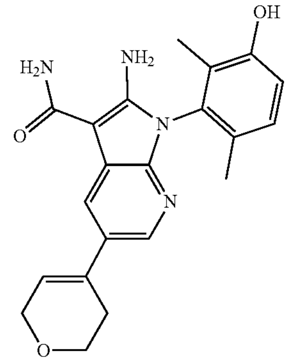 [SMILES: Cc1ccc(O)c(C)c1-n1c(N)c(C(N)=O)c2cc(C3=CCOCC3)cnc21]
304
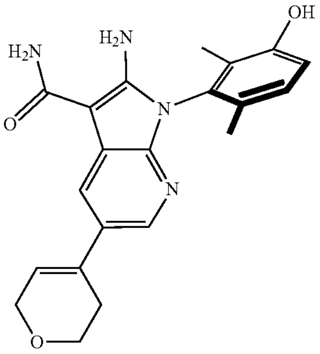
305
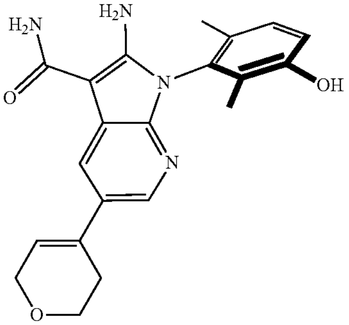
306
TABLE 1-continued
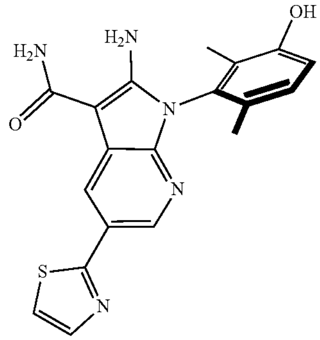
307
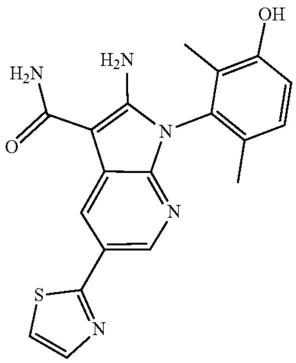 [SMILES: Cc1ccc(O)c(C)c1-n1c(N)c(C(N)=O)c2cc(-c3nccs3)cnc21]
308
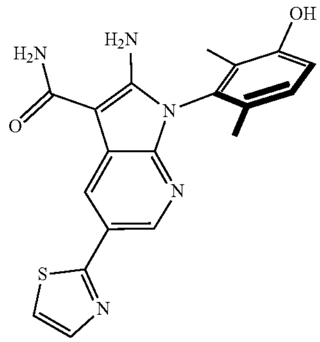
309
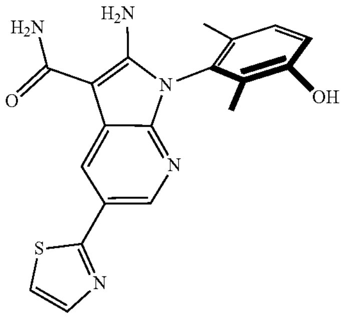
310

TABLE 1-continued
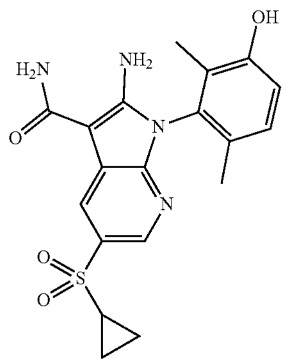 [SMILES: Cc1ccc(O)c(C)c1-n1c(N)c(C(N)=O)c2cc(S(=O)(=O)C3CC3)cnc21]
311
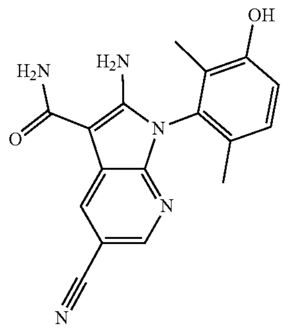 [SMILES: Cc1ccc(O)c(C)c1-n1c(N)c(C(N)=O)c2cc(C#N)cnc21]
312
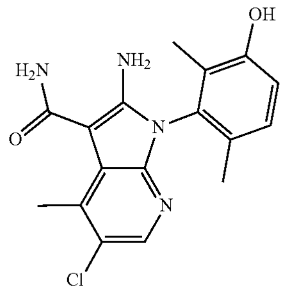 [SMILES: Cc1ccc(O)c(C)c1-n1c(N)c(C(N)=O)c2c(C)c(Cl)cnc21]
313
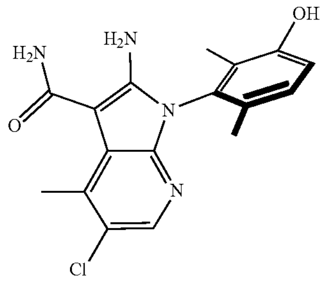
314
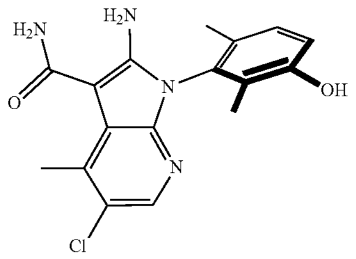
315
TABLE 1-continued
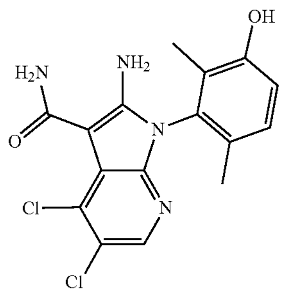 [SMILES: Cc1ccc(O)c(C)c1-n1c(N)c(C(N)=O)c2c(Cl)c(Cl)cnc21]
316
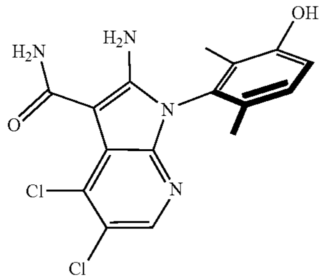
317
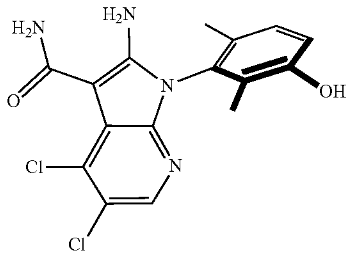
318
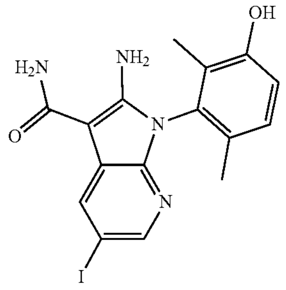 [SMILES: Cc1ccc(O)c(C)c1-n1c(N)c(C(N)=O)c2cc(I)cnc21]
319
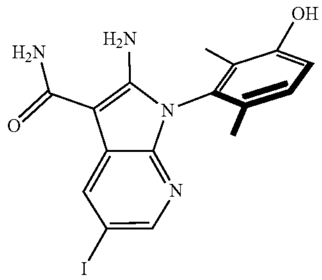
320

TABLE 1-continued
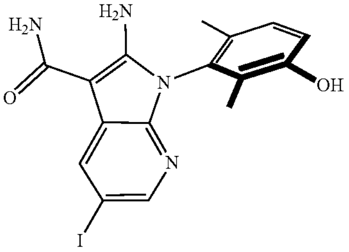
321
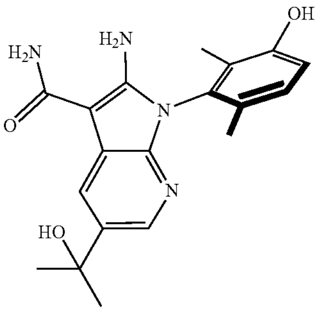
322
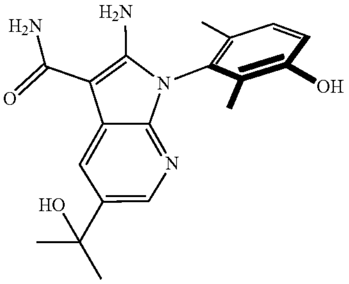
323
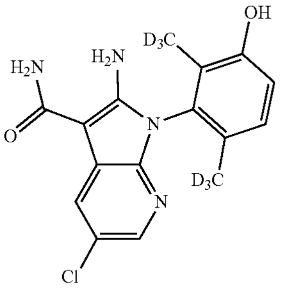 [SMILES: [2H]C([2H])([2H])c1ccc(O)c(C([2H])([2H])[2H])c1-n1c(N)c(C(N)=O)c2cc(Cl)cnc21]
324
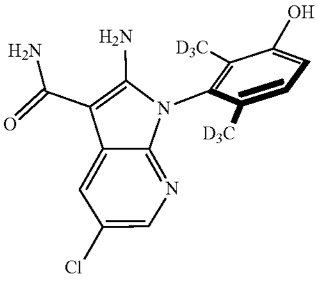
325
TABLE 1-continued
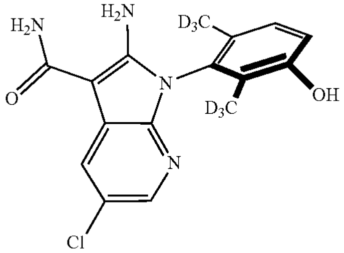
326
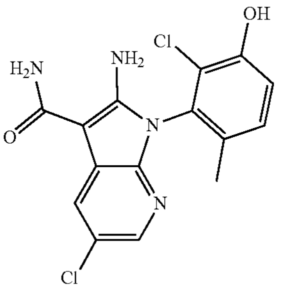 [SMILES: Cc1ccc(O)c(Cl)c1-n1c(N)c(C(N)=O)c2cc(Cl)cnc21]
327
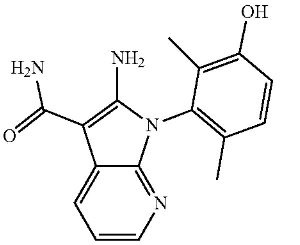 [SMILES: Cc1ccc(O)c(C)c1-n1c(N)c(C(N)=O)c2cccnc21]
328
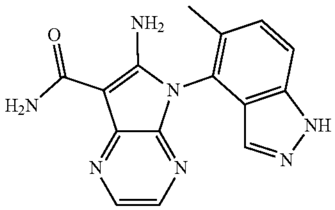 [SMILES: Cc1ccc2[nH]ncc2c1-n1c(N)c(C(N)=O)c2nccnc21]
329
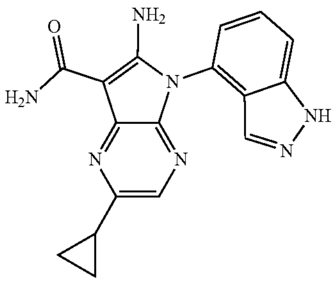 [SMILES: NC(=O)c1c(N)n(-c2cccc3[nH]ncc23)c2ncc(C3CC3)nc12]
330

TABLE 1-continued
331
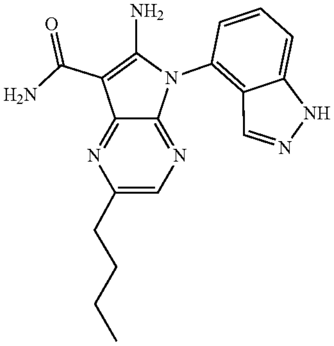 [SMILES: CCCCc1cnc2c(n1)c(C(N)=O)c(N)n2-c1cccc2[nH]ncc12]
332
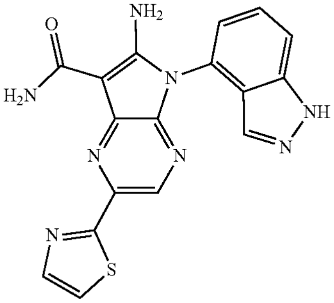 [SMILES: NC(=O)c1c(N)n(-c2cccc3[nH]ncc23)c2ncc(-c3nccs3)nc12]
333
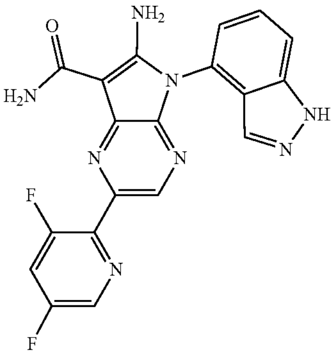 [SMILES: NC(=O)c1c(N)n(-c2cccc3[nH]ncc23)c2ncc(-c3ncc(F)cc3F)nc12]
334
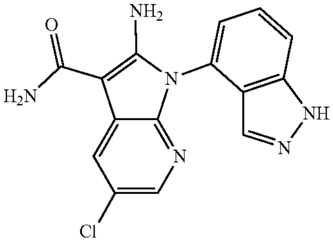 [SMILES: NC(=O)c1c(N)n(-c2cccc3[nH]ncc23)c2ncc(Cl)cc12]
335
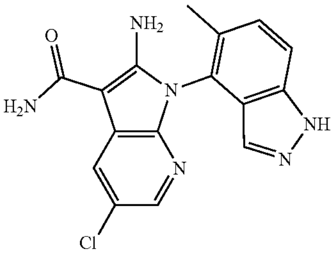 [SMILES: Cc1ccc2[nH]ncc2c1-n1c(N)c(C(N)=O)c2cc(Cl)cnc21]
TABLE 1-continued
336
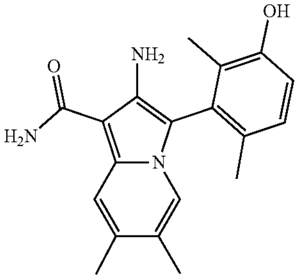 [SMILES: Cc1cc2c(C(N)=O)c(N)c(-c3c(C)ccc(O)c3C)n2cc1C]
337
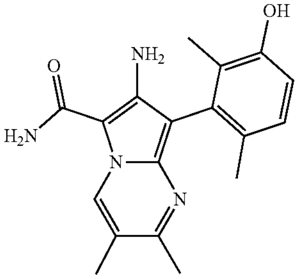
338
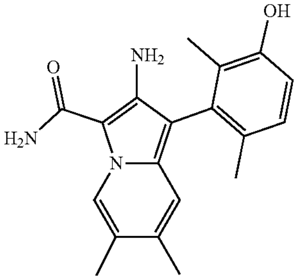 [SMILES: Cc1cc2c(-c3c(C)ccc(O)c3C)c(N)c(C(N)=O)n2cc1C]
339
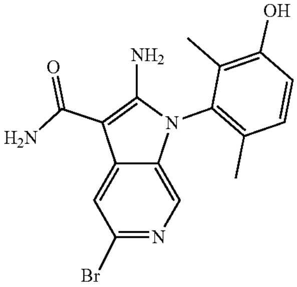 [SMILES: Cc1ccc(O)c(C)c1-n1c(N)c(C(N)=O)c2cc(Br)ncc21]
340
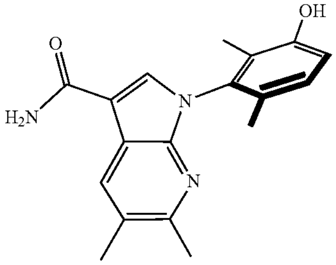

TABLE 1-continued

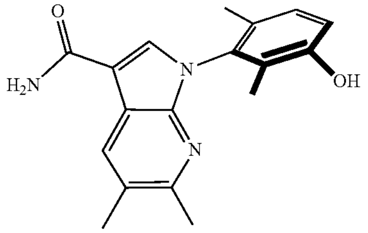

341

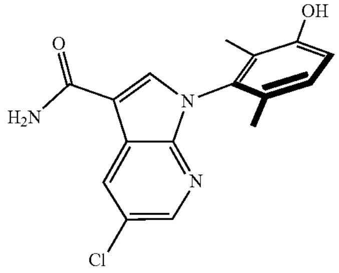

342

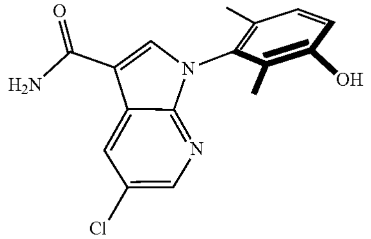

343

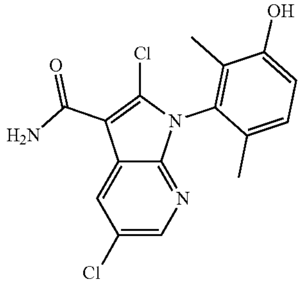 [SMILES: Cc1ccc(O)c(C)c1-n1c(Cl)c(C(N)=O)c2cc(Cl)cnc21]

344

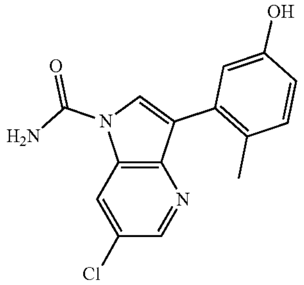 [SMILES: Cc1ccc(O)cc1-c1cn(C(N)=O)c2cc(Cl)cnc12]

345

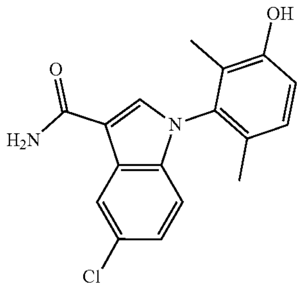 [SMILES: Cc1ccc(O)c(C)c1-n1cc(C(N)=O)c2cc(Cl)ccc21]

346

The invention includes (where possible) individual diastereomers, enantiomers, epimers, and atropisomers of the compounds disclosed herein, and mixtures of diastereomers and/or enantiomers thereof including racemic mixtures. Although the specific stereochemistries disclosed herein are preferred, other stereoisomers, including diastereomers, enantiomers, epimers, atropisomers, and mixtures of these may also have utility in treating Myt1-mediated diseases. Inactive or less active diastereoisomers and enantiomers may be useful, e.g., for scientific studies relating to the receptor and the mechanism of activation.

It is understood that certain molecules can exist in multiple tautomeric forms. This invention includes all tautomers even though only one tautomer may be indicated in the examples.

The invention also includes pharmaceutically acceptable salts of the compounds, and pharmaceutical compositions comprising the compounds and a pharmaceutically acceptable carrier. The compounds are especially useful, e.g., in certain kinds of cancer and for slowing the progression of cancer once it has developed in a patient.

The compounds disclosed herein may be used in pharmaceutical compositions comprising (a) the compound(s) or pharmaceutically acceptable salts thereof, and (b) a pharmaceutically acceptable carrier. The compounds may be used in pharmaceutical compositions that include one or more other active pharmaceutical ingredients. The compounds may also be used in pharmaceutical compositions in which the compound disclosed herein or a pharmaceutically acceptable salt thereof is the only active ingredient.

Optical Isomers-Diastereomers-Geometric Isomers-Tautomers

Compounds disclosed herein may contain, e.g., one or more stereogenic centers and can occur as racemates, racemic mixtures, single enantiomers, individual diastereomers, and mixtures of diastereomers and/or enantiomers. The invention includes all such isomeric forms of the compounds disclosed herein. It is intended that all possible stereoisomers (e.g., enantiomers and/or diastereomers) in mixtures and as pure or partially purified compounds are included within the scope of this invention (i.e., all possible combinations of the stereogenic centers as pure compounds or in mixtures).

Some of the compounds described herein may contain bonds with hindered rotation such that two separate rotomers, or atropisomers, may be separated and found to have different biological activity which may be advantageous. It is intended that all of the possible atropisomers are included within the scope of this invention.

Some of the compounds described herein may contain olefinic double bonds, and unless specified otherwise, are meant to include both E and Z geometric isomers.

Some of the compounds described herein may exist with different points of attachment of hydrogen, referred to as tautomers. An example is a ketone and its enol form, known as keto-enol tautomers. The individual tautomers as well as mixtures thereof are encompassed by the invention.

Compounds disclosed herein having one or more asymmetric centers may be separated into diastereoisomers, enantiomers, and the like by methods well known in the art.

Alternatively, enantiomers and other compounds with chiral centers may be synthesized by stereospecific synthesis using optically pure starting materials and/or reagents of known configuration.

Metabolites—Prodrugs

The invention includes therapeutically active metabolites, where the metabolites themselves fall within the scope of the claims. The invention also includes prodrugs, which are compounds that are converted to the claimed compounds as they are being administered to a patient or after they have been administered to a patient. The claimed chemical structures of this application in some cases may themselves be prodrugs.

Isotopically Enriched Derivatives

The invention includes molecules which have been isotopically enriched at one or more position within the molecule. Thus, compounds enriched for deuterium fall within the scope of the claims.

Methods of Preparing a Compound of the Invention

Compounds of the present invention may be prepared using reactions and techniques known in the art and those described herein. One of skill in the art will appreciate that methods of preparing compounds of the invention described herein are non-limiting and that steps within the methods may be interchangeable without affecting the structure of the end product.

Method A

Compounds of the present invention may be prepared as shown in Scheme A and described herein. The amino group of the commercially available 5-bromo-6-chloropyrazin-2-amine can be converted to a hydroxyl that can be benzylated with benzyl bromide in presence of a base to generate key Intermediate B. The bromo may be substituted by an aromatic amine under metal-mediated conditions. Depending on the nature of the arylamine, a protecting group may be required to be in place prior to this reaction. The chloro may be substituted by malononitrile under SNAr or palladium-mediated conditions to afford the aminopyrrole Intermediate C. The nitrile may be hydrolyzed to the carboxamide upon treatment with an acid with concomitant cleavage of the benzyl group. The resulting hydroxyl may be converted to the triflate to generate the triflate key Intermediate D that can be derivatized in a number of different ways to provide compounds of the present invention. For example, a metal-mediated coupling or SNAr displacement may be used to install a group at $R^2$. Depending on the nature of the $R^2$ group, a protecting group may be required to be in place prior to the triflate derivatization reaction. In the case where the $R^2$ group bears an unsaturation, a hydrogenation reaction may be required to give compound of the present invention. In the case where the arylamine and/or the $R^2$ group bear a protecting group, a deprotection step(s) may be required using acid, base and/or fluoride to give compounds of the present invention. Depending on the nature of the arylamine, an atropisomeric mixture may be obtained. In such cases it may be necessary to isolate the atropisomer of interest to give compounds of the present invention. Alternatively, an atropisomerically pure intermediate can be isolated and may be derivatized further to give compounds of the present invention. For example, key intermediate D may be purified by chiral chromatography to provide an atropisomerically pure intermediate that may be manipulated similarly to intermediate D described above to provide compounds of the present invention.

Scheme A

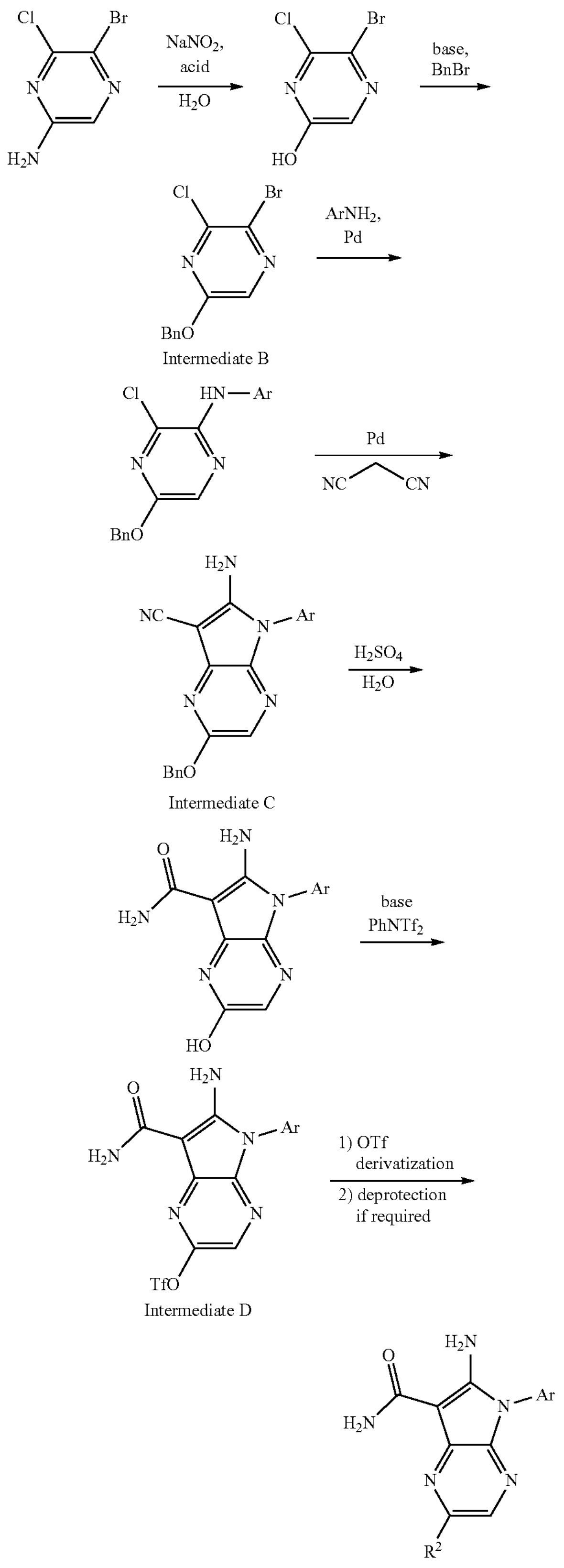

-continued

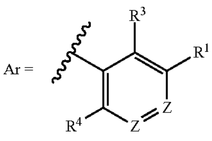

Method B

Compounds of the present invention may be prepared as shown in Scheme B and described herein. The chloro of Intermediate B can be displaced by an aromatic amine under give compound of the present invention. In the case where the arylamine and/or the $R^2$ group bear a protecting group, a deprotection step(s) may be required using acid, base and/or fluoride to give compounds of the present invention. Depending on the nature of the arylamine, an atropisomeric mixture may be obtained. In such cases it may be necessary to isolate the atropisomer of interest to give compounds of the present invention. Alternatively, an atropisomerically pure intermediate can be isolated and may be derivatized further to give compounds of the present invention.

Scheme B

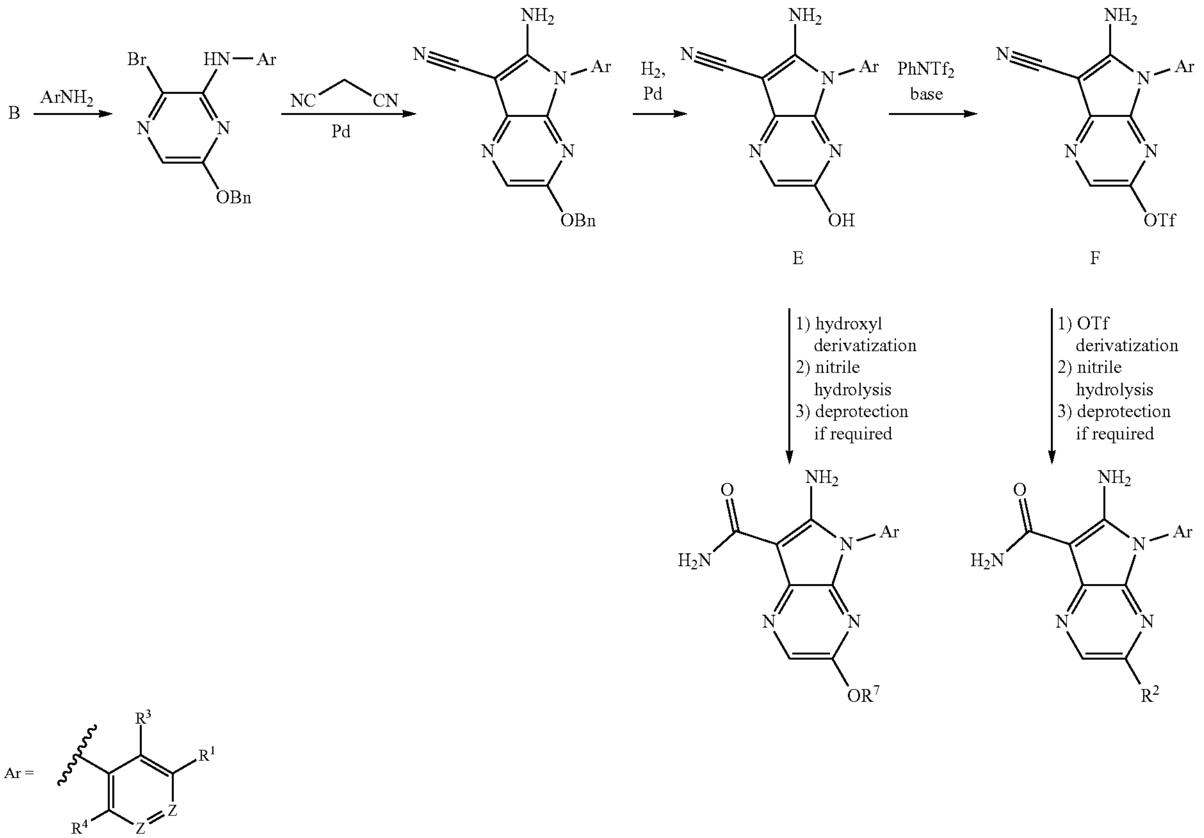

SNAr conditions. Depending on the nature of the arylamine, a protecting group may be required to be in place prior to this reaction. The bromo may then be substituted by malononitrile under metal-mediated conditions to afford an aminopyrrole. The OBn may be hydrogenolyzed to afford the key Intermediate E that may be derivatized in a number of different ways to give compounds of the present invention following nitrile hydrolysis. For example, Mitsunobu or alkylation conditions may be used to install a group at $R^2$. Alternatively, Intermediate E may be converted to the triflate key Intermediate F that may be derivatized in a number of different ways to give compounds of the present invention following nitrile hydrolysis. For example, a metal-mediated coupling may be used to install a group at $R^2$. Depending on the nature of the $R^2$ group, a protecting group may be required to be in place prior to the hydroxyl or triflate derivatization reaction. In the case where the $R^2$ group bears an unsaturation, a hydrogenation reaction may be required to Method C Compounds of the present invention may be prepared as shown in Scheme C and described herein. The 2-chloro of the commercially available 3-bromo-2,6-dichloropyridine can be substituted by malononitrile under SNAr conditions with a base. The bromo may be substituted by an aromatic amine under metal-mediated conditions to afford an amino-azaindole. Depending on the nature of the arylamine, a protecting group may be required to be in place prior to this reaction. Protecting group(s) may be removed before the nitrile may be hydrolyzed to the carboxamide upon treatment with an acid to yield Intermediate G. The remaining chloro can be derivatized in a number of different ways to provide compounds of the present invention. For example, a metal-mediated coupling may be used to install a group at $R^2$. Depending on the nature of $R^2$, a protecting group may be required to be in place prior to the chloro derivatization reaction. In the case where $R^2$ bears an unsaturation, a hydrogenation reaction may be required to give a compound of the present invention. In the case where the arylamine and/or $R^2$ bear a protecting group, a deprotection step(s) may be required using acid, base and/or fluoride to give compounds of the present invention. Depending on the nature of the arylamine, an atropisomeric mixture may be obtained. In such cases it may be necessary to isolate the atropisomer of interest to give compounds of the present invention. Alternatively, an atropisomerically pure intermediate can be isolated and may be derivatized further to give compounds of the present invention.

Scheme C

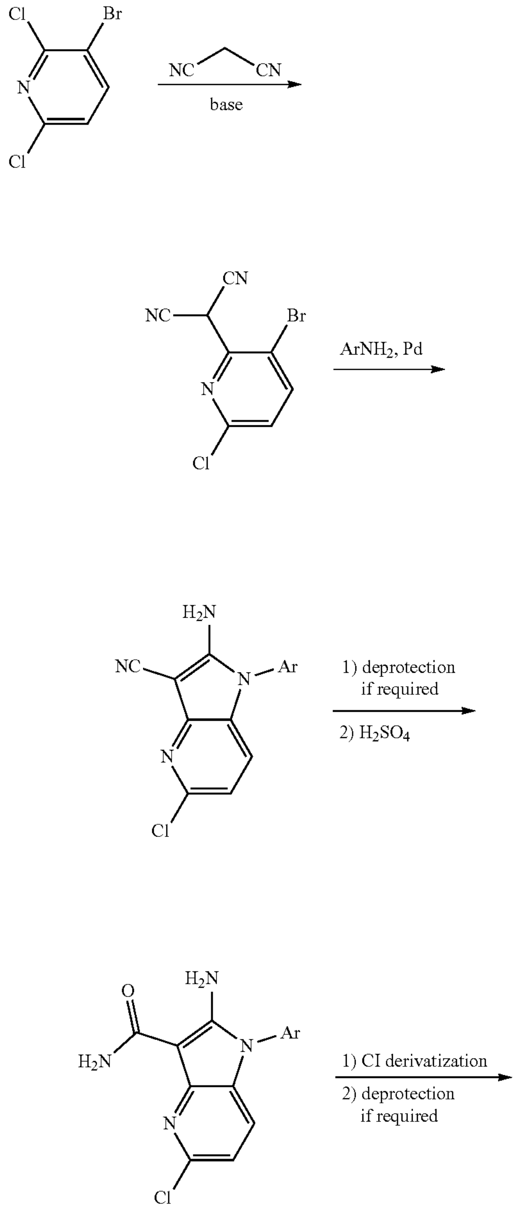

Intermediate G

-continued

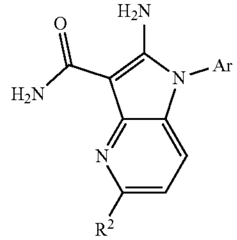

Ar = 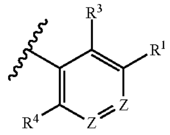

Method D

Compounds of the present invention may be prepared as shown in Scheme D and described herein. The halogen at position 2 of an adequately substituted 5-nitropyridine may be substituted with an aromatic amine under SNAr conditions or a metal-mediated C—N coupling conditions. Depending on the nature of the arylamine, a protecting group may be required to be in place prior to this reaction. The 3-bromo may be substituted by malononitrile under palladium-mediated conditions to afford an aminoazaindole. The resulting amino group can be protected with a suitable protecting group, e.g. BOC. The nitro can be reduced and the resulting amino can be converted to a halogen under Sandmeyer conditions yielding halogenated derivatives. The aminopyrrole N-protecting group may be cleaved and the nitrile can be hydrolyzed to the carboxamide to yield Intermediate I that can be derivatized in a number of different ways to provide compounds of the present invention. For example, a metal-mediated coupling may be used to install a group at $R^2$. In the case where $R^2$ bears an unsaturation, a hydrogenation reaction may be required to give a compound of the present invention. Depending on the nature of the $R^1$ group, a protecting group may be required to be in place prior to the halogen derivatization reaction. In the case where the arylamine and/or $R^2$ bear a protecting group, a deprotection step(s) may be required using acid, base and/or fluoride to give compounds of the present invention. Depending on the nature of the arylamine, an atropisomeric mixture may be obtained. In such cases it may be necessary to isolate the atropisomer of interest to give compounds of the present invention. Alternatively, an atropisomerically pure intermediate can be isolated and may be derivatized further to give compounds of the present invention.

Scheme D

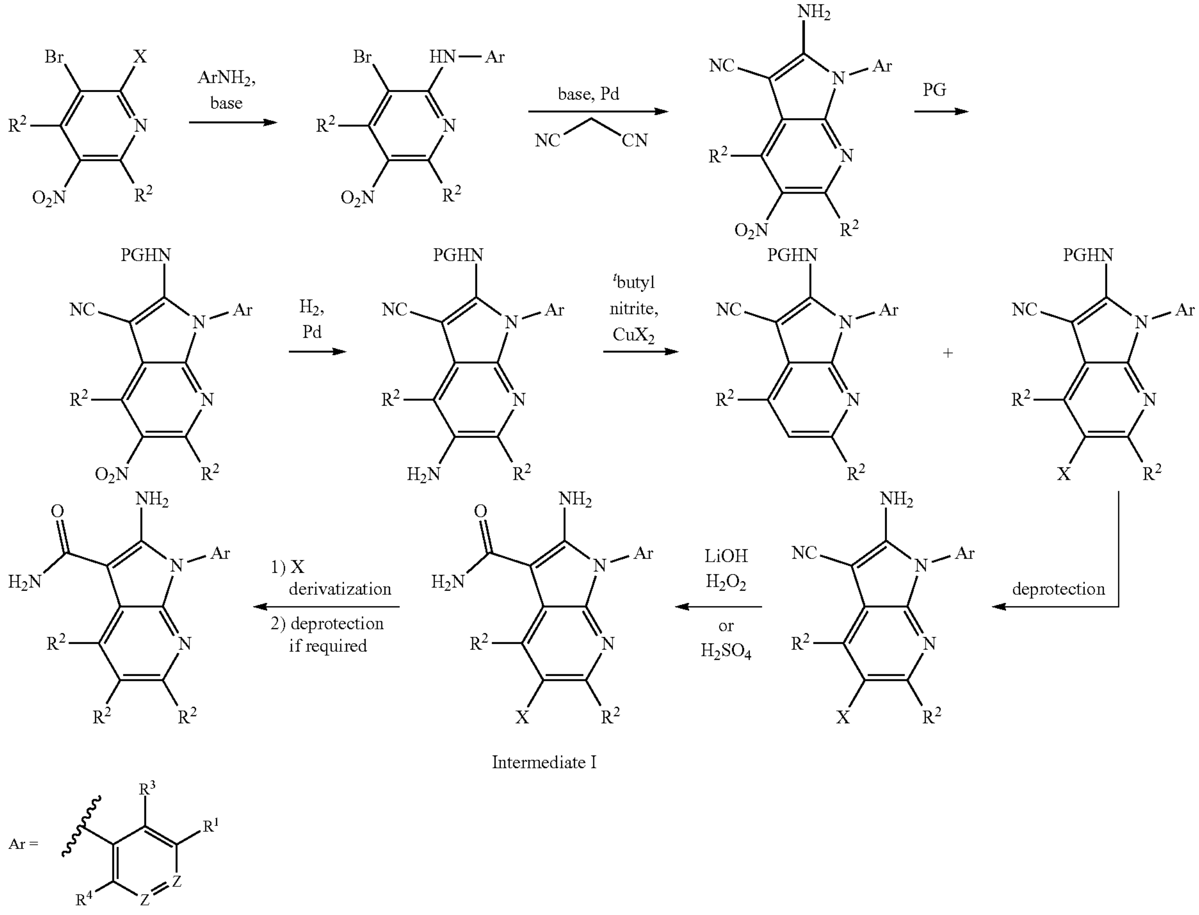

Method E

Compounds of the present invention may be prepared as shown in Scheme E and described herein. One chloro of commercially available 2,3-dichloro-pyrazine can be substituted by malononitrile under SNAr or palladium-mediated conditions. The remaining chloro can be substituted with an aromatic amine under SNAr or palladium-mediated conditions to afford an aminopyrrole. Depending on the nature of the arylamine, a protecting group may be required to be in place prior to this reaction. Hydrolysis of the nitrile can be done under acidic or basic conditions to give compounds of the present invention. In the case where the arylamine group bear a protecting group, a deprotection step(s) may be required using acid, base and/or fluoride to give compounds of the present invention. $R^2$ may each independently be functional groups that can be substituted and/or derivatized at any step in the synthesis including at the end. Depending on the nature of the arylamine, an atropisomeric mixture may be obtained. In such cases it may be necessary to isolate the atropisomer of interest to give compounds of the present invention. Alternatively, an atropisomerically pure intermediate can be isolated and may be derivatized further to give compounds of the present invention.

Scheme E

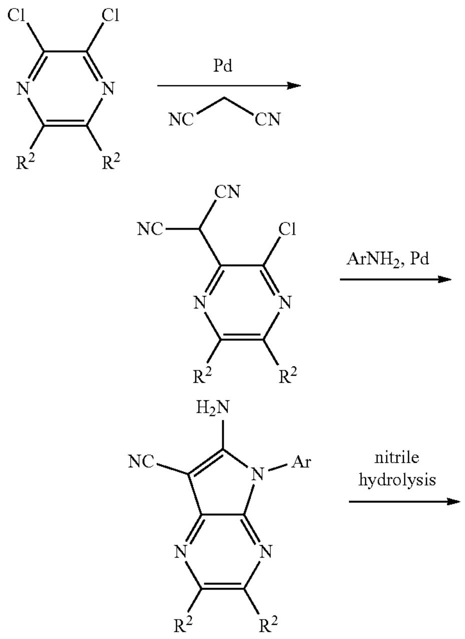

-continued

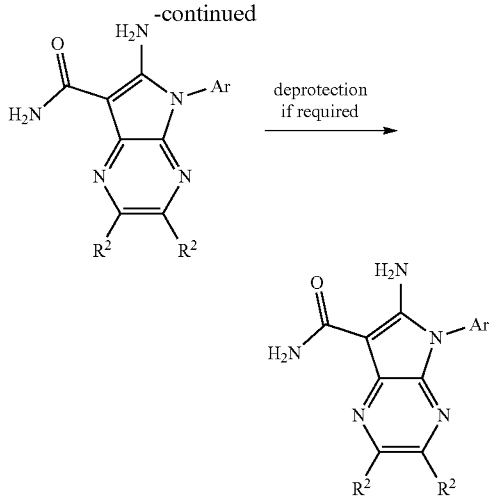

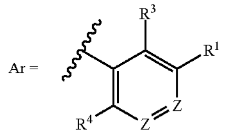

Method F

Compounds of the present invention may be prepared as shown in Scheme F and described herein. One chloro of commercially available 2,3-dichloropyrazine can be substituted by malononitrile under SNAr or palladium-mediated conditions. The other chloro can be substituted with an aromatic amine under SNAr or palladium-mediated conditions to afford an aminopyrrole. Depending on the nature of the arylamine, a protecting group may be required to be in place prior to this reaction. The pyrazine ring can be brominated using a suitable bromination reagent such as NBS. Hydrolysis of the nitrile can be done under acidic or basic conditions and protecting group may be cleaved to give key Intermediate H that may be derivatized in a number of different ways to give compounds of the present invention. For example, a metal-mediated coupling may be used to install a group at $R^2$. Depending on the nature of the $R^2$ group, a protecting group may be required to be in place prior to the bromo derivatization reaction. In the case where the $R^2$ group bears an unsaturation, a hydrogenation reaction may be required to give compound of the present invention. In the case where the arylamine and/or the $R^2$ group bear a protecting group, a deprotection step(s) may be required using acid, base and/or fluoride to give compounds of the present invention. Depending on the nature of the arylamine, an atropisomeric mixture may be obtained. In such cases it may be necessary to isolate the atropisomer of interest to give compounds of the present invention. Alternatively, an atropisomerically pure intermediate can be isolated and may be derivatized further to give compounds of the present invention.

Scheme F

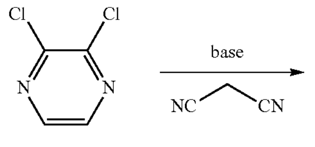

-continued

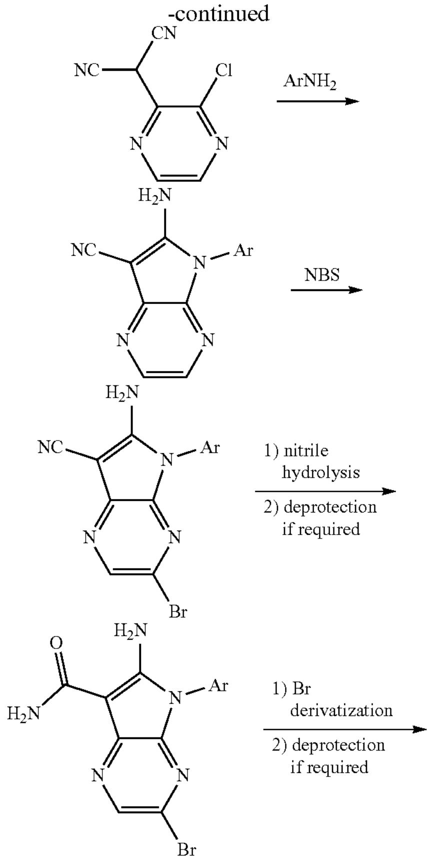

Intermediate H

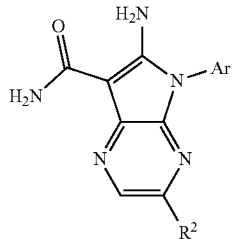

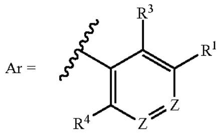

Method G

Compounds of the present invention may be prepared as shown in Scheme G and described herein. The chloro of commercially available 2-chloro-3-bromopyridines can be substituted by malononitrile under SNAr conditions. The bromo can be substituted with an aromatic amine under palladium-mediated conditions to afford an aminopyrrole. Depending on the nature of the arylamine, a protecting group may be required to be in place prior to this reaction. Hydrolysis of the nitrile can be done under acidic or basic conditions to give compounds of the present invention. For an arylamine group bearing a protecting group, a deprotection step(s) may be required using acid, base and/or fluoride to give compounds of the present invention. Depending on the nature of the arylamine, an atropisomeric mixture may be obtained. In such cases it may be necessary to isolate the atropisomer of interest to give compounds of the present invention. Alternatively, an atropisomerically pure intermediate can be isolated and may be derivatized further to give compounds of the present invention.

Scheme G

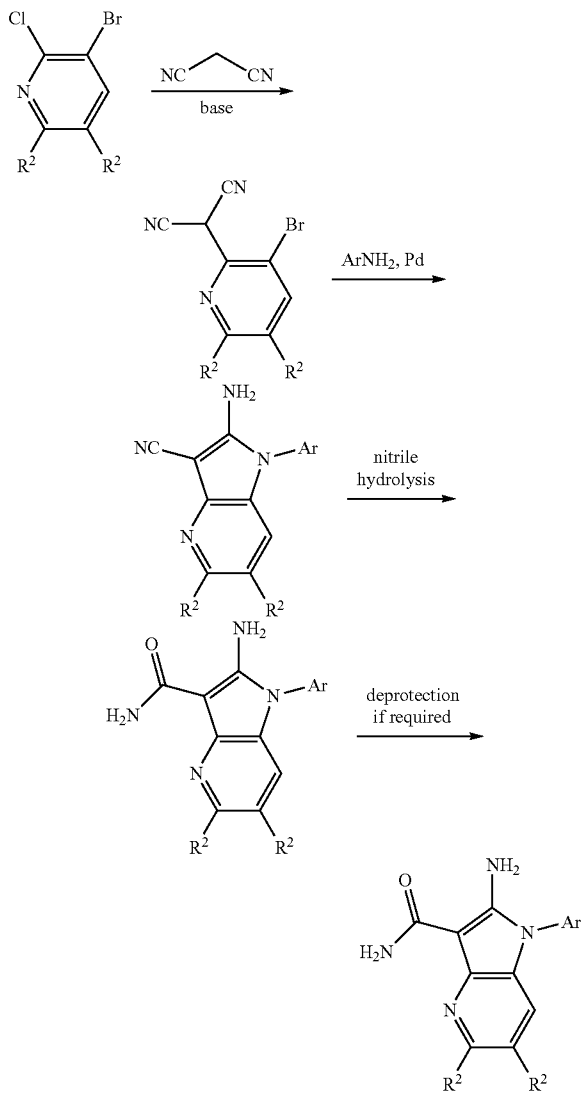

-continued

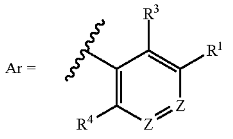

Method H

Compounds of the present invention may be prepared as shown in Scheme H and described herein. Key Intermediate C may be brominated using a suitable bromination reagent such as NBS. The nitrile may be hydrolyzed to the carboxamide upon treatment with an acid with concomitant cleavage of the benzyl group. The resulting hydroxyl may be converted to the triflate. The bromo and the triflate may be derivatized sequentially with different groups or, alternatively the bromo and the triflate may be derivatized simultaneously with the same groups. The bromo and triflate may be derivatized in a number of different ways to give compounds of the present invention. For example, metal-mediated couplings may be used to install a group at $R^2$ sequentially or simultaneously. Depending on the nature of $R^2$, a protecting group may be required to be in place prior to the bromo or triflate derivatization reaction. In the case where the arylamine and/or $R^2$ bear a protecting group, a deprotection step(s) may be required using acid, base and/or fluoride to give compounds of the present invention. Depending on the nature of the arylamine used to prepare intermediate C, an atropisomeric mixture may be obtained. In such cases it may be necessary to isolate the atropisomer of interest to give compounds of the present invention. Alternatively, an atropisomerically pure intermediate can be isolated and may be derivatized further to give compounds of the present invention.

Scheme H

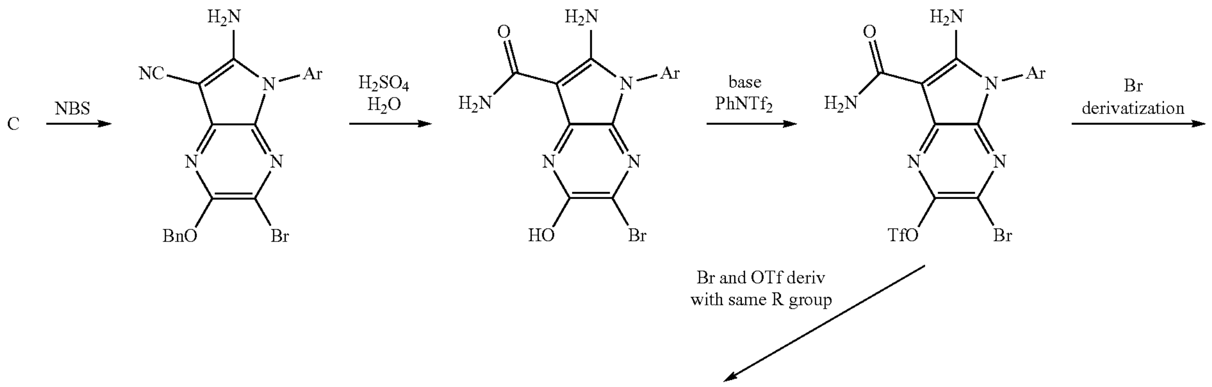

-continued

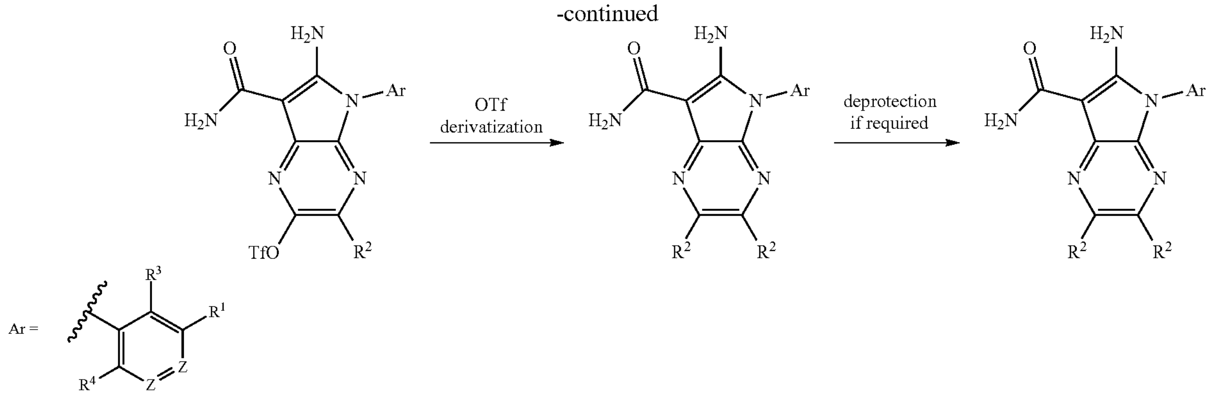

Method I

Compounds of the present invention may be prepared as shown in Scheme I and described herein. The chloro of commercially available 3-bromo-2-chloro-5-(trifluoromethyl)pyridine can be substituted with an aromatic amine under SNAr or palladium-mediated conditions. Depending on the nature of the arylamine, a protecting group may be required to be in place prior to this reaction. The bromo can be substituted with malononitrile under palladium-mediated conditions to afford an aminopyrrole. Hydrolysis of the nitrile can be done under acidic or basic conditions to give compounds of the present invention. In the case where the arylamine group bear a protecting group, a deprotection step(s) may be required using acid, base and/or fluoride to give compounds of the present invention. Depending on the nature of the arylamine, an atropisomeric mixture may be obtained. In such cases it may be necessary to isolate the atropisomer of interest to give compounds of the present invention. Alternatively, an atropisomerically pure intermediate can be isolated and may be derivatized further to give compounds of the present invention.

Scheme I

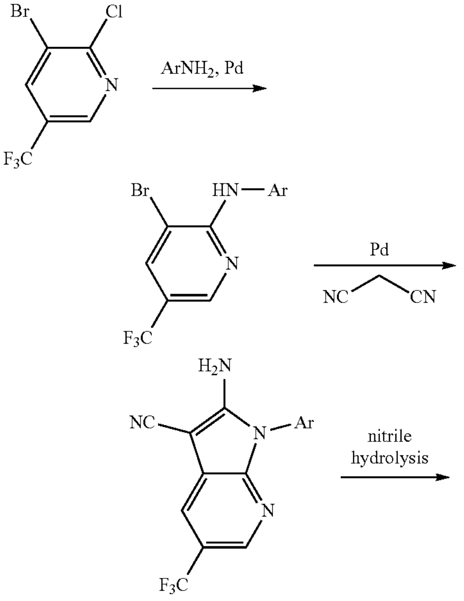

-continued

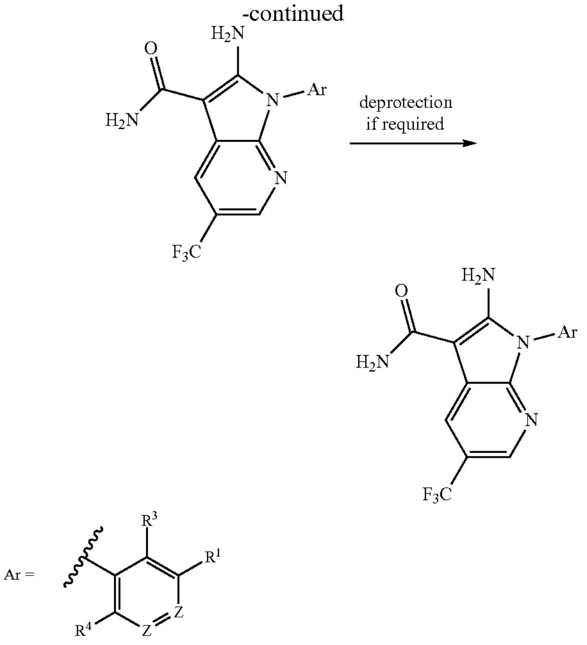

Method J

Compounds of the present invention may be prepared as shown in Scheme J and described herein. Key Intermediate C may be halogenated using a suitable halogenating reagent such as NBS or NIS. The halogen can be derivatized in a number of different ways. For example, a metal-mediated coupling may be used to install a group at $R^2$. The nitrile may be hydrolyzed to the carboxamide upon treatment with an acid with concomitant cleavage of the benzyl group. The resulting hydroxyl may be converted to the triflate. The triflate may be derivatized in a number of different ways to give compounds of the present invention. For example, a metal-mediated coupling may be used to install a group at $R^1$. Depending on the nature of $R^2$, a protecting group may be required to be in place prior to the halogen and/or triflate derivatization reaction. In the case where the arylamine and/or $R^2$ group bear a protecting group, a deprotection step(s) may be required using acid, base and/or fluoride to give compounds of the present invention. Depending on the nature of the arylamine used to prepared intermediate C, an atropisomeric mixture may be obtained. In such cases it may be necessary to isolate the atropisomer of interest to give compounds of the present invention. Alternatively, an atropisomerically pure intermediate can be isolated and may be derivatized further to give compounds of the present invention.

Scheme J

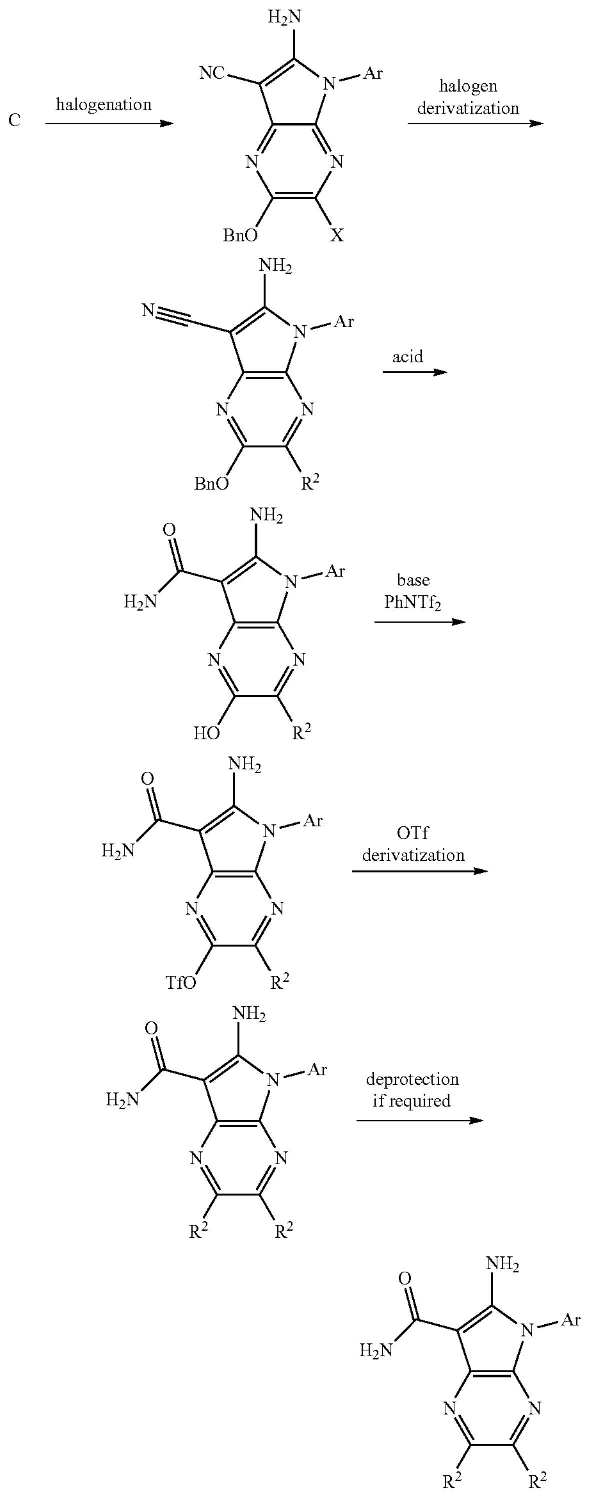

-continued

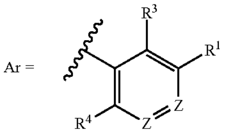

Method K

Compounds of the present invention may be prepared as shown in Scheme K and described herein. The fluoro of a 3-bromo-2-fluoro-pyridine can be substituted with an aromatic amine under SNAr conditions. Depending on the nature of the arylamine, a protecting group may be required to be in place prior to this reaction. The bromo can be substituted with malononitrile under palladium-mediated conditions to afford an aminoazaindole. Hydrolysis of the nitrile can be done under acidic or basic conditions to give compounds of the present invention. In the case where the arylamine or $R^2$ bear a protecting group, a deprotection step(s) may be required using acid, base and/or fluoride to give compounds of the present invention. $R^2$ may be a functional group that can be substituted and/or derivatized at any step in the synthesis including at the end. Depending on the nature of the arylamine, an atropisomeric mixture may be obtained. In such cases it may be necessary to isolate the atropisomer of interest to give compounds of the present invention. Alternatively, an atropisomerically pure intermediate can be isolated and may be derivatized further to give compounds of the present invention.

Scheme K

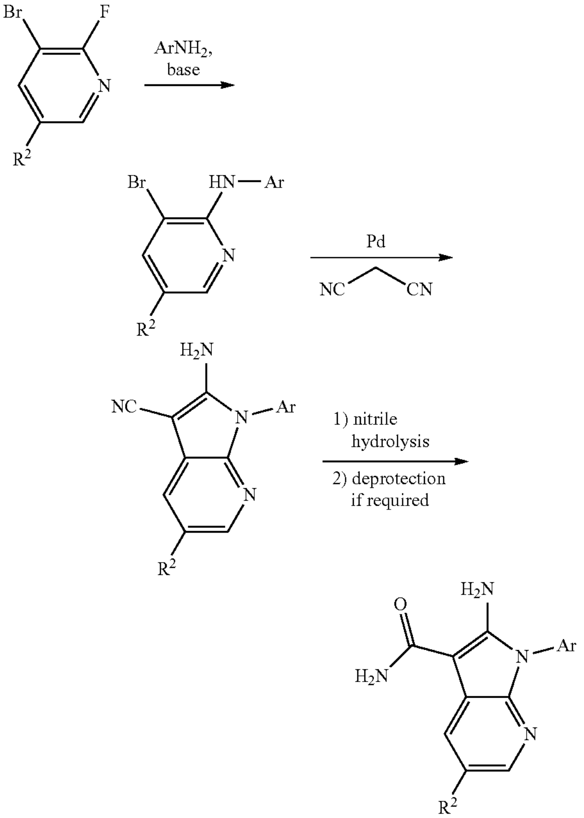

-continued

Ar =
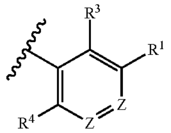

Method L

Compounds of the present invention may be prepared as shown in Scheme L and described herein. The triflate of key Intermediate D may be derivatized in a number of different ways to give compounds of the present invention. For example, a metal-mediated coupling may be used to install a group at $R^1$. the pyrazine may be brominated using a suitable bromination reagent such as NBS. The bromo may be derivatized in a number of different ways to give compounds of the present invention. For example, a metal-mediated coupling may be used to install a group at $R^2$. Depending on the nature of $R^2$, a protecting group may be required to be in place prior to the triflate and/or bromo derivatization reaction. In the case where the arylamine and/or $R^2$ bear a protecting group, a deprotection step(s) may be required using acid, base and/or fluoride to give compounds of the present invention. Depending on the nature of the arylamine used to prepare intermediate D, an atropisomeric mixture may be obtained. In such cases it may be necessary to isolate the atropisomer of interest to give compounds of the present invention. Alternatively, an atropisomerically pure intermediate can be isolated and may be derivatized further to give compounds of the present invention.

Scheme L

D
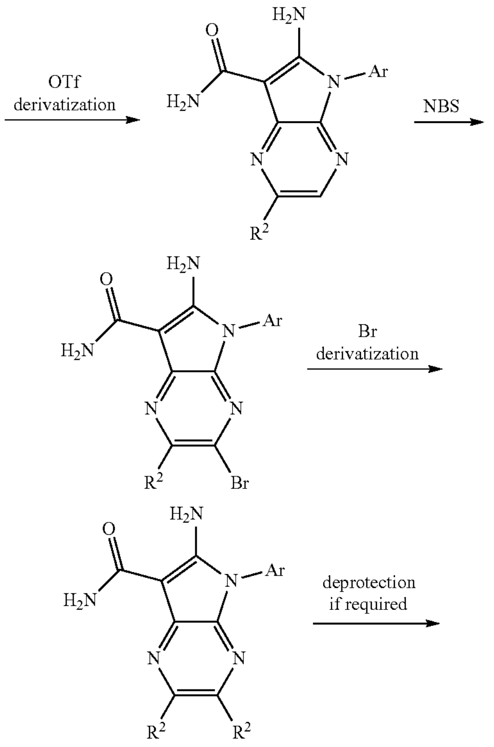

-continued

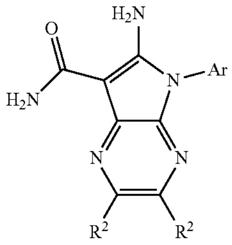

Ar =
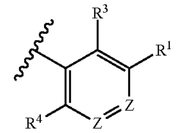

Method M

Compounds of the present invention may be prepared as shown in Scheme M and described herein. The nitrile of key Intermediate C can yield a ketone upon treatment with a Grignard reagent. The benzyl group can be cleaved under acidic conditions. The resulting hydroxyl may be converted to a triflate that can be derivatized in a number of different ways to provide compounds of the present invention. For example, a metal-mediated coupling may be used to install a group at $R^2$. Depending on the nature of $R^2$, a protecting group may be required to be in place prior to the triflate derivatization reaction. In the case where $R^2$ bears an unsaturation, a hydrogenation reaction may be required to give compound of the present invention. In the case where the arylamine and/or $R^2$ bear a protecting group, a deprotection step(s) may be required using acid, base and/or fluoride to give compounds of the present invention. Depending on the nature of the arylamine used to prepare intermediate C, an atropisomeric mixture may be obtained. In such cases it may be necessary to isolate the atropisomer of interest to give compounds of the present invention. Alternatively, an atropisomerically pure intermediate can be isolated and may be derivatized further to give compounds of the present invention.

Scheme M

C
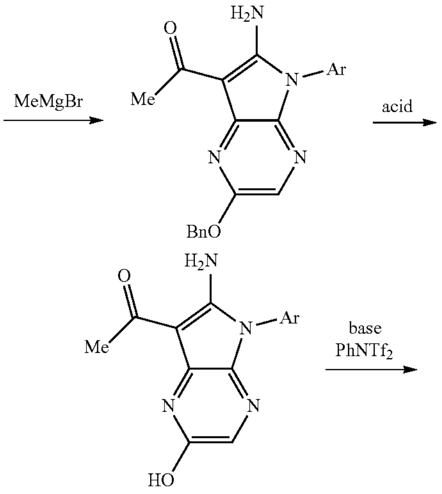

-continued

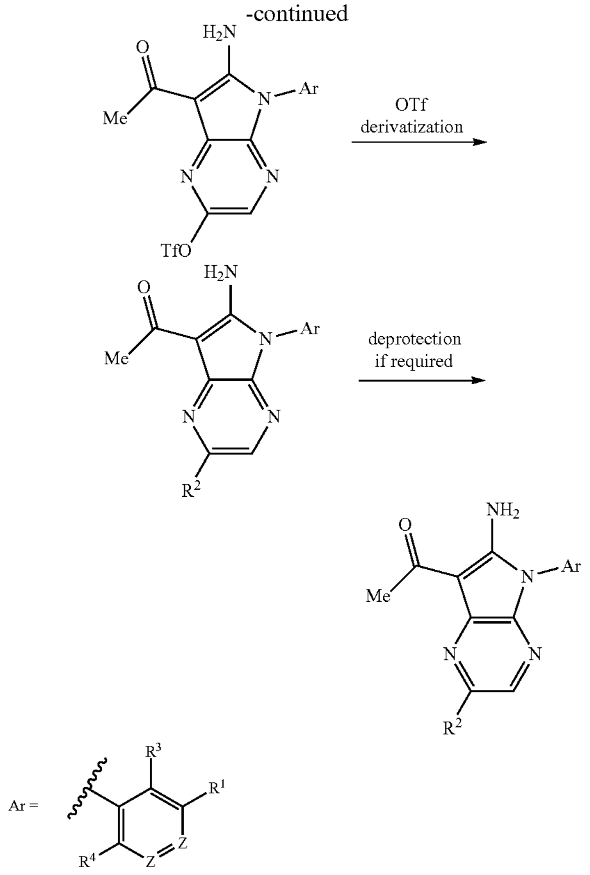

Method N

Compounds of the present invention may be prepared as shown in Scheme N and described herein. The amino of an aminopyrrole described herein can be substituted by a proton under diazotization conditions. The nitrile can be hydrolyzed to the carboxamide under acidic or basic conditions to give compounds of the present invention. Alternatively, the nitrile may be hydrolyzed prior to substitution of the amino group. In the case where the arylamine and/or $R^2$ bear a protecting group, a deprotection step(s) may be required using acid, base and/or fluoride to give compounds of the present invention. $R^2$ may be a functional group that can be substituted and/or derivatized at any step in the synthesis including at the end. Alternatively, the proton can be substituted by chlorine by way of deprotonation and treatment with a suitable chlorine source. In the case where the arylamine and/or $R^2$ bear a protecting group, a deprotection step(s) may be required using acid, base and/or fluoride to give compounds of the present invention. $R^2$ may be a functional group that can be substituted and/or derivatized at any step in the synthesis including at the end. A similar protocol may be applied to the other fused bicycles from the methods to substitute the amino group by a proton or chlorine. Depending on the nature of the N-aryl group, an atropisomeric mixture may be obtained. In such cases it may be necessary to isolate the atropisomer of interest to give compounds of the present invention. Alternatively, an atropisomerically pure intermediate can be isolated and may be derivatized further to give compounds of the present invention.

Scheme N

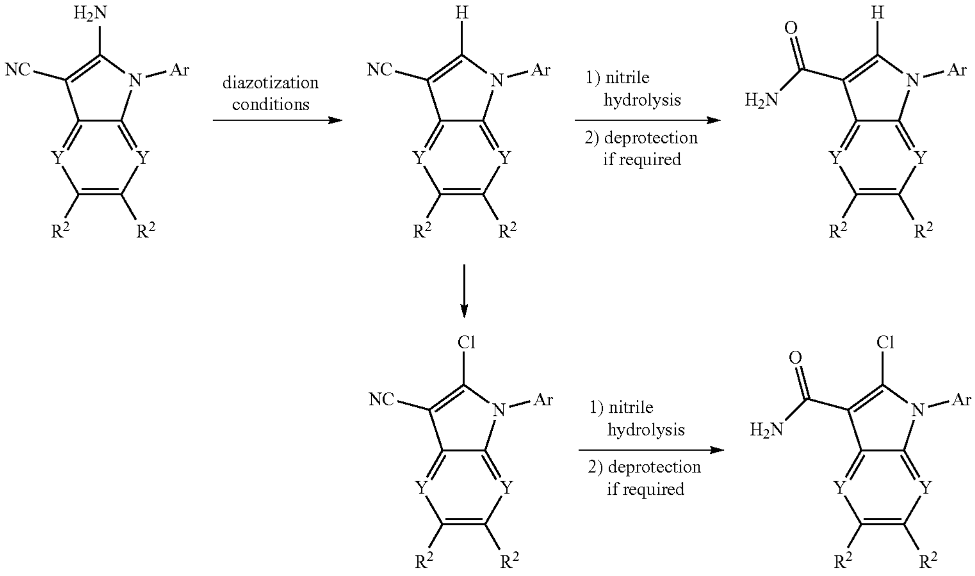

-continued

Ar =
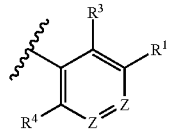

Method O

Compounds of the present invention may be prepared as shown in Scheme O and described herein. The 2-aminopyridine can be converted to the 2-hydroxypyridine which can be converted to the 2-bromopyridine. The 2-bromo can be substituted with an aromatic amine under palladium-mediated conditions. Depending on the nature of the arylamine, a protecting group may be required to be in place prior to this reaction. The 3-bromo can be substituted with malononitrile under palladium-mediated conditions to afford an aminopyrrole. Hydrolysis of the nitrile can be done under acidic or basic conditions to give compounds of the present invention. In the case where the arylamine group bears a protecting group, a deprotection step(s) may be required using acid, base and/or fluoride to give compounds of the present invention. $R^2$ may each independently be functional groups that can be substituted and/or derivatized at any step in the synthesis including at the end. Depending on the nature of the arylamine, an atropisomeric mixture may be obtained. In such cases it may be necessary to perform chiral chromatography to isolate the atropisomer of interest to give compounds of the present invention. Alternatively, an atropisomerically pure intermediate can be isolated and may be derivatized further to give compounds of the present invention.

Scheme O

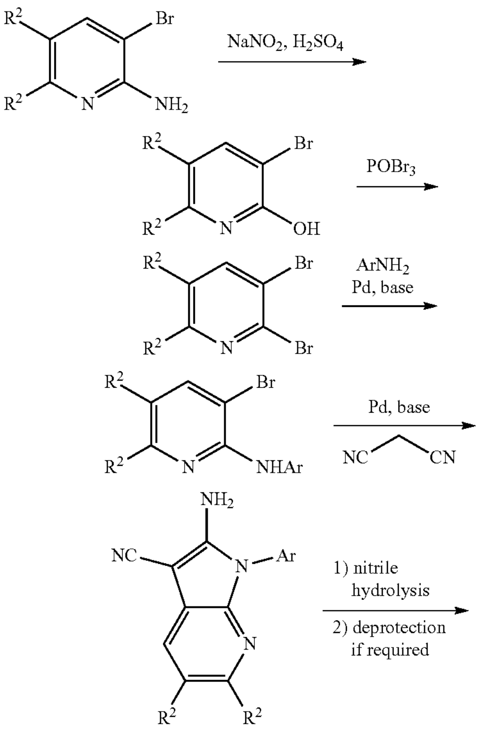

-continued

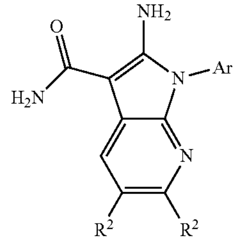

Ar =
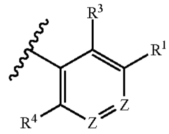

Method P

Compounds of the present invention may be prepared as shown in Scheme P and described herein. A pyridone can be N-alkylated with an electrophile, such as a substituted benzyl bromide under basic conditions and may require a phase transfer catalyst. The resulting N-substituted pyridone can be dehydrated using $POCl_3$ to afford an ortho-chloro pyridinium. The chloro may be substituted by malononitrile which can then be cyclized to provide a substituted indolizine. Hydrolysis of the nitrile can be done under acidic or basic conditions to give compounds of the present invention. In the case where the aryl group and/or $R^2$ bear a protecting group, a deprotection step(s) may be required using acid, base and/or fluoride to give compounds of the present invention. $R^2$ may each independently be functional groups that can be substituted and/or derivatized at any step in the synthesis including at the end. Depending on the nature of the aryl, an atropisomeric mixture may be obtained. In such cases it may be necessary to isolate the atropisomer of interest to give compounds of the present invention. Alternatively, an atropisomerically pure intermediate can be isolated and may be derivatized further to give compounds of the present invention.

Scheme P

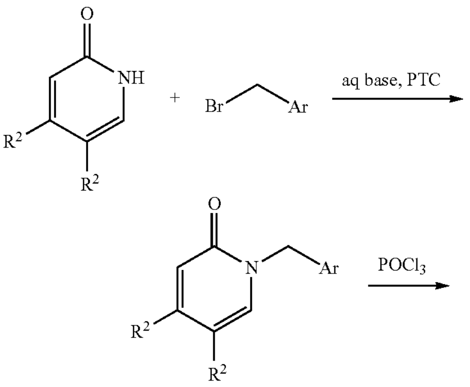

-continued

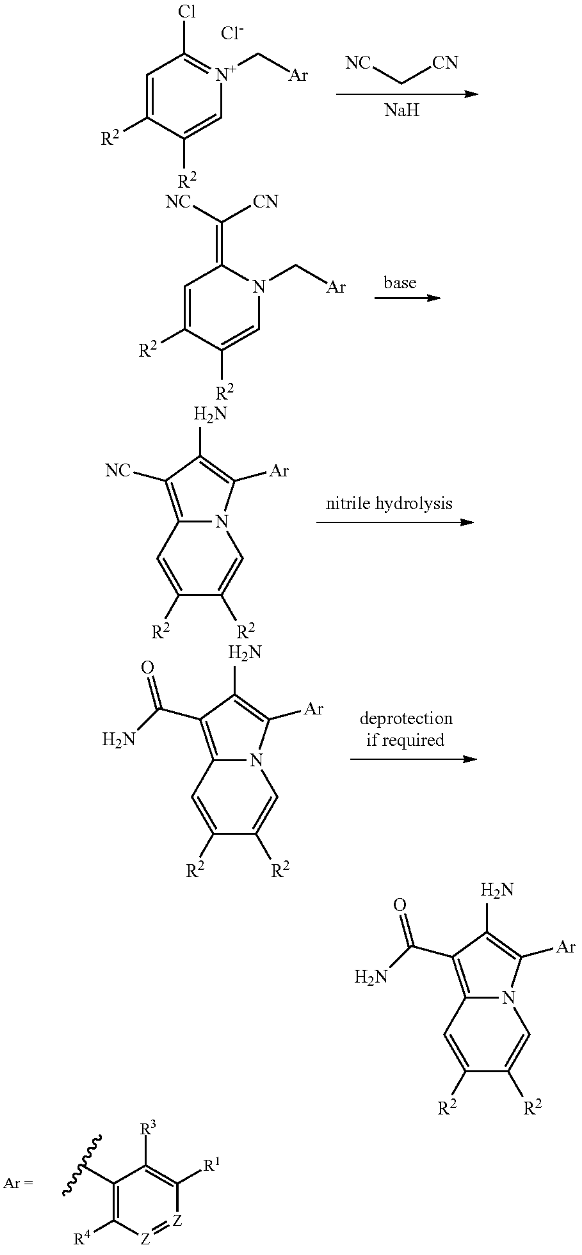

Method Q

Compounds of the present invention may be prepared as shown in Scheme Q and described herein. The chloro of a 2-chloropyrimidine or the fluoro of a 2-fluoro pyridine can be substituted with the anion of 2-arylacetonitrile, providing an intermediate that can be condensed with 2-bromoacetonitrile to provide a substituted pyrrolo[1,2-a]pyrimidine or a substituted indolizine intermediate. Hydrolysis of the nitrile can be done under acidic or basic conditions to give compounds of the present invention. In the case where the aryl group and/or $R^2$ bear a protecting group, a deprotection step(s) may be required using acid, base and/or fluoride to give compounds of the present invention. $R^2$ may each independently be functional groups that can be substituted and/or derivatized at any step in the synthesis including at the end. Depending on the nature of the aryl, an atropisomeric mixture may be obtained. In such cases it may be necessary to isolate the atropisomer of interest to give compounds of the present invention. Alternatively, an atropisomerically pure intermediate can be isolated and may be derivatized further to give compounds of the present invention.

Scheme Q

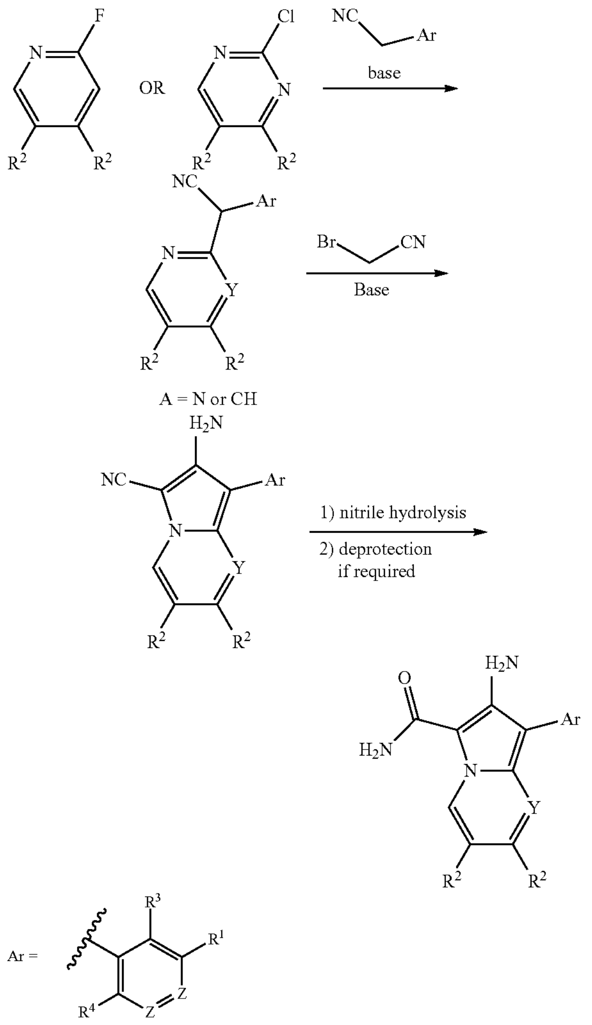

Method R

Compounds of the present invention may be prepared as shown in Scheme R and described herein. 5-bromo-4-chloropyridin-2-amine can be oxidized to the corresponding nitro. The bromide can be substituted with an aromatic amine under palladium-mediated conditions. The remaining chloride can be substituted by the anion of malononitrile under palladium-mediated conditions, affording a substituted 1H-pyrrolo[2,3-c]pyridine. After Boc protection of the amino group, the nitro group can be reduced and the remaining unprotected amino group can be derivatized a number of ways. After Boc removal, hydrolysis of the nitrile can be done under acidic or basic conditions to give compounds of the present invention. Boc removal and nitrile hydrolysis can be concomitant under acidic conditions. In the case where the arylamine and/or $R^2$ group bear a protecting group, a deprotection step(s) may be required using acid, base and/or fluoride to give compounds of the present invention. Alternatively, compounds of the present invention may be prepared as shown in Scheme $R^1$ and described herein. The bromo of a 3-bromo-4-chloropyridine can be substituted with an aromatic amine under palladium-mediated conditions. The remaining chloride can be substituted by the anion of malononitrile under palladium-mediated conditions, affording a substituted 1H-pyrrolo[2,3-c]pyridine. Hydrolysis of the nitrile can be done under acidic or basic conditions to give compounds of the present invention. In the case where the arylamine and/or $R^2$ bear a protecting group, a deprotection step(s) may be required using acid, base and/or fluoride to give compounds of the present invention. Alternatively, compounds of the present invention may be prepared as shown in Scheme $R^2$ and described herein. The iodo of a 1-iodo-2-bromophenyl can be substituted with an aromatic amine under palladium-mediated conditions. The remaining bromide can be substituted by the anion of malononitrile under palladium-mediated conditions, affording a substituted indole. Hydrolysis of the nitrile can be done under acidic or basic conditions to give compounds of the present invention. In the case where the arylamine and/or $R^2$ bear a protecting group, a deprotection step(s) may be required using acid, base and/or fluoride to give compounds of the present invention. In all three cases, $R^2$ may be a functional group that can be substituted and/or derivatized at any step in the synthesis including at the end. Depending on the nature of the aryl, an atropisomeric mixture may be obtained. In such cases it may be necessary to isolate the atropisomer of interest to give compounds of the present invention. Alternatively, an atropisomerically pure intermediate can be isolated and may be derivatized further to give compounds of the present invention.

Scheme R

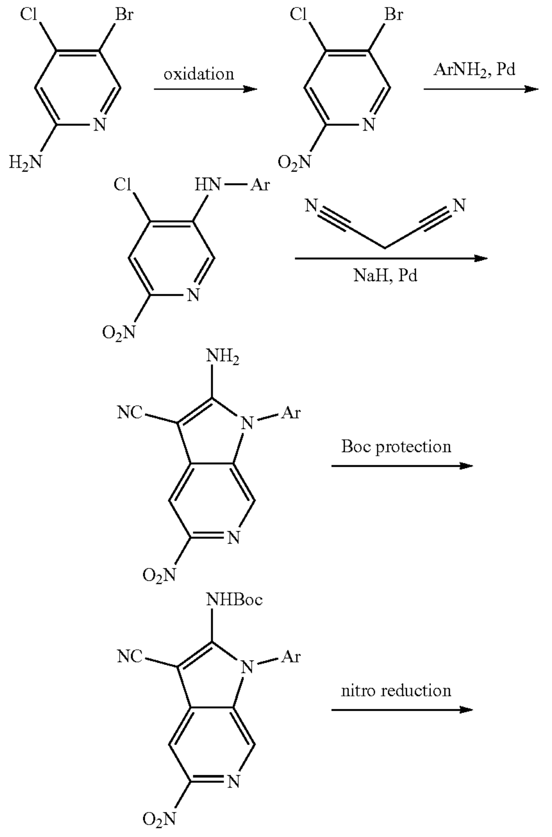

-continued

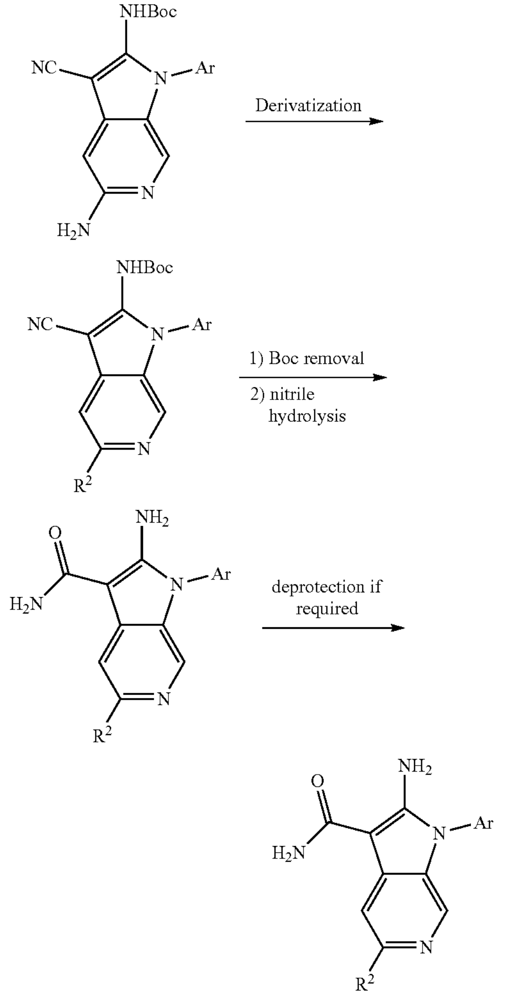

Ar =

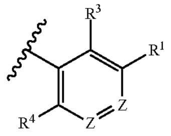

Scheme R1

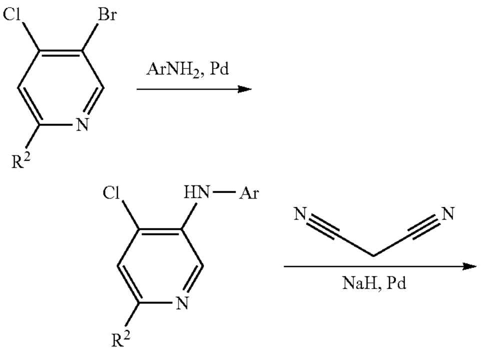

-continued

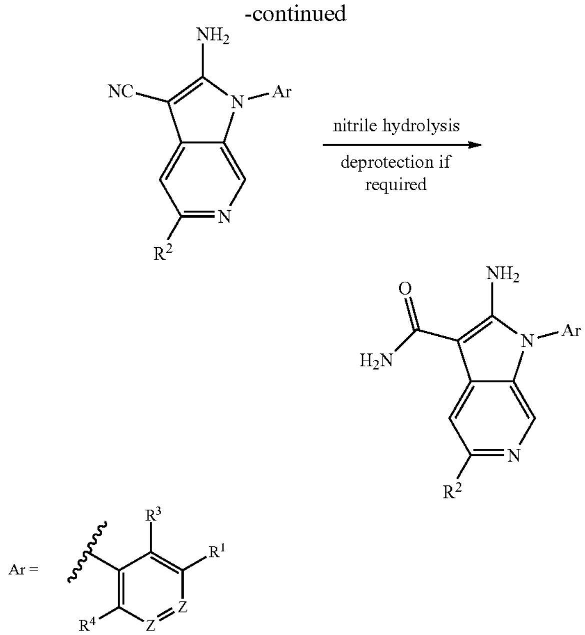

Scheme R2

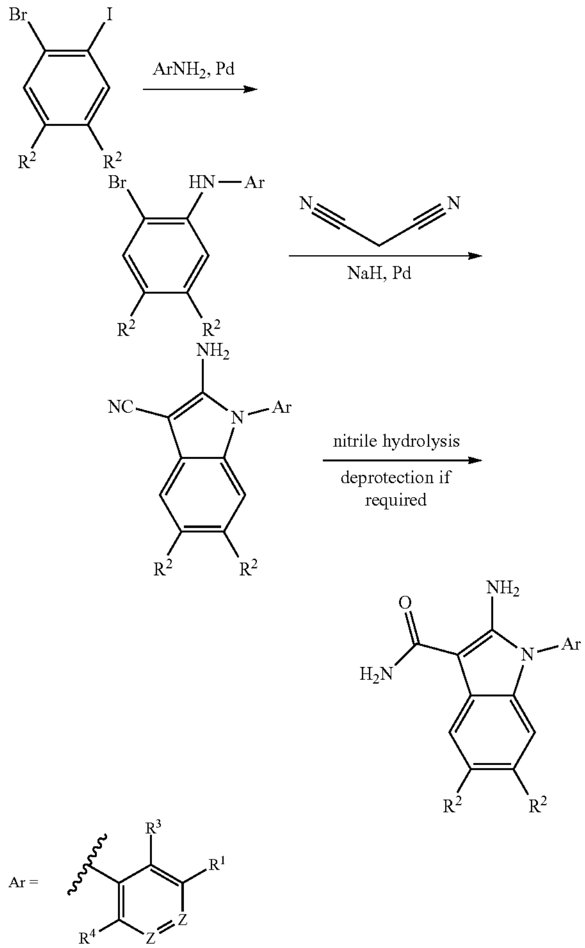

Method S

Compounds of the present invention may be prepared as shown in Scheme S and described herein. Substituted indole or aza-indole may be halogenated using a suitable halogenating reagent such as NBS or NIS. The halogen can be coupled with an arylboronate under palladium mediated conditions. R2 may be a functional group that can be substituted and/or derivatized at any step in the synthesis including at the end. The indolic NH can be converted to the corresponding urea via an activated carbonyl intermediate such as p-nitrophenol carbamate which can be treated with a source of ammonia such as ammonium carbonate. In the case where the arylamine and/or R2 group bear a protecting group, a deprotection step(s) may be required using acid, base and/or fluoride to give compounds of the present invention. Depending on the nature of the arylboronate used, an atropisomeric mixture may be obtained. In such cases it may be necessary to isolate the atropisomer of interest to give compounds of the present invention. Alternatively, an atropisomerically pure intermediate can be isolated and may be derivatized further to give compounds of the present invention.

Scheme S

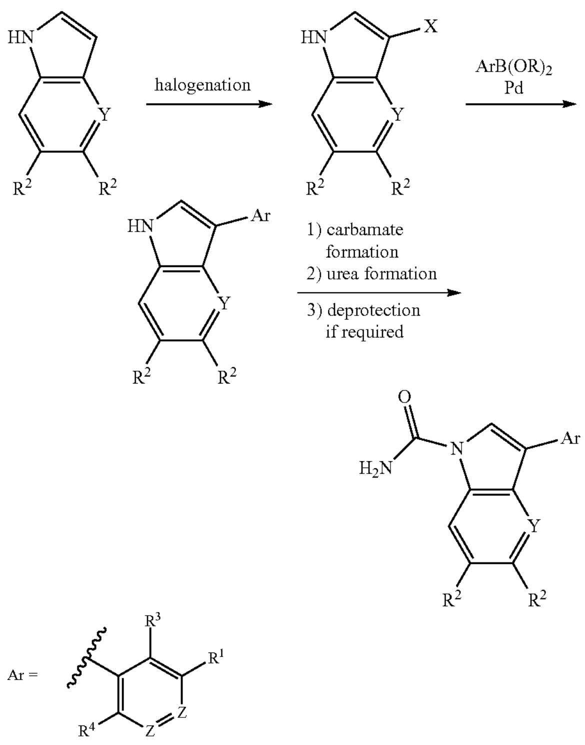

Methods of Treatment

Compounds of the invention may be used for the treatment of a disease or condition (e.g., a cancer overexpressing CCNE1 or having an inactivating mutation in the FBXW7 gene) which depend on the activity of Myt1 (Gene name PKMYT1).

The disease or condition may have the symptom of cell hyperproliferation. For example, the disease or condition may be a cancer (e.g., a cancer overexpressing CCNE1 or having an inactivating mutation in the FBXW7 gene).

Cancers which have a high incidence of CCNE1 overexpression include e.g., uterine cancer, ovarian cancer, breast cancer, stomach cancer, esophageal cancer, lung cancer, and endometrial cancer.

Cancers which have a deficiency in FBXW7 include, e.g., uterine cancer, colorectal cancer, breast cancer, lung cancer, and esophageal cancer.

A compound of the invention may be administered by a route selected from the group consisting of oral, sublingual, buccal, transdermal, intradermal, intramuscular, parenteral, intravenous, intra-arterial, intracranial, subcutaneous, intraorbital, intraventricular, intraspinal, intraperitoneal, intranasal, inhalation, intratumoral, and topical administration.

Pharmaceutical Compositions

The compounds used in the methods described herein are preferably formulated into pharmaceutical compositions for administration to human subjects in a biologically compatible form suitable for administration in vivo. Pharmaceutical compositions typically include a compound as described herein and a pharmaceutically acceptable excipient. Certain pharmaceutical compositions may include one or more additional pharmaceutically active agents described herein.

The compounds described herein can also be used in the form of the free base, in the form of salts, zwitterions, solvates, or as prodrugs, or pharmaceutical compositions thereof. All forms are within the scope of the invention. The compounds, salts, zwitterions, solvates, prodrugs, or pharmaceutical compositions thereof, may be administered to a patient in a variety of forms depending on the selected route of administration, as will be understood by those skilled in the art. The compounds used in the methods described herein may be administered, for example, by oral, parenteral, buccal, sublingual, nasal, rectal, patch, pump, or transdermal administration, and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

For human use, a compound of the invention can be administered alone or in admixture with a pharmaceutical carrier selected with regard to the intended route of administration and standard pharmaceutical practice. Pharmaceutical compositions for use in accordance with the present invention thus can be formulated in a conventional manner using one or more physiologically acceptable carriers including excipients and auxiliaries that facilitate processing of a compound of the invention into preparations which can be used pharmaceutically.

This invention also includes pharmaceutical compositions which can contain one or more pharmaceutically acceptable carriers. In making the pharmaceutical compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of tablets, powders, lozenges, sachets, cachets, elixirs, suspensions, emulsions, solutions, syrups, and soft and hard gelatin capsules. As is known in the art, the type of diluent can vary depending upon the intended route of administration. The resulting compositions can include additional agents, e.g., preservatives.

The excipient or carrier is selected on the basis of the mode and route of administration. Suitable pharmaceutical carriers, as well as pharmaceutical necessities for use in pharmaceutical formulations, are described in Remington: The Science and Practice of Pharmacy, 21st Ed., Gennaro, Ed., Lippincott Williams & Wilkins (2005), a well-known reference text in this field, and in the USP/NF (United States Pharmacopeia and the National Formulary). Examples of suitable excipients are lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents, e.g., talc, magnesium stearate, and mineral oil; wetting agents; emulsifying and suspending agents; preserving agents, e.g., methyl- and propylhydroxy-benzoates; sweetening agents; and flavoring agents. Other exemplary excipients are described in Handbook of Pharmaceutical Excipients, 6th Edition, Rowe et al., Eds., Pharmaceutical Press (2009).

These pharmaceutical compositions can be manufactured in a conventional manner, e.g., by conventional mixing, dissolving, granulating, dragee-making, levigating, emulsifying, encapsulating, entrapping, or lyophilizing processes. Methods well known in the art for making formulations are found, for example, in Remington: The Science and Practice of Pharmacy, 21st Ed., Gennaro, Ed., Lippincott Williams & Wilkins (2005), and Encyclopedia of Pharmaceutical Technology, eds. J. Swarbrick and J. C. Boylan, 1988-1999, Marcel Dekker, New York. Proper formulation is dependent upon the route of administration chosen. The formulation and preparation of such compositions is well-known to those skilled in the art of pharmaceutical formulation. In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

Dosages

The dosage of the compound used in the methods described herein, or pharmaceutically acceptable salts or prodrugs thereof, or pharmaceutical compositions thereof, can vary depending on many factors, e.g., the pharmacodynamic properties of the compound; the mode of administration; the age, health, and weight of the recipient; the nature and extent of the symptoms; the frequency of the treatment, and the type of concurrent treatment, if any; and the clearance rate of the compound in the animal to be treated. One of skill in the art can determine the appropriate dosage based on the above factors. The compounds used in the methods described herein may be administered initially in a suitable dosage that may be adjusted as required, depending on the clinical response. In general, a suitable daily dose of a compound of the invention will be that amount of the compound that is the lowest dose effective to produce a therapeutic effect. Such an effective dose will generally depend upon the factors described above.

A compound of the invention may be administered to the patient in a single dose or in multiple doses. When multiple doses are administered, the doses may be separated from one another by, for example, 1-24 hours, 1-7 days, 1-4 weeks, or 1-12 months. The compound may be administered according to a schedule or the compound may be administered without a predetermined schedule. An active compound may be administered, for example, 1, 2, 3, 4, 5, 6, 7, 8, 9, 10, 11, or 12 times per day, every 2nd, 3rd, 4th, 5th, or 6th day, 1, 2, 3, 4, 5, 6, or 7 times per week, 1, 2, 3, 4, 5, or 6 times per month, or 1, 2, 3, 4, 5, 6, 7, 8, 9, 10, 11, or 12 times per year. It is to be understood that, for any particular subject, specific dosage regimes should be adjusted over time according to the individual need and the professional judgment of the person administering or supervising the administration of the compositions.

While the attending physician ultimately will decide the appropriate amount and dosage regimen, an effective amount of a compound of the invention may be, for example, a total daily dosage of, e.g., between 0.05 mg and 3000 mg of any of the compounds described herein. Alternatively, the dosage amount can be calculated using the body weight of the patient. Such dose ranges may include, for example, between 10-1000 mg (e.g., 50-800 mg). In some embodiments, 50, 100, 150, 200, 250, 300, 350, 400, 450, 500, 550, 600, 650, 700, 750, 800, 850, 900, 950, or 1000 mg of the compound is administered.

In the methods of the invention, the time period during which multiple doses of a compound of the invention are administered to a patient can vary. For example, in some embodiments, doses of the compounds of the invention are administered to a patient over a time period that is 1-7 days; 1-12 weeks; or 1-3 months. In some embodiments, the compounds are administered to the patient over a time period that is, for example, 4-11 months or 1-30 years. In some embodiments, the compounds are administered to a patient at the onset of symptoms. In any of these embodiments, the amount of compound that is administered may vary during the time period of administration. When a compound is administered daily, administration may occur, for example, 1, 2, 3, 4, 5, 6, 7, 8, 9, 10, 11, or 12 times per day.

Formulations

A compound identified as capable of treating any of the conditions described herein, using any of the methods described herein, may be administered to patients or animals with a pharmaceutically acceptable diluent, carrier, or excipient, in unit dosage form. The chemical compounds for use in such therapies may be produced and isolated by any standard technique known to those in the field of medicinal chemistry. Conventional pharmaceutical practice may be employed to provide suitable formulations or compositions to administer the identified compound to patients suffering from a disease or condition. Administration may begin before the patient is symptomatic.

Exemplary routes of administration of the compounds (e.g., a compound of the invention), or pharmaceutical compositions thereof, used in the present invention include oral, sublingual, buccal, transdermal, intradermal, intramuscular, parenteral, intravenous, intra-arterial, intracranial, subcutaneous, intraorbital, intraventricular, intraspinal, intraperitoneal, intranasal, inhalation, and topical administration. The compounds desirably are administered with a pharmaceutically acceptable carrier. Pharmaceutical formulations of the compounds described herein formulated for treatment of the disorders described herein are also part of the present invention.

Formulations for Oral Administration

The pharmaceutical compositions contemplated by the invention include those formulated for oral administration ("oral dosage forms"). Oral dosage forms can be, for example, in the form of tablets, capsules, a liquid solution or suspension, a powder, or liquid or solid crystals, which contain the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

Formulations for oral administration may also be presented as chewable tablets, as hard gelatin capsules where the active ingredient is mixed with an inert solid diluent (e.g., potato starch, lactose, microcrystalline cellulose, calcium carbonate, calcium phosphate or kaolin), or as soft gelatin capsules where the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Controlled release compositions for oral use may be constructed to release the active drug by controlling the dissolution and/or the diffusion of the active drug substance. Any of a number of strategies can be pursued in order to obtain controlled release and the targeted plasma concentration versus time profile. In one example, controlled release is obtained by appropriate selection of various formulation parameters and ingredients, including, e.g., various types of controlled release compositions and coatings. Examples include single or multiple unit tablet or capsule compositions, oil solutions, suspensions, emulsions, microcapsules, microspheres, nanoparticles, patches, and liposomes. In some embodiments, compositions include biodegradable, pH, and/or temperature-sensitive polymer coatings.

Dissolution or diffusion-controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

The liquid forms in which the compounds and compositions of the present invention can be incorporated for administration orally include aqueous solutions, suitably flavored syrups, aqueous or oil suspensions, and flavored emulsions with edible oils, e.g., cottonseed oil, sesame oil, coconut oil, or peanut oil, as well as elixirs and similar pharmaceutical vehicles.

Formulations for Parenteral Administration

The compounds described herein for use in the methods of the invention can be administered in a pharmaceutically acceptable parenteral (e.g., intravenous or intramuscular) formulation as described herein. The pharmaceutical formulation may also be administered parenterally (intravenous, intramuscular, subcutaneous or the like) in dosage forms or formulations containing conventional, non-toxic pharmaceutically acceptable carriers and adjuvants. In particular, formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. For example, to prepare such a composition, the compounds of the invention may be dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution and isotonic sodium chloride solution. The aqueous formulation may also contain one or more preservatives, for example, methyl, ethyl, or n-propyl p-hydroxybenzoate. Additional information regarding parenteral formulations can be found, for example, in the United States Pharmacopeia-National Formulary (USP—NF), herein incorporated by reference.

The parenteral formulation can be any of the five general types of preparations identified by the USP—NF as suitable for parenteral administration:

(1) Drug Injection: a liquid preparation that is a drug substance (e.g., a compound of the invention), or a solution thereof;

(2) Drug for Injection: the drug substance (e.g., a compound of the invention) as a dry solid that will be combined with the appropriate sterile vehicle for parenteral administration as a drug injection;

(3) Drug Injectable Emulsion: a liquid preparation of the drug substance (e.g., a compound of the invention) that is dissolved or dispersed in a suitable emulsion medium;

(4) Drug Injectable Suspension: a liquid preparation of the drug substance (e.g., a compound of the invention) suspended in a suitable liquid medium; and (5) Drug for Injectable Suspension: the drug substance (e.g., a compound of the invention) as a dry solid that will be combined with the appropriate sterile vehicle for parenteral administration as a drug injectable suspension.

Formulations for parenteral administration include solutions of the compound prepared in water suitably mixed with a surfactant, e.g., hydroxypropylcellulose. Dispersions can also be prepared in glycerol, liquid polyethylene glycols, DMSO and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in Remington: The Science and Practice of Pharmacy, 21st Ed., Gennaro, Ed., Lippincott Williams & Wilkins (2005) and in The United States Pharmacopeia: The National Formulary (USP 36 NF31), published in 2013.

Formulations for parenteral administration may, for example, contain excipients, sterile water, or saline, polyalkylene glycols, e.g., polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The parenteral formulation can be formulated for prompt release or for sustained/extended release of the compound. Exemplary formulations for parenteral release of the compound include: aqueous solutions, powders for reconstitution, cosolvent solutions, oil/water emulsions, suspensions, oil-based solutions, liposomes, microspheres, and polymeric gels.

Combinations

Compounds of the present invention may be administered to a subject in combination with one or more additional agents, e.g.:

(a) a cytotoxic agent;
(b) an antimetabolite;
(c) an alkylating agent;
(d) an anthracycline;
(e) an antibiotic;
(f) an anti-mitotic agent;
(g) a hormone therapy;
(h) a signal transduction inhibitor;
(i) a gene expression modulator;
(j) an apoptosis inducer;
(k) an angiogenesis inhibitor;
(l) an immunotherapy agent;
(m) a DNA damage repair inhibitor;
or
a combination thereof.

The cytotoxic agent may be, e.g., actinomycin-D, alemtuzumab, alitretinoin, allopurinol, altretamine, amifostine, amphotericin, amsacrine, arsenic trioxide, asparaginase, azacitidine, azathioprine, Bacille Calmette-Guérin (BCG), bendamustine, bexarotene, bevacuzimab, bleomycin, bortezomib, busulphan, capecitabine, carboplatin, carfilzomib, carmustine, cetuximab, cisplatin, chlorambucil, cladribine, clofarabine, colchicine, crisantaspase, cyclophosphamide, cyclosporine, cytarabine, cytochalasin B, dacarbazine, dactinomycin, darbepoetin alfa, dasatinib, daunorubicin, 1-dehydrotestosterone, denileukin, dexamethasone, dexrazoxane, dihydroxy anthracin dione, disulfiram, docetaxel, doxorubicin, emetine, epirubicin, erlotinib, epigallocatechin gallate, epoetin alfa, estramustine, ethidium bromide, etoposide, everolimus, filgrastim, finasunate, floxuridine, fludarabine, flurouracil (5-FU), fulvestrant, ganciclovir, geldanamycin, gemcitabine, glucocorticoids, gramicidin D, histrelin acetate, hydroxyurea, ibritumomab, idarubicin, ifosfamide, imatinib, irinotecan, interferons, interferon alfa-2a, interferon alfa-2b, ixabepilone, lactate dehydrogenase A (LDH-A), lenalidomide, letrozole, leucovorin, levamisole, lidocaine, lomustine, mechlorethamine, melphalan, 6-mercaptopurine, mesna, methotrexate, methoxsalen, metoprine, metronidazole, mithramycin, mitomycin-C, mitoxantrone, nandrolone, nelarabine, nilotinib, nofetumomab, oprelvekin, oxaliplatin, paclitaxel, pemetrexed, pentostatin, palifermin, pamidronate, pegademase, pegaspargase, pegfilgrastim, pemetrexed disodium, plicamycin, porfimer sodium, procaine, procarbazine, propranolol, puromycin, quinacrine, radicicol, radioactive isotopes, raltitrexed, rapamycin, rasburicase, salinosporamide A, sargramostim, sunitinib, temozolomide, teniposide, tetracaine, 6-thioguanine, thiotepa, topotecan, toremifene, trastuzumab, treosulfan, tretinoin, valrubicin, vinblastine, vincristine, vindesine, vinorelbine, zoledronate, or a combination thereof.

The antimetabolites may be, e.g., methotrexate, 6-mercaptopurine, 6-thioguanine, cytarabine, 5-fluorouracil decarbazine, cladribine, pemetrexed, gemcitabine, capecitabine, hydroxyurea, mercaptopurine, fludarabine, pralatrexate, clofarabine, cytarabine, decitabine, floxuridine, nelarabine, trimetrexate, thioguanine, pentostatin, or a combination thereof.

The alkylating agent may be, e.g., mechlorethamine, thiotepa, chlorambucil, melphalan, carmustine (BSNU), lomustine (CCNU), cyclothosphamide, busulfan, dibromomannitol, streptozotocin, mitomycin C, cis-dichlorodiamine platinum (II) (DDP) cisplatin, altretamine, cyclophosphamide, ifosfamide, hexamethylmelamine, altretamine, procarbazine, dacarbazine, temozolomide, streptozocin, carboplatin, cisplatin, oxaliplatin, uramustine, bendamustine, trabectedin, semustine, or a combination thereof.

The anthracycline may be, e.g., daunorubicin, doxorubicin, aclarubicin, aldoxorubicin, amrubicin, annamycin, carubicin, epirubicin, idarubicin, mitoxantrone, valrubicin, or a combination thereof.

The antibiotic may be, e.g., dactinomycin, bleomycin, mithramycin, anthramycin (AMC), ampicillin, bacampicillin, carbenicillin, cloxacillin, dicloxacillin, flucloxacillin, mezlocillin, nafcillin, oxacillin, piperacillin, pivampicillin, pivmecillinam, ticarcillin, aztreonam, imipenem, doripenem, ertapenem, meropenem, cephalosporins, clarithromycin, dirithromycin, roxithromycin, telithromycin, lincomycin, pristinamycin, quinupristin, amikacin, gentamicin, kanamycin, neomycin, netilmicin, paromomycin, tobramycin, streptomycin, sulfamethizole, sulfamethoxazole, sulfisoxazole, demeclocycline, minocycline, oxytetracycline, tetracycline, penicillin, amoxicillin, cephalexin, erythromycin, clarithromycin, azithromycin, ciprofloxacin, levofloxacin, ofloxacin, doxycycline, clindamycin, metronidazole, tigecycline, chloramphenicol, metronidazole, tinidazole, nitrofurantoin, vancomycin, teicoplanin, telavancin, linezolid, cycloserine, rifamycins, polymyxin B, bacitracin, viomycin, capreomycin, quinolones, daunorubicin, doxorubicin, 4'-deoxydoxorubicin, epirubicin, idarubicin, plicamycin, mitomycin-c, mitoxantrone, or a combination thereof.

The anti-mitotic agent may be, e.g., vincristine, vinblastine, vinorelbine, docetaxel, estramustine, ixabepilone, paclitaxel, maytansinoid, a dolastatin, a cryptophycin, or a combination thereof.

The signal transduction inhibitor may be, e.g., imatinib, trastuzumab, erlotinib, sorafenib, sunitinib, temsirolimus, vemurafenib, lapatinib, bortezomib, cetuximab panitumumab, matuzumab, gefitinib, STI 571, rapamycin, flavopiridol, imatinib mesylate, vatalanib, semaxinib, motesanib, axitinib, afatinib, bosutinib, crizotinib, cabozantinib, dasatinib, entrectinib, pazopanib, lapatinib, vandetanib, or a combination thereof.

The gene expression modulator may be, e.g., a siRNA, a shRNA, an antisense oligonucleotide, an HDAC inhibitor, or a combination thereof. An HDAC inhibitor may be, e.g., trichostatin A, trapoxin B, valproic acid, vorinostat, belinostat, LAQ824, panobinostat, entinostat, tacedinaline, mocetionstat, givinostat, resminostat, abexinostat, quisinostat, rocilinostat, practinostat, CHR-3996, butyric acid, phenylbutyric acid, 4SC202, romidepsin, sirtinol, cambinol, EX-527, nicotinamide, or a combination thereof. An antisense oligonucleotide may be, e.g., custirsen, apatorsen, AZD9150, trabadersen, EZN-2968, LErafAON-ETU, or a combination thereof. An siRNA may be, e.g., ALN-VSP, CALAA-01, Atu-027, SPC2996, or a combination thereof.

The hormone therapy may be, e.g., a luteinizing hormone-releasing hormone (LHRH) antagonist. The hormone therapy may be, e.g., firmagon, leuproline, goserelin, buserelin, flutamide, bicalutadmide, ketoconazole, aminoglutethimide, prednisone, hydroxyl-progesterone caproate, medroxy-progesterone acetate, megestrol acetate, diethylstil-bestrol, ethinyl estradiol, tamoxifen, testosterone propionate, fluoxymesterone, flutamide, raloxifene, droloxifene, iodoxyfene, 4-hydroxytamoxifen, trioxifene, keoxifene, LY117018, onapristone, toremifine citrate, megestrol acetate, exemestane, fadrozole, vorozole, letrozole, anastrozole, nilutamide, tripterelin, histerelin, arbiraterone, medroxyprogesterone acetate, diethylstilbestrol, premarin, fluoxymesterone, tretinoin, fenretinide, troxacitabine, or a combination thereof.

The apoptosis inducers may be, e.g., a recombinant human TNF-related apoptosis-inducing ligand (TRAIL), camptothecin, bortezomib, etoposide, tamoxifen, or a combination thereof.

The angiogenesis inhibitors may be, e.g., sorafenib, sunitinib, pazopanib, everolimus or a combination thereof.

The immunotherapy agent may be, e.g., a monoclonal antibody, cancer vaccine (e.g., a dendritic cell (DC) vaccine), oncolytic virus, cytokine, adoptive T cell therapy, Bacille Calmette-Guérin (BCG), GM-CSF, thalidomide, lenalidomide, pomalidomide, imiquimod, or a combination thereof. The monoclonal antibody may be, e.g., anti-CTLA4, anti-PD1, anti-PD-L1, anti-LAG3, anti-KIR, or a combination thereof. The monoclonal antibody may be, e.g., alemtuzumab, trastuzumab, ibritumomab tiuxetan, brentuximab vedotin, trastuzumab, ado-trastuzumab emtansine, blinatumomab, bevacizumab, cetuximab, pertuzumab, panitumumab, ramucirumab, obinutuzumab, ofatumumab, rituximab, pertuzumab, tositumomab, gemtuzumab ozogamicin, tositumomab, or a combination thereof. The cancer vaccine may be, e.g., Sipuleucel-T, BioVaxID, NeuVax, DCVax, SuVaxM, CIMAvax®, Provenge,®, hsp110 chaperone complex vaccine, CDX-1401, MIS416, CDX-110, GVAX Pancreas, HyperAcute™ Pancreas, GTOP-99 (MyVax®), or Imprime PGG®. The oncolytic virus may be, e.g., talimogene laherparepvec. The cytokine may be, e.g., IL-2, IFNα, or a combination thereof. The adoptive T cell therapy may be, e.g., tisagenlecleucel, axicabtagene ciloleucel, or a combination thereof.

The DNA damage repair inhibitor may be, e.g., a PARP inhibitor, a cell checkpoint kinase inhibitor, or a combination thereof. The PARP inhibitor may be, e.g., olaparib, rucaparib, veliparib (ABT-888), niraparib (ZL-2306), iniparib (BSI-201), talazoparib (BMN 673), 2X-121, CEP-9722, KU-0059436 (AZD2281), PF-01367338 or a combination thereof. The cell checkpoint kinase inhibitor may be, e.g., MK-1775 or AZD1775, AZD7762, LY2606368, PF-0477736, AZD0156, GDC-0575, ARRY-575, CCT245737, PNT-737 or a combination thereof.

EXAMPLES

The following examples were meant to illustrate the invention. They were not meant to limit the invention in any way.

Reactions were typically performed at room temperature (rt) under a nitrogen atmosphere using dry solvents (Sure/Seal™) if not described otherwise in the Examples below. Reactions were monitored by TLC or by injection of a small aliquot on a Waters Acquity-H UPLC® Class system using an Acquity® UPLC HSS C18 2.1×30 mm column eluting with a gradient (1.86 min) of acetonitrile (15% to 98%) in water (both containing 0.1% formic acid). Purifications by preparative HPLC were performed on a Teledyne Isco Combi Flash®EZ Prep system using either Phenomenex Gemini® 5 μm NX—C18 110 Å 150×21.2 mm column at a flow of 40 mL/min over 12 min (<100 mg or multiple injections of <100 mg) or HP C18 RediSep®Rf gold column (>100 mg) eluting with an appropriate gradient of acetonitrile in water (both containing 0.1% formic acid) unless otherwise specified. The gradient was selected based on the retention time observed by reaction monitoring on the Waters Acquity-H UPLC® Class system (see above). Fractions containing the desired compounds were combined and finally lyophilized. Purifications by silica gel chromatography were performed on a Teledyne Isco Combi Flash®Rf system using RediSep®Rf silica gel columns of appropriate sizes. Purity of final Compounds was assessed by injection of a small aliquot on a Waters Acquity-H UPLC® Class system using an Acquity® UPLC BEH C18 2.1×50 mm column eluting with a gradient (7 min) of acetonitrile (2% to 98%) in water (both containing 0.1% formic acid).

Example 1. Preparation of Compounds

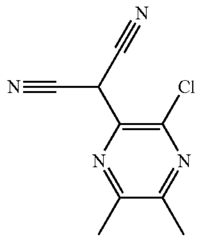

Intermediate A (2-(3-chloro-5,6-dimethyl-pyrazin-2-yl) propanedinitrile)

To a suspension of NaH (3.54 g, 92 mmol, 60% dispersion in mineral oil) in THF (100 mL) at 0° C. was added malononitrile (3.99 g, 60.4 mmol) in THF (30 mL) dropwise via an addition funnel. The cold bath was removed at the end of the addition and the resulting mixture was allowed to stir for 45 min at rt. 2,3-dichloro-5,6-dimethyl-pyrazine (5.49 g, 31.0 mmol) and $Pd(PPh_3)_4$ (1.76 g, 1.52 mmol) were added, the reaction mixture was refluxed for 3.25 h, cooled to rt, poured into 200 mL 1:1 crushed ice and 1N HCl, and extracted with DCM (3×). The combined organic layers were washed with brine, dried over $Na_2SO_4$, filtered and concentrated. The crude product was adsorbed on silica using DCM/THF and purified by silica gel chromatography eluting with a gradient of 0 to 100% EtOAc in hexanes. Mix fractions were re-purified by a second silica gel chromatography using same conditions. Clean fractions from both columns were combined, concentrated and dried in vacuo to afford 2-(3-chloro-5,6-dimethyl-pyrazin-2-yl) propanedinitrile (intermediate A, 5.0 g, 78% yield) as an orange solid. LC-MS (ESI) m/z: 205.1 [M−H]. $^1$H NMR (400 MHZ, Chloroform-d) δ 5.44 (s, 1H), 2.62 (s, 3H), 2.61 (s, 3H).

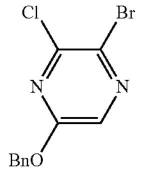

Intermediate B (5-benzyloxy-2-bromo-3-chloro-pyrazine)

Step 1. Sodium nitrite (40 g, 580 mmol) was added portion wise to a solution of 5-bromo-6-chloro-pyrazin-2-amine (110 g, 528 mmol) in sulfuric acid (770 mL) at 0° C. under mechanical stirring. The resulting thick mixture was stirred at 0° C. for 1 h and was then slowly poured in 6 L of cold water containing crushed ice maintaining temperature below 30° C. The resulting precipitate was collected by filtration, washed with water then dried by co-evaporation with toluene under vacuum twice to give 5-bromo-6-chloro-pyrazin-2-ol (104.6 g, 95% yield) as a pale beige solid.

Step 2. Benzyl bromide (48 mL, 404 mmol) was added dropwise to a suspension of 5-bromo-6-chloro-pyrazin-2-ol (80 g, 382 mmol) and silver carbonate (216 g, 778 mmol) in toluene (2 L). After stirring for 3 h, the suspension was filtered on Celite. The filtrate was evaporated to dryness to provide a yellow oil that was dissolved in warm EtOH. After slow addition of water under sonication, the precipitate was collected by filtration to provide 5-benzyloxy-2-bromo-3-chloro-pyrazine (85.2 g, 75% yield) as a beige solid. 1H NMR (400 MHZ, DMSO-d6) δ 8.27 (s, 1H), 7.51-7.46 (m, 2H), 7.44-7.33 (m, 3H), 5.36 (s, 2H).

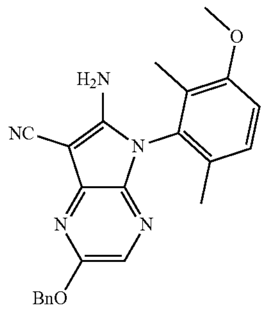 [SMILES: COc1ccc(C)c(-n2c(N)c(C#N)c3nc(OCc4ccccc4)cnc32)c1C]

Intermediate C (6-amino-2-benzyloxy-5-(3-methoxy-2,6-dimethyl-phenyl) pyrrolo[2,3-b]pyrazine-7-carbonitrile)

Step 1. To a solution of Intermediate B (90 g, 300 mmol) in toluene (1350 mL) were added potassium tert-butoxide (45.0 g, 401 mmol), 3-methoxy-2,6-dimethyl-aniline (48 g, 318 mmol), $Pd_2(dba)_3$ (14.4 g, 15.7 mmol) and Xantphos (18.0 g, 31 mmol). The mixture was degassed in vacuo and back filled with nitrogen. The resulting mixture was stirred at 80° C. for 45 min and then concentrated in vacuo. The residue was dissolved in DCM (500 mL), 200 g of silica gel was added, and the suspension was evaporated to dryness under vacuum. The residue was purified on a pad of silica gel (1 kg of silica gel) eluting with a gradient of 0 to 15% EtOAc in hexanes to provide 5-benzyloxy-3-chloro-N-(3-methoxy-2,6-dimethyl-phenyl) pyrazin-2-amine (108.4 g, 98% yield) as a pale beige solid.

Step 2. To a solution of propanedinitrile (42.1 g, 637 mmol) in DME (1800 mL) was added portion wise NaH (25.0 g, 628 mmol, 60% dispersion in mineral oil). The resulting mixture was stirred for 30 min, then 5-benzyloxy-3-chloro-N-(3-methoxy-2,6-dimethyl-phenyl) pyrazin-2-amine (115 g, 311 mmol) in DME (500 mL) and $Pd(PPh_3)_4$ (17.7 g, 15.3 mmol) were added. The resulting mixture was stirred at reflux for 2 h, and then concentrated in vacuo to 1 L. Water (1 L) was added slowly and the resulting biphasic mixture was stirred for 18 h with a mechanical stirrer. The resulting solid was recovered by filtration, washed with water, and dried in vacuo. Trituration in DCM provided the first batch of the desired material as a beige solid isolated by filtration. The mother liquor was concentrated in vacuo, and the residue was purified by silica gel chromatography (dry load) eluting with a gradient of 10 to 60% EtOAc in hexanes to provide a second batch of the desired material. The two batches were combined to provide 6-amino-2-benzyloxy-5-(3-methoxy-2,6-dimethyl-phenyl) pyrrolo[2,3-b]pyrazine-7-carbonitrile (103.1 g, 83% yield) as a beige solid. 1H NMR (400 MHZ, Chloroform-d) δ 7.60 (s, 1H), 7.53-7.47 (m, 2H), 7.42-7.34 (m, 2H), 7.33-7.27 (m, 1H), 7.21-7.15 (m, 1H), 6.94 (d, J=8.5 Hz, 1H), 5.45 (s, 2H), 4.91 (s, 2H), 3.84 (s, 3H), 1.90 (d, J=0.7 Hz, 3H), 1.83 (s, 3H). MS: [M+1]: 400.4.

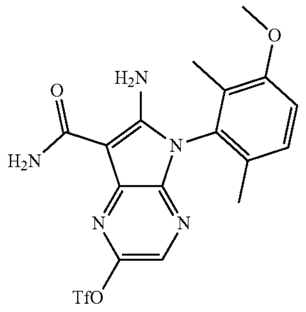 [SMILES: COc1ccc(C)c(-n2c(N)c(C(N)=O)c3nc(OS(=O)(=O)C(F)(F)F)cnc32)c1C]

Intermediate D ([6-amino-7-carbamoyl-5-(3-methoxy-2,6-dimethyl-phenyl) pyrrolo[2,3-b] pyrazin-2-yl] trifluoromethanesulfonate)

Step 1. A solution of Intermediate C (83 g, 208 mmol) in sulfuric acid (550 mL) was stirred with a mechanical stirrer for 18 h. The thick brown mixture was poured slowly in icy water (2 L) in an ice bath maintaining internal temperature below 20° C. while stirred with a mechanical stirrer. A pale-yellow solid precipitated out. The resulting suspension in an ice bath was slowly neutralized to basic pH with aqueous ammonium hydroxide (28% solution; 850 mL) while maintaining the internal temperature below 40° C. The precipitate was collected by filtration, washed with water, and dried in vacuo to provide 6-amino-2-hydroxy-5-(3-methoxy-2,6-dimethyl-phenyl) pyrrolo[2,3-b]pyrazine-7-carboxamide (65.1 g, 96% yield) as a pale beige solid.

Step 2. To a solution of 6-amino-2-hydroxy-5-(3-methoxy-2,6-dimethyl-phenyl) pyrrolo[2,3-b]pyrazine-7-carboxamide (30.5 g, 93.2 mmol) and $Cs_2CO_3$ (34.9 g, 107 mmol) in DMF (300 mL) was added 1,1,1-trifluoro-N-phenyl-N-(trifluoromethylsulfonyl) methanesulfonamide (36.6 g, 103 mmol). The reaction mixture was stirred for 1 h, diluted with water (900 mL) and extracted with EtOAc (3×300 mL). The combined organic extracts were washed with water, brine, dried over $Na_2SO_4$, filtered and concentrated in vacuo. The residue was purified by silica gel chromatography eluting with a gradient of 20 to 100% EtOAc in hexanes to provide [6-amino-7-carbamoyl-5-(3-methoxy-2,6-dimethyl-phenyl) pyrrolo[2,3-b]pyrazin-2-yl] trifluoromethanesulfonate (28 g, 65% yield) as an off-white solid. 1H NMR (400 MHZ, Chloroform-d) δ 7.75 (s, 1H), 7.22 m, 2H), 6.97 (d, J=8.5 Hz, 1H), 6.37 (s, 2H), 5.49 (s, 1H), 3.86 (s, 3H), 1.91 (s, 3H), 1.84 (s, 3H). MS: [M+1]: 528.4.

Chiral SFC separation of Intermediate D (7.0 g, 15 mmol) (Instrument: Waters Prep 100 SFC-MS; Column: Phenomenex Lux Cellulose-2, 30×250 mm, 5 μm; Conditions: Isocratic at 25% MeOH with 75% $CO_2$; Flow Rate: 70 mL/min) provided Intermediate D1 and Intermediate D2.

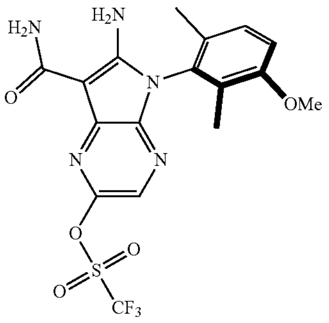

Intermediate D1 from chiral SFC separation of Intermediate D. Peak 1 (retention time 4.95 min, 99.77%): R-6-amino-7-carbamoyl-5-(3-methoxy-2,6-dimethylphenyl)-5H-pyrrolo[2,3-b]pyrazin-2-yl trifluoromethanesulfonate (1.93 g) as a white fluffy solid. 1H NMR (400 MHZ, DMSO-d6) δ 7.94 (s, 1H), 7.89 (br s, 2H), 7.50 (br s, 1H), 7.28 (dt, J=8.4, 0.8 Hz, 1H), 7.14 (d, J=8.5 Hz, 1H), 6.80 (br s, 1H), 3.85 (s, 3H), 1.82 (d, J=0.7 Hz, 3H), 1.74 (s, 3H). 19F NMR (376 MHZ, DMSO-d6) δ −72.83. MS: [M+1]: 460.0.

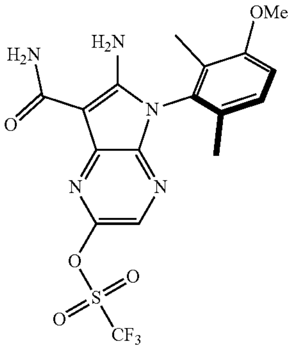

Intermediate D2 from chiral SFC separation of Intermediate D. Peak 2 (retention time 6.44 min, 99.01%): S-6-amino-7-carbamoyl-5-(3-methoxy-2,6-dimethylphenyl)-5H-pyrrolo [2,3-b]pyrazin-2-yl trifluoromethanesulfonate (1.95 g) as a white fluffy solid. 1H NMR (400 MHZ, DMSO-d6) δ 7.94 (s, 1H), 7.89 (br s, 2H), 7.50 (br s, 1H), 7.28 (dt, J=8.5, 0.7 Hz, 1H), 7.14 (d, J=8.5 Hz, 1H), 6.80 (br s, 1H), 3.85 (s, 3H), 1.82 (d, J=0.7 Hz, 3H), 1.74 (s, 3H). 19F NMR (376 MHZ, DMSO-d6) δ −72.83. MS: [M+1]: 460.0.

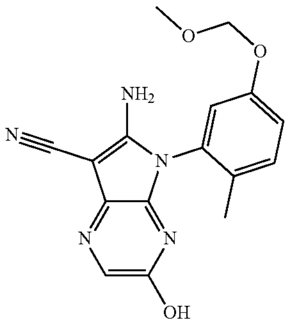 [SMILES: COCOc1ccc(C)c(-n2c(N)c(C#N)c3ncc(O)nc32)c1]

Intermediate E (6-amino-3-hydroxy-5-[5-(methoxymethoxy)-2-methyl-phenyl]pyrrolo[2,3-b]pyrazine-7-carbonitrile)

Step 1. To a solution of 5-benzyloxy-2-bromo-3-chloro-pyrazine (5.08 g, 17.0 mmol) and 5-(methoxymethoxy)-2-methyl-aniline (5.70 g, 34.1 mmol) in THF (40 mL) at 0° C. was added dropwise potassium tert-butoxide in THF (1 M, 48 mL). After stirring for 90 min at 0° C., the reaction mixture was quenched with saturated $NH_4Cl$, diluted with water, and extracted with EtOAc (3×). The combined organic extracts were washed with water, brine, dried over $Na_2SO_4$, filtered and concentrated in vacuo. The crude residue was purified by silica gel chromatography (dry load) eluting with a gradient of 0 to 20% EtOAc in hexanes to provide 6-benzyloxy-3-bromo-N-[5-(methoxymethoxy)-2-methyl-phenyl]pyrazin-2-amine (1.80 g, 25% yield) as a pale yellow solid.

Step 2. To a suspension of NaH (631 mg, 16.5 mmol, 60% dispersion in mineral oil) in THF (28 mL) at 0° C., was added malononitrile (556 mg, 8.42 mmol) in THF (12 mL) dropwise. After stirring at 0° C. for 30 min, the ice bath was removed and 6-benzyloxy-3-bromo-N-[5-(methoxymethoxy)-2-methyl-phenyl]pyrazin-2-amine (1.80 g, 4.18 mmol) and $Pd(PPh_3)_4$ (242 mg, 209 μmol) were added. The resulting mixture was flushed with nitrogen, and stirred at 60° C. for 1 h. The resulting mixture was cooled down to rt, poured slowly in saturated aqueous $NH_4Cl$ and then was extracted with EtOAc (2×). The combined organic extracts were washed with water, brine, dried over $Na_2SO_4$, filtered and concentrated in vacuo. The residue was purified by silica gel chromatography (dry load) eluting with a gradient of 0 to 100% EtOAc in hexanes to provide 6-amino-3-benzyloxy-5-[5-(methoxymethoxy)-2-methyl-phenyl]pyrrolo[2,3-b]pyrazine-7-carbonitrile (1.63 g, 94% yield) as a light tan solid.

Step 3. A mixture 6-amino-3-benzyloxy-5-[5-(methoxymethoxy)-2-methyl-phenyl]pyrrolo[2,3-b]pyrazine-7-carbonitrile (1.39 g, 3.35 mmol) and palladium on carbon (350 mg, 0.329 mmol, 10% w/w) was flushed with nitrogen and MeOH (40 mL) was added. The reaction mixture was flushed with hydrogen and stirred under a hydrogen atmosphere (1 atm) for 2 h, then flushed with nitrogen, filtered on a Celite pad using DCM and MeOH. The filtrate was concentrated in vacuo, then dried to afford 6-amino-3-hydroxy-5-[5-(methoxymethoxy)-2-methyl-phenyl]pyrrolo[2,3-b]pyrazine-7-carbonitrile (1.12 g, 100%) as an ochre solid. MS: [M+1]: 326.1.

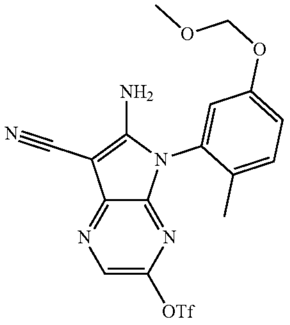 [SMILES: COCOc1ccc(C)c(-n2c(N)c(C#N)c3ncc(OS(=O)(=O)C(F)(F)F)nc32)c1]

Intermediate F ([6-amino-7-cyano-5-[5-(methoxymethoxy)-2-methyl-phenyl]pyrrolo[2,3-b]pyrazin-3-yl] trifluoromethanesulfonate)

Step 1. To a solution of 6-amino-3-hydroxy-5-[5-(methoxymethoxy)-2-methyl-phenyl]pyrrolo[2,3-b]pyrazine-7-carbonitrile (1.12 g, 3.44 mmol) and 1,1,1-trifluoro-N-phenyl-N-(trifluoromethylsulfonyl) methanesulfonamide (1.49 g, 4.17 mmol) in THF (45 mL) was added $Et_3N$ (1.23 g, 12.2 mmol, 1.70 mL). The reaction mixture was stirred for 18 h, then concentrated in vacuo. The residue was purified by silica gel chromatography (dry load) eluting with a gradient of 0 to 100% EtOAc in hexanes to afford [6-amino-7-cyano-5-[5-(methoxymethoxy)-2-methyl-phenyl]pyrrolo[2,3-b]pyrazin-3-yl] trifluoromethanesulfonate (1.72 g, 100%) as a dark yellow solid. 1H NMR (400 MHZ, DMSO-d6) δ8.38 (s, 1H), 8.13 (br s, 2H), 7.41 (dd, J=8.5, 0.9 Hz, 1H), 7.19 (dd, J=8.5, 2.6 Hz, 1H), 7.11 (d, J=2.6 Hz, 1H), 5.22 (d, J=6.8 Hz, 1H), 5.17 (d, J=6.8 Hz, 1H), 3.38 (s, 3H), 1.90 (s, 3H). MS: [M+1]: 458.0.

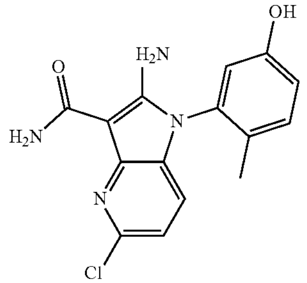 [SMILES: Cc1ccc(O)cc1-n1c(N)c(C(N)=O)c2nc(Cl)ccc21]

Intermediate G (2-amino-5-chloro-1-(5-hydroxy-2-methyl-phenyl) pyrrolo[3,2-b]pyridine-3-carboxamide)

Step 1. To a solution of propanedinitrile (11.8 g, 179 mmol) in DME (200 mL) at 0° C. was added portion wise NaH (7.0 g, 175.00 mmol, 60% dispersion in mineral oil). 3-bromo-2,6-dichloro-pyridine (20 g, 88.15 mmol) was then added and the resulting mixture was stirred at 90° C. for 6 h. The reaction mixture was cooled to rt, neutralized with 1M HCl, diluted with water and extracted with EtOAc (3×). The combined organic extracts were washed with brine, filtered and concentrated in vacuo. The residue was purified by preparative HPLC in multiple batches. The desired fractions were combined and concentrated to dryness to provide 2-(3-bromo-6-chloro-2-pyridyl) propanedinitrile (8.0 g, 35% yield) as an off-white solid.

Step 2. To a solution of 2-(3-bromo-6-chloro-2-pyridyl) propanedinitrile (5 g, 19.5 mmol) in DMF (75 mL) were added $Pd_2(dba)_3$ (1.75 g, 1.91 mmol), 5-(methoxymethoxy)-2-methyl-aniline (3.6 g, 21.53 mmol), $Cs_2CO_3$ (12.7 g) and Xantphos (1.12 g, 1.94 mmol). The mixture was degassed in vacuo and back filled with nitrogen 3 times. The resulting mixture was stirred at 130° C. for 8 h then cooled to rt. The resulting mixture was diluted with water and extracted with EtOAc (3×). The combined organic extracts were washed with brine, dried over $Na_2SO_4$, filtered and concentrated in vacuo. The residue was purified by silica gel chromatography eluting with a gradient of 10 to 60% EtOAc in hexanes. The desired fractions were concentrated to dryness, and the residue was triturated with DCM to provide 2-amino-5-chloro-1-[5-(methoxymethoxy)-2-methyl-phenyl]pyrrolo[3,2-b]pyridine-3-carbonitrile (2.2 g, 33% yield) as an off-white solid.

Step 3. To the suspension of 2-amino-5-chloro-1-[5-(methoxymethoxy)-2-methyl-phenyl]pyrrolo[3,2-b]pyridine-3-carbonitrile (2.20 g, 6.42 mmol) in DCM (5 mL) was added hydrogen chloride 4M in dioxane (4 M, 5 mL). The mixture was stirred for 30 min. The volatiles were removed in vacuo to provide 2-amino-5-chloro-1-(5-hydroxy-2-methyl-phenyl) pyrrolo[3,2-b]pyridine-3-carbonitrile HCl salt (2.10 g, 98% yield) as an off-white solid.

Step 4. The solution of 2-amino-5-chloro-1-(5-hydroxy-2-methyl-phenyl) pyrrolo[3,2-b]pyridine-3-carbonitrile (2.3 g, 7.70 mmol) in conc. sulfuric acid (25 mL) was stirred at rt for 1 h. Then it was diluted with crushed ice, basified with conc. aqueous ammonia to pH 8. The suspension was filtered. The precipitate was washed with water, dried in vacuo to provide an off-white mixture mainly containing 2-amino-5-chloro-1-(5-hydroxy-2-methyl-phenyl) pyrrolo[3,2-b]pyridine-3-carboxamide (2 g, 82% yield) which was used directly in the next step without further purification. $^1H$ NMR (400 MHZ, DMSO-d6) δ 9.77 (s, 1H), 7.42 (s, 1H), 7.30 (d, J=8.3 Hz, 1H), 7.16 (m, 3H), 6.98-6.91 (m, 2H), 6.87 (d, J=8.1 Hz, 1H), 6.71 (d, J=2.6 Hz, 1H), 1.81 (s, 3H). MS: [M+1]: 317.1.

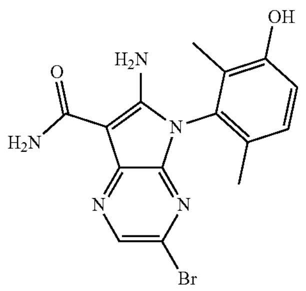 [SMILES: Cc1ccc(O)c(C)c1-n1c(N)c(C(N)=O)c2ncc(Br)nc21]

Intermediate H (6-amino-3-bromo-5-(3-hydroxy-2,6-dimethyl-phenyl) pyrrolo[2,3-b]pyrazine-7-carboxamide)

Step 1. Propanedinitrile (26.6 g, 403 mmol) was added dropwise with vigorous stirring to a suspension of NaH 60% dispersion in mineral oil (16 g, 418 mmol) in DME (600 mL). The mixture was stirred for 30 min and then 2,3-dichloropyrazine (30 g, 201 mmol) was added. The reaction mixture was stirred for 3 h and then heated to reflux for 1 h. The DME was evaporated under vacuum and the resulting residue was treated with cold aqueous HCl 1 M to give a yellow product that was recovered by filtration, washed with water and a minimum of ethanol to afford 2-(3-chloropyrazin-2-yl) propanedinitrile (34.2 g, 95% yield) as a yellow solid.

Step 2. A microwave vial containing 2-(3-chloropyrazin-2-yl) propanedinitrile (1.00 g, 5.60 mmol), 3-methoxy-2,6-dimethyl-aniline (2.54 g, 16.8 mmol) and NMP (10 mL) was capped, stirred at 150° C. for 1 h then at 200° C. for 8 h. The reaction mixture was cooled to rt, poured into saturated aqueous $NaHCO_3$ and diluted with water and EtOAc. The mixture was filtered through a pad of Celite and the layers were separated. The organic layer was dried over $Na_2SO_4$, filtered, adsorbed on silica and purified by silica gel chromatography eluting with a gradient of 0 to 100% EtOAc in hexanes. The appropriate fractions were combined, concentrated in vacuo. The residue was purified again by silica gel chromatography eluting with a gradient of 0 to 20% MeOH in DCM. The appropriate fractions were combined, concentrated and dried in vacuo to provide 6-amino-5-(3-methoxy-2,6-dimethyl-phenyl) pyrrolo[2,3-b]pyrazine-7-carbonitrile (346 mg, 21% yield) as a beige solid.

Step 3. To a solution of 6-amino-5-(3-methoxy-2,6-dimethyl-phenyl) pyrrolo[2,3-b]pyrazine-7-carbonitrile (600 mg, 2.05 mmol) in DMF (10 mL) was added NBS (436 mg, 2.45 mmol). The mixture was stirred for 10 min, diluted with water, stirred for 20 min then filtered. The solid was washed with water and dried in vacuo. Purification by silica gel chromatography eluting with a gradient of 0 to 100% EtOAc in hexanes provided 6-amino-3-bromo-5-(3-methoxy-2,6-dimethyl-phenyl) pyrrolo[2,3-b]pyrazine-7-carbonitrile (350 mg, 46% yield).

Step 4. To a solution of 6-amino-3-bromo-5-(3-methoxy-2,6-dimethyl-phenyl) pyrrolo[2,3-b]pyrazine-7-carbonitrile (350 mg, 940 μmol) in DCM (10 mL) was added $H_2SO_4$ (1.88 mmol, 1 mL). The mixture was stirred 60 min, quenched with crushed ice and extracted with DCM. The organic phase was dried over $Na_2SO_4$, filtered and concentrated in vacuo. The residue was purified on silica gel using a gradient of 0 to 20% MeOH in DCM to provide 6-amino-2-bromo-5-(3-methoxy-2,6-dimethyl-phenyl) pyrrolo[2,3-b]pyrazine-7-carboxamide (300 mg, 82% yield).

Step 5. To a solution of 6-amino-3-bromo-5-(3-methoxy-2,6-dimethyl-phenyl) pyrrolo[2,3-b]pyrazine-7-carboxamide (300 mg, 769 μmol) in DCM (3 mL) was added $BBr_3$ solution in DCM (1 M, 2.31 mL). The mixture was stirred for 2 h. The volatiles were removed in vacuo to afford a crude mixture of 6-amino-3-bromo-5-(3-hydroxy-2,6-dimethyl-phenyl) pyrrolo[2,3-b]pyrazine-7-carboxamide (263 mg, 91% yield) that was used in the next step without further purification. 1H NMR (400 MHZ, DMSO-d6) δ8.29 (s, 1H), 7.55 (s, 2H), 7.31 (s, 1H), 7.21 (s, 1H), 7.13-7.06 (m, 1H), 6.96 (d, J=8.3 Hz, 1H), 1.78 (s, 3H), 1.70 (s, 3H). MS: [M+1]: 378.3.

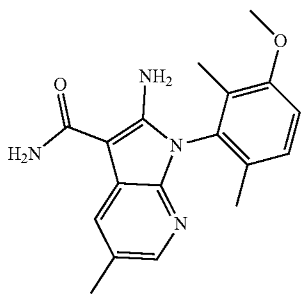 [SMILES: COc1ccc(C)c(-n2c(N)c(C(N)=O)c3cc(C)cnc32)c1C]

Intermediate I (2-amino-5-bromo-1-(3-methoxy-2,6-dimethyl-phenyl) pyrrolo[2,3-b]pyridine-3-carboxamide)

Step 1. To a solution of 2,3-dibromo-5-nitro-pyridine (20 g, 63.85 mmol) in NMP (120 mL) were added 2,6-dimethylpyridine (11.08 g, 103.4 mmol, 12 mL), 3-methoxy-2,6-dimethyl-aniline (14 g, 95.23 mmol). The mixture was heated at 130° C. overnight. After it was cooled to rt, it was diluted with water dropwise, stirred at rt for 20 min, filtered. The solid was washed with water, dried in vacuo. The residue was purified using 2×330 g silica gel eluting with a gradient of 10 to 30% EtOAc in heptane to provide 3-bromo-N-(3-methoxy-2,6-dimethyl-phenyl)-5-nitro-pyridin-2-amine (12 g, 53% yield) as an off-white solid.

Step 2. To a solution of propanedinitrile (4.4 g, 66.6 mmol, 4.19 mL) in DME (120 mL) was added portion wise NaH (2.90 g, 66.9 mmol, 60% dispersion in mineral oil). The resulting mixture was stirred for 5 min, then 3-bromo-N-(3-methoxy-2,6-dimethyl-phenyl)-5-nitro-pyridin-2-amine (11.6 g, 32.9 mmol) and $PdCl_2(dppf)\cdot CH_2Cl_2$ (1.34 g, 1.65 mmol) were added. The mixture was stirred 2 h at 110° C. The mixture was cooled to rt, diluted with water and extracted twice with EtOAc. The combined organic extracts were washed with brine, dried over $Na_2SO_4$, filtered and concentrated in vacuo. The residue was purified by silica gel chromatography eluting with a gradient of 0 to 60% EtOAc in hexanes to provide 2-amino-1-(3-methoxy-2,6-dimethyl-phenyl)-5-nitro-pyrrolo[2,3-b]pyridine-3-carbonitrile (11 g, 99% yield) as a yellow solid.

Step 3. To a solution of 2-amino-1-(3-methoxy-2,6-dimethyl-phenyl)-5-nitro-pyrrolo[2,3-b]pyridine-3-carbonitrile (1.130 g, 3.35 mmol) in THF (15 mL) were added $Et_3N$ (3.37 mmol, 470 uL), DMAP (45 mg, 368 μmol) and tert-butoxycarbonyl tert-butyl carbonate (1.47 g, 6.73 mmol). The mixture was stirred at 50° C. for 1 h then cooled to rt. Ethylenediamine (500 μL) was added and the mixture was stirred for 2 h. The resulting mixture was diluted with water, extracted with DCM (2×). The combined organic extracts were washed with brine, dried over $Na_2SO_4$, filtered and concentrated in vacuo. The residue was purified by silica gel chromatography eluting with a gradient of 20 to 60% EtOAc in to provide tert-butyl N-[3-cyano-1-(3-methoxy-2,6-dimethyl-phenyl)-5-nitro-pyrrolo[2,3-b]pyridin-2-yl]carbamate (1.27 g, 87% yield).

Step 4. To a solution of tert-butyl N-[3-cyano-1-(3-methoxy-2,6-dimethyl-phenyl)-5-nitro-pyrrolo[2,3-b]pyridin-2-yl]carbamate (2.94 g, 6.72 mmol) in DCM (30 mL) and MeOH (30 mL) was added palladium on carbon (10% w/w, 400 mg, 376 μmol). The mixture was stirred for 3 h under 1 atm of $H_2$. The suspension was filtered over a pad of Celite and concentrated in vacuo to provide tert-butyl N-[5-amino-3-cyano-1-(3-methoxy-2,6-dimethyl-phenyl) pyrrolo[2,3-b]pyridin-2-yl]carbamate (2.7 g, 99% yield) as an off-white solid.

Step 5. To a solution of tert-butyl N-[5-amino-3-cyano-1-(3-methoxy-2,6-dimethyl-phenyl) pyrrolo[2,3-b]pyridin-2-yl]carbamate (15.1 g, 37.1 mmol) in a mixture of DMF (60 mL) and acetonitrile (80 mL) was added tert-butyl nitrite (5.72 g, 55.5 mmol, 6.6 mL) followed by Copper (II) bromide (10 g, 44.8 mmol). The mixture was stirred at 60° C. for 20 min, then it was diluted with water, treated with ammonia, extracted with EtOAc (3×). The combined organic extracts were washed with brine, dried over $Na_2SO_4$, filtered. The filtrate was concentrated to dryness. The residue was purified using 3×330 silica gel column eluting with a gradient of 0 to 5% EtOAc in DCM to provide tert-butyl N-[5-bromo-3-cyano-1-(3-methoxy-2,6-dimethyl-phenyl) pyrrolo[2,3-b]pyridin-2-yl]carbamate (9.67 g, 55% yield) as an off-white solid. MS: 471.2 (M+H)+. The following side product was also isolated from the purification: tert-butyl (3-cyano-1-(3-methoxy-2,6-dimethylphenyl)-1H-pyrrolo[2,3-b]pyridin-2-yl) carbamate (350 mg, 2% yield).

Step 6. To a solution of tert-butyl N-[5-bromo-3-cyano-1-(3-methoxy-2,6-dimethyl-phenyl) pyrrolo[2,3-b]pyridin-2-yl]carbamate (1.05 g, 2.23 mmol) in EtOH (15 mL) at 80° C. was added aqueous HCl (6 M, 6 mL). The mixture was stirred for 20 min then concentrated to dryness, coevaporated with MeOH, treated with $Et_3N$ and then concentrated to dryness. The residue was purified by reverse phase flash chromatography on a $C_{18}$ cartridge eluting with $CH_3CN$/water/0.1% formic acid to provide 2-amino-5-bromo-1-(3-methoxy-2,6-dimethyl-phenyl) pyrrolo[2,3-b]pyridine-3-carbonitrile (515 mg, 60% yield) as an off-white solid.

Step 7. To a solution of 2-amino-5-bromo-1-(3-methoxy-2,6-dimethyl-phenyl) pyrrolo[2,3-b]pyridine-3-carbonitrile (580 mg, 1.56 mmol) in a mixture of EtOH (6 mL) and water (2 mL) were added $LiOH\cdot H_2O$ (500 mg, 11.9 mmol) and $H_2O_2$ (27% w/w aq. solution, 21.02 mmol, 650 uL). The mixture was stirred at 60° C. for 20 min, cooled to rt, diluted with water and filtered. The solid was washed with water, dried in vacuo to provide 2-amino-5-bromo-1-(3-methoxy-2,6-dimethyl-phenyl) pyrrolo[2,3-b]pyridine-3-carboxamide (600 mg, 99% yield) as an off-white solid. 1H NMR (400 MHZ, DMSO-d6) δ 8.21 (d, J=2.0 Hz, 1H), 7.77 (d, J=2.0 Hz, 1H), 7.20 (dt, J=8.4, 0.7 Hz, 1H), 7.13 (s, 2H), 7.05 (d, J=8.5 Hz, 1H), 6.83 (s, 2H), 3.73 (s, 3H), 1.75 (d, J=0.7 Hz, 3H), 1.65 (s, 3H). MS: [M+1]: 469.1.

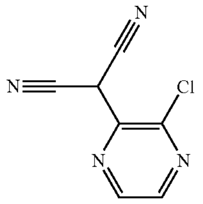 [SMILES: N#CC(C#N)c1nccnc1Cl]

Intermediate J (2-(3-chloropyrazin-2-yl) propanedinitrile)

Malononitrile (26.6 g, 403 mmol) was added dropwise with vigorous stirring to a suspension of sodium hydride (60% dispersion in mineral oil, 16 g, 418 mmol) in DME (600 mL). After the addition, the stirring was continued for 30 min. and then 2,3-dichloropyrazine (30 g, 201 mmol) was added. The reaction mixture was stirred at rt for 3 h and then heated under reflux for 1 h. The DME was evaporated and the resulting residue was treated with cold aqueous hydrochloric acid 1M to give a yellow product that was recovered by filtration, washed with water and a minimum of ethanol to afford 2-(3-chloropyrazin-2-yl) propanedinitrile (intermediate J, 34.2 g, 95% yield) as a yellow solid. LC-MS (ESI) m/z: 177.0 [M−H]—.

Intermediate K (2-(bromomethyl)-4-methoxy-1,3-dimethylbenzene)

Compounds of the present invention can be prepared from bromomethyl aryl K which can be prepared as shown in the Scheme below and described herein. Starting from arylamine A2, described previously, the amino group can be converted to iodo via diazo formation using sodium nitrite and substitution with an iodide. Transmetallation using a base such as n-butyllithium and quenching the anion with DMF can provide an aromatic aldehyde which can be reduced to the corresponding alcohol. Treatment of this alcohol with PBrs can provide the desired bromomethyl aryl K.

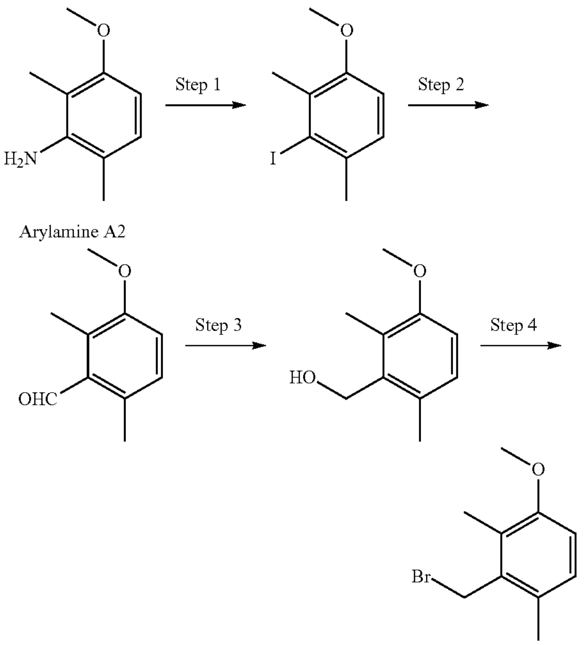

Arylamine A2

K

Step 1. A solution of 3-methoxy-2,6-dimethylaniline (A2, 25 g, 165 mmol) in MeCN (60 mL) was added dropwise to a mixture of sulfuric acid (230 g, 2.35 mol, 125 mL) and $H_2O$ (125 mL) at 0° C. (ice bath). After the addition, the mixture was stirred for 5 min. Then to it was added dropwise a cold solution of sodium nitrite (20.5 g, 297 mmol) in $H_2O$ (150 mL) while maintaining the temperature at 0° C. After the addition, the mixture was stirred for 30 min. Then to the mixture was added dropwise a solution of potassium iodide (96 g, 578 mmol) in $H_2O$ (200 mL). After the addition, the mixture was stirred at rt for 1 h. Then it was quenched with addition of 20% $Na_2S_2O_3$ aqueous, dropwise. The mixture was then extracted with EtOAc. The combined organic extracts were washed with water and brine consecutively, dried over sodium sulfate and filtered. The filtrate was concentrated to dryness in vacuo. The residue was purified by flash chromatography on silica gel (0-20% DCM in hexanes) to provide 3-iodo-1-methoxy-2,4-dimethyl-benzene (21 g, 48% yield) as a yellowish liquid. 1H NMR (400 MHZ, $CDCl_3$) δ 7.14-6.93 (m, 1H), 6.72 (d, J=8.3 HZ, 1H), 3.79 (s, 3H), 2.41 (2s, 6H).

Step 2. To a solution of 2-iodo-4-methoxy-1,3-dimethyl-benzene (4.81 mL, 16.0 mmol) in THF (42.7 mL) at −78° C. was slowly added tert-Butyllithium (1.7 M in pentane, 20.7 mL, 35.3 mmol). This mixture was stirred at −78° C. for 2 h, followed by the addition of DMF (21.4 mL). The reaction mixture was warmed to RT and stirred overnight. Water was added slowly to quench the reaction, followed by extraction with EtOAc. The combined organic extracts were dried over $Na_2SO_4$ and concentrated to dryness. The residue was purified by Combi-Flash (12 g Gold SiO2) by eluting from 100% hexanes to 90% EtOAc/hexanes over 20 min. Tubes were selected by TLC and concentrated in vacuo to obtain 2.63 g of 3-methoxy-2,6-dimethylbenzaldehyde. LC-MS (ESI) m/z: 165.1 $[M+H]^+$.

Step 3. A solution of 3-methoxy-2,6-dimethylbenzaldehyde (2.63 g, 16.0 mmol) in MeOH (50.0 mL) was cooled down to 0° C., and sodium borohydride (909 mg, 24.0 mmol) was added slowly. After 30 min, ice bath was removed and the reaction was stirred at RT overnight. At this point, water (20 mL) was added to the reaction, and the MeOH was removed in vacuo. The remaining aqueous phase was extracted with EtOAc (3×40 mL). The combined organic layers were washed with brine, dried over anhydrous $Na_2SO_4$, filtered, and concentrated in vacuo to yield the crude (3-methoxy-2,6-dimethylphenyl) methanol as a white solid, which was used in the next step without further purification. LC-MS (ESI) m/z: 149.0 [M−OH+H]+.

Step 4. A solution of (3-methoxy-2,6-dimethylphenyl) methanol (4.36 g, 26.2 mmol) in $Et_2O$ (82.0 mL) was cooled down to 0° C., and to it was added phosphorus tribromide (3.05 mL, 31.5 mmol) dropwise. The ice bath was removed, and the reaction mixture was stirred at RT for 1 h. Then, the reaction was cooled down to 0° C., and brine (100 mL) was added slowly. The layers were separated, and the organic layer was dried over anhydrous $Na_2SO_4$, filtered, and concentrated in vacuo to afford the crude 2-(bromomethyl)-4-methoxy-1,3-dimethylbenzene (intermediate K), which was used in the next step without further purification. 1H-NMR (400 MHZ, $CDCl_3$): δ 7.00 (d; J=8.34 Hz; 1H); 6.75 (d; J=8.34 Hz; 1H); 4.57 (s; 2H); 3.81 (s; 3H); 2.37 (s; 3H); 2.29 (s; 3H).

Intermediate L (2-(3-methoxy-2,6-dimethylphenyl) acetonitrile)

Compounds of the present invention can be prepared from 2-aryl acetonitrile L which can be prepared as shown in the scheme below and described herein. Displacement of the bromide of bromomethyl aryl K with a cyanide anion can provide the required 2-aryl acetonitrile L.

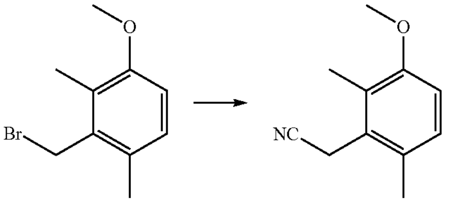

K L

To a solution of 2-(bromomethyl)-4-methoxy-1,3-dimethylbenzene (intermediate K, 3.80 g, 16.6 mmol) in ACN (96.4 mL) was added trimethylsilylcyanide (4.15 mL, 33.2 mmol), followed by TBAF (1 M in THF, 28.2 mL, 28.2 mmol) at 0° C. The mixture was warmed up to RT and stirred for 2 h. The reaction was quenched with aqueous saturated $NaHCO_3$. The aqueous layer was extracted with EtOAc. The combined organic layers were washed with brine, dried over anhydrous $Na_2SO_4$, filtered and concentrated. The crude residue was purified by flash chromatography on silica gel eluting with 0-50% EtOAc/hexanes to afford 2.32 g of 2-(3-methoxy-2,6-dimethylphenyl) acetonitrile (intermediate L). 1H-NMR (400 MHZ, $CDCl_3$): δ 7.03 (d; J=8.37 Hz; 1H); 6.76 (d; J=8.37 Hz; 1H); 3.81 (s; 3H); 3.64 (s; 2H); 2.34 (s; 3H); 2.27 (s; 3H).

General Procedure 1 for Nitrile Hydrolysis

The nitrile intermediate was stirred in concentrated $H_2SO_4$ for an appropriate time to complete nitrile hydrolysis and concomitant removal of acid labile protecting groups such as benzyl, THP and PMB in some cases. The reaction mixture was then poured into ice water and/or crushed ice and neutralized or made slightly alkaline with $NH_4OH$ (7 or 14M). The solid formed was collected by filtration and washed with portions of $H_2O$. It was then air-dried then dried in vacuo. Alternatively, the product was extracted from the aqueous solution using DCM or EtOAc. When a subsequent deprotection step was needed, the crude product was often used as such. In other cases, the crude product was purified by prep HPLC, reverse phase flash chromatography on C18 cartridge or flash chromatography on silica gel as appropriate.

General Procedure 2 for Methoxy Deprotection

To a solution of the appropriate methoxy phenyl intermediate in DCM was added 3 or more eq of tribromoborane (1M solution in DCM). After stirring for the appropriate time at rt (sometime heating was required to complete deprotection), the reaction mixture was concentrated to dryness and coevaporated with DCM/MeOH and/or MeOH a few times, then the residue was taken in MeOH, made basic with $Et_3N$ and concentrated again. The residue was then purified by prep HPLC, reverse phase flash chromatography on C18 or flash chromatography on silica gel as appropriate.

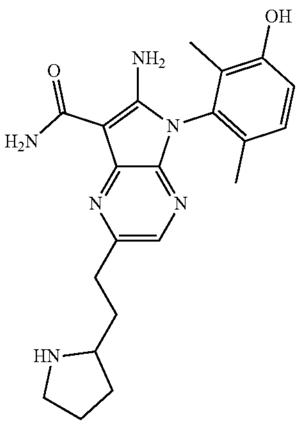 [SMILES: Cc1ccc(O)c(C)c1-n1c(N)c(C(N)=O)c2nc(CCC3CCCN3)cnc21]

Compound 2 (6-amino-5-(3-hydroxy-2,6-dimethylphenyl)-2-(2-(pyrrolidin-2-yl)ethyl)-5H-pyrrolo[2,3-b]pyrazine-7-carboxamide)

Step 1. To a solution of Intermediate D (0.25 g, 0.55 mmol) in DMF was added tert-butyl 2-ethynylpyrrolidine-1-carboxylate (0.213 g, 1.08 mmol) and $Et_3N$ (234 μL, 1.66 mmol). Nitrogen gas was bubbled in the reaction mixture for 10 min. CuI (10 mg, 0.054 mmol) and $PdCl_2(PPh_3)_2$ (20 mg, 0.027 mmol) were then added and the reaction mixture was heated at 100° C. for 1.5 h. The reaction mixture was cooled to rt, diluted with cold water and extracted with EtOAc (3×). The combined organic layers were dried over $Na_2SO_4$, filtered and concentrated in vacuo. The residue was purified by silica gel chromatography eluting with 60% EtOAc in hexanes to afford of tert-butyl 2-((6-amino-7-carbamoyl-5-(3-methoxy-2,6-dimethylphenyl)-5H-pyrrolo[2,3-b]pyrazin-2-I) ethynyl) pyrrolidine-1-carboxylate (0.27 g, 83% yield) as a yellow solid.

Step 2. To a solution of tert-butyl 2-((6-amino-7-carbamoyl-5-(3-methoxy-2,6-dimethylphenyl)-5H-pyrrolo[2,3-b]pyrazin-2-I) ethynyl) pyrrolidine-1-carboxylate (0.13 g, 0.55 mmol) in methanol was added palladium on carbon (10% w/w, 50% moisture). The suspension was stirred under hydrogen atmosphere for 2 h. The reaction mixture was filtered on Celite and washed with methanol. The filtrate was concentrated in vacuo and the residue was purified by silica gel chromatography eluting with 30% EtOAc in hexanes to provide tert-butyl 2-(2-(6-amino-7-carbamoyl-5-(3-methoxy-2,6-dimethylphenyl)-5H-pyrrolo[2,3-b]pyrazin-2-yl)ethyl) pyrrolidine-1-carboxylate (0.105 g, 49% yield) as an off-white solid.

Step 3. For O-Me deprotection using $BBr_3$, following general procedure 2 provided a residue which was purified by preparative HPLC to provide 6-amino-5-(3-hydroxy-2,6-dimethylphenyl)-2-(2-(pyrrolidin-2-yl)ethyl)-5H-pyrrolo[2,3-b]pyrazine-7-carboxamide (2.7 mg, 3.5% yield) as a white solid. 1H NMR (400 MHZ, DMSO-$d_6$) δ 9.79 (bs, 1H), 8.40 (s, 1H), 7.65 (s, 1H), 7.47 (s, 1H), 7.35 (s, 2H), 7.27 (s, 1H), 7.07 (d, J=8 Hz, 1H), 6.95 (d, J=8.4 Hz, 1H), 3.39 (s, 2H), 3.06 (s, 1H), 2.99 (s, 1H), 2.80 (s, 2H), 2.02 (s, 3H), 1.83 (s, 1H), 1.76 (s, 3H), 1.68 (s, 3H), 1.46 (s, 1H). MS: [M+1]: 395.5.

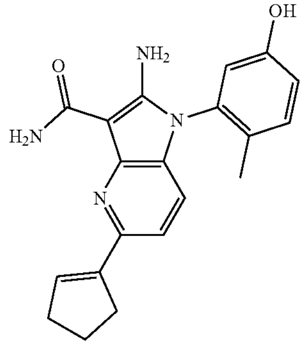 [SMILES: Cc1ccc(O)cc1-n1c(N)c(C(N)=O)c2nc(C3=CCCC3)ccc21]

Compound 6 (2-amino-5-(cyclopenten-1-yl)-1-(5-hydroxy-2-methyl-phenyl) pyrrolo[3,2-b]pyridine-3-carboxamide)

To a solution of Intermediate G (33 mg, 104 μmol) in dioxane (1.5 mL) were added 2-(cyclopenten-1-yl)-4,4,5,5-tetramethyl-1,3,2-dioxaborolane (40 mg, 206 μmol), $PdCl_2$(dppf)·$CH_2Cl_2$ (8 mg, 10 μmol) and aqueous $Na_2CO_3$ (2 M, 200 μL). The mixture was stirred at 100° C. for 5 h. The volatiles were removed in vacuo. The residue was purified by preparative HPLC to provide 2-amino-5-(cyclopenten-1-yl)-1-(5-hydroxy-2-methyl-phenyl) pyrrolo[3,2-b]pyridine-3-carboxamide (5 mg, 14% yield) as an off-white solid. 1H NMR (400 MHZ, DMSO-d6) δ 9.77 (s, 1H), 8.03 (s, 1H), 7.25 (d, J=8.3 Hz, 1H), 6.99 (d, J=8.1 Hz, 2H), 6.91 (s, 2H), 6.88 (dd, J=8.3, 2.6 Hz, 1H), 6.82 (d, J=8.1 Hz, 1H), 6.66 (d, J=2.5 Hz, 1H), 6.41 (t, J=2.1 Hz, 1H), 2.72 (m, 2H), 2.50 (m, 2H), 1.94 (m, 2H), 1.78 (s, 3H). MS: [M+1]: 349.1.

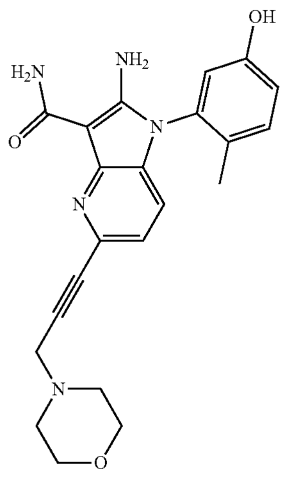 [SMILES: Cc1ccc(O)cc1-n1c(N)c(C(N)=O)c2nc(C#CCN3CCOCC3)ccc21]

Compound 16 (2-amino-1-(5-hydroxy-2-methyl-phenyl)-5-(3-morpholinoprop-1-ynyl) pyrrolo[3,2-b] pyridine-3-carboxamide)

A solution of 4-prop-2-ynylmorpholine (40 mg, 0.32 mmol), Intermediate G (50 mg, 0.16 mmol), Copper (I) iodide (3 mg, 16 μmol), $Na_2CO_3$ (70 mg, 0.66 mmol), tri-tert-butylphosphonium tetrafluoroborate (9 mg, 31 μmol) and $PdCl_2$ (3 mg, 17 μmol) in DMF (2 mL) was degassed in vacuo and back-filled with nitrogen. The mixture was stirred at 100° C. for 5 h. The mixture was purified by preparative HPLC eluting with $CH_3CN$/water/10 mM ammonium bicarbonate (pH 10). The desired fractions were combined and lyophilized to provide 2-amino-1-(5-hydroxy-2-methyl-phenyl)-5-(3-morpholinoprop-1-ynyl) pyrrolo[3,2-b]pyridine-3-carboxamide (22 mg, 35% yield) as an off-white solid. 1H NMR (400 MHZ, DMSO-d6) δ 9.76 (s, 1H), 7.74 (d, J=3.6 Hz, 1H), 7.38-7.16 (m, 1H), 7.06 (s, 3H), 6.98 (d, J=8.1 Hz, 1H), 6.88 (dd, J=8.4, 2.6 Hz, 1H), 6.83 (d, J=8.0 Hz, 1H), 6.66 (d, J=2.5 Hz, 1H), 3.57 (m, 4H), 3.50 (s, 2H), 2.52-2.47 (m, 4H), 1.77 (s, 3H). MS: [M+1]: 406.2.

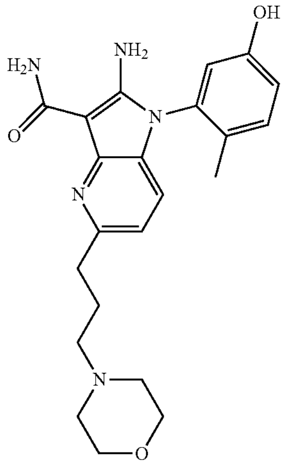 [SMILES: Cc1ccc(O)cc1-n1c(N)c(C(N)=O)c2nc(CCCN3CCOCC3)ccc21]

Compound 18 (2-amino-1-(5-hydroxy-2-methyl-phenyl)-5-(3-morpholinopropyl) pyrrolo[3,2-b]pyridine-3-carboxamide)

To a solution of 2-amino-1-(5-hydroxy-2-methyl-phenyl)-5-(3-morpholinoprop-1-ynyl) pyrrolo[3,2-b]pyridine-3-carboxamide (20 mg, 49 μmol) in MeOH (2 mL) was added palladium on carbon (10% w/w, 6 mg). The mixture was stirred under a hydrogen atmosphere for 30 min. The resulting mixture was filtered and concentrated in vacuo to provide 2-amino-1-(5-hydroxy-2-methyl-phenyl)-5-(3-morpholinopropyl) pyrrolo[3,2-b]pyridine-3-carboxamide (17.8 mg, 88% yield) as a white solid. 1H NMR (400 MHZ, DMSO-d6) δ 9.74 bs, 1H), 8.01 (d, J=4.0 Hz, 1H), 7.24 (dd, J=8.3, 0.8 Hz, 1H), 6.97 (d, J=4.0 Hz, 1H), 6.90-6.81 (m, 3H), 6.76 (d, J=8.0 Hz, 1H), 6.67 (d, J=8.1 Hz, 1H), 6.63 (d, J=2.5 Hz, 1H), 3.51 (m, 4H), 2.77-2.58 (m, 2H), 2.28 (m, 6H), 1.91-1.78 (m, 2H), 1.77 (s, 3H). MS: [M+1]: 410.2.

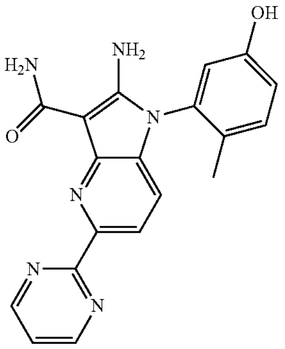 [SMILES: Cc1ccc(O)cc1-n1c(N)c(C(N)=O)c2nc(-c3ncccn3)ccc21]

Compound 23 (2-amino-1-(5-hydroxy-2-methyl-phenyl)-5-pyrimidin-2-yl-pyrrolo[3,2-b]pyridine-3-carboxamide)

To a solution of Intermediate G (50 mg, 0.158 mmol) in DMF (2 mL) were added tributyl(pyrimidin-2-yl) stannane (73 mg, 0.199 mmol, 60 μL), CuI (3 mg, 16 μmol), LiCl (7 mg, 165 μmol) and $PdCl_2(dppf)\cdot CH_2Cl_2$ (12 mg, 16 μmol). The mixture was degassed in vacuo and back filled with nitrogen three times, then stirred at 110° C. for 18 h. The mixture was then purified by preparative HPLC to provide 2-amino-1-(5-hydroxy-2-methyl-phenyl)-5-pyrimidin-2-yl-pyrrolo[3,2-b]pyridine-3-carboxamide (8 mg, 14% yield) as a yellowish solid. 1H NMR (400 MHZ, DMSO-d6) δ9.79 (s, 1H), 8.90 (d, J=4.8 Hz, 2H), 8.32 (d, J=3.9 Hz, 1H), 8.02 (d, J=8.3 Hz, 1H), 7.43 (t, J=4.8 Hz, 1H), 7.28 (d, J=8.3 Hz, 1H), 7.16 (d, J=3.8 Hz, 1H), 7.05 (s, 2H), 7.02 (d, J=8.3 Hz, 1H), 6.90 (dd, J=8.4, 2.5 Hz, 1H), 6.72 (d, J=2.5 Hz, 1H), 1.82 (s, 3H). MS: [M+1]: 361.2.

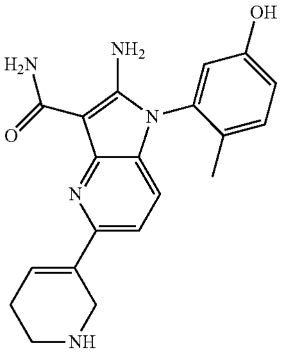 [SMILES: Cc1ccc(O)cc1-n1c(N)c(C(N)=O)c2nc(C3=CCCNC3)ccc21]

Compound 27 (2-amino-1-(5-hydroxy-2-methyl-phenyl)-5-(1,2,3,6-tetrahydropyridin-5-yl)pyrrolo[3,2-b]pyridine-3-carboxamide HCl salt)

To a solution of tert-butyl 5-[2-amino-3-carbamoyl-1-(5-hydroxy-2-methyl-phenyl) pyrrolo[3,2-b]pyridin-5-yl]-3,6-dihydro-2H-pyridine-1-carboxylate (75 mg, 0.162 mmol, prepared similarly to Compound 6) in MeOH (1 mL) was added HCl in dioxane (4 M, 0.5 mL). The mixture was stirred for 2 h. The volatiles were removed in vacuo. The residue was dissolved in water and $CH_3CN$ then lyophilized to provide 2-amino-1-(5-hydroxy-2-methyl-phenyl)-5-(1,2,3,6-tetrahydropyridin-5-yl)pyrrolo[3,2-b]pyridine-3-carboxamide HCl salt (64 mg, 99% yield) as an off-white solid. 1H NMR (400 MHZ, DMSO-d6) δ 9.76 (s, 1H), 9.20 (s, 2H), 8.01-7.41 (m, 1H), 7.26 (d, J=8.4, Hz, 1H), 7.12 (d, J=8.3 Hz, 1H), 7.02 (s, 3H), 6.92-6.82 (m, 2H), 6.72-6.61 (m, 2H), 4.11 (s, 2H), 3.44 (m 2H), 3.19 (m, 2H), 1.77 (s, 3H). MS: [M+1]: 464.2.

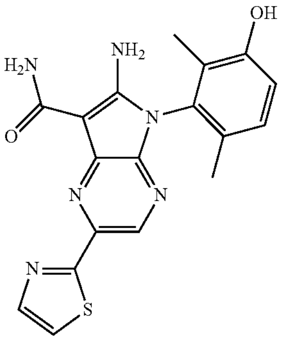 [SMILES: Cc1ccc(O)c(C)c1-n1c(N)c(C(N)=O)c2nc(-c3nccs3)cnc21]

Compound 28 (6-amino-5-(3-hydroxy-2,6-dimethyl-phenyl)-2-thiazol-2-yl-pyrrolo[2,3-b]pyrazine-7-carboxamide)

Step 1. A mixture of tributyl(thiazol-2-yl) stannane (345 mg, 0.922 mmol, 290 uL), Intermediate D (210 mg, 0.457 mmol), CuI (11 mg, 58 µmol), LiCl (40 mg, 0.943 mmol), $PdCl_2(dppf){\cdot}CH_2Cl_2$ (35 mg, 45 µmol) in DMF (3 mL) was degassed in vacuo, then back filled with nitrogen. The final mixture was stirred at 120° C. for 4 h. The volatiles were removed in vacuo. The residue was purified by silica gel chromatography eluting with a gradient of 20 to 100% EtOAc in hexanes to provide a 6-amino-5-(3-methoxy-2,6-dimethyl-phenyl)-2-thiazol-2-yl-pyrrolo[2,3-b]pyrazine-7-carboxamide (136 mg, 75% yield) as an off-white solid.

Step 2. For OMe deprotection using $BBr_3$, following general procedure 2 was done on the appropriate intermediate (23 mg, 58 µmol) to provide a residue which was purified by preparative HPLC to provide 6-amino-5-(3-hydroxy-2,6-dimethyl-phenyl)-2-thiazol-2-yl-pyrrolo[2,3-b]pyrazine-7-carboxamide (10 mg, 45% yield) as an off-white solid. 1H NMR (400 MHZ, DMSO-d6) δ 9.63 (s, 1H), 8.49 (s, 1H), 7.91 (d, J=3.2 Hz, 1H), 7.78 (d, J=3.2 Hz, 1H), 7.61 (s, 2H), 7.40 (s, 1H), 7.29 (s, 1H), 7.06 (d, J=8.4 Hz, 1H), 6.92 (d, J=8.3 Hz, 1H), 1.77 (s, 3H), 1.69 (s, 3H). MS: [M+1]: 381.2.

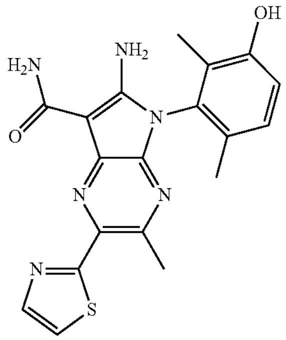 [SMILES: Cc1ccc(O)c(C)c1-n1c(N)c(C(N)=O)c2nc(-c3nccs3)c(C)nc21]

Compound 31 (6-amino-5-(3-hydroxy-2,6-dimethyl-phenyl)-3-methyl-2-thiazol-2-yl-pyrrolo[2,3-b]pyrazine-7-carboxamide)

Step 1. To a solution of 6-amino-2-benzyloxy-5-(3-methoxy-2,6-dimethyl-phenyl) pyrrolo[2,3-b]pyrazine-7-carbonitrile Intermediate C (4 g, 10 mmol) in DMF (40 mL) was added NBS (4 g, 10 mmol). The mixture was stirred for 1 h, diluted with water, and finally stirred for 20 min. The resulting solid was filtered, washed with water and dried in vacuo then purified by silica gel chromatography eluting with a gradient of 20 to 80% EtOAc in hexanes to provide 6-amino-2-benzyloxy-3-bromo-5-(3-methoxy-2,6-dimethyl-phenyl) pyrrolo[2,3-b]pyrazine-7-carbonitrile (3.86 g, 81% yield) as an off-white solid.

Step 2. To a solution of 6-amino-2-benzyloxy-3-bromo-5-(3-methoxy-2,6-dimethyl-phenyl) pyrrolo[2,3-b]pyrazine-7-carbonitrile (650 mg, 1.36 mmol) in dioxane (10 mL) and water (3 mL) were added $Pd(PPh_3)_4$ (80 mg, 69 µmol), $K_2CO_3$ (800 mg, 5.79 mmol). The mixture was degassed in vacuo and then back filled with nitrogen three times. 2,4,6-trimethyl-1,3,5,2,4,6-trioxatriborinane (712 mg, 2.84 mmol, 0.8 mL) was then added and the final mixture was stirred at 100° C. for 18 h. The mixture was cooled to rt, diluted with EtOAc, washed with water, brine, dried over $Na_2SO_4$, filtered and concentrated in vacuo. The residue was purified by silica gel chromatography eluting with a gradient of 0 to 45% EtOAc in hexanes to provide 6-amino-2-benzyloxy-5-(3-methoxy-2,6-dimethyl-phenyl)-3-methyl-pyrrolo[2,3-b]pyrazine-7-carbonitrile (300 mg, 53% yield) as an off-white solid.

Step 3. For nitrile hydrolysis using sulfuric acid, the same procedure used for Compound 164 was done on the appropriate intermediate (260 mg, 0.629 mmol) to provide 6-amino-2-hydroxy-5-(3-methoxy-2,6-dimethyl-phenyl)-3-methyl-pyrrolo[2,3-b]pyrazine-7-carboxamide (205 mg, 96% yield) as an off-white solid.

Step 4. To a solution of 6-amino-2-hydroxy-5-(3-methoxy-2,6-dimethyl-phenyl)-3-methyl-pyrrolo[2,3-b]pyrazine-7-carboxamide (206 mg, 0.603 mmol) and $Cs_2CO_3$ (390 mg, 1.20 mmol) in DMF (2 mL) was added 1,1,1-trifluoro-N-phenyl-N-(trifluoromethylsulfonyl) methanesulfonamide (235 mg, 0.658 mmol). The mixture was stirred for 1 h, then diluted with water and extracted with EtOAc (4×). The combined organic extracts were washed with brine, dried over $Na_2SO_4$, filtered, and concentrated in vacuo. The residue was purified by silica gel chromatography eluting with a gradient of 0 to 70% EtOAc in hexanes to provide [6-amino-7-carbamoyl-5-(3-methoxy-2,6-dimethyl-phenyl)-3-methyl-pyrrolo[2,3-b]pyrazin-2-yl] trifluoromethanesulfonate (160 mg, 56% yield) as an off-white solid.

Step 5. A mixture of tributyl(thiazol-2-yl) stannane (83 mg, 0.223 mmol, 70 uL), [6-amino-7-carbamoyl-5-(3-methoxy-2,6-dimethyl-phenyl)-3-methyl-pyrrolo[2,3-b]pyrazin-2-yl] trifluoromethanesulfonate (50 mg, 0.106 mmol), CuI (3 mg, 16 μmol), LiCl (7 mg, 0.165 mmol), $PdCl_2(dppf)\cdot CH_2Cl_2$ (8 mg, 11 μmol) in DMF (1.5 mL) was degassed in vacuo, then back filled with nitrogen. The reaction mixture was stirred at 110° C. for 4 h, cooled to rt and concentrated in vacuo. The residue was purified by preparative HPLC to provide 6-amino-5-(3-methoxy-2,6-dimethyl-phenyl)-3-methyl-2-thiazol-2-yl-pyrrolo[2,3-b]pyrazine-7-carboxamide (22 mg, 51% yield) as an off-white solid.

Step 6. For OMe deprotection using $BBr_3$, following general procedure 2 was done on the appropriate intermediate (22 mg, 53 μmol) to provide a residue which was purified by preparative HPLC to provide 6-amino-5-(3-hydroxy-2,6-dimethyl-phenyl)-3-methyl-2-thiazol-2-yl-pyrrolo[2,3-b]pyrazine-7-carboxamide (5 mg, 24% yield) as an off-white solid. 1H NMR (400 MHZ, DMSO-d6) δ 9.64 (s, 1H), 7.94 (d, J=3.3 Hz, 1H), 7.76 (d, J=3.3 Hz, 1H), 7.47 (s, 2H), 7.35 (s, 1H), 7.22 (s, 1H), 7.06 (d, J=8.3 Hz, 1H), 6.92 (d, J=8.3 Hz, 1H), 2.76 (s, 3H), 1.77 (s, 3H), 1.69 (s, 3H). MS: [M+1]: 395.2.

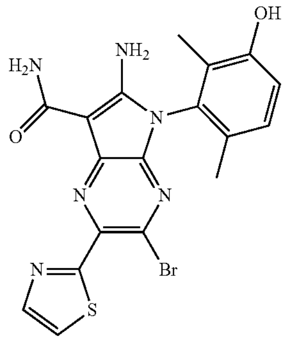 [SMILES: Cc1ccc(O)c(C)c1-n1c(N)c(C(N)=O)c2nc(-c3nccs3)c(Br)nc21]

Compound 33 (6-amino-3-bromo-5-(3-hydroxy-2,6-dimethyl-phenyl)-2-thiazol-2-yl-pyrrolo[2,3-b]pyrazine-7-carboxamide)

Step 1. To a solution of 6-amino-5-(3-methoxy-2,6-dimethyl-phenyl)-2-thiazol-2-yl-pyrrolo[2,3-b]pyrazine-7-carboxamide (Compound 28, 60 mg, 0.15 mmol) in DMF (1 mL) was added NBS (30 mg, 0.17 mmol). The mixture was stirred 18 h, diluted with water, treated with 20% aqueous $Na_2S_2O_3$, extracted with EtOAc (3×). The combined organic extracts were washed with water, brine, dried over $Na_2SO_4$, filtered and concentrated in vacuo. The residue was purified by silica gel chromatography eluting with a gradient of 20 to 100% EtOAc in hexanes to provide 6-amino-3-bromo-5-(3-methoxy-2,6-dimethyl-phenyl)-2-thiazol-2-yl-pyrrolo[2,3-b]pyrazine-7-carboxamide (45 mg, 63% yield) as an off-white solid.

Step 2. For OMe deprotection using $BBr_3$, following general procedure 2 was done on the appropriate intermediate (35 mg, 74 μmol) to provide a residue which was purified by preparative HPLC to provide 6-amino-3-bromo-5-(3-hydroxy-2,6-dimethyl-phenyl)-2-thiazol-2-yl-pyrrolo[2,3-b]pyrazine-7-carboxamide (10 mg, 29% yield) as an off-white solid. 1H NMR (400 MHZ, DMSO-d6) δ 9.71 (s, 1H), 7.97 (d, J=3.3 Hz, 1H), 7.88 (d, J=3.3 Hz, 1H), 7.75 (s, 2H), 7.45 (s, 1H), 7.19-7.00 (m, 2H), 6.94 (d, J=8.3 Hz, 1H), 1.79 (s, 3H), 1.71 (s, 3H). MS: [M+1]: 460.2.

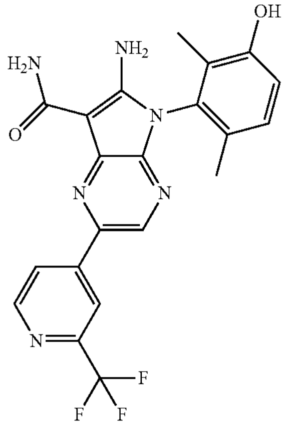 [SMILES: Cc1ccc(O)c(C)c1-n1c(N)c(C(N)=O)c2nc(-c3ccnc(C(F)(F)F)c3)cnc21]

Compound 35 (6-amino-5-(3-hydroxy-2,6-dimethyl-phenyl)-2-[2-(trifluoromethyl)-4-pyridyl]pyrrolo[2,3-b]pyrazine-7-carboxamide)

Step 1. To a solution of Intermediate D (50 mg, 0.109 mmol) in dioxane (1 mL) were added $PdCl_2(dppf)\cdot CH_2Cl_2$ (8 mg, 10 μmol). [2-(trifluoromethyl)-4-pyridyl]boronic acid (40 mg, 0.209 mmol) and aqueous $Na_2CO_3$ (2 M, 200 μL). The mixture was degassed in vacuo and back filled with nitrogen. The reaction mixture was stirred at 100° C. for 4 h, cooled to rt, diluted with water and then filtered. The solid was washed with water, dried in vacuo and finally purified by silica gel chromatography eluting with a gradient of 20 to 100% EtOAc in hexanes to provide 6-amino-5-(3-methoxy-2,6-dimethyl-phenyl)-2-[2-(trifluoromethyl)-4-pyridyl]pyrrolo[2,3-b]pyrazine-7-carboxamide (36 mg, 72% yield) as an off-white solid.

Step 2. Deprotection of 6-amino-5-(3-methoxy-2,6-dimethyl-phenyl)-2-[2-(trifluoromethyl)-4-pyridyl]pyrrolo[2,3-b]pyrazine-7-carboxamide (36 mg, 79 μmol) following general procedure 2 provided 6-amino-5-(3-hydroxy-2,6-dimethyl-phenyl)-2-[2-(trifluoromethyl)-4-pyridyl]pyrrolo[2,3-b]pyrazine-7-carboxamide (16 mg, 46% yield) as an off-white solid, after purification by prep HPLC. 1H NMR (400 MHz, DMSO-d6) δ 9.63 (s, 1H), 8.81 (m, 1H), 8.62 (s, 1H), 8.48 (s, 1H), 8.41 (m, 1H), 7.63 (s, 2H), 7.45 (s, 1H), 7.33 (s, 1H), 7.07 (d, J=8.3 Hz, 1H), 6.93 (d, J=8.3 Hz, 1H), 1.77 (s, 3H), 1.69 (s, 3H). MS: [M+1]: 443.2.

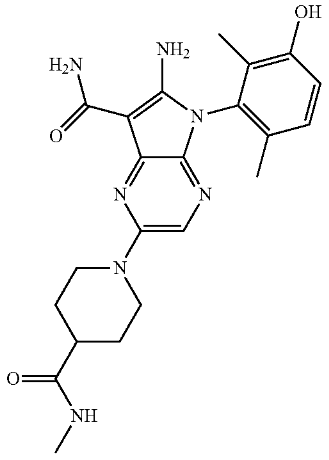 [SMILES: CNC(=O)C1CCN(c2cnc3c(n2)c(C(N)=O)c(N)n3-c2c(C)ccc(O)c2C)CC1]

Compound 46 (6-amino-5-(3-hydroxy-2,6-dimethyl-phenyl)-2-[4-(methylcarbamoyl)-1-piperidyl]pyrrolo[2,3-b]pyrazine-7-carboxamide)

Step 1. To a solution of Intermediate D (50 mg, 0.109 mmol) in DMSO (1 mL) was added N-methylpiperidine-4-carboxamide (80 mg, 0.563 mmol). The mixture was stirred at 130° C. for 2 h in a sealed vial, then cooled to rt and purified by preparative HPLC to provide 6-amino-5-(3-methoxy-2,6-dimethyl-phenyl)-2-[4-(methylcarbamoyl)-1-piperidyl]pyrrolo[2,3-b]pyrazine-7-carboxamide (14 mg, 28% yield) as an off-white solid.

Step 2. For OMe deprotection using $BBr_3$, following general procedure 2 was done on the appropriate intermediate (15 mg, 32 μmol) to provide a residue which was purified by preparative HPLC to provide 6-amino-5-(3-hydroxy-2,6-dimethyl-phenyl)-2-[4-(methylcarbamoyl)-1-piperidyl]pyrrolo[2,3-b]pyrazine-7-carboxamide (10 mg, 69% yield) as an off-white solid. 1H NMR (400 MHZ, DMSO-d6) δ 9.51 (s, 1H), 7.72 (d, J=4.8 Hz, 1H), 7.35 (s, 1H), 7.27 (s, 1H), 7.14-6.96 (m, 4H), 6.87 (d, J=8.2 Hz, 1H), 4.13 (d, J=12.4 Hz, 2H), 2.85-2.68 (m, 2H), 2.53 (d, J=4.6 Hz, 3H), 2.35-2.20 (m, 1H), 1.74 (m, 5H), 1.65 (s, 3H), 1.64-1.50 (m, 2H). MS: [M+1]: 438.2.

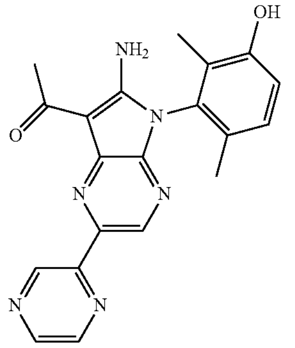 [SMILES: CC(=O)c1c(N)n(-c2c(C)ccc(O)c2C)c2ncc(-c3cnccn3)nc12]

Compound 97 (1-[6-amino-5-(3-hydroxy-2,6-dimethyl-phenyl)-2-pyrazin-2-yl-pyrrolo[2,3-b]pyrazin-7-yl]ethenone)

Step 1. To a solution of Intermediate C (2.5 g, 6.26 mmol) in THF (20 mL) was added MeMgBr solution in THF (3 M, 6.50 mL) at 0° C. The mixture was warmed and stirred 18 h. An additional amount of MeMgBr solution in THF (3 M, 4.00 mL) was added and the mixture was stirred an extra 5 h. The resulting mixture was quenched with sat. aqueous $NH_4Cl$, diluted with water, extracted with EtOAc. The organic extract was washed with water and brine, dried over $Na_2SO_4$, filtered and concentrated in vacuo. The residue was purified by silica gel column eluting with a gradient of 0 to 30% EtOAc in hexanes to provide 1-[6-amino-2-benzyloxy-5-(3-methoxy-2,6-dimethyl-phenyl) pyrrolo[2,3-b]pyrazin-7-yl]ethanone (120 mg, 5% yield).

Step 2. To a solution of 1-[6-amino-2-benzyloxy-5-(3-methoxy-2,6-dimethyl-phenyl) pyrrolo[2,3-b]pyrazin-7-yl] ethanone (100 mg, 0.240 mmol) in DCM (1 mL) was added TFA (500 μL). The mixture was stirred at 50° C. for 10 h. The volatiles were removed in vacuo. The residue was purified by preparative HPLC to provide 1-[6-amino-2-hydroxy-5-(3-methoxy-2,6-dimethyl-phenyl) pyrrolo[2,3-b] pyrazin-7-yl]ethanone (43 mg, 55% yield).

Step 3. To a mixture of 1-[6-amino-2-hydroxy-5-(3-methoxy-2,6-dimethyl-phenyl) pyrrolo[2,3-b]pyrazin-7-yl] ethanone (43 mg, 0.132 mmol) and $Cs_2CO_3$ (50 mg, 0.153 mmol) in DMF (1 mL) was added 1, 1, 1-trifluoro-N-phenyl-N-(trifluoromethylsulfonyl) methanesulfonamide (52 mg, 0.146 mmol). The mixture was stirred for 1 h. The volatiles were removed in vacuo. The residue was purified by silica gel chromatography eluting with a gradient of 0 to 70% EtOAc in hexanes to provide [7-acetyl-6-amino-5-(3-methoxy-2,6-dimethyl-phenyl) pyrrolo[2,3-b]pyrazin-2-yl] trifluoromethanesulfonate (46 mg, 76% yield) as an off-white solid.

Step 4. To a solution of [7-acetyl-6-amino-5-(3-methoxy-2,6-dimethyl-phenyl) pyrrolo[2,3-b]pyrazin-2-yl] trifluoromethanesulfonate (46 mg, 0.100 mmol) in DMF (1 mL) were added LiCl (9 mg, 0.212 mmol), tributyl(pyrazin-2-yl) stannane (74 mg, 0.200 mmol), and $PdCl_2(dppf)\cdot CH_2Cl_2$ (7 mg, 9.6 μmol). The mixture was stirred at 120° C. for 10 h. The volatiles were removed in vacuo. The residue was purified by preparative HPLC to provide 1-[6-amino-5-(3-methoxy-2,6-dimethyl-phenyl)-2-pyrazin-2-yl-pyrrolo[2,3-b]pyrazin-7-yl]ethanone (38 mg, 97% yield) as an off-white solid.

Step 5. For OMe deprotection using $BBr_3$, following general procedure 2 was done on the appropriate intermediate (38 mg, 98 μmol) to provide a residue which was purified by preparative HPLC to provide 1-[6-amino-5-(3-hydroxy-2,6-dimethyl-phenyl)-2-pyrazin-2-yl-pyrrolo[2,3-b]pyrazin-7-yl]ethanone (18 mg, 49% yield) as an off-white solid. 1H NMR (400 MHZ, DMSO-d6) δ 9.62 (s, 1H), 9.55 (s, 1H), 8.72 (s, 1H), 8.69-8.62 (m, 2H), 8.13 (s, 2H), 7.07 (d, J=8.3 Hz, 1H), 6.93 (d, J=8.3 Hz, 1H), 2.76 (s, 3H), 1.77 (s, 3H), 1.69 (s, 3H). MS: [M+1]: 375.

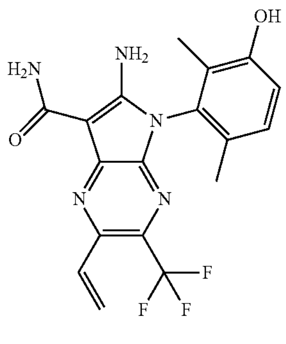 [SMILES: C=Cc1nc2c(C(N)=O)c(N)n(-c3c(C)ccc(O)c3C)c2nc1C(F)(F)F]

Compound 102 (6-amino-5-(3-hydroxy-2,6-dimethyl-phenyl)-3-(trifluoromethyl)-2-vinyl-pyrrolo[2,3-b]pyrazine-7-carboxamide)

Step 1. To a solution of Intermediate C (800 mg, 2.00 mmol) in DMF (10 mL) was added NIS (450 mg, 2.00 mmol). The mixture was stirred for 30 min, diluted with water and stirred for 20 min. The resulting precipitate was collected by filtration and then purified by silica gel chromatography eluting with a gradient of 20 to 60% EtOAc in hexanes to provide 6-amino-2-benzyloxy-3-iodo-5-(3-methoxy-2,6-dimethyl-phenyl) pyrrolo[2,3-b]pyrazine-7-carbonitrile (820 mg, 78% yield) as an off-white solid.

Step 2. To a solution of 6-amino-2-benzyloxy-3-iodo-5-(3-methoxy-2,6-dimethyl-phenyl) pyrrolo[2,3-b]pyrazine-7-carbonitrile (745 mg, 1.42 mmol) in DMF (10 mL) was added (1,10-phenanthroline) (trifluoromethyl) copper (I) (900 mg, 2.88 mmol). The mixture was stirred at 70° C. for 4 h. The volatiles were removed in vacuo. The residue was purified by silica gel chromatography eluting with a gradient of 20 to 60% EtOAc in hexanes to provide 6-amino-2-benzyloxy-5-(3-methoxy-2,6-dimethyl-phenyl)-3-(trifluoromethyl) pyrrolo[2,3-b]pyrazine-7-carbonitrile (300 mg, 45% yield).

Step 3. A solution of 6-amino-2-benzyloxy-5-(3-methoxy-2,6-dimethyl-phenyl)-3-(trifluoromethyl) pyrrolo [2,3-b]pyrazine-7-carbonitrile (300 mg, 0.642 mmol) in sulfuric acid (1 mL) was stirred for 5 h, poured in crushed ice, neutralized with ammonia solution and the resulting precipitate was filtered. The precipitate was washed with water, dried in vacuo to provide 6-amino-2-hydroxy-5-(3-methoxy-2,6-dimethyl-phenyl)-3-(trifluoromethyl) pyrrolo [2,3-b]pyrazine-7-carboxamide (232 mg, 91% yield) as a yellow solid.

Step 4. To a solution of 6-amino-2-hydroxy-5-(3-methoxy-2,6-dimethyl-phenyl)-3-(trifluoromethyl) pyrrolo [2,3-b]pyrazine-7-carboxamide (232 mg, 0.587 mmol) and $Cs_2CO_3$ (200 mg, 0.615 mmol) in DMF (2 mL) was added 1,1,1-trifluoro-N-phenyl-N-(trifluoromethylsulfonyl) methanesulfonamide (210 mg, 0.588 mmol). The mixture was stirred for 1 h, diluted with water and stirred for 20 min. The resulting precipitate was filtered, washed with water, dried in vacuo. Further purification by silica gel chromatography eluting with a gradient of 20 to 100% EtOAc in hexanes provided [6-amino-7-carbamoyl-5-(3-methoxy-2,6-dimethyl-phenyl)-3-(trifluoromethyl) pyrrolo[2,3-b]pyrazin-2-yl] trifluoromethanesulfonate (190 mg, 61% yield) as an off-white solid.

Step 5. To the solution of [6-amino-7-carbamoyl-5-(3-methoxy-2,6-dimethyl-phenyl)-3-(trifluoromethyl) pyrrolo [2,3-b]pyrazin-2-yl] trifluoromethanesulfonate (90 mg, 0.171 mmol) in dioxane (1 mL) were added $PdCl_2(dppf)\cdot CH_2Cl_2$ (14 mg, 17 umol), 4,4,5,5-tetramethyl-2-vinyl-1,3,2-dioxaborolane (30 mg, 0.195 mmol) and aqueous $Na_2CO_3$ (2M, 100 μL). The mixture was stirred at 120° C. for 18 h. The volatiles were removed in vacuo. The residue was purified by preparative HPLC to provide 6-amino-5-(3-methoxy-2,6-dimethyl-phenyl)-3-(trifluoromethyl)-2-vinyl-pyrrolo[2,3-b]pyrazine-7-carboxamide (10 mg, 14% yield) as an off-white solid.

Step 6. For OMe deprotection using $BBr_3$, following general procedure 2 was done on the appropriate intermediate (10 mg, 25 μmol) to provide a residue which was purified by preparative HPLC to provide 6-amino-5-(3-hydroxy-2,6-dimethyl-phenyl)-3-(trifluoromethyl)-2-vinyl-pyrrolo[2,3-b]pyrazine-7-carboxamide (3 mg, 31% yield) as an off-white solid. 1H NMR (400 MHZ, DMSO-d6) δ 9.67 (s, 1H), 7.85 (s, 2H), 7.41 (m, 2H), 7.10-6.89 (m, 3H), 6.50 (m, 1H), 5.60 (m, 1H), 1.76 (s, 3H), 1.68 (s, 3H). MS: [M+1]: 392.2.

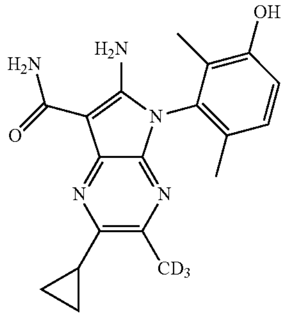 [SMILES: [2H]C([2H])([2H])c1nc2c(nc1C1CC1)c(C(N)=O)c(N)n2-c1c(C)ccc(O)c1C]

Compound 110 (6-amino-2-cyclopropyl-5-(3-hydroxy-2,6-dimethyl-phenyl)-3-(trideuteriomethyl) pyrrolo[2,3-b]pyrazine-7-carboxamide)

Step 1. To a suspension of magnesium turnings (140 mg, 5.76 mmol) in THF (10 mL) was added iodine (13 mg, 52 μmol). The mixture was stirred for 10 min, $CD_3I$ (5.14 mmol, 320 μL) was then added and the mixture was stirred for 18 h under nitrogen to generate an off-white suspension. To the mixture was added $ZnCl_2$ (0.5 M in THF, 10.5 mL) dropwise. After addition, the mixture was stirred for 20 min, then 6-amino-2-benzyloxy-3-bromo-5-(3-methoxy-2,6-dimethyl-phenyl) pyrrolo[2,3-b]pyrazine-7-carbonitrile (500 mg, 1.05 mmol) and $Pd(PPh_3)_4$ (120 mg, 0.103 mmol) were added. The final mixture was stirred at 70° C. for 6 h. The reaction was quenched with HCl 1M, diluted with water, and extracted with EtOAc (2×). The combined organic extracts were washed with water, brine, dried over $Na_2SO_4$, filtered and concentrated in vacuo. The residue was purified by silica gel chromatography eluting with a gradient of 0 to 60% EtOAc in hexanes to provide 6-amino-2-benzyloxy-5-(3-methoxy-2,6-dimethyl-phenyl)-3-(trideuteriomethyl) pyrrolo[2,3-b]pyrazine-7-carbonitrile (328 mg, 75% yield) as an off-white solid.

Step 2. A mixture of 6-amino-2-benzyloxy-5-(3-methoxy-2,6-dimethyl-phenyl)-3-(trideuteriomethyl) pyrrolo[2,3-b]pyrazine-7-carbonitrile (328 mg, 0.788 mmol) in $H_2SO_4$ (2 mL) was stirred for 4 h. The mixture was cooled to 0° C. then neutralized to pH 7 using concentrated aqueous ammonia. The resulting mixture was lyophilized, and the residue was triturated with water and filtered. The solid was dried in vacuo to provide 6-amino-2-hydroxy-5-(3-methoxy-2,6-dimethyl-phenyl)-3-(trideuteriomethyl) pyrrolo[2,3-b]pyrazine-7-carboxamide (220 mg, 81% yield) as an off-white solid.

Step 3. To a solution of 6-amino-2-hydroxy-5-(3-methoxy-2,6-dimethyl-phenyl)-3-(trideuteriomethyl) pyrrolo[2,3-b]pyrazine-7-carboxamide (232 mg, 0.674 mmol) in DMF (3 mL) were added $Cs_2CO_3$ (320 mg, 0.982 mmol) and 1,1,1-trifluoro-N-phenyl-N-(trifluoromethylsulfonyl) methanesulfonamide (360 mg, 1.01 mmol). The mixture was stirred for 1 h. The volatiles were removed in vacuo. The residue was purified by silica gel chromatography eluting with a gradient of 20 to 100% EtOAc in hexanes to provide [6-amino-7-carbamoyl-5-(3-methoxy-2,6-dimethyl-phenyl)-3-(trideuteriomethyl) pyrrolo[2,3-b]pyrazin-2-yl] trifluoromethanesulfonate (200 mg, 62% yield) as an off-white solid.

Step 4. To the solution of [6-amino-7-carbamoyl-5-(3-methoxy-2,6-dimethyl-phenyl)-3-(trideuteriomethyl) pyrrolo[2,3-b]pyrazin-2-yl] trifluoromethanesulfonate (200 mg, 0.420 μmol) in DMF (3 mL) were added lithium chloride (36 mg, 0.849 mmol) and tributyl(cyclopropyl) stannane (275 mg, 0.831 mmol). The mixture was stirred at 120° C. for 10 h. The volatiles were removed in vacuo. The residue was purified by preparative HPLC to provide 6-amino-2-cyclopropyl-5-(3-methoxy-2,6-dimethyl-phenyl)-3-(trideuteriomethyl) pyrrolo[2,3-b]pyrazine-7-carboxamide (80 mg, 52% yield) as an off-white solid.

Step 5. For OMe deprotection using $BBr_3$, following general procedure 2 was done on the appropriate intermediate (35 mg, 95 μmol) to provide a residue which was purified by preparative HPLC to provide 6-amino-2-cyclopropyl-5-(3-hydroxy-2,6-dimethyl-phenyl)-3-(trideuteriomethyl) pyrrolo[2,3-b]pyrazine-7-carboxamide (20 mg, 59% yield) as an off-white solid. 1H NMR (400 MHZ, DMSO-d6) δ 9.49 (s, 1H), 7.24 (s, 1H), 7.14-6.98 (m, 4H), 6.89 (d, J=8.2 Hz, 1H), 2.11 (m, 1H), 1.84-1.68 (s, 3H), 1.64 (s, 3H), 1.04-0.81 (m, 4H). MS: [M+1]: 356.2.

Chiral SFC separation of Compound 110 (20 mg, 0.056 mmol) (Instrument: Waters Prep 15 SFC-MS; Column: Phenomenex Lux Cellulose-2, 10×250 mm, 5 μm; Conditions: Isocratic at 55% MeOH with 45% $CO_2$; Flow Rate: 10 mL/min) provided Compound 111 and Compound 112.

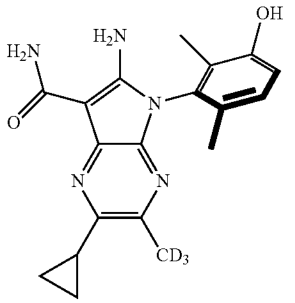

Compound 111 from chiral SFC separation of 110. Peak 1 (retention time 5.33 min, 99.95%): S-6-amino-2-cyclopropyl-5-(3-hydroxy-2,6-dimethyl-phenyl)-3-(trideuteriomethyl) pyrrolo[2,3-b]pyrazine-7-carboxamide (7.8 mg) is obtained as an off-white solid. 1H NMR (400 MHZ, DMSO-d6) δ 9.49 (s, 1H), 7.24 (s, 1H), 7.14-6.98 (m, 4H), 6.89 (d, J=8.2 Hz, 1H), 2.11 (m, 1H), 1.84-1.68 (s, 3H), 1.64 (s, 3H), 1.04-0.81 (m, 4H). MS: [M+1]: 356.2.

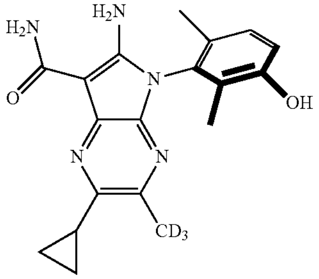

Compound 112 from chiral SFC separation of 110. Peak 2 (retention time 6.00 min, 99.78%): R-6-amino-2-cyclopropyl-5-(3-hydroxy-2,6-dimethyl-phenyl)-3-(trideuteriomethyl) pyrrolo[2,3-b]pyrazine-7-carboxamide (5.3 mg) is obtained as an off-white solid. 1H NMR (400 MHZ, DMSO-d6) δ 9.49 (s, 1H), 7.24 (s, 1H), 7.14-6.98 (m, 4H), 6.89 (d, J=8.2 Hz, 1H), 2.11 (m, 1H), 1.84-1.68 (s, 3H), 1.64 (s, 3H), 1.04-0.81 (m, 4H). MS: [M+1]: 356.2.

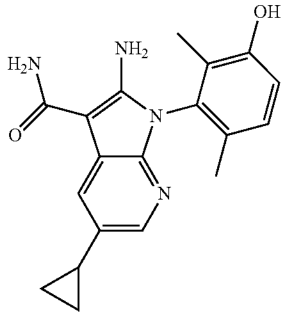 [SMILES: Cc1ccc(O)c(C)c1-n1c(N)c(C(N)=O)c2cc(C3CC3)cnc21]

Compound 116 (2-amino-5-cyclopropyl-1-(3-hydroxy-2,6-dimethyl-phenyl) pyrrolo[2,3-b]pyridine-3-carboxamide)

Step 1. To a solution of tert-butyl N-[5-bromo-3-cyano-1-(3-methoxy-2,6-dimethyl-phenyl) pyrrolo[2,3-b]pyridin-2-yl]carbamate (described in the synthesis of intermediate I) (110 mg, 0.233 mmol) in water (0.5 mL) and dioxane (2 mL) were added cyclopropylboronic acid (41 mg, 0.477 mmol), $Cs_2CO_3$ (270 mg, 0.829 mmol), $PdCl_2(dppf)\cdot CH_2Cl_2$ (18 mg, 22 μmol) in a sealed vial. The mixture was degassed and back filled with nitrogen 3 times. The resulting mixture was heated to 100° C. and stirred 18 h. The volatiles were removed in vacuo. The residue was purified by silica gel chromatography eluting with a gradient of 0 to 60% EtOAc in hexanes to provide 2-amino-5-cyclopropyl-1-(3-methoxy-2,6-dimethyl-phenyl) pyrrolo[2,3-b]pyridine-3-carbonitrile (63 mg, 81% yield) as an off-white solid.

Step 2. To a solution of 2-amino-5-cyclopropyl-1-(3-methoxy-2,6-dimethyl-phenyl) pyrrolo[2,3-b]pyridine-3-carbonitrile (73 mg, 0.220 mmol) in EtOH (1.5 mL) and water (300 μL) were added $LiOH\cdot H_2O$ (50 mg, 1.19 mmol) and $H_2O_2$ (700 uL, 27% w/w aq. soln). The mixture was stirred at 60° C. for 20 min, then the volatiles were removed in vacuo. The residue was purified by silica gel chromatography eluting with a gradient of 20 to 60% EtOAc in hexanes to provide 2-amino-5-cyclopropyl-1-(3-methoxy-2,6-dimethyl-phenyl) pyrrolo[2,3-b]pyridine-3-carboxamide (22 mg, 29% yield) as an off-white solid. Step 3. For OMe deprotection using $BBr_3$, following general procedure 2 was done on the appropriate intermediate (22 mg, 63 μmol) to provide a residue which was purified by preparative HPLC to provide 2-amino-5-cyclopropyl-1-(3-hydroxy-2,6-dimethyl-phenyl) pyrrolo[2,3-b]pyridine-3-carboxamide (15 mg, 71% yield) as an off-white solid. 1H NMR (400 MHZ, DMSO-d6) δ 9.43 (s, 1H), 7.58 (s, 1H), 7.50 (s, 1H), 7.00 (d, J=8.3 Hz, 1H), 6.86 (m, 3H), 6.69 (s, 2H), 1.88 m, 1H), 1.69 (s, 3H), 1.61 (s, 3H), 0.86 (m, 2H), 0.81-0.68 (m, 2H). MS: [M+1]: 337.2.

Chiral SFC separation of Compound 116 (410 mg, 1.22 mmol) (Instrument: Waters Prep 100 SFC-MS; Column: Phenomenex Lux Cellulose-2, 30×250 mm, 5 μm; Conditions: Isocratic at 50% ACN/EtOH 1:1 with 50% CO2; Flow Rate: 70 mL/min) provided Compound 117 and Compound 118.

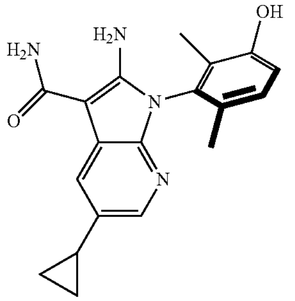

Compound 117 from chiral SFC separation of 116. Peak 1 (retention time 5.60 min, 99.83%): S-2-amino-5-cyclopropyl-1-(3-hydroxy-2,6-dimethyl-phenyl) pyrrolo[2,3-b]pyridine-3-carboxamide (130 mg) is obtained as an off-white solid. 1H NMR (400 MHZ, DMSO-d6) δ 9.52 (s, 1H), 8.12 (d, J=2.2 Hz, 1H), 8.08-7.92 (m, 2H), 7.46 (s, 1H), 7.00 (d, J=8.2 Hz, 2H), 6.86 (d, J=8.3 Hz, 1H), 2.03 (m, 1H), 1.70 (s, 3H), 1.59 (s, 3H), 0.96 (m, 2H), 0.68 (m, 2H). MS: [M+1]: 337.2.

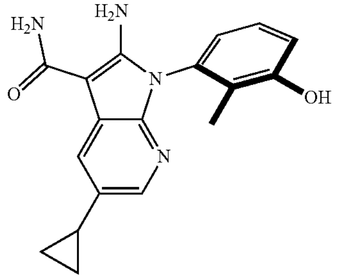

Compound 118 from chiral SFC separation of 116. Peak 2 (retention time 7.81 min, 98.81%): R-2-amino-5-cyclopropyl-1-(3-hydroxy-2,6-dimethyl-phenyl) pyrrolo[2,3-b]pyridine-3-carboxamide (130 mg). 1H NMR (400 MHZ, DMSO-d6) δ9.52 (s, 1H), 8.12 (d, J=2.2 Hz, 1H), 8.08-7.92 (m, 2H), 7.46 (s, 1H), 7.00 (d, J=8.2 Hz, 2H), 6.86 (d, J=8.3 Hz, 1H), 2.03 (m, 1H), 1.70 (s, 3H), 1.59 (s, 3H), 0.96 (m, 2H), 0.68 (m, 2H). MS: [M+1]: 337.2.

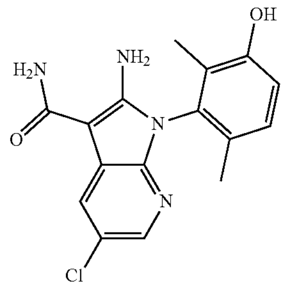 [SMILES: Cc1ccc(O)c(C)c1-n1c(N)c(C(N)=O)c2cc(Cl)cnc21]

Compound 132 (2-amino-5-chloro-1-(3-hydroxy-2, 6-dimethyl-phenyl) pyrrolo[2,3-b]pyridine-3-carboxamide)

Step 1. To a solution of 3-methoxy-2,6-dimethyl-aniline (3.61 g, 23.9 mmol) and 3-bromo-5-chloro-2-fluoro-pyridine (5.02 g, 23.9 mmol) in THF (50 mL) was added LiHMDS solution in THF (1 M, 48 mL) dropwise over 18 min. A 16° C. exotherm was observed. After 30 min, the reaction mixture was diluted with saturated aqueous $NH_4Cl$ and extracted with EtOAc. The organic layer was separated, washed with brine, dried over $Na_2SO_4$, filtered and concentrated. The crude product was purified by flash chromatography (dry load) eluting with a gradient of 0 to 20% EtOAc in heptane. The fractions were combined, concentrated and dried in vacuo to provide 3-bromo-5-chloro-N-(3-methoxy-2,6-dimethyl-phenyl)pyridin-2-amine (6.58 g, 81% yield) as a peach solid.

Step 2. To a suspension of NaH (1.08 g, 24.9 mmol, 60% dispersion in mineral oil) in DME (60 mL) is added propanedinitrile (1.62 g, 24.6 mmol) in DME (15 mL) dropwise. After stirring for 30 min, 3-bromo-5-chloro-N-(3-methoxy-2,6-dimethyl-phenyl)pyridin-2-amine (4.00 g, 11.7 mmol) in DME (15 mL) and $PdCl_2(dppf)\cdot CH_2Cl_2$ (1.08 g, 1.32 mmol) were added. The reaction mixture was flushed with nitrogen bubbling through the solution, then stirred at 100° C. for 5 h. The reaction mixture was cooled to rt and icy water (250 mL) was added dropwise. The resulting precipitate was collected by filtration and washed with water. The solid was air-dried then co-evaporated with toluene (2×), dried in vacuo to afford 4.67 g crude product. Purification by silica gel chromatography (dry load) eluting with a gradient of 0 to 100% EtOAc in heptane. The fractions were combined, concentrated and dried in vacuo, to afford 2-amino-5-chloro-1-(3-methoxy-2,6-dimethyl-phenyl) pyrrolo[2,3-b]pyridine-3-carbonitrile (3.27 g, 85% yield) as an ivory crystalline solid.

Step 3. To a suspension of 2-amino-5-chloro-1-(3-methoxy-2,6-dimethyl-phenyl) pyrrolo[2,3-b]pyridine-3-carbonitrile (7.50 g, 23.0 mmol) in water (60 mL) and reagent alcohol (180 mL) was added $LiOH\cdot H_2O$, 98% (7.22 g, 172 mmol) and $H_2O_2$ (27% w/w aq. solution, 9.8 mL). The mixture was stirred at 60° C. for 30 min, then cooled to rt. Water was added dropwise (500 mL) and the solid was collected by filtration, washed with water and air-dried. The filtrate was diluted with water and a second crop of solid was obtained. Finally the filtrate was extracted with EtOAc (3×). The combined organic extracts were dried over $Na_2SO_4$, filtered and concentrated then dried in vacuo affording a third crop of crude product. The combined crude material was purified by silica gel chromatography using a gradient of 50 to 100% EtOAc in heptane. Pure fractions were combined and concentrated, dried in vacuo to provide 2-amino-5-chloro-1-(3-methoxy-2,6-dimethyl-phenyl) pyrrolo[2,3-b]pyridine-3-carboxamide (3.90 g, 49% yield) as a light yellow solid. Alternatively, nitrile hydrolysis could be performed under $H_2SO_4$ conditions (using the same procedure used for Compound 164) affording 2-amino-5-chloro-1-(3-methoxy-2,6-dimethyl-phenyl) pyrrolo[2,3-b]pyridine-3-carboxamide in quantitative yield.

Step 4. For OMe deprotection using $BBr_3$, following general procedure 2 was used on the appropriate intermediate (3.90 g, 11.3 mmol) to provide a residue which was co-evaporated with MeOH (4×), dried in vacuo, triturated with saturated aqueous $NaHCO_3$ and filtered. The crude product was purified by silica gel chromatography silica using a gradient of 0 to 20% MeOH in $CH_2Cl_2$ to provide 2-amino-5-chloro-1-(3-hydroxy-2,6-dimethyl-phenyl) pyrrolo[2,3-b]pyridine-3-carboxamide (3.54 g, 95% yield) as a light beige solid. 1H NMR (400 MHZ, DMSO-d6) δ 9.54 (s, 1H), 8.14 (d, J=2.2 Hz, 1H), 7.74 (d, J=2.1 Hz, 1H), 7.14 (br s, 2H), 7.06 (d, J=8.3 Hz, 1H), 6.91 (d, J=8.3 Hz, 1H), 6.86 (br s, 2H), 1.74 (s, 3H), 1.65 (s, 3H). MS: [M+1]: 331.1.

Chiral SFC separation of Compound 132 (3.54 g, 10.7 mmol) (Instrument: Waters Prep 100 SFC-MS; Column: Phenomenex Lux Cellulose-2, 30×250 mm, 5 μm; Conditions: Isocratic at 45% ACN/EtOH 1:1 with 55% $CO_2$; Flow Rate: 70 mL/min) provided Compound 133 and Compound 134.

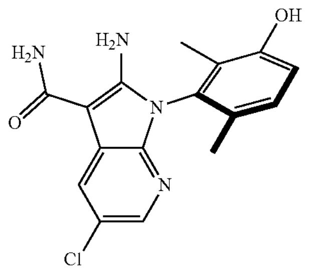

Compound 133 from chiral SFC separation of 132. Peak 1 (retention time 5.37 min, 99.70%): S-2-amino-5-chloro-1-(3-hydroxy-2,6-dimethyl-phenyl) pyrrolo[2,3-b]pyridine-3-carboxamide (1.26 g) is obtained as an off-white solid. 1H NMR (400 MHZ, DMSO-d6) δ 9.54 (s, 1H), 8.14 (d, J=2.2 Hz, 1H), 7.74 (d, J=2.1 Hz, 1H), 7.14 (br s, 2H), 7.06 (dt, J=8.2, 0.7 Hz, 1H), 6.91 (d, J=8.3 Hz, 1H), 6.86 (br s, 2H), 1.74 (d, J=0.7 Hz, 3H), 1.65 (s, 3H). MS: [M+1]: 331.1.

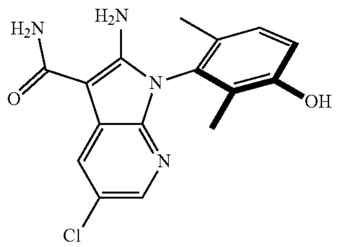

Compound 134 from chiral SFC separation of 132. Peak 2 (retention time 7.79 min, 99.19%): R-2-amino-5-chloro-1-(3-hydroxy-2,6-dimethyl-phenyl) pyrrolo[2,3-b]pyridine-3-carboxamide (1.26 g). 1H NMR (400 MHz, DMSO-d6) δ9.54 (s, 1H), 8.14 (d, J=2.2 Hz, 1H), 7.74 (d, J=2.1 Hz, 1H), 7.14 (br s, 2H), 7.06 (dt, J=8.2, 0.7 Hz, 1H), 6.91 (d, J=8.3 Hz, 1H), 6.86 (br s, 2H), 1.74 (d, J=0.7 Hz, 3H), 1.65 (s, 3H). MS: [M+1]: 331.1.

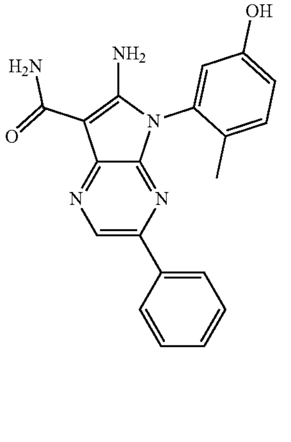 [SMILES: Cc1ccc(O)cc1-n1c(N)c(C(N)=O)c2ncc(-c3ccccc3)nc21]

Compound 150 (6-amino-5-(5-hydroxy-2-methyl-phenyl)-3-phenyl-pyrrolo[2,3-b]pyrazine-7-carboxamide)

Step 1. Intermediate F (101 mg, 0.236 mmol), phenyl boronic acid (29 mg, 0.24 mmol). $Pd(PPh_3)_4$ (30 mg, 0.026 mmol) and potassium phosphate tribasic anhydrous (176 mg, 0.829 mmol) were loaded in a microwave vial, which was flushed with nitrogen, then dioxane (2 mL) was added, the vial was capped and placed in a heat block set to 90° C. After 90 min, the reaction mixture was cooled to rt, diluted with water, extracted with EtOAc (3×). The combined organic extracts were washed with brine, dried over $Na_2SO_4$, filtered and concentrated. The residue was purified by silica gel chromatography eluting with a gradient of 0 to 100% EtOAc in hexanes to provide 6-amino-5-(5-methoxy-2-methyl-phenyl)-3-phenyl-pyrrolo[2,3-b]pyrazine-7-carbonitrile (30 mg, 36% yield) as an orange solid.

Step 2. For nitrile hydrolysis using sulfuric acid, the same procedure used for Compound 164 was done on the appropriate intermediate (28 mg, 0.079 mmol) to provide 6-amino-5-(5-methoxy-2-methyl-phenyl)-3-phenyl-pyrrolo[2,3-b]pyrazine-7-carboxamide (20 mg, 68% yield) as a pale yellow solid.

Step 3. For OMe deprotection using $BBr_3$, following general procedure 2 provided a residue which was purified by preparative HPLC to provide 6-amino-5-(5-hydroxy-2-methyl-phenyl)-3-phenyl-pyrrolo[2,3-b]pyrazine-7-carboxamide (11 mg, 57% yield) as a white fluffy solid. 1H NMR (400 MHZ, DMSO-d6) δ 9.71 (br s, 1H), 8.73 (s, 1H), 7.92-7.76 (m, 2H), 7.49 (br s, 2H), 7.45-7.37 (m, 3H), 7.35-7.28 (m, 2H), 7.26 (br s, 1H), 6.92 (dd, J=8.3, 2.6 Hz, 1H), 6.77 (d, J=2.5 Hz, 1H), 1.89 (s, 3H). MS: [M+1]: 360.2.

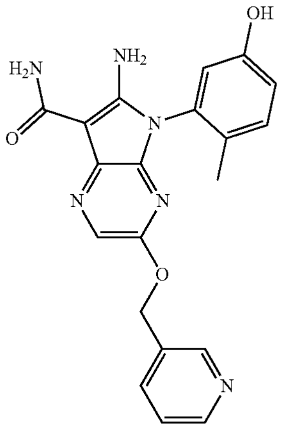 [SMILES: Cc1ccc(O)cc1-n1c(N)c(C(N)=O)c2ncc(OCc3cccnc3)nc21]

Compound 153 (6-amino-5-(5-hydroxy-2-methyl-phenyl)-3-(3-pyridylmethoxy) pyrrolo[2,3-b]pyrazine-7-carboxamide)

Step 1. To a mixture of Intermediate E (51 mg, 0.16 mmol), 3-pyridylmethanol (41 mg, 0.38 mmol) and triphenylphosphine (62 mg, 0.24 mmol) in THF (2 mL) was added diisopropyl azodicarboxylate (47 uL, 0.24 mmol). The resulting mixture was stirred 18 h. Additional triphenylphosphine (62 mg, 0.24 mmol), 3-pyridylmethanol (41 mg, 0.38 mmol) and diisopropyl azodicarboxylate (47 uL, 0.24 mmol) were added and the mixture was stirred for another 2.5 h and concentrated to dryness. The crude residue was purified by silica gel chromatography eluting with a gradient of 0 to 100% EtOAc in hexanes to provide 6-amino-5-[5-(methoxymethoxy)-2-methyl-phenyl]-3-(3-pyridylmethoxy) pyrrolo[2,3-b]pyrazine-7-carbonitrile (115 mg) as an impure amber gum (containing triphenyl phosphine oxide), that was carried to next step without further purification.

Step 2. To a solution of 6-amino-5-[5-(methoxymethoxy)-2-methyl-phenyl]-3-(3-pyridylmethoxy) pyrrolo[2,3-b]pyrazine-7-carbonitrile (65.0 mg, 0.156 mmol) in MeOH (1.5 mL) was added HCl in dioxane (4 M, 1.50 mL). After stirring for 75 min, the reaction mixture was concentrated and dried in vacuo. Crude 6-amino-5-(5-hydroxy-2-methyl-phenyl)-3-(3-pyridylmethoxy) pyrrolo[2,3-b]pyrazine-7-carbonitrile assumed bis HCl salt was carried to the next step without further purification.

Step 3. To a solution of crude 6-amino-5-(5-hydroxy-2-methyl-phenyl)-3-(3-pyridylmethoxy) pyrrolo[2,3-b]pyrazine-7-carbonitrile (70 mg, 0.156 mmol, assuming bis HCl salt) in MeOH (1.0 mL) was added aqueous NaOH solution (4 M, 1.0 mL). Reaction mixture was transferred to a preheated heat block at 90° C. and stirred for 18 h. After cooling down to rt, the mixture was neutralized with 3N HCl and diluted with water. The precipitate was collected by filtration and washed with water, then air-dried. Purification by preparative HPLC provided 6-amino-5-(5-hydroxy-2-methyl-phenyl)-3-(3-pyridylmethoxy) pyrrolo[2,3-b]pyrazine-7-carboxamide (4 mg, 7% yield) as a white fluffy solid. 1H NMR (400 MHZ, DMSO-d6) δ 9.68 (br s, 1H), 8.48 (d, J=2.2 Hz, 1H), 8.42 (dd, J=4.8, 1.7 Hz, 1H), 7.85 (s, 1H), 7.65 (dt, J=7.8, 2.0 Hz, 1H), 7.26 (ddd, J=7.9, 4.9, 0.9 Hz, 1H), 7.23 (d, J=8.6 Hz, 1H), 7.15 (br s, 1H), 7.04 (br s, 1H), 7.00 (br s, 2H), 6.87 (dd, J=8.3, 2.6 Hz, 1H), 6.66 (d, J=2.5 Hz, 1H), 5.09 (d, J=12.2 Hz, 1H), 5.08 (d, J=12.2 Hz, 1H), 1.72 (s, 3H). MS: [M+1]: 391.2.

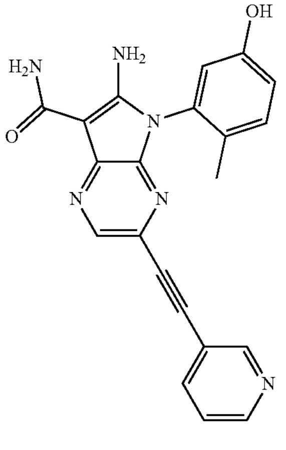 [SMILES: Cc1ccc(O)cc1-n1c(N)c(C(N)=O)c2ncc(C#Cc3cccnc3)nc21]

Compound 160 (6-amino-5-(5-hydroxy-2-methyl-phenyl)-3-[2-(3-pyridyl) ethynyl]pyrrolo[2,3-b]pyrazine-7-carboxamide)

Step 1. To a microwave vial charged with Intermediate F (251 mg, 0.549 mmol), $Pd(PPh_3)_4$ (65 mg, 0.056 mmol), CuI (43 mg, 0.023 mmol) and flushed with nitrogen was added 3-ethynylpyridine (72 mg, 0.698 mmol) in DMF (2.5 mL) followed by $Et_3N$ (610 UL, 4.39 mmol). The vial was capped then transferred to a preheated heat block (120° C.). After 1 h, the reaction mixture was concentrated under vacuum, then taken in THF and adsorbed on silica. The volatiles were evaporated under vacuum and the residue was purified by silica gel chromatography eluting with a gradient of 0 to 100% EtOAc in hexanes then 0 to 20% MeOH in EtOAc, to provide 6-amino-5-[5-(methoxymethoxy)-2-methyl-phenyl]-3-[2-(3-pyridyl)ethynyl]pyrrolo[2,3-b]pyrazine-7-carbonitrile (260 mg, 99%) as a tan solid.

Step 2. To a suspension of 6-amino-5-[5-(methoxymethoxy)-2-methyl-phenyl]-3-[2-(3-pyridyl)ethynyl]pyrrolo[2,3-b]pyrazine-7-carbonitrile (225 mg, 0.548 mmol) in MeOH (3 mL) was added HCl in dioxane (4 M, 3 mL). After stirring for 30 min, the reaction mixture was concentrated to dryness then dried in vacuo, affording 6-amino-5-(5-hydroxy-2-methyl-phenyl)-3-[2-(3-pyridyl) ethynyl]pyrrolo[2,3-b]pyrazine-7-carbonitrile (319 mg, bis HCl salt) as a tan sticky solid which was used in the next step without further purification.

Step 3. 6-amino-5-(5-hydroxy-2-methyl-phenyl)-3-[2-(3-pyridyl)ethynyl]pyrrolo[2,3-b]pyrazine-7-carbonitrile bis HCl salt (241 mg, 0.548 mmol) was stirred in conc. $H_2SO_4$ (2 mL). After 3 days, the reaction mixture was quenched with crushed ice, placed in ice bath and made alkaline (pH about 10) with 1:1 $NH_4OH/H_2O$. The solids were collected by filtration and air-dried overnight, affording crude product as an ochre yellow solid (249 mg). A portion (67 mg) was purified by preparative HPLC to provide 6-amino-5-(5-hydroxy-2-methyl-phenyl)-3-[2-(3-pyridyl)ethynyl]pyrrolo [2,3-b]pyrazine-7-carboxamide (26 mg, 46% calculated yield) as a light yellow fluffy solid. 1H NMR (400 MHZ, DMSO-d6) δ 9.77 (br s, 1H), 8.75 (dd, J=2.3, 0.9 Hz, 1H), 8.57 (dd, J=4.9, 1.7 Hz, 1H), 8.42 (s, 1H), 7.98 (dt, J=7.9, 1.9 Hz, 1H), 7.73 (br s, 2H), 7.44 (ddd, J=8.0, 4.9, 0.9 Hz, 1H), 7.35 (br d, J=4.4 Hz, 2H), 7.29 (d, J=8.4 Hz, 1H), 6.94 (dd, J=8.3, 2.6 Hz, 1H), 6.77 (d, J=2.6 Hz, 1H), 1.85 (s, 3H). MS: [M+1]: 385.3.

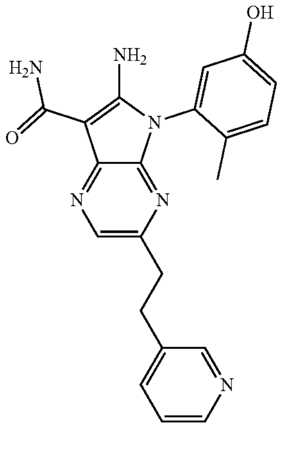 [SMILES: Cc1ccc(O)cc1-n1c(N)c(C(N)=O)c2ncc(CCc3cccnc3)nc21]

Compound 162 (6-amino-5-(5-hydroxy-2-methyl-phenyl)-3-[2-(3-pyridyl)ethyl]pyrrolo[2,3-b]pyrazine-7-carboxamide)

Step 1. 6-amino-5-(5-hydroxy-2-methyl-phenyl)-3-[2-(3-pyridyl)ethynyl]pyrrolo[2,3-b]pyrazine-7-carboxamide (102 mg, 0.265 mmol) and palladium on carbon (30 mg, 0.028 mmol, 10% w/w) was stirred in MeOH (3 mL) under hydrogen atmosphere overnight, filtered on disk filter using MeOH, concentrated and purified by preparative HPLC to provide 6-amino-5-(5-hydroxy-2-methyl-phenyl)-3-[2-(3-pyridyl)ethyl]pyrrolo[2,3-b]pyrazine-7-carboxamide (7 mg, 7% yield) as an off-white fluffy solid. 1H NMR (400 MHZ, DMSO-d6) δ 8.34 (dd, J=4.8, 1.7 Hz, 1H), 8.31 (dd, J=2.3, 0.8 Hz, 1H), 7.95 (s, 1H), 7.55 (ddd, J=7.8, 2.4, 1.7 Hz, 1H), 7.34 (br s, 1H), 7.30 (br s, 2H), 7.28 (dd, J=8.4, 0.8 Hz, 1H), 7.23 (ddd, J=7.8, 4.8, 0.9 Hz, 1H), 7.15 (br s, 1H), 6.92 (dd, J=8.3, 2.6 Hz, 1H), 6.72 (d, J=2.6 Hz, 1H), 3.01-2.93 (m, 2H), 2.92-2.84 (m, 2H), 1.82 (s, 3H). MS: [M+1]: 389.2.

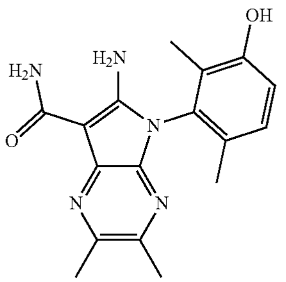 [SMILES: Cc1ccc(O)c(C)c1-n1c(N)c(C(N)=O)c2nc(C)c(C)nc21]

Compound 164 (6-amino-5-(3-hydroxy-2,6-dimethyl-phenyl)-2,3-dimethyl-pyrrolo[2,3-b]pyrazine-7-carboxamide)

Step 1. To a suspension of NaH (3.54 g, 92 mmol, 60% dispersion in mineral oil) in THF (100 mL) at 0° C. was added malononitrile (3.99 g, 60.4 mmol) in THF (30 mL) dropwise via an addition funnel. The cold bath was removed at the end of the addition and the resulting mixture was allowed to stir for 45 min at rt. 2,3-dichloro-5,6-dimethyl-pyrazine (5.49 g, 31.0 mmol) and $Pd(PPh_3)_4$ (1.76 g, 1.52 mmol) were added, the reaction mixture was refluxed for 3.25 h, cooled to rt, poured into 200 mL 1:1 crushed ice and 1N HCl, and extracted with DCM (3×). The combined organic layers were washed with brine, dried over $Na_2SO_4$, filtered and concentrated. The crude product was adsorbed on silica using DCM/THF and purified by silica gel chromatography eluting with a gradient of 0 to 100% EtOAc in hexanes. Mix fractions were re-purified by a second silica gel chromatography using same conditions. Clean fractions from both columns were combined, concentrated and dried in vacuo to afford 2-(3-chloro-5,6-dimethyl-pyrazin-2-yl) propanedinitrile (5.0 g, 78% yield) as an orange solid.

Step 2. The reaction was split in 3 vials containing ⅓ of the amounts each. The microwave vials were charged with 2-(3-chloro-5,6-dimethyl-pyrazin-2-yl) propanedinitrile (3.04 g, 14.7 mmol), 3-methoxy-2,6-dimethyl-aniline (6.61 g, 43.7 mmol), potassium tert-butoxide (3.30 g, 29.4 mmol) and Pd-PEPPSI™—SIPr catalyst (513 mg, 0.752 mmol), flushed with nitrogen three times, then dry NMP (30 mL) was added, flushed again with nitrogen, capped and submitted to microwave irradiation (100° C.) for 30 min. The vials were combined and diluted with EtOAc, saturated aqueous $NH_4Cl$ and water. The layers were separated, and the aqueous layer was extracted twice with EtOAc. The combined organic extracts were washed with brine, dried over $Na_2SO_4$, filtered and concentrated in vacuo. The crude product was purified by silica gel chromatography eluting with a gradient of 0 to 100% EtOAc in heptane. Desired fractions were combined, concentrated and dried in vacuo to provide 6-amino-5-(3-methoxy-2,6-dimethyl-phenyl)-2,3-dimethyl-pyrrolo[2,3-b]pyrazine-7-carbonitrile (2.57 g, 54% yield) as a yellow solid.

Step 3. (General procedure for nitrile hydrolysis using sulfuric acid) 6-amino-5-(3-methoxy-2,6-dimethyl-phenyl)-2,3-dimethyl-pyrrolo[2,3-b]pyrazine-7-carbonitrile (7.11 g, 22.1 mmol) was dissolved in concentrated sulfuric acid (70 mL), then stirred for 45 min. The reaction mixture was slowly poured into crushed ice (500 cc), then placed in an ice bath and neutralized to pH 8-9 with concentrated $NH_4OH$ (about 190 mL), maintaining internal temperature below 35° C. After stirring for 1 h, the precipitate was filtered, washed with water, air-dried, then further dried by co-evaporation with toluene under vacuum then dried in vacuo to afford 6-amino-5-(3-methoxy-2,6-dimethyl-phenyl)-2,3-dimethyl-pyrrolo[2,3-b]pyrazine-7-carboxamide (7.5 g, quantitative yield) as a yellow solid.

Step 4. To a suspension of 6-amino-5-(3-methoxy-2,6-dimethyl-phenyl)-2,3-dimethyl-pyrrolo[2,3-b]pyrazine-7-carboxamide (7.50 g, 22.1 mmol) in DCM (132 mL) was added $BBr_3$ (66.3 mmol, 6.4 mL) slowly. After stirring for 70 min, the reaction mixture was concentrated to dryness, resuspended in DCM, and MeOH was added (exotherm observed). After concentrating, the crude mixture was co-evaporated again with DCM/MeOH then carefully triturated with saturated aqueous $NaHCO_3$ (100 mL), diluted with water and stirred for 1.5 h. The precipitate was filtered, washed with water and air-dried then purified by silica gel chromatography (dry load) eluting with a gradient of 0 to 20% MeOH in DCM. Mixed fractions were combined and re-purified by silica gel chromatography using the same conditions. The clean material from both columns was combined, concentrated then dried in vacuo, affording 6-amino-5-(3-hydroxy-2,6-dimethyl-phenyl)-2,3-dimethyl-pyrrolo[2,3-b]pyrazine-7-carboxamide (5.3 g, 74% yield). 1H NMR (400 MHZ, DMSO-d6) δ9.57 (s, 1H), 7.45 (br s, 1H), 7.18-7.02 (m, 4H), 6.93 (d, J=8.3 Hz, 1H), 2.48-2.45 (m, 3H), 2.35-2.24 (m, 3H), 1.81-1.73 (m, 3H), 1.68 (s, 3H). MS: [M+1]: 326.4.

Chiral SFC separation of Compound 164 (5.40 g, 16.6 mmol) (Instrument: Waters Prep 100 SFC-MS; Column: Phenomenex Lux Cellulose-2, 30×250 mm, 5 μm; Conditions: Isocratic at 55% ACN/EtOH 1:1 with 45% CO2; Flow Rate: 70 mL/min) provided Compound 165 and Compound 166.

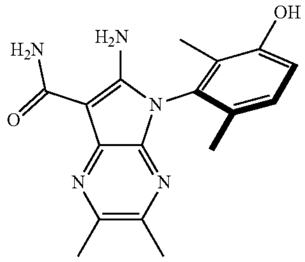

Compound 165 from chiral SFC separation of 164. Peak 1 (retention time 4.07 min, 99.99%): S-6-amino-5-(3-hydroxy-2,6-dimethyl-phenyl)-2,3-dimethyl-pyrrolo[2,3-b]pyrazine-7-carboxamide (1.31 g) was obtained as a light beige solid. 1H NMR (400 MHZ, DMSO-d6) δ 9.57 (s, 1H), 7.45 (br s, 1H), 7.12 (br s, 1H), 7.09 (br s, 2H), 7.06 (d, J=8.8 Hz, 1H), 6.93 (d, J=8.3 Hz, 1H), 2.47 (s, 3H), 2.31 (s, 3H), 1.76 (s, 3H), 1.68 (s, 3H). MS: [M+1]: 327.3.

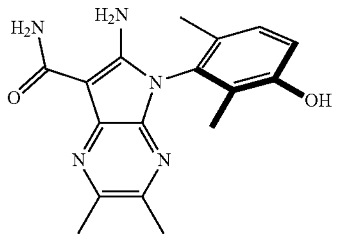

Compound 166 from chiral SFC separation of 164. Peak 2 (retention time 4.81 min, 99.83%): R-6-amino-5-(3-hydroxy-2,6-dimethyl-phenyl)-2,3-dimethyl-pyrrolo[2,3-b]pyrazine-7-carboxamide (1.43 g) was obtained as a light beige solid. 1H NMR (400 MHZ, DMSO-d6) δ 9.57 (s, 1H), 7.45 (br s, 1H), 7.12 (br s, 1H), 7.09 (br s, 2H), 7.07 (d, J=8.4 Hz, 1H), 6.93 (d, J=8.3 Hz, 1H), 2.47 (s, 3H), 2.31 (s, 3H), 1.76 (s, 3H), 1.68 (s, 3H). MS: [M+1]: 327.3.

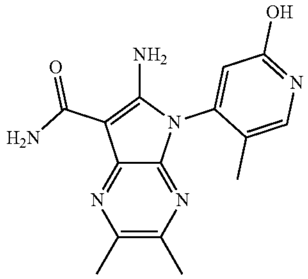 [SMILES: Cc1cnc(O)cc1-n1c(N)c(C(N)=O)c2nc(C)c(C)nc21]

Compound 169 (6-amino-5-(2-hydroxy-5-methyl-4-pyridyl)-2,3-dimethyl-pyrrolo[2,3-b]pyrazine-7-carboxamide)

Step 1. A MW vial was charged with 2-(3-chloro-5,6-dimethyl-pyrazin-2-yl) propanedinitrile (intermediate A, 98 mg, 0.47 mmol), 2-[(4-methoxyphenyl) methoxy]-5-methyl-pyridin-4-amine (arylamine A13, 343 mg, 1.40 mmol), potassium tert-butoxide (109 mg, 0.971 mmol) and Pd-PEPPSI™—SIPr catalyst (19 mg, 0.028 mmol), flushed with $N_2$ (house-vac then $N_2$, 3×), dry NMP (1 mL) was added, flushed again with $N_2$, capped and submitted to MW irradiation (100° C.) for 30 min then heated overnight to 100° C. (heat block). The reaction mixture was cooled down to RT, adsorbed on silica using DCM. Purification by flash chromatography on silica gel (0-100% EtOAc in heptanes then 0-10% MeOH in EtOAc) and evaporation of the appropriate fractions furnished material which was purified again by flash chromatography on silica gel (0-100% EtOAc in DCM). Appropriate fractions were combined, concentrated and dried in vacuo to provide 6-amino-5-[2-[(4-methoxyphenyl) methoxy]-5-methyl-4-pyridyl]-2,3-dimethyl-pyrrolo[2,3-b]pyrazine-7-carbonitrile (34 mg, 17% yield) as a light yellow solid. MS: [M+1]: 415.2.

Step 2: Following general procedure 1, 6-amino-5-[2-[(4-methoxyphenyl) methoxy]-5-methyl-4-pyridyl]-2,3-dimethyl-pyrrolo[2,3-b]pyrazine-7-carbonitrile (34 mg, 0.082 mmol) was treated with $H_2SO_4$ to provide 6-amino-5-(2-hydroxy-5-methyl-4-pyridyl)-2,3-dimethyl-pyrrolo[2,3-b]pyrazine-7-carboxamide (compound 169, 15 mg, 59% yield) as a fluffy yellow solid after precipitation from the reaction mixture, redissolving the sample in $MeCN/H_2O$ and lyophilization. 1H NMR (400 MHZ, DMSO-d6) δ 7.48 (br s, 1H), 7.43 (br s, 3H), 7.17 (br s, 1H), 6.44 (s, 1H), 2.47 (s, 3H), 2.36 (s, 3H), 1.64 (s, 3H). MS: [M+1]: 313.1.

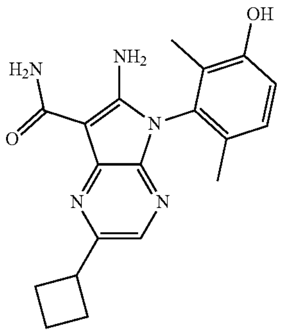 [SMILES: Cc1ccc(O)c(C)c1-n1c(N)c(C(N)=O)c2nc(C3CCC3)cnc21]

Compound 173 (6-amino-2-cyclobutyl-5-(3-hydroxy-2,6-dimethyl-phenyl) pyrrolo[2,3-b]pyrazine-7-carboxamide)

Step 1. A microwave vial was loaded with [6-amino-7-carbamoyl-5-(3-methoxy-2,6-dimethyl-phenyl) pyrrolo[2,3-b]pyrazin-2-yl] trifluoromethanesulfonate (200 mg, 0.435 μmol) and $Pd(PPh_3)_4$ (56 mg, 49 μmol), flushed with nitrogen, THF (2 mL) was added, bubbled through with nitrogen, cyclobutyl zinc bromide solution (0.5 M, 4.35 mL) added, bubbled through with nitrogen, capped and transferred to a heat block preheated at 70° C. The reaction mixture was stirred 90 min, cooled to rt, quenched with saturated aqueous $NH_4Cl$ and extracted with EtOAc (2×). The combined organic extracts were washed with brine, dried over $Na_2SO_4$, filtered and concentrated. The residue was purified by silica gel chromatography eluting with a gradient of 0 to 100% EtOAc in hexanes to provide 6-amino-2-cyclobutyl-5-(3-methoxy-2,6-dimethyl-phenyl) pyrrolo[2,3-b]pyrazine-7-carboxamide (110 mg, 69% yield) as a white/beige solid.

Step 2. For OMe deprotection using $BBr_3$, following general procedure 2 was done on the appropriate intermediate (110 mg, 0.301 mmol) to provide a residue which was purified by preparative HPLC to provide 6-amino-2-cyclobutyl-5-(3-hydroxy-2,6-dimethyl-phenyl) pyrrolo[2,3-b]pyrazine-7-carboxamide (54 mg, 51% yield) as an off-white fluffy solid. 1H NMR (400 MHZ, DMSO-d6) δ 9.58 (s, 1H), 7.61 (s, 1H), 7.59 (br s, 1H), 7.32 (br s, 2H), 7.23 (br s, 1H), 7.07 (d, J=8.3 Hz, 1H), 6.93 (d, J=8.3 Hz, 1H), 3.66 (p, J=8.6 Hz, 1H), 2.42-2.17 (m, 4H), 2.10-1.94 (m, 1H), 1.88 (td, J=8.5, 4.0 Hz, 1H), 1.76 (s, 3H), 1.68 (s, 3H). MS: [M+1]: 352.4.

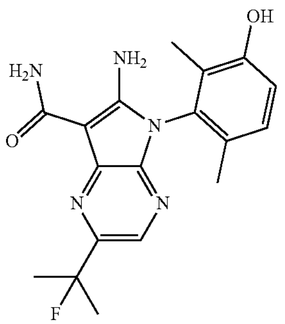 [SMILES: Cc1ccc(O)c(C)c1-n1c(N)c(C(N)=O)c2nc(C(C)(C)F)cnc21]

Compound 178 (6-amino-2-(1-fluoro-1-methyl-ethyl)-5-(3-hydroxy-2,6-dimethyl-phenyl) pyrrolo[2,3-b]pyrazine-7-carboxamide)

Step 1. To a solution of 6-amino-5-(3-hydroxy-2,6-dimethyl-phenyl)-2-(1-hydroxy-1-methyl-ethyl) pyrrolo[2,3-b]pyrazine-7-carboxamide (Compound 190, 46.0 mg, 0.129 mmol) in DCM (2 mL) at −78° C. was added Deoxo-Fluor® solution (315 mg, 0.712 mmol, 50% in THF) dropwise. The mixture was stirred at 0° C. for 45 min, concentrated and purified by preparative HPLC to provide 6-amino-2-(1-fluoro-1-methyl-ethyl)-5-(3-hydroxy-2,6-dimethyl-phenyl) pyrrolo[2,3-b]pyrazine-7-carboxamide (23 mg, 50% yield) as an off-white fluffy solid. 1H NMR (400 MHZ, DMSO-d6) δ9.63 (s, 1H), 7.92 (d, J=0.6 Hz, 1H), 7.46 (br s, 2H), 7.37 (br s, 1H), 7.26 (br s, 1H), 7.08 (d, J=8.3 Hz, 1H), 6.94 (d, J=8.3 Hz, 1H), 1.75 (d, J=22.4 Hz, 6H), 1.77 (s, 3H), 1.69 (s, 3H). 19F NMR (376 MHZ, DMSO-d6) δ −137.78 (hept, J=22.1 Hz). MS: [M+1]: 358.2.

Chiral SFC separation of Compound 178 (19 mg, 0.053 mmol) (Instrument: Mettler Toledo Minigram SFC; Column: Phenomenex Lux Cellulose-2, 10×250 mm, 5 μm; Conditions: Isocratic at 45% ACN/EtOH 1:1 with 55% $CO_2$; Flow Rate: 10 mL/min) provided Compound 179 and Compound 180.

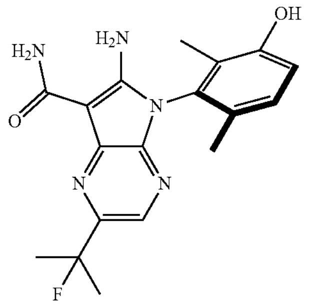

Compound 179 from chiral SFC separation of 178. Peak 1 (retention time 3.63 min, 99.87%): S-6-amino-2-(1-fluoro-1-methyl-ethyl)-5-(3-hydroxy-2,6-dimethyl-phenyl) pyrrolo[2,3-b]pyrazine-7-carboxamide (5 mg) as a white fluffy solid. 1H NMR (400 MHZ, DMSO-d6) δ 9.63 (s, 1H), 7.92 (s, 1H), 7.46 (br s, 2H), 7.42-7.32 (m, 1H), 7.30-7.19 (m, 1H), 7.08 (d, J=8.3 Hz, 1H), 6.94 (d, J=8.2 Hz, 1H), 1.77 (s, 3H), 1.75 (d, J=22.4 Hz, 6H), 1.69 (s, 3H). 19F NMR (376 MHZ, DMSO-d6) δ −137.75 (hept, J=22.1 Hz). MS: [M+1]: 358.2.

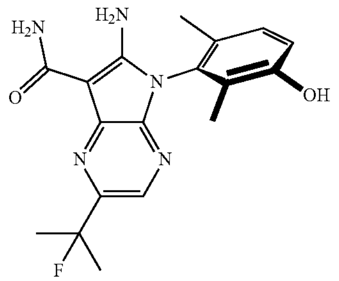

Compound 180 from chiral SFC separation of 178. Peak 2 (retention time 4.00 min, 99.90%): R-6-amino-2-(1-fluoro-1-methyl-ethyl)-5-(3-hydroxy-2,6-dimethyl-phenyl) pyrrolo[2,3-b]pyrazine-7-carboxamide (5 mg) as a white fluffy solid. 1H NMR (400 MHZ, DMSO-d6) δ 9.63 (s, 1H), 7.92 (s, 1H), 7.46 (br s, 2H), 7.37 (br s, 1H), 7.26 (br s, 1H), 7.08 (d, J=8.5 Hz, 1H), 6.94 (d, J=8.3 Hz, 1H), 1.77 (s, 3H), 1.74 (d, J=22.4 Hz, 6H), 1.69 (s, 3H). 19F NMR (376 MHZ, DMSO-d6) δ −137.75 (hept, J=22.1 Hz). MS: [M+1]: 358.2.

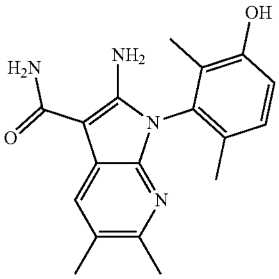 [SMILES: Cc1cc2c(C(N)=O)c(N)n(-c3c(C)ccc(O)c3C)c2nc1C]

Compound 181 2-amino-1-(3-hydroxy-2,6-dimethyl-phenyl)-5,6-dimethyl-pyrrolo[2,3-b]pyridine-3-carboxamide (from method D)

Step 1. A pressure vessel was loaded with 3-bromo-2-chloro-6-methyl-5-nitro-pyridine (10.11 g, 40.2 mmol) and 3-methoxy-2,6-dimethylaniline (Aniline A2, 9.20 g, 60.8 mmol). NMP (40 mL) and 2,6-dimethylpyridine (8.58 g, 80.1 mmol, 9.3 mL) were added and the reaction mixture was heated to 130° C. (pellet bath) for 5 days until satisfactory conversion as assessed by UPLCMS was achieved. The reaction mixture was cooled to RT and the resulting paste transferred to a conical flask and 500 mL HCl 0.5 N was added dropwise while stirring, resulting in a sticky gum. The supernatant was filtered on a Buchner funnel. The remaining gum was washed with $H_2O$, dissolved in DCM, and combined with the solid which had also been dissolved in DCM (200 mL total). The DCM solution was dried over $Na_2SO_4$, filtered and concentrated. The crude residue was purified by silica gel chromatography (dry load) eluting with a gradient of 0 to 100% DCM in heptanes to provide 3-bromo-N-(3-methoxy-2,6-dimethyl-phenyl)-6-methyl-5-nitro-pyridin-2-amine (10.5 g, 71% yield) as a light yellow solid.

Step 2. To a RBF containing sodium hydride (3.13 g, 72.2 mmol, 60% w/w in mineral oil) in DME (150 mL) was added a solution of propanedinitrile (4.75 g, 71.9 mmol) in DME (50 mL) slowly. After stirring for 1 h, 3-bromo-N-(3-methoxy-2,6-dimethyl-phenyl)-6-methyl-5-nitro-pyridin-2-amine (10.5 g, 28.7 mmol) and Pd(dppf)$Cl_2$·DCM (2.31 g, 2.83 mmol) were added. The resulting mixture was degassed by bubbling $N_2$ through solution, equipped with a condenser, and heated to 95° C. for 1 h. The reaction mixture was cooled to RT, poured into saturated aqueous $NH_4Cl$ and extracted with DCM (3×). The combined organic extracts were washed with $H_2O$, brine, dried over $Na_2SO_4$, filtered and adsorbed on silica. The crude residue was purified by silica gel chromatography (dry load) eluting with a gradient of 0 to 100% EtOAc in heptanes. Appropriate fractions were combined, concentrated and the resulting solid was triturated with DCM, filtered, and dried in vacuo, affording 2-amino-1-(3-methoxy-2,6-dimethyl-phenyl)-6-methyl-5-nitro-pyrrolo[2,3-b]pyridine-3-carbonitrile (7.97 g, 79% yield) as a bright yellow solid. A second crop of material was obtained from the filtrate from the previous trituration by purification by flash chromatography and trituration in the same fashion, providing additional 2-amino-1-(3-methoxy-2,6-dimethyl-phenyl)-6-methyl-5-nitro-pyrrolo[2,3-b]pyridine-3-carbonitrile (1.04 g, 10% yield) as a dark yellow solid.

Step 3. To a solution of 2-amino-1-(3-methoxy-2,6-dimethyl-phenyl)-6-methyl-5-nitro-pyrrolo[2,3-b]pyridine-3-carbonitrile (9.0 g, 25.6 mmol) in THF (120 mL) was added triethylamine (7.99 g, 78.9 mmol, 11 mL), DMAP (312 mg, 2.55 mmol) and tert-butoxycarbonyl tert-butyl carbonate (17.0 g, 77.9 mmol). The mixture was stirred at 50° C. for 40 min. The heating was stopped, and ethylenediamine (6.20 g, 103 mmol, 6.90 mL) was added and the mixture was stirred at RT for 45 min, then diluted with $H_2O$ and DCM. The layers were separated and the aqueous layer was extracted with DCM (2×). The combined organic extracts were washed with half-saturated brine, dried over $Na_2SO_4$, filtered and concentrated. The crude residue was purified by silica gel chromatography eluting with a gradient of 0 to 60% EtOAc in heptanes to provide tert-butyl N-[3-cyano-1-(3-methoxy-2,6-dimethyl-phenyl)-6-methyl-5-nitro-pyrrolo[2,3-b]pyridin-2-yl]carbamate (13.94 g, quantitative yield) as an off-white solid, which was contaminated with tert-butyl N-[2-(tert-butoxycarbonylamino)ethyl]carbamate (50 mol % by 1H NMR).

Step 4. To a RBF containing tert-butyl N-[3-cyano-1-(3-methoxy-2,6-dimethyl-phenyl)-6-methyl-5-nitro-pyrrolo[2,3-b]pyridin-2-yl]carbamate (13.94 g, 25.6 mmol) (assumed quantitative from the previous step) in DCM (280 mL) and MeOH (280 mL) was added palladium on carbon (2.08 g, 1.95 mmol, 10% w/w) as a slurry in some of the solvent mixture. The reaction mixture was flushed with $H_2$ and stirred under $H_2$ atmosphere (balloon) overnight. The reaction mixture was flushed with $N_2$, filtered on a celite pad, rinsed with DCM and MeOH. The filtrate was concentrated and dried in vacuo, affording a light yellow solid which was purified by silica gel chromatography (dry load) eluting with a gradient of EtOAc (20 to 100%) in heptanes. Appropriate fractions were combined and concentrated in vacuo to afford tert-butyl N-[5-amino-3-cyano-1-(3-methoxy-2,6-dimethyl-phenyl)-6-methyl-pyrrolo[2,3-b]pyridin-2-yl]carbamate (9.34 g, 87% yield) as an off-white solid.

Step 5. To a solution of tert-butyl N-[5-amino-3-cyano-1-(3-methoxy-2,6-dimethyl-phenyl)-6-methyl-pyrrolo[2,3-b]pyridin-2-yl]carbamate (10.34 g, 24.5 mmol) in acetonitrile (100 mL) and DMF (60 mL) was added tert-butyl nitrite (5.20 g, 50.5 mmol, 6.0 mL), followed by copper (II) bromide (6.58 g, 29.4 mmol). The mixture was heated to 70° C. for 35 min, cooled to RT, diluted with $H_2O$ (600 mL) and $NH_4OH$ conc (30 mL) and extracted with EtOAc (3×). The combined organic extracts were washed with saturated $NH_4Cl$ (2×), half-saturated brine, dried over $Na_2SO_4$, filtered and concentrated. The residue was purified by silica gel chromatography (dry load) eluting with a gradient of EtOAc (0 to 100%) in heptanes. Appropriate fractions were combined and concentrated in vacuo to afford tert-butyl N-[5-bromo-3-cyano-1-(3-methoxy-2,6-dimethyl-phenyl)-6-methyl-pyrrolo[2,3-b]pyridin-2-yl]carbamate (6.18 g, 52% yield) as an ivory solid.

Step 6. Tert-butyl N-[5-bromo-3-cyano-1-(3-methoxy-2,6-dimethyl-phenyl)-6-methyl-pyrrolo[2,3-b]pyridin-2-yl]carbamate (6.18 g, 12.7 mmol) in EtOH (60 mL) was treated with aqueous HCl (6M, 34 mL) and stirred for 70 min at 80° C. then cooled to RT and concentrated. The residue was dissolved in MeOH, made alkaline with excess $Et_3N$ and concentrated again. The residue was purified by silica gel chromatography (dry load) eluting with a gradient of EtOAc (0 to 100%) in heptanes. Appropriate fractions were combined and concentrated in vacuo to afford 2-amino-5-bromo-1-(3-methoxy-2,6-dimethyl-phenyl)-6-methyl-pyrrolo[2,3-b]pyridine-3-carbonitrile (3.70 g, 75% yield) as a dark magenta solid.

Step 7. 2-Amino-5-bromo-1-(3-methoxy-2,6-dimethyl-phenyl)-6-methyl-pyrrolo[2,3-b]pyridine-3-carbonitrile (3.70 g, 9.6 mmol) was stirred in concentrated sulfuric acid (18M, 25 mL) for 55 min, then the reaction mixture was quenched with crushed ice, placed in an ice bath and made alkaline to pH 8-9 with saturated $NH_4OH$ added slowly. The resulting solid was collected by filtration on a Buchner funnel and washed with $H_2O$. The material was air-dried then co-evaporated twice with toluene and dried in vacuo, then stirred in 10% MeOH/DCM and filtered on a silica plug, eluting with 10% MeOH/DCM to remove residual ammonium salts. The filtrate was concentrated then dried in vacuo, affording 2-amino-5-bromo-1-(3-methoxy-2,6-dimethyl-phenyl)-6-methyl-pyrrolo[2,3-b]pyridine-3-carboxamide (3.80 g, 98% yield) as a pink solid.

Step 8. To a solution of methyl magnesium chloride (3M, 18.8 mL) in THF (160 mL) in a RBF under $N_2$ was added a solution of zinc dichloride in THF (0.5M, 112 mL) at RT dropwise via an addition funnel. After the addition, the resulting white suspension was stirred at RT for 35 min. To the zincate solution was added 2-amino-5-bromo-1-(3-methoxy-2,6-dimethyl-phenyl)-6-methyl-pyrrolo[2,3-b]pyridine-3-carboxamide (4.48 g, 11.1 mmol), the flask was rinsed with 20 mL THF, and palladium (0) tetrakis(triphenylphosphine) (1.14 g, 0.987 mmol) was added. The mixture was bubbled through with $N_2$ then equipped with a condenser and refluxed (heat block set to 80° C.) for 24 h. The reaction mixture was cooled to RT, then diluted with saturated aqueous $NH_4Cl$ and extracted with EtOAc (3×). The combined organic extracts were washed with brine, dried over $Na_2SO_4$, filtered and concentrated. The residue was purified by silica gel chromatography (dry load) eluting with a gradient of EtOAc (0 to 100%) in heptanes then purified again by silica gel chromatography (dry load) eluting with a gradient of MeOH (1 to 15%) in DCM. Appropriate fractions from the two columns were combined and concentrated in vacuo to afford 2-amino-1-(3-methoxy-2,6-dimethyl-phenyl)-5,6-dimethyl-pyrrolo[2,3-b]pyridine-3-carboxamide (2.22 g, 59% yield, 77% purity) as a light pink solid, which contained some 2-amino-1-(3-methoxy-2,6-dimethyl-phenyl)-6-methyl-pyrrolo[2,3-b]pyridine-3-carboxamide side product (19% by UPLCMS).

Step 9. To a suspension of 2-amino-1-(3-methoxy-2,6-dimethyl-phenyl)-5,6-dimethyl-pyrrolo[2,3-b]pyridine-3-carboxamide (2.22 g, 6.56 mmol, 77% purity) in DCM (25 mL) was added tribromoborane in DCM (1M, 26 mmol, 26 mL) dropwise. The reaction mixture was stirred at RT for 45 min, then concentrated to dryness. The crude product was taken in DCM and placed in an ice bath and MeOH was added carefully (exotherm). The mixture was concentrated to dryness then co-evaporated twice with MeOH. The residue was triturated with saturated aqueous $NaHCO_3$. The solids were collected by filtration on a Buchner funnel, washed with $H_2O$ and air-dried. The still wet solid was dissolved in DCM/MeOH, concentrated to dryness and triturated in 20% MeOH/DCM (50 mL). The solid was collected by filtration, washed with 20% MeOH/DCM, air-dried then dried in vacuo to afford 2-amino-1-(3-hydroxy-2,6-dimethyl-phenyl)-5,6-dimethyl-pyrrolo[2,3-b]pyridine-3-carboxamide (1.60 g, 75% yield) as a light beige solid. MS: [M+1]: 325.1. A different batch was purified by preparative HPLC to yield 2-amino-1-(3-hydroxy-2,6-dimethyl-phenyl)-5,6-dimethyl-pyrrolo[2,3-b]pyridine-3-carboxamide (63% yield) as an off-white fluffy solid. 1H NMR (400 MHZ, DMSO-d6) δ 9.51 (s, 1H), 7.82 (s, 1H), 7.05 (d, J=8.3 Hz, 1H), 6.90 (d, J=8.2 Hz, 1H), 6.71 (br s, 2H), 6.64 (br s, 2H), 2.26 (s, 3H), 2.23 (s, 3H), 1.74 (s, 3H), 1.65 (s, 3H). MS: [M+1]: 325.1.

Chiral SFC separation of Compound 181 (1.60 g, 4.93 mmol) (Instrument: Waters Prep 100 SFC-MS; Column: Phenomenex Lux Cellulose-2, 30×250 mm, 5 μm; Conditions: isocratic at 55% IPA+10 mM Ammonium Formate with 45% $CO_2$; Flow Rate: 70 mL/min) provided Compound 182 and Compound 183.

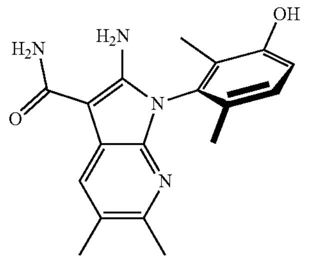

Compound 182 from SFC separation of 181. Peak 1 (retention time 3.94 min, 99.86%): (S)-2-amino-1-(3-hydroxy-2,6-dimethyl-phenyl)-5,6-dimethyl-pyrrolo[2,3-b]pyridine-3-carboxamide (381 mg) was obtained as an off white fluffy solid. 1H NMR (400 MHZ, DMSO-d6) δ 9.50 (s, 1H), 7.83 (s, 1H), 7.05 (d, J=8.3 Hz, 1H), 6.90 (d, J=8.3 Hz, 1H), 6.72 (s, 2H), 6.65 (s, 2H), 2.26 (s, 3H), 2.24 (s, 3H), 1.74 (s, 3H), 1.65 (s, 3H). MS: [M+1]: 325.1.

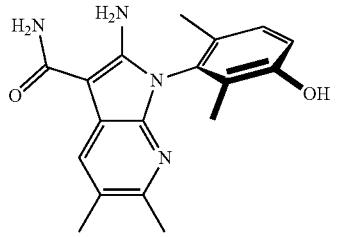

Compound 183 from SFC separation of 181. Peak 2 (retention time 4.35 min, 98.09%): (R)-2-amino-1-(3-hydroxy-2,6-dimethyl-phenyl)-5,6-dimethyl-pyrrolo[2,3-b]pyridine-3-carboxamide (495 mg) was obtained as an off white fluffy solid. 1H NMR (400 MHZ, DMSO-d6) δ 9.50 (s, 1H), 7.83 (s, 1H), 7.05 (d, J=8.2 Hz, 1H), 6.90 (d, J=8.2 Hz, 1H), 6.72 (s, 2H), 6.66 (s, 2H), 2.26 (s, 3H), 2.24 (s, 3H), 1.74 (s, 3H), 1.65 (s, 3H). MS: [M+1]: 325.1.

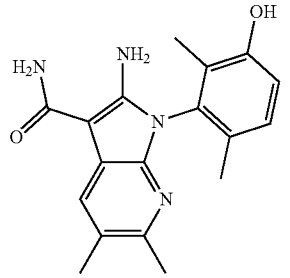 [SMILES: Cc1cc2c(C(N)=O)c(N)n(-c3c(C)ccc(O)c3C)c2nc1C]

Compound 181 2-amino-1-(3-hydroxy-2,6-dimethyl-phenyl)-5,6-dimethyl-pyrrolo[2,3-b]pyridine-3-carboxamide (From method O)

Step 1. Sulfuric acid (140.1 mL, 2575 mmol) was added slowly to water (1.15 L) and the solution was cooled at 25° C. 2-Amino-3-bromo-5,6-dimethylpyridine (114.8 g, 571.0 mmol) was added in one portion to get a solution. The solution was cooled to 0° C.-5° C. with an ice-water bath to give a suspension. Under strong stirring, a solution of sodium nitrite (49.25 g, 713.7 mmol) in water (175.0 mL) was added dropwise over 90 minutes. The ice-water bath was removed, and the suspension was warmed up slowly to 11° C. and stirred for 1 hour. A solution of sodium hydroxide (175 g, 4.37 mol) in 400 mL of water was added dropwise to maintain the temperature under 20° C. The pH of the solution was adjusted to 7 with K2HPO4 (~58 g, 0.33 mol) in 70 ml of water. The suspension was filtered at 10° C. The filter cake was triturated in water (250 mL) and filtered. The filter cake was washed profusely with ice-cooled water and dried by vacuum suction. The product was oven-dried under vacuum at 60° C. overnight to get 3-bromo-5,6-dimethylpyridin-2-ol as a light yellow crystalline solid (105.69 g, 91.6%) 1H NMR (400 MHZ, DMSO-d6) δ 11.96 (br s, 1H), 7.73 (s, 1H), 2.11 (s, 3H), 1.96 (s, 3H). MS: [M+1]: 202.0, 204.0

Step 2. To a solution of 3-bromo-5,6-dimethylpyridin-2-ol (105.3 g, 521.2 mmol) in N,N-dimethylformamide (316 mL) and toluene (527 mL) at 90° C. under nitrogen was added phosphorus oxybromide (1.3:1, 56.5% (w/w) in xylenes) (278 mL, 781.7 mmol) dropwise over 90 min. After the addition was complete, the mixture was stirred at 90° C. overnight. The mixture was cooled to room temperature and was slowly added to water (2 L). The flask was washed with 500 ml of water. The combined aqueous phases were extracted with MTBE (3×1 L). The organic phases were combined and washed with 0.5N NaOH (1 L), water (3×1 L) and brine (1 L) then dried with sodium sulfate and concentrated. The solid was partially dissolved in MTBE (400 mL) and heptanes (300 mL) was added. The mixture was concentrated under reduced pressured to ~1.7 volume to provide a precipitate. The mixture was filtered and rinsed with heptanes. The residue was dried to afford 2,3-dibromo-5,6-dimethylpyridine as a beige solid (114.290 g, 82.8%). The filtrate was further concentrated and filtered to provide a second crop of solid: (8.73 g, 6.32%). 1H NMR (400 MHZ, DMSO-d6) δ 7.95 (s, 1H), 2.36 (s, 3H), 2.21 (s, 3H). MS: [M+1]: 264.0, 266.0, 268.0.

Step 3. A 2000 mL 4-neck round-bottomed flask was charged with intermediate A2 (33.0 g, 218.0 mmol), degassed 1,2-dimethoxyethane (750 mL), 2,3-dibromo-5,6-dimethylpyridine (55 g, 207.6 mmol), 4,5-bis(diphenylphosphino)-9,9-dimethylxanthene (10.8 g, 18.68 mmol) and cesium carbonate (169.1 g, 519.0 mmol). The reaction mixture was sonicated for 20 minutes while sparging the suspension with nitrogen. Tris(dibenzylideneacetone) dipalladium (0) (8.55 g, 9.341 mmol) was added and the suspension was heated to reflux. After 13 hours of stirring, the reaction mixture was cooled to room temperature and was filtered over a pad of silica gel. The filter cake was washed with ethyl acetate (1.2 L). The filtrate was evaporated to a volume of ~200 mL and heptanes (300 mL) was added. The solvents were evaporated to provide a suspension in ~2 volumes of solvent. The suspension was filtered and washed with heptanes to provide 3-bromo-N-(3-methoxy-2,6-dimethylphenyl)-5,6-dimethylpyridin-2-amine as a light yellow solid. (56.2 g, 80.8%). 1H NMR (400 MHZ, DMSO-d6) δ

7.57 (s, 1H), 7.26 (s, 1H), 7.02 (d, J=8.6 Hz, 1H), 6.77 (d, J=8.3 Hz, 1H), 3.76 (s, 3H), 2.07 (s, 3H), 2.04 (s, 3H), 2.03 (s, 3H), 1.94 (s, 3H). MS: [M+1]: 335.2, 337.2.

Step 4. To a degassed solution of malononitrile (33.3 g, 503.5 mmol) in 1,2-dimethoxyethane (1000 mL) was added sodium tert-butoxide (46.3 g, 482.0 mmol) in 4 portions. The reaction mixture was stirred 30 minutes at room temperature to get a solution. 3-bromo-N-(3-methoxy-2,6-dimethylphenyl)-5,6-dimethylpyridin-2-amine (80 g, 238.6 mmol) and 1,1'-bis(diphenylphosphino) ferrocene palladium(II) chloride, complex with dichloromethane (14.9 g, 18.26 mmol) were added in one portion and the suspension was heated to strong reflux. After 17 hours of stirring, the reaction mixture was transferred into a 5000 mL flask and ethyl acetate (1.5 L) was added. A solution of N-acetyl-L-cysteine (12.1 g, 74 mmol, 4× Pd mol content) and $Na_2CO_3$ (15.7 g, 148 mmol) in water (500 mL) were added. The biphasic solution was stirred for 10 minutes at 60° C. and then cooled slowly to 40° C. over 75 minutes. Inside the 5000 ml flask, the two layers were separated at 40° C. and the organic phase was washed with water (2×250 mL) and brine (200 mL) and then filtered over a pad of silica gel (3 inches, 185 g). The filter cake was rinsed with DCM/EtOAc. The filtrate was evaporated, and the solvents were switched for EtOAc during rotavap evaporation to provide a suspension. The suspension was filtered at room temperature and the filter cake was triturated in 50 mL of ice-cooled ethyl acetate. The product was filtered and the filter cake was rinsed with 50 mL of ice-cooled ethyl acetate. The product was oven-dried under vacuum at 60° C. overnight to afford 2-amino-1-(3-methoxy-2,6-dimethylphenyl)-5,6-dimethyl-1H-pyrrolo[2,3-b]pyridine-3-carbonitrile as a light yellow solid. (65.38 g, 85.5%, 8% (w/w) DME). 1H NMR (400 MHZ, DMSO-d6) δ7.38 (s, 1H), 7.22 (d, J=8.4 Hz, 1H), 7.07 (d, J=8.6 Hz, 1H), 6.76 (br s, 2H), 3.84 (s, 3H), 2.26 (s, 3H), 2.23 (s, 3H), 1.78 (s, 3H), 1.69 (s, 3H). MS: [M+1]: 321.2.

Step 5. To methanesulfonic acid (600 mL, 9239 mmol) was added slowly a solution of sulfuric acid (93 mL)/water (7.0 mL) over 5 minutes at room temperature. 2-amino-1-(3-methoxy-2,6-dimethylphenyl)-5,6-dimethyl-1H-pyrrolo [2,3-b]pyridine-3-carbonitrile (80 g, 249.7 mmol) was added portion wise over 15 minutes to keep the reaction temperature below 40° C. The resulting solution was stirred at room temperature for 90 minutes. DL-Methionine (149.028 g, 998.8 mmol) was added portion wise over 20 minutes below 40° C. The solution was stirred at 40° C. After 37 hours of stirring, the reaction mixture was cooled to room temperature and then added slowly over 1.5 h to a solution of $K_2HPO_4$ (100 g) and NaOH (540 g) in water (5 L). EtOAc (1 L) was added and the biphasic mixture was stirred for 5 min to get a precipitate. The product was filtered. The mother liquors were extracted with EtOAc (3×1 L). The organic phases were combined, dried over $Na_2SO_4$, filtered and concentrated under reduced pressure to ~100 mL to get a suspension. The suspension was filtered and rinse with EtOAc (50 mL). The solids were combined and triturated in water (800 mL) two times. The residue was suspended in EtOAc (500 mL), stirred for 10 minutes and filtered. The product was oven-dried under reduced pressure to get 67.8 g of crude product. The compound was suspended in DMSO (350 mL, 5 vol) and the mixture was heated to 65° C. to get a solution. The solution was cooled slowly at 28° C. with a water bath. Water (1.05 L) was added dropwise over 2 hours to get a suspension. After 5 minutes of stirring at room temperature, the product was filtered. The solid was triturated in 100 ml of water and filtered. The filter cake was washed with 2×100 ml of water. The product was oven dried at 60° C. under vacuum to get 2-amino-1-(3-hydroxy-2,6-dimethyl-phenyl)-5,6-dimethyl-pyrrolo[2,3-b]pyridine-3-carboxamide as a light yellow solid. 61.5 g, (75%, 3% (w/w) EtOAc and 6% (w/w) DMSO). 1H NMR (400 MHZ, DMSO-d6) δ 9.47 (s, 1H), 7.82 (s, 1H), 7.05 (d, J=8.2 Hz, 1H), 6.90 (d, J=8.2 Hz, 1H), 6.71 (br. s, 2H), 6.64 (br. s., 2H), 2.27 (s, 3H), 2.24 (s, 3H), 1.75 (s, 3H), 1.66 (s, 3H). MS: [M+1]: 325.2.

Compound 184

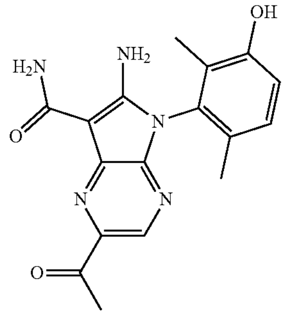

and

Compound 190

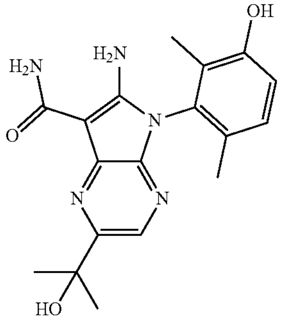

Step 1. To a solution of Intermediate D (1.07 g, 2.33 mmol) in DCM (9 mL) was added $BBr_3$ solution in DCM (1 M, 9.3 mL, 9.3 mmol). The mixture was stirred at 0° C. for 2 h, silica was added, the mixture was concentrated, then purified by silica gel chromatography (dry load) eluting with a gradient of 0 to 20% MeOH in DCM to provide [6-amino-7-carbamoyl-5-(3-hydroxy-2,6-dimethyl-phenyl) pyrrolo[2,3-b]pyrazin-2-yl] trifluoromethanesulfonate (744 mg, 72% yield) as an off-white solid.

Step 2. A solution of [6-amino-7-carbamoyl-5-(3-hydroxy-2,6-dimethyl-phenyl) pyrrolo[2,3-b]pyrazin-2-yl] trifluoromethanesulfonate (744 mg, 1.67 mmol), $PdCl_2(PPh_3)_2$ (117 mg, 0.167 mmol) in a mixture of DMF (8 mL) and MeOH (8 mL) and $Et_3N$ (1.40 mL, 10.0 mmol) was heated at 70° C. under an atmosphere of carbon monoxide (balloon). The apparatus was previously flushed with carbon monoxide once. After 2 h, more $PdCl_2(PPh_3)_2$ (117 mg, 0.167 mmol) was added and the reaction mixture was continued for 18 h. The reaction mixture was cooled to rt, filtered through Celite, rinsing with MeOH and the filtrate was concentrated. The residue was purified by silica gel chromatography (dry load) eluting with a gradient of 0 to 20% of MeOH in DCM to provide a dark green sticky solid. The solid was dissolved in EtOAc, passed through a silica plug using EtOAc/MeOH (5%) that provided upon evaporating the volatiles methyl 6-amino-7-carbamoyl-5-(3-hydroxy-2,6-dimethyl-phenyl) pyrrolo[2,3-b]pyrazine-2-carboxylate (418 mg, 70% yield) as a light brown sticky solid.

Step 3. A solution of methyl 6-amino-7-carbamoyl-5-(3-hydroxy-2,6-dimethyl-phenyl) pyrrolo[2,3-b]pyrazine-2-carboxylate (322 mg, 0.906 mmol) in THF (12 mL) was cooled to −40° C. and MeMgCl solution in THF (3 M, 4.53 mL, 13.1 mmol) was added dropwise. The mixture was left to warm to rt overnight, quenched with saturated aqueous $NH_4Cl$ (25 mL), the pH was adjusted to 7-8 with 1N HCl and the mixture was extracted with DCM (3×). The combined organic extracts were washed with brine, dried over $Na_2SO_4$, filtered and concentrated. The residue was purified by silica gel chromatography eluting with a gradient of 0 to 20% MeOH in DCM to provide 6-amino-5-(3-hydroxy-2,6-dimethyl-phenyl)-2-(1-hydroxy-1-methyl-ethyl) pyrrolo[2,3-b]pyrazine-7-carboxamide Compound 190 (103 mg, 32% yield) as a light tan solid. 1H NMR (400 MHZ, DMSO-d6) δ 9.61 (s, 1H), 7.99 (s, 1H), 7.50 (br s, 1H), 7.42 (br s, 2H), 7.23 (br s, 1H), 7.08 (d, J=8.5 Hz, 1H), 6.94 (d, J=8.3 Hz, 1H), 5.95-5.81 (m, 1H), 5.30-5.17 (m, 1H), 2.19 (s, 3H), 1.78 (s, 3H), 1.70 (s, 3H). MS: [M+1]: 338.1; and 2-acetyl-6-amino-5-(3-hydroxy-2,6-dimethyl-phenyl) pyrrolo[2,3-b]pyrazine-7-carboxamide Compound 184 (31 mg, 10% yield) as a light tan solid. 1H NMR (400 MHZ, DMSO-d6) δ9.83 (br s, 1H), 8.38 (d, J=1.9 Hz, 1H), 7.68 (br s, 2H), 7.40 (s, 2H), 7.09 (d, J=8.2 Hz, 1H), 6.97 (d, J=8.1 Hz, 1H), 2.68 (s, 3H), 1.77 (s, 3H), 1.69 (s, 3H). MS: [M+1]: 340.1.

Chiral SFC separation of Compound 190 (39 mg, 0.110 mmol) (Instrument: Mettler Toledo Minigram SFC; Column: Phenomenex Lux Cellulose-2, 10×250 mm, 5 μm; Conditions: Isocratic at 40% IPA+10 mM Ammonium Formate with 60% CO2; Flow Rate: 10 mL/min) provided Compound 191 and Compound 192.

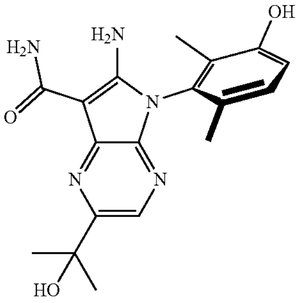

Compound 191 from chiral SFC separation of 190. Peak 1 (retention time 3.83 min, 100%): S-6-amino-5-(3-hydroxy-2,6-dimethyl-phenyl)-2-(1-hydroxy-1-methyl-ethyl) pyrrolo [2,3-b]pyrazine-7-carboxamide (10 mg) as an off-white solid. 1H NMR (400 MHZ, DMSO-d6) δ 9.61 (br s, 1H), 7.99 (s, 1H), 7.52 (br d, J=3.0 Hz, 1H), 7.32 (br s, 2H), 7.18 (br d, J=3.1 Hz, 1H), 7.08 (dt, J=8.2, 0.8 Hz, 1H), 6.93 (d, J=8.3 Hz, 1H), 5.26 (s, 1H), 1.77 (s, 3H), 1.68 (s, 3H), 1.51 (s, 6H). MS: [M+1]: 356.2.

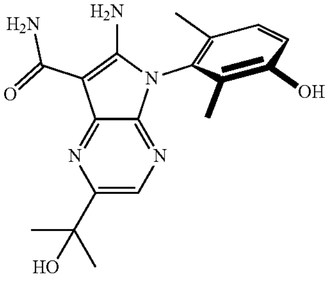

Compound 192 from chiral SFC separation of 190. Peak 2 (retention time 4.07 min): R-6-amino-5-(3-hydroxy-2,6-dimethyl-phenyl)-2-(1-hydroxy-1-methyl-ethyl) pyrrolo[2,3-b]pyrazine-7-carboxamide (10 mg). 1H NMR (400 MHZ, DMSO-d6) δ 9.62 (br s, 1H), 7.99 (s, 1H), 7.52 (br d, J=3.2 Hz, 1H), 7.32 (br s, 2H), 7.18 (br d, J=3.1 Hz, 1H), 7.08 (dt, J=8.3, 0.8 Hz, 1H), 6.93 (d, J=8.3 Hz, 1H), 5.26 (s, 1H), 1.77 (s, 3H), 1.68 (s, 3H), 1.51 (s, 6H). MS: [M+1]: 356.2.

Chiral SFC separation of Compound 184 (103 mg, 0.290 mmol) (Instrument: Mettler Toledo Minigram SFC; Column: Phenomenex Lux Cellulose-2, 10×250 mm, 5 μm; Conditions: Isocratic at 40% IPA+10 mM Ammonium Formate with 60% $CO_2$; Flow Rate: 10 mL/min) provided Compound 185 and Compound 186.

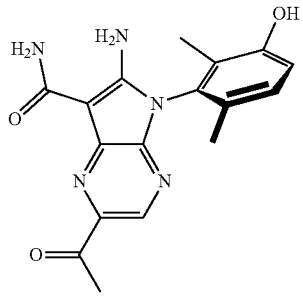

Compound 185 from chiral SFC separation of 184. Peak 1 (retention time 3.87 min, 100%): S-2-acetyl-6-amino-5-(3-hydroxy-2,6-dimethyl-phenyl) pyrrolo[2,3-b]pyrazine-7-carboxamide (9 mg) as a yellow fluffy solid. 1H NMR (400 MHZ, DMSO-d6) δ 9.68 (br s, 1H), 8.38 (s, 1H), 7.69 (br s, 2H), 7.41 (br s, 2H), 7.09 (dt, J=8.3, 0.7 Hz, 1H), 6.95 (d, J=8.3 Hz, 1H), 2.68 (s, 3H), 1.77 (d, J=0.8 Hz, 3H), 1.69 (s, 3H). MS: [M+1]: 340.2.

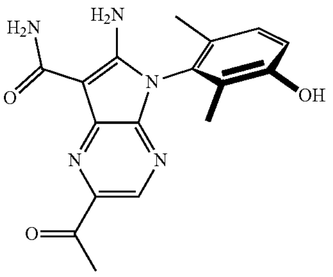

Compound 186 from chiral SFC separation of 184. Peak 2 (retention time 4.21 min, 99.80%): R-2-acetyl-6-amino-5-(3-hydroxy-2,6-dimethyl-phenyl) pyrrolo[2,3-b]pyrazine-7-carboxamide (9 mg) as a yellow fluffy solid. 1H NMR (400 MHZ, DMSO-d6) δ 9.69 (br s, 1H), 8.38 (s, 1H), 7.69 (br s, 2H), 7.41 (br s, 2H), 7.09 (dt, J=8.2, 0.7 Hz, 1H), 6.95 (d, J=8.3 Hz, 1H), 2.68 (s, 3H), 1.77 (d, J=0.7 Hz, 3H), 1.69 (s, 3H). MS: [M+1]: 340.1.

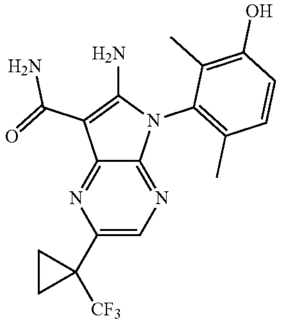 [SMILES: Cc1ccc(O)c(C)c1-n1c(N)c(C(N)=O)c2nc(C3(C(F)(F)F)CC3)cnc21]

Compound 198 (6-amino-5-(3-hydroxy-2,6-dimethyl-phenyl)-2-[1-(trifluoromethyl)cyclopropyl]pyrrolo[2,3-b]pyrazine-7-carboxamide)

Step 1. A microwave vial was loaded with Intermediate D (500 mg, 1.09 mmol), 4,4,6-trimethyl-2-[1-(trifluoromethyl)vinyl]-1,3,2-dioxaborinane (502 mg, 2.26 mmol), dioxane (5 mL) and aqueous $Na_2CO_3$ (2 M, 1.63 mL, 3.26 mmol), flushed with nitrogen (house vac then nitrogen, 3×). $PdCl_2$(dppf)·$CH_2Cl_2$ (444 mg, 0.544 mmol) added, the vial was flushed again, capped and transferred to a preheated (80° C.) heat block and stirred overnight. After cooling to rt, the reaction mixture was filtered on Celite, washed with water and DCM and diluted with brine. The layers were separated (phase separator). The aqueous layer was extracted with DCM (2×). The combined organic extracts were concentrated and purified by silica gel chromatography eluting with a gradient of 0 to 50% EtOAc in DCM affording 6-amino-5-(3-methoxy-2,6-dimethyl-phenyl)-2-[1-(trifluoromethyl)vinyl]pyrrolo[2,3-b]pyrazine-7-carboxamide (169 mg, 38% yield) as a dark yellow gum.

Step 2. To a solution of 6-amino-5-(3-methoxy-2,6-dimethyl-phenyl)-2-[1-(trifluoromethyl)vinyl]pyrrolo[2,3-b]pyrazine-7-carboxamide (42.0 mg, 0.104 mmol) in DCM (2 mL) at 0° C. was added diazomethane solution in $Et_2O$ (0.5 M, 400 μL) then warmed to rt. Another portion of diazomethane solution (0.5 M, 400 μL) was added. After reaction was deemed complete by UPLCMS, the reaction mixture was quenched with AcOH (200 μL), stirred for a few minutes and concentrated to dryness, then taken in saturated aqueous $NaHCO_3$ and DCM. The layers were separated (phase separator). The aqueous layer was extracted with DCM (3×). The combined organic extracts were concentrated then dried in vacuo, affording 6-amino-5-(3-methoxy-2,6-dimethyl-phenyl)-2-[5-(trifluoromethyl)-3,4-dihydropyrazol-5-yl]pyrrolo[2,3-b]pyrazine-7-carboxamide (48 mg, quantitative yield) as a yellow gum.

Step 3. 6-amino-5-(3-methoxy-2,6-dimethyl-phenyl)-2-[5-(trifluoromethyl)-3,4-dihydropyrazol-5-yl]pyrrolo[2,3-b]pyrazine-7-carboxamide (48.0 mg, 0.107 mmol) was dissolved in xylenes (3 mL) and heated to 130° C. with a reflux condenser open to air for a total of 75 min. The reaction mixture was concentrated then purified by silica gel chromatography eluting with a gradient of 0 to 100% EtOAc in heptane, then a gradient of 0 to 20% MeOH in EtOAc to provide 6-amino-5-(3-methoxy-2,6-dimethyl-phenyl)-2-[1-(trifluoromethyl)cyclopropyl]pyrrolo[2,3-b]pyrazine-7-carboxamide (35 mg, 81% yield) as a light yellow solid.

Step 4. For OMe deprotection using $BBr_3$, following general procedure 2 provided a residue which was purified by preparative HPLC to provide 6-amino-5-(3-hydroxy-2,6-dimethyl-phenyl)-2-[1-(trifluoromethyl)cyclopropyl]pyrrolo[2,3-b]pyrazine-7-carboxamide (17 mg, 50% yield) as a white fluffy solid. 1H NMR (400 MHZ, DMSO-d6) δ 9.62 (s, 1H), 7.88 (s, 1H), 7.49 (br s, 2H), 7.36 (br s, 1H), 7.28 (br s, 1H), 7.08 (d, J=8.2 Hz, 1H), 6.94 (d, J=8.3 Hz, 1H), 1.76 (s, 3H), 1.69 (s, 3H), 1.46-1.29 (m, 4H). 19F NMR (376 MHZ, DMSO-d6) δ −66.85. MS: [M+1]: 406.1.

Chiral SFC separation of Compound 198 (14.5 mg, 0.358 mmol) (Instrument: Mettler Toledo Minigram SFC; Column: Phenomenex Lux Cellulose-2, 10×250 mm, 5 μm; Conditions: Isocratic at 40% ACN/EtOH 1:1 with 60% $CO_2$; Flow Rate: 10 mL/min) provided Compound 199 and Compound 200.

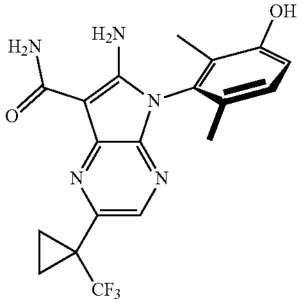

Compound 199 from chiral SFC separation of 198. Peak 1 (retention time 3.50 min, 99.99%): S-6-amino-5-(3-hydroxy-2,6-dimethyl-phenyl)-2-[1-(trifluoromethyl)cyclopropyl]pyrrolo[2,3-b]pyrazine-7-carboxamide (5 mg) as a white fluffy solid. 1H NMR (400 MHZ, DMSO-d6) δ 9.61 (s, 1H), 7.88 (s, 1H), 7.48 (br s, 2H), 7.36 (br s, 1H), 7.27 (br s, 1H), 7.08 (d, J=8.3 Hz, 1H), 6.94 (d, J=8.3 Hz, 1H), 1.76 (s, 3H), 1.68 (s, 3H), 1.43-1.33 (m, 4H). MS: [M+1]: 406.2.

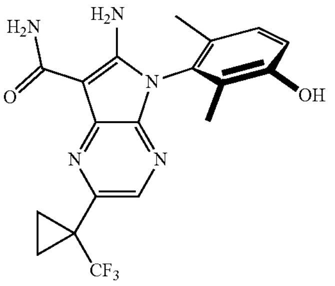

Compound 200 from chiral SFC separation of 198. Peak 2 ((retention time 3.81 min, 99.95%): R-6-amino-5-(3-hydroxy-2,6-dimethyl-phenyl)-2-[1-(trifluoromethyl)cyclopropyl]pyrrolo[2,3-b]pyrazine-7-carboxamide (5 mg) as a white fluffy solid. 1H NMR (400 MHZ, DMSO-d6) δ 9.61 (s, 1H), 7.87 (s, 1H), 7.48 (br s, 2H), 7.36 (br s, 1H), 7.27 (br s, 1H), 7.08 (d, J=8.3 Hz, 1H), 6.94 (d, J=8.3 Hz, 1H), 1.76 (s, 3H), 1.69 (s, 3H), 1.43-1.35 (m, 4H). MS: [M+1]: 406.2.

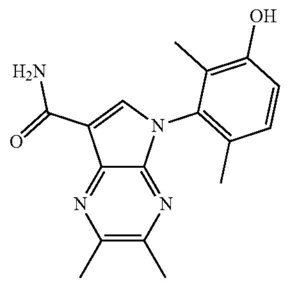 [SMILES: Cc1ccc(O)c(C)c1-n1cc(C(N)=O)c2nc(C)c(C)nc21]

Compound 209 (5-(3-hydroxy-2,6-dimethyl-phenyl)-2,3-dimethyl-pyrrolo[2,3-b]pyrazine-7-carboxamide)

Step 1. To a solution of 6-amino-5-(3-methoxy-2,6-dimethyl-phenyl)-2,3-dimethyl-pyrrolo[2,3-b]pyrazine-7-carbonitrile (298 mg, 0.927 mmol) in THF (7 mL) was added tert-butyl nitrite (550 μL, 4.63 mmol). After stirring 30 min, the mixture was refluxed for 3.5 h then cooled down to rt and concentrated to dryness and purified by silica gel chromatography eluting with a gradient of 0 to 100% EtOAc in hexanes. The combined pure fractions were concentrated and dried in vacuo to provide 5-(3-methoxy-2,6-dimethyl-phenyl)-2,3-dimethyl-pyrrolo[2,3-b]pyrazine-7-carbonitrile (150 mg, 53% yield) as a light yellow solid.

Step 2. For nitrile hydrolysis using sulfuric acid, the same procedure used for Compound 164 was done on the appropriate intermediate (150 mg, 0.490 mmol) to provide 5-(3-methoxy-2,6-dimethyl-phenyl)-2,3-dimethyl-pyrrolo[2,3-b]pyrazine-7-carboxamide (144 mg, 91% yield) was obtained as an off-white solid.

Step 3. For OMe deprotection using $BBr_3$, following general procedure 2 provided a residue which was purified by preparative HPLC to provide 5-(3-hydroxy-2,6-dimethyl-phenyl)-2,3-dimethyl-pyrrolo[2,3-b]pyrazine-7-carboxamide (76 mg, 55% yield) as an off-white fluffy solid. 1H NMR (400 MHZ, DMSO-d6) δ 9.65 (br s, 1H), 8.13 (s, 1H), 7.86 (br s, 1H), 7.60 (br s, 1H), 7.05 (d, J=8.2 Hz, 1H), 6.92 (d, J=8.3 Hz, 1H), 2.64 (s, 3H), 1.75 (s, 3H), 1.64 (s, 3H). 1 Me singlet likely buried under dmso peak. MS: [M+1]: 311.1.

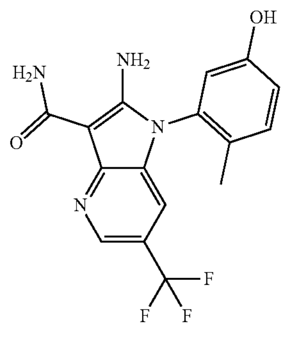 [SMILES: Cc1ccc(O)cc1-n1c(N)c(C(N)=O)c2ncc(C(F)(F)F)cc21]

Compound 212 (2-amino-1-(5-hydroxy-2-methyl-phenyl)-6-(trifluoromethyl) pyrrolo[3,2-b]pyridine-3-carboxamide)

Step 1. To a suspension of NaH (108 mg, 2.83 mmol, 60% dispersion in mineral oil) in DME (3 mL) was added dropwise 3-bromo-2-chloro-5-(trifluoromethyl)pyridine (300 mg, 1.15 mmol) in DME (3 mL). After the addition, the mixture was stirred for 25 min then propanedinitrile (188 mg, 2.85 mmol) was added. The resulting mixture was refluxed for 18 h, cooled to rt and concentrated under vacuum. The residue was purified by preparative HPLC to provide 2-[3-bromo-5-(trifluoromethyl)-2-pyridyl]propanedinitrile (100 mg, 30% yield).

Step 2. To a solution of 2-[3-bromo-5-(trifluoromethyl)-2-pyridyl]propanedinitrile (50 mg, 172 μmol) in DMF (2 mL) were added $Pd_2dba_3$ (16 mg, 17 μmol), 5-(methoxymethoxy)-2-methyl-aniline (33.3 mg, 199 μmol), $Cs_2CO_3$ (84 mg, 259 μmol) and Xantphos (10.0 mg, 17.3 μmol). The mixture was degassed in vacuo and back filled with nitrogen (3 times). The mixture was stirred at 130° C. for 8 h, cooled to rt, diluted with water and extracted with EtOAc (3×). The combined organic extracts were washed with brine, dried over $Na_2SO_4$, filtered and concentrated in vacuo. The residue was purified by silica gel chromatography eluting with a gradient of 5 to 100% EtOAc in hexanes to provide 2-amino-1-[5-(methoxymethoxy)-2-methyl-phenyl]-6-(trifluoromethyl) pyrrolo[3,2-b]pyridine-3-carbonitrile (30 mg, 46% yield).

Step 3. 2-amino-1-[5-(methoxymethoxy)-2-methyl-phenyl]-6-(trifluoromethyl) pyrrolo[3,2-b]pyridine-3-carbonitrile (30 mg, 135 μmol) was stirred in $H_2SO_4$ (1 mL). After 90 min, the reaction mixture was poured into crushed ice, placed in an ice bath and neutralized with 1:1 $NH_4OH/H_2O$. The precipitate was filtered, washed with water and air-dried overnight. Purification by preparative HPLC provided 2-amino-1-(5-hydroxy-2-methyl-phenyl)-6-(trifluoromethyl) pyrrolo[3,2-b]pyridine-3-carboxamide (3.2 mg, 11% yield) as an orange solid. 1H NMR (400 MHZ, DMSO-d6) δ 9.76 (s, 1H), 8.45 (s, 1H), 7.77 (s, 1H), 7.34 (s, 2H), 7.31-7.13 (m, 2H), 6.98 (s, 1H), 6.91 (d, J=8.5 Hz, 1H), 6.71 (s, 1H), 1.78 (s, 3H). MS: [M+1]: 351.3.

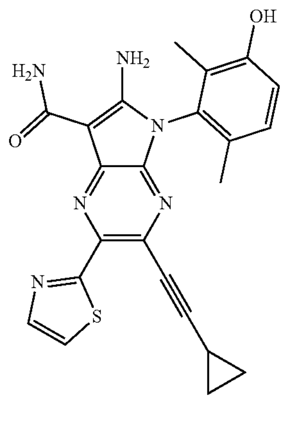 [SMILES: Cc1ccc(O)c(C)c1-n1c(N)c(C(N)=O)c2nc(-c3nccs3)c(C#CC3CC3)nc21]

Compound 214 (6-amino-3-(2-cyclopropylethynyl)-5-(3-hydroxy-2,6-dimethyl-phenyl)-2-thiazol-2-yl-pyrrolo[2,3-b]pyrazine-7-carboxamide)

Step 1. A solution of 6-amino-2-benzyloxy-3-bromo-5-(3-methoxy-2,6-dimethyl-phenyl) pyrrolo[2,3-b]pyrazine-7-carbonitrile (400 mg, 836 μmol, described in the preparation of compound 31) in conc. $H_2SO_4$ (2 mL) and DCM (2 mL) was stirred 10 min. NaOH 0.4 M was added then water and the resulting precipitate was recovered by filtration. The crude product was purified by silica gel chromatography using a gradient of 0 to 20% MeOH in DCM to afford 6-amino-3-bromo-2-hydroxy-5-(3-methoxy-2,6-dimethyl-phenyl) pyrrolo[2,3-b]pyrazine-7-carboxamide (300 mg, 88% yield)

Step 2. To a solution of 6-amino-3-bromo-2-hydroxy-5-(3-methoxy-2,6-dimethyl-phenyl) pyrrolo[2,3-b]pyrazine-7-carboxamide (300 mg, 739 μmol) and $Cs_2CO_3$ (440 mg, 1.35 mmol) in DMF (3 mL) was added 1,1,1-trifluoro-N-phenyl-N-(trifluoromethylsulfonyl) methanesulfonamide (288 mg, 807 μmol). The mixture was stirred for 1 h, diluted with water, extracted with EtOAc twice. The combined organic extracts were washed with brine, dried over $Na_2SO_4$, filtered and concentrated. The residue was purified by silica gel chromatography using a gradient of 0 to 100% EtOAc in hexanes to afford 6-amino-3-bromo-7-carbamoyl-5-(3-methoxy-2,6-dimethylphenyl)-5H-pyrrolo[2,3-b] pyrazin-2-yl trifluoromethanesulfonate (460 mg, 43% yield).

Step 3. A microwave vial charged with [6-amino-3-bromo-7-carbamoyl-5-(3-methoxy-2,6-dimethyl-phenyl) pyrrolo[2,3-b]pyrazin-2-yl] trifluoromethanesulfonate (35 mg, 65 μmol), ethynylcyclopropane (5.0 mg, 75 μmol), CuI (1.3 mg, 7 μmol) and $PdCl_2(PPh_3)_2$ (5.0 mg, 7 μmol) in DMF (1 mL) was flushed with nitrogen, then $Et_3N$ (520 μmol, 73 uL) was added and the mixture was stirred for 1 h. The mixture was filtered and purified by preparative HPLC to provide [6-amino-7-carbamoyl-3-(2-cyclopropylethynyl)-5-(3-methoxy-2,6-dimethyl-phenyl) pyrrolo[2,3-b]pyrazin-2-yl] trifluoromethanesulfonate (10 mg, 29% yield).

Step 4. A mixture of tributyl(thiazol-2-yl) stannane (38.5 μmol, 12.1 uL), [6-amino-7-carbamoyl-3-(2-cyclopropylethynyl)-5-(3-methoxy-2,6-dimethyl-phenyl) pyrrolo[2,3-b] pyrazin-2-yl] trifluoromethanesulfonate (10.0 mg, 19.1 μmol). CuI (0.5 mg, 2.5 μmol), LiCl (1.7 mg, 40 μmol). $PdCl_2(dppf)·CH_2Cl_2$ (1.5 mg, 2 μmol) in DMF (3 mL) was degassed in vacuo, then back filled with nitrogen. The reaction mixture was stirred at 120° C. for 3 h. Water was added, and the resulting precipitate was recovered by filtration to afford crude 6-amino-3-(2-cyclopropylethynyl)-5-(3-methoxy-2,6-dimethyl-phenyl)-2-thiazol-2-yl-pyrrolo[2,3-b]pyrazine-7-carboxamide (5 mg, 57% yield).

Step 5. For OMe deprotection using $BBr_3$, following general procedure 2 provided a residue which was purified by preparative HPLC to provide 6-amino-3-(2-cyclopropylethynyl)-5-(3-hydroxy-2,6-dimethyl-phenyl)-2-thiazol-2-yl-pyrrolo[2,3-b]pyrazine-7-carboxamide (1.1 mg, 23% yield). 1H NMR (400 MHZ, Methanol-d4) δ 9.16 (d, J=4.2 Hz, 1H), 8.47 (d, J=4.2 Hz, 2H), 7.89 (d, J=1.1 Hz, 1H), 7.15 (d, J=8.3 Hz, 1H), 6.98 (d, J=8.3 Hz, 1H), 2.55-2.47 (m, 1H), 1.88 (d, J=21.7 Hz, 6H), 1.37-1.31 (m, 2H), 1.11-1.05 (m, 2H). MS: [M+1]: 445.3.

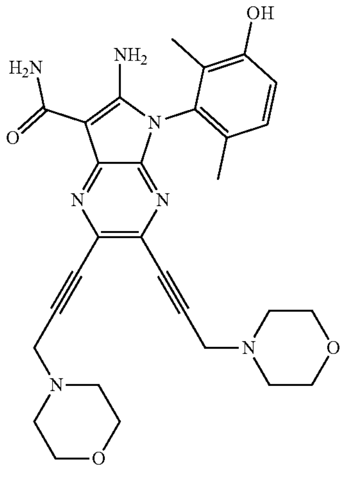 [SMILES: Cc1ccc(O)c(C)c1-n1c(N)c(C(N)=O)c2nc(C#CCN3CCOCC3)c(C#CCN3CCOCC3)nc21]

Compound 215 (2-amino-1-(3-hydroxy-2,6-dimethyl-phenyl)-5-(trifluoromethyl) pyrrolo[2,3-b]pyridine-3-carboxamide)

Step 1. A microwave vial charged with 4-prop-2-ynylmorpholine (26 mg, 204 μmol), copper (I) iodide (3.5 mg, 19 μmol), and triethylamine (1.49 mmol, 207 uL) was flushed with $N_2$, then 6-amino-3-bromo-7-carbamoyl-5-(3-methoxy-2,6-dimethylphenyl)-5H-pyrrolo[2,3-b]pyrazin-2-yl trifluoromethanesulfonate (100 mg, 186 μmol) in DMF (1 mL) was added followed by $PdCl_2(PPh_3)_2$ (14 mg, 19 μmol). The vial was capped heated to 120° C. After 1 h, concentrated under vacuum then adsorbed on silica (4 g) using THF. Purified by silica gel chromatography eluting with a gradient of 0 to 100% EtOAc in hexanes, then 0 to 20% MeOH in EtOAc to provide 6-amino-5-(3-methoxy-2,6-dimethyl-phenyl)-2,3-bis(3-morpholinoprop-1-ynyl) pyrrolo[2,3-b]pyrazine-7-carboxamide (16 mg, 15% yield) Step 2. For OMe deprotection using $BBr_3$, following general procedure 2 provided a residue which was purified by preparative HPLC to provide 2-amino-1-(3-hydroxy-2,6-dimethyl-phenyl)-5-(trifluoromethyl) pyrrolo[2,3-b]pyridine-3-carboxamide (7 mg, 45% yield). 1H NMR (400 MHZ, DMSO-d6) δ 9.63 (s, 1H), 7.70 (s, 2H), 7.35-7.13 (m, 2H), 7.05 (d, J=8.3 Hz, 1H), 6.92 (d, J=8.3 Hz, 1H), 3.62-3.51 (m, 11H), 3.49 (s, 2H), 2.52 (q, J=4.3, 3.9 Hz, 4H), 1.74 (s, 3H), 1.66 (s, 3H). MS: [M+1]: 544.5.

Compound 219

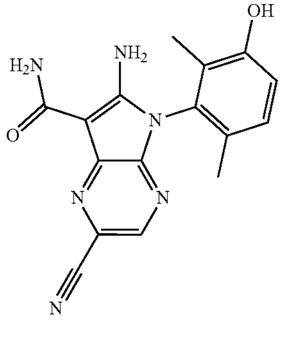

and

-continued

Compound 220

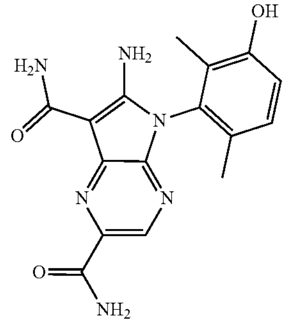

Step 1. A mixture of Intermediate D (150 mg, 327 μmol), $Zn(CN)_2$ (38.3 mg, 327 μmol) and Zn powder (4 mg, 65 μmol) in NMP (3 mL) was degassed. $Pd(PPh_3)_4$ (38 mg, 33 μmol) was added, and the mixture was stirred at 120° C. for 24 h, cooled to rt, quenched with saturated aqueous $NH_4Cl$, and extracted with EtOAc (3×). The combined extracts were washed with brine, dried over $Na_2SO_4$, and concentrated. The residue was purified by preparative HPLC to provide 6-amino-2-cyano-5-(3-methoxy-2,6-dimethyl-phenyl) pyrrolo[2,3-b]pyrazine-7-carboxamide (50 mg, 46% yield).

Step 2. For OMe deprotection using $BBr_3$, following general procedure 2 provided a residue which was purified by preparative HPLC to provide 6-amino-2-cyano-5-(3-hydroxy-2,6-dimethyl-phenyl) pyrrolo[2,3-b]pyrazine-7-carboxamide compound 219 (2.6 mg, 9% yield) 1H NMR (400 MHZ, DMSO-d6) δ9.64 (s, 1H), 8.28 (s, 1H), 7.88 (s, 2H), 7.38 (s, 1H), 7.05 (d, J=8.4 Hz, 2H), 6.92 (d, J=8.3 Hz, 1H), 1.73 (s, 3H), 1.65 (s, 3H), MS: [M+1]: 324.2; and 6-amino-5-(3-hydroxy-2,6-dimethyl-phenyl) pyrrolo[2,3-b] pyrazine-2,7-dicarboxamide compound 220 (10 mg, 33% yield). 1H NMR (400 MHZ, DMSO-d6) δ9.57 (s, 1H), 8.67 (s, 1H), 8.35 (s, 1H), 7.64 (s, 3H), 7.41 (s, 1H), 7.13 (s, 1H), 7.11-6.97 (m, 1H), 6.91 (d, J=8.3 Hz, 1H), 1.73 (s, 3H), 1.65 (s, 3H). MS: [M+1]: 341.4.

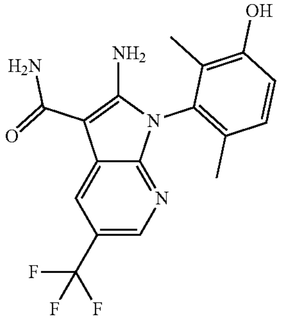 [SMILES: Cc1ccc(O)c(C)c1-n1c(N)c(C(N)=O)c2cc(C(F)(F)F)cnc21]

Compound 221 (2-amino-1-(3-hydroxy-2,6-dimethyl-phenyl)-5-(trifluoromethyl) pyrrolo[2,3-b]pyridine-3-carboxamide)

Step 1. To the solution of 3-methoxy-2,6-dimethyl-aniline (2.02 g, 13.4 mmol) in toluene (15 mL) were added potassium tert-butoxide (1.64 g, 14.6 mmol), 3-bromo-2-chloro-5-(trifluoromethyl)pyridine (3.16 g, 12.1 mmol). $Pd_2dba_3$ (582 mg, 635 μmol) and Xantphos (723 mg, 1.26 mmol). The mixture was degassed in vacuo and back filled with nitrogen. The resulting mixture was stirred at 120° C. for 2 h. The reaction mixture was cooled to rt, diluted with EtOAc, washed with water, brine, dried over $Na_2SO_4$, filtered and concentrated to dryness. The residue was purified by flash silica gel chromatography eluting with a gradient of 0 to 70% EtOAc in hexanes to provide 3-bromo-N-(3-methoxy-2,6-dimethyl-phenyl)-5-(trifluoromethyl) pyridin-2-amine (1.55 g, 34% yield).

Step 2. To a solution of propanedinitrile (556 mg, 8.41 mmol) in DME (20 mL) was added NaH (361 mg, 8.34 mmol, 60% dispersion in mineral oil). The mixture was stirred for 5 min then 3-bromo-N-(3-methoxy-2,6-dimethyl-phenyl)-5-(trifluoromethyl)pyridin-2-amine (1.55 g, 4.13 mmol) and $Pd(PPh_3)_4$ (231 mg, 200 μmol) were added. The resulting mixture was stirred at 120° C. for 17 h in a pressure vial. DME was removed under reduced pressure, then the mixture was diluted with EtOAc, washed with water, brine, dried over $Na_2SO_4$, filtered and concentrated to dryness. The residue was purified by flash chromatography eluting with a gradient of 0 to 100% EtOAc in hexanes to provide 2-amino-1-(3-methoxy-2,6-dimethyl-phenyl)-5-(trifluoromethyl) pyrrolo[2,3-b]pyridine-3-carbonitrile (44 mg, 3% yield).

Step 3. For nitrile hydrolysis using sulfuric acid, the same procedure used for Compound 164 was done on the appropriate intermediate (44 mg, 0.121 mmol) to provide 2-amino-1-(3-methoxy-2,6-dimethyl-phenyl)-5-(trifluoromethyl) pyrrolo[2,3-b]pyridine-3-carboxamide (40 mg, 87% yield).

Step 4. For OMe deprotection using $BBr_3$, following general procedure 2 provided a residue which was purified by preparative HPLC to provide 2-amino-1-(3-hydroxy-2,6-dimethyl-phenyl)-5-(trifluoromethyl) pyrrolo[2,3-b]pyridine-3-carboxamide (25 mg, 59% yield). 1H NMR (400 MHZ, DMSO-d6) δ 9.66 (s, 1H), 8.47 (dt, J=2.0, 1.0 Hz, 1H), 7.77 (s, 1H), 7.31 (s, 2H), 7.23 (s, 1H), 7.10 (dt, J=8.3, 0.8 Hz, 1H), 7.00-6.80 (m, 2H), 1.82-1.57 (m, 6H). MS: [M+1]: 365.3.

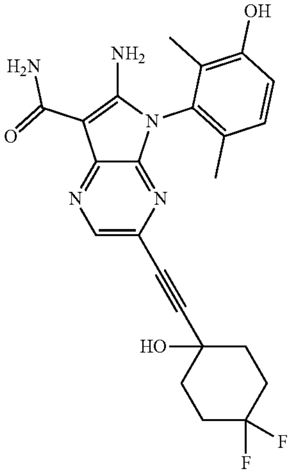 [SMILES: Cc1ccc(O)c(C)c1-n1c(N)c(C(N)=O)c2ncc(C#CC3(O)CCC(F)(F)CC3)nc21]

Compound 242 (6-amino-3-[2-(4,4-difluoro-1-hydroxy-cyclohexyl) ethynyl]-5-(3-hydroxy-2,6-dimethyl-phenyl) pyrrolo[2,3-b]pyrazine-7-carboxamide)

To a microwave vial charged with Intermediate H (20.0 mg, 53.2 μmol), CuI (1.0 mg, 5.3 μmol), 1-ethynyl-4,4-difluoro-cyclohexanol (43 mg, 266 μmol) in DMF (1 mL)

was added $PdCl_2(PPh_3)_2$ (4 mg, 6 μmol) and $Et_3N$ (425 μmol, 60 uL). The vial was capped and heated to 80° C. for 3 h. After cooling to rt, the mixture was filtered and purified by preparative HPLC to provide 6-amino-3-[2-(4,4-difluoro-1-hydroxy-cyclohexyl) ethynyl]-5-(3-hydroxy-2,6-dimethyl-phenyl) pyrrolo[2,3-b]pyrazine-7-carboxamide (5.1 mg, 21% yield). 1H NMR (400 MHZ, DMSO-d6) δ 9.63 (s, 1H), 8.21 (s, 1H), 7.57 (d, J=10.6 Hz, 2H), 7.28 (s, 2H), 7.05 (d, J=8.3 Hz, 1H), 6.92 (d, J=8.3 Hz, 1H), 5.77 (s, 1H), 2.11-1.74 (m, 8H), 1.73 (s, 3H), 1.65 (s, 3H). MS: [M+1]: 456.4.

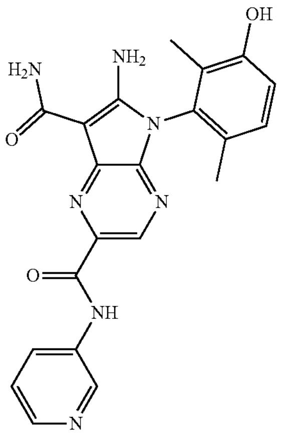 [SMILES: Cc1ccc(O)c(C)c1-n1c(N)c(C(N)=O)c2nc(C(=O)Nc3cccnc3)cnc21]

Compound 243 (6-amino-5-(3-hydroxy-2,6-dimethyl-phenyl)-$N_2$-(3-pyridyl) pyrrolo[2,3-b]pyrazine-2,7-dicarboxamide)

Step 1. A mixture of Intermediate D (1.00 g, 2.18 mmol), $PdCl_2(PPh_3)_2$ (319 mg, 435 □ mol) in a mixture of DMF (5 mL), MeOH (5 mL) and $Et_3N$ (1.90 mL, 13.6 mmol) was heated at 70° C. under an atmosphere of carbon monoxide (balloon) for 18 h. The apparatus was previously flushed with carbon monoxide once. The volatiles were evaporated in vacuo and the residue was purified by preparative HPLC to provide methyl 6-amino-7-carbamoyl-5-(3-methoxy-2,6-dimethyl-phenyl) pyrrolo[2,3-b]pyrazine-2-carboxylate (689 mg, 86% yield).

Step 2. To methyl 6-amino-7-carbamoyl-5-(3-methoxy-2,6-dimethyl-phenyl) pyrrolo[2,3-b]pyrazine-2-carboxylate (689 mg, 1.87 mmol) in THF (5 mL) was added NaOH (1 M, 5.60 mL) and the mixture was stirred for 1.5 h. The pH was acidified using conc. HCl, DMSO was added, volatiles were removed under reduced pressure and the residue was purified by preparative HPLC to provide 6-amino-7-carbamoyl-5-(3-methoxy-2,6-dimethyl-phenyl) pyrrolo[2,3-b]pyrazine-2-carboxylic acid (366 mg, 55% yield).

Step 3. To pyridin-3-amine (7.95 mg, 84.4 μmol), 6-amino-7-carbamoyl-5-(3-methoxy-2,6-dimethyl-phenyl) pyrrolo[2,3-b]pyrazine-2-carboxylic acid (25 mg, 70 μmol) and HATU (29 mg, 77 μmol) in DCM (5 mL) was added DIPEA (211 μmol, 37 μL). The reaction mixture was stirred for 18 h. Water was added to the mixture, the organic phase was separated, dried over $Na_2SO_4$, filtered and concentrated in vacuo to afford crude 6-amino-5-(3-methoxy-2,6-dimethyl-phenyl)-$N_2$-(3-pyridyl) pyrrolo[2,3-b]pyrazine-2,7-dicarboxamide (21 mg, 34% yield, 49% purity).

Step 4. For OMe deprotection using $BBr_3$, following general procedure 2 provided a residue which was purified by preparative HPLC to provide 6-amino-5-(3-hydroxy-2,6-dimethyl-phenyl)-$N_2$-(3-pyridyl) pyrrolo[2,3-b]pyrazine-2,7-dicarboxamide (3.5 mg, 12% yield). 1H NMR (400 MHZ, DMSO-d6) δ10.82 (s, 1H), 9.61 (s, 1H), 8.92 (d, J=2.5 Hz, 1H), 8.49 (s, 1H), 8.32 (dd, J=4.8, 1.6 Hz, 1H), 8.20-8.10 (m, 1H), 7.75 (d, J=9.0 Hz, 3H), 7.40 (dd, J=8.3, 4.7 Hz, 1H), 7.30 (s, 1H), 7.07 (d, J=8.3 Hz, 1H), 6.93 (d, J=8.3 Hz, 1H), 1.75 (s, 3H), 1.67 (s, 3H). MS: [M+1]: 418.3.

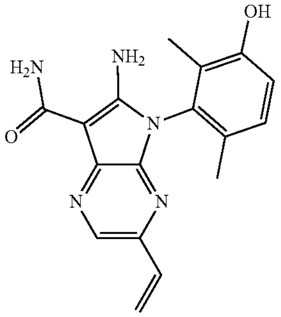 [SMILES: C=Cc1cnc2c(C(N)=O)c(N)n(-c3c(C)ccc(O)c3C)c2n1]

Compound 257 (6-amino-5-(3-hydroxy-2,6-dimethyl-phenyl)-3-vinyl-pyrrolo[2,3-b]pyrazine-7-carboxamide)

Step 1. A mixture of tributyl(vinyl) stannane (37.1 mg, 117 μmol), Intermediate H (40.0 mg, 106 μmol), CuI (2.56 mg, 13.4 μmol), LiCl (9.30 mg, 220 μmol), $PdCl_2(dppf)\cdot CH_2Cl_2$ (8.1 mg, 10 μmol) in DMF (1 mL) was degassed in vacuo, then back filled with nitrogen. The final mixture was stirred at 130° C. for 3 h, cooled to rt, filtered and purified preparative HPLC to provide 6-amino-5-(3-hydroxy-2,6-dimethyl-phenyl)-3-vinyl-pyrrolo[2,3-b]pyrazine-7-carboxamide (1.4 mg, 4% yield). 1H NMR (400 MHZ, DMSO-d6) δ9.59 (s, 1H), 8.29 (s, 1H), 8.19 (s, 1H), 7.38 (d, J=24.4 Hz, 2H), 7.20 (s, 1H), 7.05 (d, J=8.3 Hz, 1H), 6.91 (d, J=8.3 Hz, 1H), 6.69 (dd, J=17.3, 10.8 Hz, 1H), 5.80 (dd, J=17.3, 1.8 Hz, 1H), 5.15 (dd, J=10.7, 1.8 Hz, 1H), 1.75 (s, 3H), 1.67 (s, 3H). MS: [M+1]: 324.3.

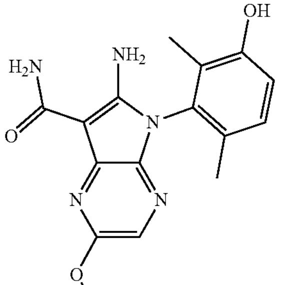

Compound 260 (6-amino-2-(cyclopropoxy)-5-(3-hydroxy-2,6-dimethyl-phenyl) pyrrolo[2,3-b]pyrazine-7-carboxamide)

Step 1. A solution of cyclopropanol (12 mg, 202 μmol), Intermediate D (31 mg, 67 μmol) and $Cs_2CO_3$ (66 mg, 202 μmol) in NMP (1 mL) was stirred at 140° C. for 16 h. The mixture was cooled to rt, filtered and purified by preparative HPLC to provide 6-amino-2-(cyclopropoxy)-5-(3-methoxy-2,6-dimethyl-phenyl) pyrrolo[2,3-b]pyrazine-7-carboxamide (3 mg, 12% yield)

Step 2. For OMe deprotection using $BBr_3$, following general procedure 2 provided a residue which was purified by preparative HPLC to provide 6-amino-2-(cyclopropoxy)-5-(3-hydroxy-2,6-dimethyl-phenyl) pyrrolo[2,3-b]pyrazine-7-carboxamide (0.52 mg, 18% yield). 1H NMR (400 MHZ, DMSO-d6) δ 9.57 (s, 1H), 8.45 (s, 1H), 7.35 (s, 1H), 7.19 (d, J=19.0 Hz, 3H), 7.02 (d, J=8.3 Hz, 1H), 6.88 (d, J=8.3 Hz, 1H), 4.25-4.14 (m, 1H), 1.73 (s, 3H), 1.65 (s, 3H), 0.73 (t, J=5.0 Hz, 2H), 0.68 (s, 2H). MS: [M+1]: 354.4.

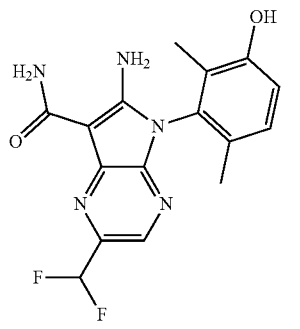 [SMILES: Cc1ccc(O)c(C)c1-n1c(N)c(C(N)=O)c2nc(C(F)F)cnc21]

Compound 263 (6-amino-2-(difluoromethyl)-5-(3-hydroxy-2,6-dimethyl-phenyl) pyrrolo[2,3-b]pyrazine-7-carboxamide)

Step 1. A microwave flask was charged with $PdCl_2(PPh_3)_2$ (79.6 mg, 109 μmol), Intermediate D (1.00 g, 2.18 mmol) and sodium formate (222 mg, 3.27 mmol). The flask was flushed with carbon monoxide. DMF (5 mL) was added and a slow stream of carbon monoxide was passed into the suspension. The mixture was vigorously stirred at 100° C. for 2 h under an atmosphere of carbon monoxide. The resulting mixture was cooled to rt, filtered and the supernatant was purified by preparative HPLC to provide a crude mixture of 6-amino-2-formyl-5-(3-methoxy-2,6-dimethyl-phenyl) pyrrolo[2,3-b]pyrazine-7-carboxamide (556 mg, 75% yield).

Step 2. To a solution of 6-amino-2-formyl-5-(3-methoxy-2,6-dimethyl-phenyl) pyrrolo[2,3-b]pyrazine-7-carboxamide (180 mg, 530 μmol) in DCM (2 mL) at 0° C. was added Deoxo-Fluor® solution (50% in THF, 1.46 M, 2.00 mL) dropwise. The mixture was warmed to rt. After 2 h, extra Deoxo-Fluor® solution (50% in THF, 1.17 g, 2.65 mmol) was added. After 1 h more Deoxo-Fluor® solution (50% in THF, 2.35 g, 5.30 mmol) was added and the final mixture was stirred for 4 h then diluted with DCM and saturated aqueous $Na_2CO_3$ was added. The biphasic mixture was stirred for 1 h. The organic layer was separated, dried over $Na_2SO_4$, filtered and concentrated. The residue was purified by preparative HPLC to provide 6-amino-2-(difluoromethyl)-5-(3-methoxy-2,6-dimethyl-phenyl) pyrrolo[2,3-b]pyrazine-7-carboxamide (10 mg, 5% yield).

Step 3. For OMe deprotection using $BBr_3$, following general procedure 2 provided a residue which was purified by preparative HPLC to provide 6-amino-2-(difluoromethyl)-5-(3-hydroxy-2,6-dimethyl-phenyl) pyrrolo[2,3-b]pyrazine-7-carboxamide (3.0 mg, 31% yield). $^1$H NMR (400 MHZ, DMSO-d6) δ 9.66 (s, 1H), 8.29 (s, 1H), 8.00 (s, 1H), 7.65 (s, 2H), 7.30 (d, J=34.1 Hz, 2H), 7.11-6.98 (m, 2H), 6.99-6.69 (m, 1H), 1.73 (s, 3H), 1.65 (s, 3H). MS: [M+1]: 348.2.

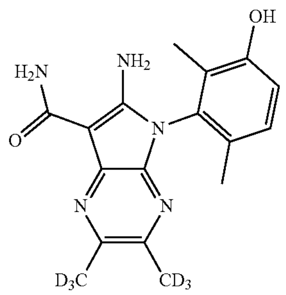 [SMILES: [2H]C([2H])([2H])c1nc2c(C(N)=O)c(N)n(-c3c(C)ccc(O)c3C)c2nc1C([2H])([2H])[2H]]

Compound 266 (6-amino-5-(3-hydroxy-2,6-dimethyl-phenyl)-2,3-bis(trideuteriomethyl) pyrrolo[2,3-b]pyrazine-7-carboxamide)

Step 1. To a suspension of magnesium turnings (380 mg, 15.7 mmol) in $Et_2O$ (20 mL) was added iodine (33 mg, 130 μmol). The mixture was stirred for 10 min and then $CD_3I$ (975 μL, 15.7 mmol) was added. The mixture was stirred 18 h under nitrogen atmosphere to generate an off-white suspension. $ZnCl_2$ (0.5 M in THF, 1.4 mL) was added dropwise and the mixture was stirred for 20 min. Intermediate D (1.2 g, 2.61 mmol) and $Pd(PPh_3)_4$ (300 mg, 259 μmol) were added. The mixture was stirred at 70° C. for 72 h under nitrogen atmosphere. The reaction was quenched with aqueous HCl 1M, diluted with water, and extracted with EtOAc twice. The combined organic extracts were washed with water, brine, dried over $Na_2SO_4$, filtered and concentrated to dryness. The residue was purified by silica gel chromatography eluting with a gradient of 0 to 80% EtOAc in hexanes to provide 6-amino-5-(3-methoxy-2,6-dimethyl-phenyl)-2-(trideuteriomethyl) pyrrolo[2,3-b]pyrazine-7-carboxamide (400 mg, 46% yield).

Step 2. To a solution of 6-amino-5-(3-methoxy-2,6-dimethyl-phenyl)-2-(trideuteriomethyl) pyrrolo[2,3-b]pyrazine-7-carboxamide (400 mg, 1.22 mmol) in DMF (2 mL) was added NBS (259 mg, 1.46 mmol). The mixture was stirred for 10 min, diluted with water, stirred for 20 min and filtered. The precipitate was purified by preparative HPLC to provide 6-amino-3-bromo-5-(3-methoxy-2,6-dimethyl-phenyl)-2-(trideuteriomethyl) pyrrolo[2,3-b]pyrazine-7-carboxamide (400 mg, 81% yield).

Step 3. To a suspension of magnesium (177 mg, 7.3 mmol) in ether (10 mL) was added iodine (16 mg, 61 μmol). The mixture was stirred for 10 min and then to it was added $CD_3I$ (455 μL, 7.31 mmol). The mixture was stirred for 18 h under nitrogen atmosphere to yield an off-white suspension. $ZnCl_2$ (0.5 M in THF, 14.6 mL) was added dropwise. After the addition, the mixture was stirred for 20 min. 6-amino-3-bromo-5-(3-methoxy-2,6-dimethyl-phenyl)-2-(trideuteriomethyl) pyrrolo[2,3-b]pyrazine-7-carboxamide (496 mg, 1.22 mmol), $Pd_2dba_3$ (111 mg, 122 μmol), and tritert-butylphosphonium tetrafluoroborate (71 mg, 244 μmol) were added and the mixture was stirred at 70° C. for 18 h under nitrogen atmosphere. The reaction was quenched with aqueous HCl 1M, diluted with water and extracted with EtOAc twice. The combined organic extracts were washed with water, brine, dried over $Na_2SO_4$, filtered and concentrated to dryness. The residue was purified by silica gel chromatography eluting with a gradient of 0 to 60% EtOAc in hexanes to provide 6-amino-5-(3-methoxy-2,6-dimethyl-phenyl)-2,3-bis(trideuteriomethyl) pyrrolo[2,3-b]pyrazine-7-carboxamide (400 mg, 95% yield).

Step 4. For OMe deprotection using $BBr_3$, following general procedure 2 provided a residue which was purified by preparative HPLC to provide 6-amino-5-(3-hydroxy-2,6-dimethyl-phenyl)-2,3-bis(trideuteriomethyl) pyrrolo[2,3-b]pyrazine-7-carboxamide (65 mg, 17% yield). 1H NMR (400 MHZ, DMSO-d6) δ9.55 (s, 1H), 7.41 (s, 1H), 7.22-6.98 (m, 4H), 6.89 (d, J=8.3 Hz, 1H), 1.74-1.69 (m, 3H), 1.63 (s, 3H). MS: [M+1]: 332.2.

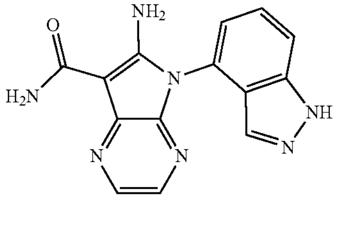 [SMILES: NC(=O)c1c(N)n(-c2cccc3[nH]ncc23)c2nccnc12]

Compound 277 (6-amino-5-(1H-indazol-4-yl)pyrrolo[2,3-b]pyrazine-7-carboxamide)

Step 1. 2-(3-chloropyrazin-2-yl) propanedinitrile (intermediate J, 300 mg, 1.68 mmol), NMP (4 mL) and 1H-indazol-4-amine (670 mg, 5.03 mmol) in NMP (4 mL) was heated at 150° C. for 4 h and brought back to rt. Saturated aqueous $NaHCO_3$ (10 mL) was added dropwise under stirring and the resulting solid was collected by filtration and washed with $H_2O$ then purified by prep HPLC (20-80% MeCN in $H_2O$, 0.1% formic acid modifier). The appropriate fractions were combined and lyophilized to provide 6-amino-5-(1H-indazol-4-yl)pyrrolo[2,3-b]pyrazine-7-carbonitrile (45 mg, 10% yield). 1H NMR (400 MHZ, DMSO-d6) δ13.39 (s, 1H), 8.09 (dt, J=2.9, 1.4 Hz, 1H), 7.80-7.62 (m, 4H), 7.49 (ddd, J=8.5, 7.1, 1.3 Hz, 1H), 7.37-7.13 (m, 1H). MS: [M+1]: 276.1.

Step 2. Following general procedure 1, 6-amino-5-(1H-indazol-4-yl)pyrrolo[2,3-b]pyrazine-7-carbonitrile (40 mg, 0.145 mmol) was treated with $H_2SO_4$ to provide 6-amino-5-(1H-indazol-4-yl) pyrrolo[2,3-b]pyrazine-7-carboxamide (compound 277, 18 mg, 39% yield) as a yellow solid after purification by prep HPLC (30-60% MeCN in $H_2O$, 0.1% formic acid modifier). 1H NMR (400 MHZ, DMSO-d6) δ13.62-13.24 (m, 1H), 8.11 (d, J=3.1 Hz, 1H), 7.84-7.62 (m, 3H), 7.57-7.38 (m, 4H), 7.30-7.14 (m, 2H). MS: [M+1]: 294.1.

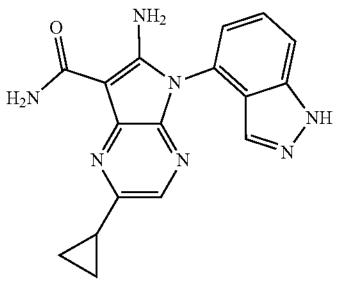 [SMILES: NC(=O)c1c(N)n(-c2cccc3[nH]ncc23)c2ncc(C3CC3)nc12]

Compound 330 (6-amino-2-cyclopropyl-5-(1H-indazol-4-yl)pyrrolo[2,3-b]pyrazine-7-carboxamide)

Step 1. To a solution of 5-benzyloxy-2-bromo-3-chloro-pyrazine (intermediate B, 5.00 g, 16.7 mmol) in toluene (60 mL) were added potassium tert-butoxide (2.5 g, 22 mmol), 1-tetrahydropyran-2-ylindazol-4-amine (4 g, 18 mmol), $Pd_2dba_3$ (800 mg, 0.874 mmol) and Xantphos (1.00 g, 1.73 mmol). The mixture was degassed in vacuo and back-filled with $N_2$, then stirred at 110° C. for 1 h. After cooling down to rt, the mixture was diluted with EtOAc, washed with water and brine, dried over sodium sulfate, filtered and concentrated to dryness. The residue was purified by flash chromatography on silica gel (0-35% EtOAc in hexanes) to provide N-(5-benzyloxy-3-chloro-pyrazin-2-yl)-1-tetrahydropyran-2-yl-indazol-4-amine (3.3 g, 45% yield) as an off-white solid. MS: [M+1]: 436.2.

Step 2. To a solution of malononitrile (1.02 g, 15.51 mmol) in DME (40 mL) was added sodium hydride (60% dispersion in mineral oil, 660 mg, 15.22 mmol) portionwise. After the, addition, the mixture was stirred at rt for 5 min after which were added N-(5-benzyloxy-3-chloro-pyrazin-2-yl)-1-tetrahydropyran-2-yl-indazol-4-amine (3.30 g, 7.57 mmol) and $Pd(PPh_3)_4$ (430 mg, 0.372 mmol). The mixture was degassed in vacuo and back-filled with $N_2$, then refluxed for 2 h under $N_2$. After cooling down to rt, the mixture was diluted with water, stirred at rt for 20 min, and the solid formed was collected by filtration, washed with $H_2O$ and dried in vacuo, affording a first crop of desired product. The filtrate was concentrated to a residue which was purified by flash chromatography on silica gel (0-10% MeOH in DCM). The appropriate fractions were combined and concentrated, affording a second crop. The two batches were combined to obtain 6-amino-2-benzyloxy-5-(1-tetrahydropyran-2-ylindazol-4-yl)pyrrolo[2,3-b]pyrazine-7-carbonitrile (3.05 g, 87% yield) as a yellowish solid. MS: [M+1]: 466.2.

Step 3. Following general procedure 1, 6-amino-2-benzyloxy-5-(1-tetrahydropyran-2-ylindazol-4-yl) pyrrolo[2,3-b]pyrazine-7-carbonitrile (2.95 g, 6.34 mmol) was treated with $H_2SO_4$ to provide crude 6-amino-2-hydroxy-5-(1H-indazol-4-yl)pyrrolo[2,3-b]pyrazine-7-carboxamide (1.71 g, 87% yield) as an off-white solid. MS: [M+1]: 310.2.

Step 4a. To a solution of 6-amino-2-hydroxy-5-(1H-indazol-4-yl)pyrrolo[2,3-b]pyrazine-7-carboxamide (50 mg, 0.162 mmol) and cesium carbonate (65 mg, 0.20 mmol) in DMF (1 mL) was added 1,1,1-trifluoro-N-phenyl-N-(trifluoromethylsulfonyl) methanesulfonamide (69 mg, 0.19 mmol). The mixture was stirred at rt for 2 h, filtered and the filtrate was purified by prep HPLC (30-70% MeCN in $H_2O$, 0.1% formic acid modifier) to provide [6-amino-7-carbamoyl-5-(1H-indazol-4-yl)pyrrolo[2,3-b]pyrazin-2-yl] trifluoromethanesulfonate (23 mg, 32% yield) as an off-white solid. MS: [M+1]: 442.2.

Step 4b. Alternatively, treating 6-amino-2-hydroxy-5-(1H-indazol-4-yl)pyrrolo[2,3-b]pyrazine-7-carboxamide (700 mg, 2.26 mmol) with more equivalents of cesium carbonate (1.62 g, 4.98 mmol) and 1,1,1-trifluoro-N-phenyl-N-(trifluoromethylsulfonyl) methanesulfonamide (1.7 g, 4.76 mmol) provided [6-amino-7-carbamoyl-5-[1-(trifluoromethylsulfonyl) indazol-4-yl]pyrrolo[2,3-b]pyrazin-2-yl] trifluoromethanesulfonate (450 mg, 35% yield) after purification by reverse-phase flash chromatography on C18 (10-95% MeCN in $H_2O$, 0.1% formic acid modifier). MS: [M+1]: 574.2.

Step 5. To a solution of [6-amino-7-carbamoyl-5-[1-(trifluoromethylsulfonyl) indazol-4-yl]pyrrolo[2,3-b]pyrazin-2-yl] trifluoromethanesulfonate (130 mg, 0.227 mmol) in DMF (1 mL) were added lithium chloride (22 mg, 0.52 mmol), Pd(dppf)$Cl_2$ (17 mg, 0.023 mmol), copper (I) iodide (9 mg, 0.047 mmol) and tributyl(cyclopropyl) stannane (150 mg, 0.453 mmol). The mixture was stirred at 120° C. for 18 h. The crude reaction mixture was filtered, and the filtrate was purified by prep HPLC (10-95% MeCN in $H_2O$, 0.1% formic acid modifier). Appropriate fractions were combined and lyophilized to afford 6-amino-2-cyclopropyl-5-[1-(trifluoromethylsulfonyl) indazol-4-yl]pyrrolo[2,3-b]pyrazine-7-carboxamide (40 mg, 38% yield). MS: [M+1]: 466.2.

Step 6. To a solution of 6-amino-2-cyclopropyl-5-[1-(trifluoromethylsulfonyl) indazol-4-yl]pyrrolo[2,3-b]pyrazine-7-carboxamide (40 mg, 0.086 mol) in MeOH (0.5 mL) was added sodium methoxide (0.5 M in MeOH, 540 μL). The mixture was submitted to microwave irradiation for 30 min at 120° C. It was then acidified with AcOH, and purified by prep HPLC (10-95% MeCN in $H_2O$, 0.1% formic acid modifier) to provide 6-amino-2-cyclopropyl-5-(1H-indazol-4-yl)pyrrolo[2,3-b]pyrazine-7-carboxamide (compound 330, 16 mg, 56% yield) as an off-white solid. 1H NMR (400 MHZ, Methanol-d4) δ 7.77-7.69 (m, 2H), 7.67 (s, 1H), 7.59 (m, 1H), 7.27 (d, J=7.2 Hz, 1H), 2.10 (m, 1H), 1.26-0.70 (m, 4H). MS: [M+1]: 334.2.

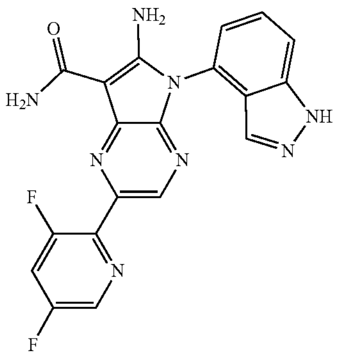 [SMILES: NC(=O)c1c(N)n(-c2cccc3[nH]ncc23)c2ncc(-c3ncc(F)cc3F)nc12]

Compound 333 (6-amino-2-(3,5-difluoro-2-pyridyl)-5-(1H-indazol-4-yl)pyrrolo[2,3-b]pyrazine-7-carboxamide)

Following the procedure described for compound 330 step 5, using [6-amino-7-carbamoyl-5-(1H-indazol-4-yl) pyrrolo[2,3-b]pyrazin-2-yl] trifluoromethanesulfonate (22 mg, 0.050 mmol) and tributyl-(3,5-difluoro-2-pyridyl) stannane (40 mg, 0.099 mmol) led to 6-amino-2-(3,5-difluoro-2-pyridyl)-5-(1H-indazol-4-yl) pyrrolo[2,3-b]pyrazine-7-carboxamide (compound 333, 6 mg, 30% yield) as an off-white solid, after purification by prep HPLC (30-65% MeCN in $H_2O$, 0.1% formic acid modifier). 1H NMR (400 MHZ, DMSO-d6) δ13.41 (s, 1H), 8.61 (d, J=2.4 Hz, 1H), 8.31 (s, 1H), 8.06 (m, 1H), 7.80 (s, 1H), 7.74 (d, J=8.5 Hz, 1H), 7.64-7.49 (m, 4H), 7.32 (s, 1H), 7.27 (d, J=7.2 Hz, 1H). MS: [M+1]: 407.2.

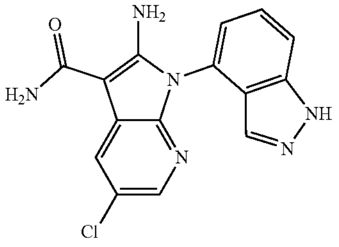 [SMILES: NC(=O)c1c(N)n(-c2cccc3[nH]ncc23)c2ncc(Cl)cc12]

Compound 334 (2-amino-5-chloro-1-(1H-indazol-4-yl)pyrrolo[2,3-b]pyridine-3-carboxamide)

Step 1. To a solution of 1-tetrahydropyran-2-ylindazol-4-amine (1.15 g, 5.27 mmol) in THF (10 mL) was added nBuLi (2.4 M in hexane, 2.20 mL) dropwise. After 10 min, this anion solution was added dropwise (over 20 min) to a solution of 3-bromo-5-chloro-2-fluoro-pyridine (1.0 g, 4.75 mmol) in THF (10 mL). After stirring for 2.75 h, the reaction mixture was quenched with saturated aqueous $NH_4Cl$ (50 mL) and extracted with EtOAc (3×). The combined organic extracts were washed with brine, dried over $Na_2SO_4$, filtered and concentrated. The crude residue was adsorbed on silica using DCM and purified by flash chromatography on silica gel (0-50% EtOAc in heptanes). The appropriate fractions were combined, concentrated and dried in vacuo to provide N-(3-bromo-5-chloro-2-pyridyl)-1-tetrahydropyran-2-yl-indazol-4-amine (460 mg, 24% yield). MS: [M+1]: 409.0.

Step 2. To a MW vial containing sodium hydride (60% dispersion in mineral oil, 98 mg, 2.5 mmol) in DME (6 mL) was added malononitrile (158 mg, 2.39 mmol) as a solution in DME (3 mL). After stirring for 20 min, N-(3-bromo-5-chloro-2-pyridyl)-1-tetrahydropyran-2-yl-indazol-4-amine (460 mg, 1.13 mmol) in DME (3 mL) and Pd(dppf)$Cl_2$.DCM (99 mg, 0.12 mmol) were added, the vial was flushed with $N_2$ bubbling through solution, capped and transferred to a preheated (95° C.) heat block for 2 h. After cooling down to rt, the reaction mixture was poured into saturated aqueous $NH_4Cl$ (20 mL) and extracted with DCM (3×). The combined organic extracts were washed with half-saturated brine, dried over $Na_2SO_4$, filtered, adsorbed on silica and purified by flash chromatography on silica gel (0-100% EtOAc in heptanes). The appropriate fractions were combined, concentrated and dried in vacuo, affording 2-amino-5-chloro-1-(1-tetrahydropyran-2-ylindazol-4-yl)pyrrolo[2,3-b]pyridine-3-carbonitrile (419 mg, 95% yield) as a light beige solid. MS: [M+1]: 393.2.

Step 3. To a suspension of 2-amino-5-chloro-1-(1-tetrahydropyran-2-ylindazol-4-yl)pyrrolo[2,3-b]pyridine-3-carbonitrile (419 mg, 1.07 mmol) in EtOH (reagent alcohol) (12 mL) and $H_2O$ (4 mL) was added lithium hydroxide monohydrate (338 mg, 8.05 mmol) and hydrogen peroxide (27% w/w aq. soln., stab., 19.4 mmol, 600 μL). The mixture was stirred at 60° C. for 30 min. After cooling down to rt, the mixture was diluted with water (20 mL) and the solid was collected by filtration and washed with $H_2O$ and dried in vacuo to provide 2-amino-5-chloro-1-(1-tetrahydropyran-2-ylindazol-4-yl)pyrrolo[2,3-b]pyridine-3-carboxamide (211 mg, 48% yield) as a pale yellow solid. MS: [M+1]: 411.1.

Step 4. A vial containing 2-amino-5-chloro-1-(1-tetrahydropyran-2-ylindazol-4-yl)pyrrolo[2,3-b]pyridine-3-carboxamide (215 mg, 0.523 mmol), MeOH (2.75 mL) and HCl aqueous (6 M, 1.35 mL) was capped and heated to 60° C. After 50 min, the reaction mixture was cooled to rt, concentrated to dryness then coevaporated with MeOH and excess $Et_3N$. The crude residue was purified by prep HPLC (25-55% MeCN in $H_2O$, 0.1% formic acid modifier). The desired fractions were combined and lyophilized to provide material which was purified again by flash chromatography (Isco silica 12 g GOLD cartridge, 1-20% MeOH in DCM) The appropriate fractions were combined, concentrated, the residue was suspended in MeCN/$H_2O$ and freeze-dried, affording 2-amino-5-chloro-1-(1H-indazol-4-yl)pyrrolo[2,3-b]pyridine-3-carboxamide (74 mg, 43% yield) as a white fluffy solid. 1H NMR (400 MHZ, DMSO-d6) δ 13.41 (s, 1H), 8.18 (d, J=2.2 Hz, 1H), 7.76-7.72 (m, 2H), 7.65 (d, J=1.2 Hz, 1H), 7.54 (dd, J=8.4, 7.3 Hz, 1H), 7.29 (s, 2H), 7.21 (dd, J=7.3, 0.7 Hz, 1H), 6.92 (s, 2H). MS: [M+1]: 327.1.

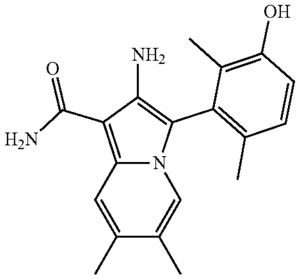 [SMILES: Cc1cc2c(C(N)=O)c(N)c(-c3c(C)ccc(O)c3C)n2cc1C]

Compound 336 (2-amino-3-(3-hydroxy-2,6-dimethylphenyl)-6,7-dimethylindolizine-1-carboxamide)

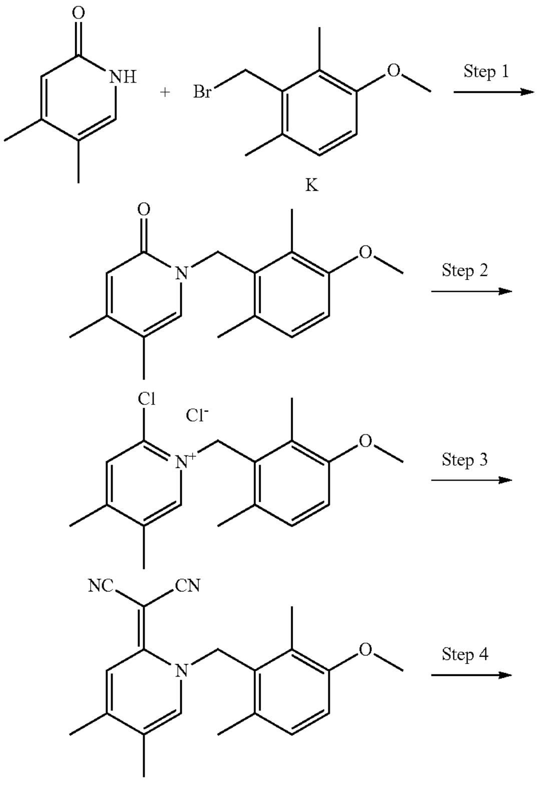

-continued

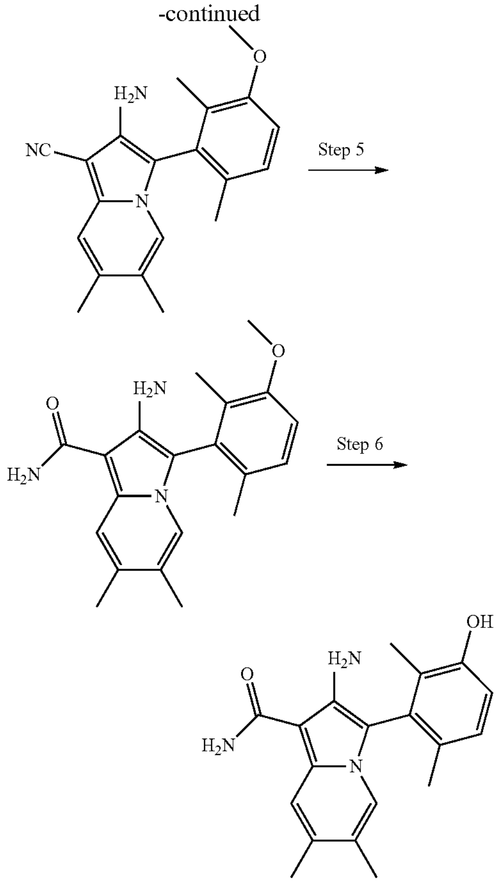

336

Step 1. To a solution of hexadecyltrimethylammonium bromide (100 mg, 274 μmol) (2% w/v) in $H_2O$ (6.17 mL) was added 4,5-dimethylpyridin-2 (1H)-one (400 mg, 3.09 mmol) followed by potassium carbonate (640 mg, 4.63 mmol). The reaction mixture was stirred at rt for 15 min. Then, 2-(bromomethyl)-4-methoxy-1,3-dimethylbenzene (intermediate K, 778 mg, 3.39 mmol) was added, and the reaction mixture was allowed to stir at 70° C. for 3 h. Upon completion, the reaction mixture was diluted with water (1 mL). The aqueous layer was extracted with EtOAc (3×3 mL); combined organic layers were washed with brine and dried over anhydrous $Na_2SO_4$. The crude product was purified by silica gel flash chromatography (0-100% EtOAc inhex) to afford 758 mg of 1-(3-methoxy-2,6-dimethylbenzyl)-4,5-dimethylpyridin-2 (1H)-one as a white solid. 1H-NMR (400 MHZ, $CDCl_3$): δ 7.06 (d; J=8.36 Hz; 1H); 6.81 (d; J=8.36 Hz; 1H); 6.44 (s; 1H); 6.42 (s; 1H); 5.10 (s; 2H); 3.83 (s; 3H); 2.19 (s; 3H); 2.11 (s; 3H); 2.09 (s; 3H); 1.83 (s; 3H). MS: [M+1]: 272.1.

Step 2. A solution of phosphorus (V) oxychloride (752 μL, 8.07 mmol) in DCE (4.48 mL) was added dropwise to a solution of 1-(3-methoxy-2,6-dimethylbenzyl)-4,5-dimethylpyridin-2 (1H)-one (730 mg, 2.69 mmol) in DCE (4.48 mL), and the resulting mixture was heated at 60° C. overnight. The mixture was concentrated to dryness under vacuum to give the crude 2-chloro-1-(3-methoxy-2,6-dimethylbenzyl)-4,5-dimethylpyridin-1-ium chloride as a viscous oil, which was used in the next step without further purification. MS: [M+1]: 290.1.

Step 3. A solution of malononitrile (444 mg, 6.73 mmol) in THF (3.50 mL) was added dropwise to a mixture of sodium hydride (60% in mineral oil, 269 mg, 6.73 mmol) in THF (3.50 mL), and the resulting mixture was stirred at RT for 30 min. Then, a solution of 2-chloro-1-(3-methoxy-2,6-dimethylbenzyl)-4,5-dimethylpyridin-1-ium chloride (878 mg, 2.69 mmol) in THF (3.50 mL) was added and the reaction mixture was stirred at RT for 1 h. The reaction was quenched with $H_2O$ (0.5 mL), aq. layer was extracted with DCM (3×2 mL). Combined organic layers were washed with brine, dried over anhydrous $Na_2SO_4$, filtered and concentrated. The crude product was purified by flash chromatography on silica gel (0-6% MeOH in DCM) to afford 350 mg of 2-(1-(3-methoxy-2,6-dimethylbenzyl)-4,5-dimethylpyridin-2 (1H)-ylidene)malononitrile as a yellow solid. 1H-NMR (400 MHZ, $CDCl_3$): δ 7.27 (s; 1H); 7.10 (d; J=8.41 Hz; 1H); 6.87 (d; J=8.40 Hz; 1H); 6.69 (s; 1H); 5.36 (s; 2H); 3.84 (s; 3H); 2.22 (s; 3H); 2.15 (s; 3H); 2.06 (s; 3H); 1.91 (s; 3H). MS: [M+1]: 320.2.

Step 4. A solution of 2-(1-(3-methoxy-2,6-dimethylbenzyl)-4,5-dimethylpyridin-2 (1H)-ylidene)malono nitrile (325 mg, 1.02 mmol) in THF (2.95 mL) was cooled down to 0° C. Then, potassium tert-butoxide (1 M in THF, 1.22 mL, 1.22 mmol) was added slowly in portions over a 10-min period. After 2 h at 0° C. and 2 h at RT, the mixture was diluted with DCM, quenched with $H_2O$, and extracted with DCM. The crude product was purified by flash chromatography on silica gel (0-7% MeOH in DCM) to obtain 281 mg of 2-amino-3-(3-methoxy-2,6-dimethylphenyl)-6,7-dimethylindolizine-1-carbonitrile as a red foamy solid. MS: [M+1]: 320.2.

Step 5. Following general procedure 1 for nitrile hydrolysis, 2-amino-3-(3-methoxy-2,6-dimethylphenyl)-6,7-dimethylindolizine-1-carbonitrile (200 mg, 0.623 mmol) was treated with $H_2SO_4$ to provide crude 2-amino-3-(3-methoxy-2,6-dimethylphenyl)-6,7-dimethylindolizine-1-carboxamide, after extraction with DCM. It was used in the next step without further purification. MS: [M+1]: 338.2.

Step 6. To a solution of 2-amino-3-(3-methoxy-2,6-dimethylphenyl)-6,7-dimethylindolizine-1-carboxamide (90 mg, 0.27 mmol) in DCM (2 mL) was added boron tribromide (1 M in DCM, 1.07 mL, 1.07 mmol) dropwise at RT. The reaction mixture was stirred at RT for 45 min. Then, it was diluted with DCM and quenched with saturated aqueous $NaHCO_3$. A red solid residue was formed, that was not soluble in aqueous or organic layers. The solid recovered from decantation was dissolved in acetone. LCMS of this solution showed the formation of isopropyl-imine. To regenerate the desired product from this by-product, acetone was evaporated, and the residue was dissolved in MeOH. HCl (12 M) was added to this solution until pH ~0, and the solution was neutralized with aqueous $NH_4OH$ to pH 9 after 2 h. The solvent was evaporated, and the resulting residue was purified by prep HPLC, affording 2-amino-3-(3-hydroxy-2,6-dimethylphenyl)-6,7-dimethylindolizine-1-carboxamide (compound 336, 20 mg). 1H-NMR (400 MHZ, $CDCl_3$): δ 7.65 (s; 1H); 7.10 (d; J=8.20 Hz; 1H); 7.03 (s; 1H); 6.89 (d; J=8.18 Hz; 1H); 5.70 (s; 2H); 5.05 (s; 1H); 4.00 (s; 2H); 2.30 (s; 3H); 2.10 (s; 3H); 1.95 (s; 3H); 1.93 (s; 3H). MS: [M+1]: 324.2.

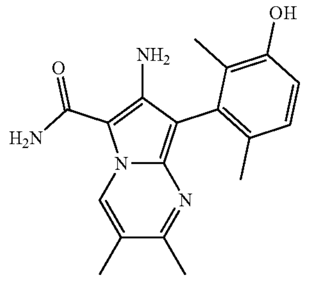 [SMILES: Cc1cn2c(C(N)=O)c(N)c(-c3c(C)ccc(O)c3C)c2nc1C]

Compound 337 (7-amino-8-(3-hydroxy-2,6-dimethylphenyl)-2,3-dimethylpyrrolo[1,2-a]pyrimidine-6-carboxamide)

Step 1. To a solution of 2-(3-methoxy-2,6-dimethylphenyl) acetonitrile (Intermediate L, 536 mg, 3.06 mmol) and 2-chloro-4,5-dimethylpyrimidine (300 mg, 2.04 mmol) in THF (6.00 mL) at rt was added dropwise potassium bis (trimethylsilyl)amide (0.5M/toluene, 6.12 mL, 3.06 mmol). The mixture was allowed to stand at rt for 2 h. Ice was added to the reaction mixture, diluted with EtOAc and saturated aqueous $NH_4Cl$ was added. The layers were partitioned and the aqueous layer was extracted with EtOAc. The combined organic layers were washed with brine, dried over anhydrous $MgSO_4$, filtered and concentrated to dryness in vacuo. The residue was adsorbed in silica gel for purification by flash chromatography on silica gel eluting with 0-60% EtOAc/hexanes. The desired fractions were concentrated to dryness to afford 330 mg of 2-(4,5-dimethylpyrimidin-2-yl)-2-(3-methoxy-2,6-dimethylphenyl) acetonitrile. 1H-NMR (400 MHZ, $CDCl_3$): δ 8.33 (s; 1H); 7.03 (d; J=8.37 Hz; 1H); 6.77 (d; J=8.37 Hz; 1H); 5.83 (s; 1H); 3.79 (s; 3H); 2.46 (s; 3H); 2.36 (s; 3H); 2.23 (s; 3H); 2.22 (s; 3H). MS: [M+1]: 282.1.

Step 2. To a suspension of 2-(4,5-dimethylpyrimidin-2-yl)-2-(3-methoxy-2,6-dimethylphenyl) acetonitrile (330 mg, 1.17 mmol) and potassium carbonate (973 mg, 7.04 mmol) in dry DMSO (3.30 mL) at rt was added dropwise bromoacetonitrile (204 L, 2.93 mmol) over 30 min. The reaction mixture was stirred at rt for 18 h and quenched with saturated aqueous $NH_4Cl$ and EtOAc. The layers were partitioned and the aqueous layer was extracted with EtOAc. The combined organic layers were washed with brine, dried over anhydrous $MgSO_4$, filtered and concentrated to dryness in vacuo. The residue was adsorbed in silica gel for purification by flash chromatography on silica gel eluting with 5-60% EtOAc/hexanes. The desired fractions were concentrated to dryness to afford 126 mg of 7-amino-8-(3-methoxy-2,6-dimethylphenyl)-2,3-dimethylpyrrolo[1,2-a]pyrimidine-6-carbonitrile as a yellow solid. $^1$H-NMR (400 MHZ, DMSO): δ 8.28 (s; 1H); 7.06 (d; J=8.33 Hz; 1H); 6.87 (d; J=8.34 Hz; 1H); 5.31 (s; 2H); 3.77 (s; 3H); 2.27 (s; 3H); 2.17 (s; 3H); 1.91 (s; 3H); 1.83 (s; 3H). MS: [M+1]: 321.1.

Step 3. Following general procedure 1, 7-amino-8-(3-methoxy-2,6-dimethylphenyl)-2,3-dimethylpyrrolo[1,2-a]pyrimidine-6-carbonitrile (126 mg, 0.393 mmol) was treated with $H_2SO_4$, to provide crude 7-amino-8-(3-methoxy-2,6-dimethylphenyl)-2,3-dimethylpyrrolo[1,2-a]pyrimidine-6-carboxamide (97 mg) as a light yellow solid which was submitted to the next step without further purification. MS: [M+1]: 339.1.

Step 4. Following general procedure 2, 7-amino-8-(3-methoxy-2,6-dimethylphenyl)-2,3-dimethylpyrrolo[1,2-a]pyrimidine-6-carboxamide (97 mg, 0.29 mmol) was treated with $BBr_3$, to provide 7-amino-8-(3-hydroxy-2,6-dimethylphenyl)-2,3-dimethylpyrrolo[1,2-a]pyrimidine-6-carboxamide (compound 337, 44 mg) as a light yellow solid, after basic aqueous work-up and purification by chromatography on silica gel (0-10% MeOH in DCM). 1H-NMR (400 MHZ, DMSO): δ 9.21 (s; 1H); 8.97 (s; 1H); 6.90 (d; J=8.16 Hz; 1H); 6.86 (s; 2H); 6.72 (d; J=8.11 Hz; 1H); 4.73 (s; 2H); 2.27 (s; 3H); 2.16 (s; 3H); 1.86 (s; 3H); 1.79 (s; 3H). MS: [M+1]: 325.1.

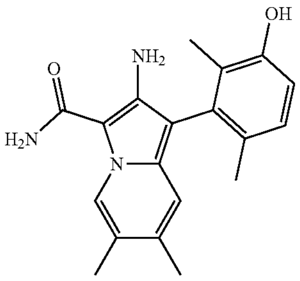 [SMILES: Cc1cc2c(-c3c(C)ccc(O)c3C)c(N)c(C(N)=O)n2cc1C]

Compound 338 (2-amino-1-(3-hydroxy-2,6-dimethylphenyl)-6,7-dimethylindolizine-3-carboxamide)

Step 1. A solution of 2-(3-methoxy-2,6-dimethylphenyl) acetonitrile (intermediate L, 500 mg, 2.85 mmol) in THF (4.0 mL) was cooled down to 0° C., and to it was added potassium bis(trimethylsilyl)amide (0.5 M in toluene, 11.4 mL, 5.71 mmol) dropwise. The resulting mixture was stirred at 0° C. for 30 min. Then, 5-bromo-2-fluoro-4-methylpyridine (657 μL, 5.71 mmol) was added dropwise, and the resulting mixture was allowed to warm up to RT and stir for 3 h. The reaction was quenched with $H_2O$, and the aqueous layer was extracted with EtOAc. The combined organic layers were washed with brine, dried over anhydrous $Na_2SO_4$, filtered and concentrated, and the crude residue was purified by flash chromatography on silica gel eluting with 0-50% EtOAc/hexanes to yield 650 mg of 2-(5-bromo-4-methylpyridin-2-yl)-2-(3-methoxy-2,6-dimethylphenyl) acetonitrile as a bright yellow foamy solid. 1H-NMR (400 MHZ, $CDCl_3$): δ 8.60 (s; 1H); 7.07 (d; J=8.35 Hz; 1H); 6.98 (s; 1H); 6.82 (d; J=8.47 Hz; 1H); 5.68 (s; 1H); 3.82 (s; 3H); 2.34 (s; 3H); 2.28 (s; 3H); 2.16 (s; 3H). MS: [M+1]: 345.0/347.0.

Step 2. Bromoacetonitrile (202 μL, 2.90 mmol) was added slowly to a mixture of 2-(4,5-dimethylpyridin-2-yl)-2-(3-methoxy-2,6-dimethylphenyl) acetonitrile (400 mg, 1.16 mmol) and potassium carbonate (961 mg, 6.95 mmol) in DMSO (4.0 mL). The mixture was stirred at RT for 72 h, water was added, and the aqueous layer was extracted with EtOAc (3×). The combined org layers were washed with brine, dried over anhydrous $Na_2SO_4$, filtered, and concentrated in vacuo. The crude was purified by flash chromatography on silica gel, eluting with 0-40% EtOAc/hexanes to yield 186 mg of 2-amino-6-bromo-1-(3-methoxy-2,6-dimethylphenyl)-7-methylindolizine-3-carbonitrile. 1H-NMR (400 MHZ, $CDCl_3$): δ 8.25 (s; 1H); 7.26 (s; 1H); 7.12 (d; J=8.39 Hz; 1H); 6.85 (d; J=8.41 Hz; 1H); 6.63 (s; 1H); 3.86 (s; 3H); 2.29 (s; 3H); 1.98 (s; 3H); 1.93 (s; 3H). MS: [M+1]: 384.1/386.0.

Step 3. A dry flask was charged with 2-amino-6-bromo-1-(3-methoxy-2,6-dimethylphenyl)-7-methylindolizine-3-carbonitrile (186 mg, 484 μmol), tri-t-butylphosphoniumtetrafluoroborate (28.1 mg, 96.8 μmol) and tris (dibenzylideneacetone)dipalladium (0) (44.3 mg, 48.4 μmol). The flask was purged with $N_2$. Then, THF (0.93 mL) was added, followed by the dropwise addition of a solution of dimethyl zinc (0.37 M in $Et_2O$, 5.23 mL, 1.94 mmol). After the addition, the mixture was heated to 70° C. for 2 h. Upon cooling to RT, the mixture was diluted with aqueous saturated $NH_4Cl$ (1 mL) and EtOAc (2 mL) and filtered through celite. The layers were partitioned, and the aqueous layer was extracted with EtOAc (×3). The combined organic layers were washed with brine, dried over anhydrous $MgSO_4$, filtered, and concentrated to dryness in vacuo. The crude product was purified by flash chromatography on silica gel eluting with 0-70% EtOAc/hexanes to yield 65 mg of 2-amino-1-(3-methoxy-2,6-dimethylphenyl)-6,7-dimethylindolizine-3-carbonitrile as an off-white foamy solid. 1H-NMR (400 MHz, $CDCl_3$): δ 7.86 (s; 1H); 7.12 (d; J=8.36 Hz; 1H); 6.84 (d; J=8.35 Hz; 1H); 6.55 (s; 1H); 3.86 (s; 3H); 3.69 (s; 2H); 2.20 (s; 3H); 2.17 (s; 3H); 2.00 (s; 3H); 1.95 (s; 3H). MS: [M+1]: 320.2.

Step 4. Following general procedure 1 for nitrile hydrolysis, 2-Amino-1-(3-methoxy-2,6-dimethylphenyl)-6,7-dimethylindolizine-3-carbonitrile (65.0 mg, 204 μmol) was stirred in conc. sulfuric acid (0.86 mL, 15.4 mmol) at RT for 2 h. Then, the reaction mixture was quenched with crushed ice, placed in an ice bath, and made alkaline to pH 9 with conc. $NH_4OH$. The aqueous layer was extracted with DCM (6×2 mL), the combined org layers were washed with brine, dried over anhydrous $Na_2SO_4$, filtered and concentrated in vacuo to afford the crude 2-amino-1-(3-methoxy-2,6-dimethylphenyl)-6,7-dimethylindolizine-3-carboxamide, which was used in the next step without further purification. MS: [M+1]: 338.2.

Step 5. Following general procedure 2, to a solution of 2-amino-1-(3-methoxy-2,6-dimethylphenyl)-6,7-dimethylindolizine-3-carboxamide (59.0 mg, 175 μmol) in DCM (1.64 mL) was added boron tribromide (1 M in DCM, 699 μL, 699 μmol) dropwise at RT. The reaction mixture was stirred at RT for 45 min. Then, it was diluted with DCM and quenched with saturated aqueous $NaHCO_3$. The aqueous layer was separated and extracted with DCM (6×2 mL). The combined organic layers were washed with brine, dried over anhydrous $Na_2SO_4$, filtered and concentrated. The crude residue was purified by flash chromatography on silica gel (treated with 0.1% TEA in DCM) eluting with 0-10% MeOH/DCM, the solid obtained was resuspended in 0.1% FA in ACN/$H_2O$ and lyophilized. to afford 24 mg of 2-amino-1-(3-hydroxy-2,6-dimethylphenyl)-6,7-dimethylindolizine-3-carboxamide as a yellow solid (compound 338, 24 mg) as a yellow solid. 1H-NMR (400 MHZ, $CDCl_3$): δ 9.35 (s; 1H); 7.06 (d; J=8.13 Hz; 1H); 6.81 (d; J=8.13 Hz; 1H); 6.58 (s; 1H); 5.80 (s; 2H); 3.47 (s; 2H); 2.23 (s; 3H); 2.19 (s; 3H); 1.97 (s; 6H). MS: [M+1]: 324.1.

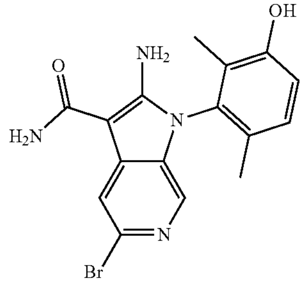 [SMILES: Cc1ccc(O)c(C)c1-n1c(N)c(C(N)=O)c2cc(Br)ncc21]

Compound 339 (2-amino-5-bromo-1-(3-hydroxy-2,6-dimethylphenyl)-1H-pyrrolo[2,3-c]pyridine-3-carboxamide)

Step 1. A solution of 30% $H_2O_2$ (70.5 mL) in $H_2SO_4$ (150 mL) at 0-5° C. was stirred for 10 min under $N_2$ atmosphere followed by a dropwise addition of 5-bromo-4-chloropyridin-2-amine (5.0 g, 24 mmol) as a solution in $H_2SO_4$ (15 mL) over a period of 30 min at 0° C. The reaction mixture was stirred at rt for 14 h. After completion of reaction (TLC, 10% ethyl acetate/hexanes), the reaction mixture was poured into cold water. The resulting precipitate was collected by filtration and dried under vacuum. The crude product was purified by flash chromatography on silica gel (EtOAc in hexanes, 2%). The desired fractions were combined and concentrated, to afford 5-bromo-4-chloro-2-nitropyridine (3.2 g, 56% yield). 1H NMR (400 MHZ, DMSO d6) δ 9.02 (s, 1H), 8.67 (s, 1H).

Step 2. 5-bromo-4-chloro-2-nitropyridine (2.0 g, 8.4 mmol) was dissolved in toluene (100 mL) and stirred at room temperature. To the resulting mixture was added 3-methoxy-2,6-dimethylaniline (Arylamine A2) (1.2 g, 7.9 mmol) and $Cs_2CO_3$ (4.5 g, 13.8 mmol). The reaction mixture was purged with $N_2$ gas for 10 min, followed by addition of $Pd(OAc)_2$ (0.28 g, 0.4 mmol) and rac-BINAP (0.39 g, 0.677 mmol). The reaction mixture was stirred at 110° C. for 6 h. After completion of reaction (TLC, 20% ethyl acetate in hexanes), the reaction mixture was quenched in water (30 mL) and extracted with EtOAc (3×), then the combined organic layer was dried over $Na_2SO_4$, filtered and concentrated under vacuum to get a crude product which was purified by flash chromatography on silica gel (10% EtOAc in hexanes). The desired fractions were combined and concentrated, to afford 4-chloro-N-(3-methoxy-2,6-dimethylphenyl)-6-nitropyridin-3-amine (1.1 g, 42% yield). MS: [M+1]: 308.4.

Step 3. To a cold (0° C.) solution of malononitrile (0.23 g, 3.5 mmol) in DMF (12 mL) was added NaH (60% dispersion in mineral oil, 0.168 g, 4.2 mmol). The resulting mixture was stirred at 0° C. for 30 min, after which 4-chloro-N-(3-methoxy-2,6-dimethylphenyl)-6-nitropyridin-3-amine (1.1 g, 3.5 mmol) and $Pd(PPh_3)_4$ (404 mg, 0.35 mmol) were added and the reaction mixture was heated to 80° C. for 10 h. After completion of the reaction (TLC, 30% EtOAc in hexanes), the reaction mixture was quenched in water (30 mL) and extracted with EtOAc (3×), then the combined organic layer was dried over $Na_2SO_4$, filtered and concentrated under vacuum to get crude product which was purified by flash chromatography on silica gel (20% EtOAc in hexanes). The desired fractions were combined and concentrated, to afford 2-amino-1-(3-methoxy-2,6-dimethylphenyl)-5-nitro-1H-pyrrolo[2,3-c]pyridine-3-carbonitrile (0.4 g, 33% yield). MS: [M+1]: 338.3.

Step 4. To a solution of 2-amino-1-(3-methoxy-2,6-dimethylphenyl)-5-nitro-1H-pyrrolo[2,3-c]pyridine-3-carbonitrile (1.7 g, 4.2 mmol) in THF (12 mL) was added TEA (1.6 g, 4.0 mmol) and DMAP (51 mg, 0.417 mmol). The resulting mixture was stirred at rt for 30 min. Boc anhydride (2.75 g, 12.6 mmol) was added and the reaction was stirred at rt for 1 h, followed by heating at 80° C. for 16 h. After completion of reaction (TLC, 60% EtOAc in hexanes), the reaction mixture was quenched in water (30 mL) and extracted with EtOAc (3×), then the combined organic layer was dried over $Na_2SO_4$, filtered and concentrated under vacuum to get the crude product which was purified by flash chromatography on silica gel (50% EtOAc in hexanes). The desired fractions were combined and concentrated, to afford tert-butyl (3-cyano-1-(3-methoxy-2,6-dimethylphenyl)-5-nitro-1H-pyrrolo[2,3-c]pyridin-2-yl) carbamate (0.8 g, 36% yield). MS: [M+1]: 382.3 $[M-tBu+H]^+$.

Step 5. To a solution of tert-butyl (3-cyano-1-(3-methoxy-2,6-dimethylphenyl)-5-nitro-1H-pyrrolo[2,3-c]pyridin-2-yl) carbamate (0.8 g, 1.83 mmol) in ethanol (2 mL) was added iron powder (0.29 g, 5.2 mmol) and ammonium chloride (289 mg, 5.2 mmol). The reaction mixture was heated at 70° C. for 6 h. After completion of reaction (TLC, 5% MeOH in DCM), the reaction mixture was filtered through a celite plug and concentrated in vacuum to get the crude product which was purified by flash chromatography on silica gel (5% MeOH in DCM). The desired fractions were combined and concentrated, to afford tert-butyl (5-amino-3-cyano-1-(3-methoxy-2,6-dimethylphenyl)-1H-pyrrolo[2,3-c]pyridin-2-yl) carbamate (0.35 g, 46% yield). MS: [M+1]: 408.3.

Step 6. To a solution of tert-butyl (5-amino-3-cyano-1-(3-methoxy-2,6-dimethylphenyl)-1H-pyrrolo[2,3-c]pyridin-2-yl) carbamate (0.35 g, 0.85 mmol) in MeCN (2 mL) was added $NaNO_2$ (0.059 g, 0.85 mmol) and CuBr (0.147 g, 1.03 mmol). After completion of the reaction (TLC, 5% MeOH in DCM), the reaction mixture was quenched in water (30 mL) and extracted with EtOAc (3×), then the combined organic layer was dried over $Na_2SO_4$, filtered and concentrated under vacuum to get the crude product which was purified by flash chromatography on silica gel (50% EtOAc in hexanes). The desired fractions were combined and concentrated, to afford tert-butyl (5-bromo-3-cyano-1-(3-methoxy-2,6-dimethylphenyl)-1H-pyrrolo[2,3-c]pyridin-2-yl) carbamate (0.14 g, 35% yield). MS: [M+1]: 471.4.

Step 7. A solution of tert-butyl (5-bromo-3-cyano-1-(3-methoxy-2,6-dimethylphenyl)-1H-pyrrolo[2,3-c]pyridin-2-yl) carbamate (0.14 g, 0.30 mmol) in MeOH (1.5 mL) was cooled to 0° C.) and aqueous HCl (6M, 1.5 mL) was added. The reaction mixture was stirred for 6 h at rt. After completion of reaction (TLC, 5% MeOH in DCM), the reaction mixture was quenched in saturated aqueous bicarbonate (10 mL) and extracted with EtOAc (3×), then the combined organic layer was dried over $Na_2SO_4$, filtered and concentrated under vacuum to get the crude product which was purified by flash chromatography on silica gel (50% EtOAc in hexanes). The desired fractions were combined and concentrated, to afford 2-amino-5-bromo-1-(3-methoxy-2,6-dimethylphenyl)-1H-pyrrolo[2,3-c]pyridine-3-carbonitrile (0.07 g, 63% yield). MS: [M+1]: 371.2.

Step 8. Treatment of 2-amino-5-bromo-1-(3-methoxy-2,6-dimethylphenyl)-1H-pyrrolo[2,3-c]pyridine-3-carbonitrile (0.07 g, 0.188 mmol) with concentrated $H_2SO_4$ (2 mL) following general procedure 1 afforded 2-amino-5-bromo-1-(3-methoxy-2,6-dimethylphenyl)-1H-pyrrolo[2,3-c]pyridine-3-carboxamide (0.045 g, 61%) after purification by flash chromatography on silica gel. MS: [M+1]: 389.3.

Step 9. Deprotection of 2-amino-5-bromo-1-(3-methoxy-2,6-dimethylphenyl)-1H-pyrrolo[2,3-c]pyridine-3-carboxamide (0.025 g, 0.0645 mmol) with $BBr_3$ following general procedure 2 afforded 2-amino-5-bromo-1-(3-hydroxy-2,6-dimethylphenyl)-1H-pyrrolo[2,3-c]pyridine-3-carboxamide (compound 339, 5 mg, 21% yield) after purification by flash chromatography on silica gel. $^1H$ NMR (400 MHZ, DMSO $d_6$) δ 9.68 (s, 1H), 7.88 (s, 1H), 7.39 (s, 1H), 7.29 (s, 1H), 7.14 (s, 2H), 6.98-6.94 (m, 2H), 1.78 (s, 3H), 1.69 (s, 3H). MS: [M−1]: 374.2.

Compounds 340 ((S)-1-(3-hydroxy-2,6-dimethylphenyl)-5,6-dimethyl-1Hpyrrolo[2,3-b]pyridine-3-carboxamide) and compound 341 ((R)-1-(3-hydroxy-2,6-dimethylphenyl)-5,6-dimethyl-1Hpyrrolo[2,3-b]pyridine-3-carboxamide)

Step 1. Following general procedure 1, [3-cyano-1-(3-methoxy-2,6-dimethyl-phenyl)-5,6-dimethyl-pyrrolo[2,3-b]

pyridin-2-yl]ammonium (see step 4 of the preparation procedure for Compound 181) was treated with $H_2SO_4$ to provide crude 2-amino-1-(3-methoxy-2,6-dimethyl-phenyl)-5,6-dimethyl-pyrrolo[2,3-b]pyridine-3-carboxamide (910 mg, 98% yield). MS: [M+1]: 339.3.

Step 2. To a suspension of 2-amino-1-(3-methoxy-2,6-dimethylphenyl)-5,6-dimethyl-1H-pyrrolo[2,3-b]pyridine-3-carboxamide (3.38 g, 9.99 mmol) in THF (60 mL) was added tert-butyl nitrite (2.70 mL, 20.5 mmol). After 90 min of stirring at rt, the reaction mixture was heated to 60° C. (oil bath) for 18 h. After cooling down to rt, the reaction mixture was evaporated to dryness and the crude residue was purified by silica gel flash chromatography (0-100% EtOAc in heptanes), then it was purified again (40-100% EtOAc in heptanes), the appropriate fractions were combined and concentrated to afford 1-(3-methoxy-2,6-dimethylphenyl)-5,6-dimethyl-1Hpyrrolo[2,3-b]pyridine-3-carboxamide (907 mg, 25%) as a brown solid. 1H NMR (400 MHZ, DMSO-d6) δ ppm 1.68 (s, 3H), 1.81 (s, 3H), 2.35 (s, 3H), 2.37 (s, 3H), 3.85 (s, 3H), 6.90-7.15 (m, 2H), 7.23 (d, J=8.6 Hz, 1H), 7.46 (br. s, 1H), 7.95 (s, 1H), 8.29 (s, 1H). MS: [M+1]: 324.2.

Step 3. To a solution of 1-(3-methoxy-2,6-dimethylphenyl)-5,6-dimethyl-1H-pyrrolo[2,3-b]pyridine-3-carboxamide (900 mg, 2.78 mmol) in methanesulfonic acid (15 mL) was added DL-methionine (1.66 g, 11.13 mmol) and the reaction mixture was stirred at 55° C. overnight. The reaction mixture was cooled to rt and was poured into an aqueous solution of $Na_2HPO_4$ (4.5 g) in water (150 mL) and the solution was basified with ~10 g of NaOH to pH 9-10. Ethyl acetate was added to get a suspension after 5 minutes of stirring. The precipitate obtained was washed with water to get a light brown solid, which was oven-dried. A portion of the crude product (300 mg) was purified by reverse phase flash chromatography on C18 (30-80% MeOH in $H_2O$, 0.1 TFA modifier). Appropriate fractions were freeze-dried to provide 1-(3-hydroxy-2,6-dimethylphenyl)-5,6-dimethyl-1Hpyrrolo[2,3-b]pyridine-3-carboxamide (TFA salt, 149 mg). MS: [M+1]: 310.1.

Chiral SFC separation of 1-(3-hydroxy-2,6-dimethylphenyl)-5,6-dimethyl-1Hpyrrolo[2,3-b]pyridine-3-carboxamide (149 mg), (Instrument: Pic Solution Hybrid 10-150; Column: Phenomenex Lux Cellulose-1 21.2×250 mm, 5 μm; Conditions: Isocratic at 35% MeOH with 65% $CO_2$; Flow Rate: 75 mL/min; outlet pressure 100 bar; column temperature 40° C.) provided Compound 340 and Compound 341.

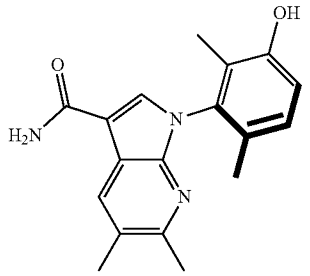

Compound 340 from chiral SFC separation of 1-(3-hydroxy-2,6-dimethylphenyl)-5,6-dimethyl-1Hpyrrolo[2,3-b]pyridine-3-carboxamide. Peak 1 (retention time 2.58 min (chiral HPLC), 0.75 min (chiral SFC), 100%). After the chiral SFC, the fractions were concentrated and purified by reverse phase flash chromatography on $C_{18}$ (10-100% MeOH in $H_2O$, ammonium bicarbonate modifier) to remove the TFA.

The fractions were concentrated then lyophilized from MeCN/$H_2O$, providing(S)-1-(3-hydroxy-2,6-dimethylphenyl)-5,6-dimethyl-1Hpyrrolo[2,3-b]pyridine-3-carboxamide (50 mg). 1H NMR (400 MHZ, DMSO-d6) δ ppm 1.64 (s, 3H), 1.75 (s, 3H), 2.34 (s, 3H), 2.37 (s, 3H), 3.32 (s, 2H), 6.90 (d, J=7.3 Hz, 1H), 6.97-7.14 (m, 2H), 7.42 (br. s, 1H), 7.94 (s, 1H), 8.28 (s, 1H), 9.53 (s, 1H). MS: [M+1]: 310.2.

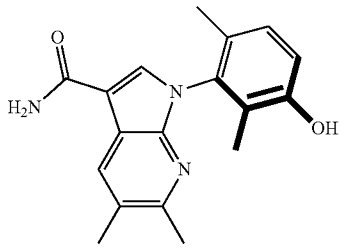

Compound 341 from chiral SFC separation of 1-(3-hydroxy-2,6-dimethylphenyl)-5,6-dimethyl-1Hpyrrolo[2,3-b]pyridine-3-carboxamide. Peak 2 (retention time 2.88 min (chiral HPLC), 1.52 min (chiral SFC), 100%). After the chiral SFC, the fractions were concentrated and purified by reverse phase flash chromatography on $C_{18}$ (10-100% MeOH in $H_2O$, ammonium bicarbonate modifier) to remove the TFA. The fractions were concentrated then lyophilized from MeCN/$H_2O$, providing (R)-1-(3-hydroxy-2,6-dimethylphenyl)-5,6-dimethyl-1Hpyrrolo[2,3-b]pyridine-3-carboxamide (51 mg). 1H NMR (400 MHZ, DMSO-d6) δ ppm 1.64 (s, 3H), 1.75 (s, 3H), 2.34 (s, 3H), 2.37 (s, 3H), 3.32 (s, 3H), 6.90 (d, J=8.1 Hz, 1H), 6.94-7.11 (m, 2H), 7.44 (br. s, 1H), 7.94 (s, 1H), 8.28 (s, 1H), 9.53 (s, 1H). MS: [M+1]: 310.1.

Compound 342 ((S)-5-chloro-1-(3-hydroxy-2,6-dimethylphenyl)-1H-pyrrolo[2,3-b]pyridine-3-carboxamide) and compound 343 ((R)-5-chloro-1-(3-hydroxy-2,6-dimethylphenyl)-1H-pyrrolo[2,3-b]pyridine-3-carboxamide)

Step 1. Intermediate 2-amino-5-chloro-1-(3-methoxy-2,6-dimethylphenyl)-1H-pyrrolo[2,3-b]pyridine-3-carbonitrile was prepared following the steps 1 and 2 from compound 334, using arylamine A2.

Step 2. To a solution of 2-amino-5-chloro-1-(3-methoxy-2,6-dimethylphenyl)-1H-pyrrolo[2,3-b]pyridine-3-carbonitrile (1.62 g, 4.96 mmol) in THF (24 mL) was added tert-butyl nitrite (1.30 mL, 9.84 mmol) at rt. After 30 minutes of stirring at rt, the solution was stirred at reflux for 1 h. The reaction mixture was evaporated to dryness and purified by flash chromatography on silica gel (0-60% EtOAc in heptanes). The appropriate fractions were combined and concentrated then dried in vacuo to afford 5-chloro-1-(3-methoxy-2,6-dimethylphenyl)-1H-pyrrolo[2,3-b]pyridine-3-carbonitrile (1.139 g, 73% yield) as a light yellow solid. 1H NMR (400 MHZ, DMSO-d6) δ ppm 1.67 (s, 3H), 1.79 (s, 3H), 3.85 (s, 3H), 7.13 (d, J=8.6 Hz, 1H), 7.26 (d, J=8.3 Hz, 1H), 8.39 (d, J=2.4 Hz, 1H), 8.46 (d, J=2.4 Hz, 1H), 8.68 (s, 1H). MS: [M+1]: 312.1.

Step 3. 5-chloro-1-(3-methoxy-2,6-dimethylphenyl)-1H-pyrrolo[2,3-b]pyridine-3-carbonitrile (1.200 g, 3.849 mmol) was added portionwise to a stirred solution of methanesulfonic acid (11 mL), sulfuric acid (1.50 mL) and water (139 μL, 7.70 mmol). The reaction mixture was stirred for 4 h at rt then the reaction mixture was heated to 35° C. for 90 minutes. DL-Methionine (2.297 g, 15.40 mmol) was added portionwise and the brown solution was stirred at 45° C. over 3 days, then more DL-methionine (600 mg) was added and the reaction mixture was stirred at 60° C. overnight. The reaction mixture was diluted with ice-cold water and the product was extracted with EtOAc (3×) and EtOAc/Me-THF (1×). The combined organic extracts were washed with water (3×) and brine, dried over sodium sulfate and evaporated to get the crude product which was purified by reverse phase flash chromatography on $C_{18}$ (10-100% MeOH in $H_2O$). The appropriate fractions were freeze-dried to provide 5-chloro-1-(3-hydroxy-2,6-dimethylphenyl)-1H-pyrrolo[2,3-b]pyridine-3-carboxamide (213 mg, 17% yield). MS: [M+1]: 316.1.

Chiral SFC separation of 5-chloro-1-(3-hydroxy-2,6-dimethylphenyl)-1H-pyrrolo[2,3-b]pyridine-3-carboxamide (120 mg), (Instrument: Pic Solution Hybrid 10-150; Column: Phenomenex Lux Cellulose-1 21.2×250 mm, 5 μm; Conditions: Isocratic at 35% MeOH with 65% $CO_2$; Flow Rate: 75 mL/min; outlet pressure 100 bar; column temperature 40° C.) provided Compound 342 and Compound 343.

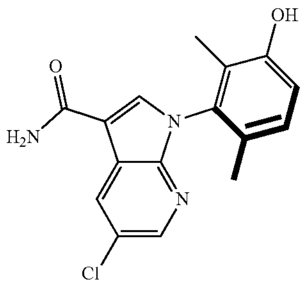

Compound 342 from chiral SFC separation of 5-chloro-1-(3-hydroxy-2,6-dimethylphenyl)-1H-pyrrolo[2,3-b]pyridine-3-carboxamide. Peak 1 (retention time 3.52 min (chiral HPLC), 0.8 min (chiral SFC), 99.6%): (S)-5-chloro-1-(3-hydroxy-2,6-dimethylphenyl)-1H-pyrrolo[2,3-b]pyridine-3-carboxamide (49 mg). 1H NMR (400 MHZ, DMSO-d6) δ ppm 1.65 (s, 3H), 1.76 (s, 3H), 6.92 (d, J=8.3 Hz, 1H), 7.06 (d, J=8.3 Hz, 1H), 7.18 (br. s, 1H), 7.61 (br. s, 1H), 8.22 (s, 1H), 8.26 (d, J=2.4 Hz, 1H), 8.55 (d, J=2.4 Hz, 1H), 9.58 (s, 1H). MS: [M+1]: 316.1.

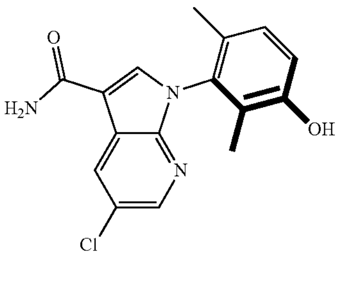

Compound 343 from chiral SFC separation of 5-chloro-1-(3-hydroxy-2,6-dimethylphenyl)-1H-pyrrolo[2,3-b]pyridine-3-carboxamide. Peak 2 (retention time 4.35 min (chiral HPLC), 1.82 min (chiral SFC), 99.6%): (R)-5-chloro-1-(3-hydroxy-2,6-dimethylphenyl)-1H-pyrrolo[2,3-b]pyridine-3-carboxamide (45 mg). 1H NMR (400 MHZ, DMSO-d6) δ ppm 1.65 (s, 3H), 1.75 (s, 3H), 6.92 (d, J=8.3 Hz, 1H), 7.06 (d, J=8.3 Hz, 1H), 7.19 (br. s, 1H), 7.61 (br. s, 1H), 8.22 (s, 1H), 8.26 (d, J=2.2 Hz, 1H), 8.55 (d, J=2.4 Hz, 1H), 9.59 (s, 1H). MS: [M+1]: 316.1.

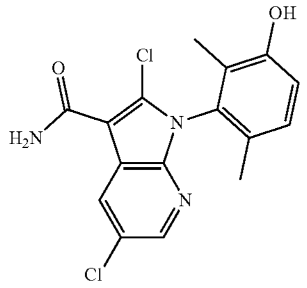 [SMILES: Cc1ccc(O)c(C)c1-n1c(Cl)c(C(N)=O)c2cc(Cl)cnc21]

Compound 344 (2,5-dichloro-1-(3-hydroxy-2,6-dimethylphenyl)-1Hpyrrolo[2,3-b]pyridine-3-carboxamide)

Step 1. To a cold (−15° C.) solution of diisopropylamine (200 μL, 1.43 mmol) in THF (2.50 mL) was added dropwise n-butyllithium in hexane (2.5M, 525 μL, 1.31 mmol) and the solution was stirred for 20 minutes at the same temperature. The resulting LDA solution was added dropwise to a cold (−78° C.) solution of 5-chloro-1-(3-methoxy-2,6-dimethylphenyl)-1H-pyrrolo[2,3-b]pyridine-3-carbonitrile prepared in step 2 of compounds 342 and 343 (341 mg, 1.09 mmol) in THF (3.50 mL) and the resulting mixture was stirred at the same temperature for 25 min then a solution of hexachloroethane (388 mg, 1.64 mmol) in THF (1.50 mL) was added dropwise. The cooling bath was removed and the solution was warmed up slowly to rt and stirred for 5 h. The reaction mixture was partitioned between EtOAc and saturated aqueous $NH_4Cl$ (sat) and the organic phase was washed with brine, dried over $Na_2SO_4$ and concentrated. The crude product was purified by flash chromatography on silica gel (0-50% EtOAc in heptanes), affording 2,5-dichloro-1-(3-methoxy-2,6-dimethylphenyl)-1Hpyrrolo[2,3-b]pyridine-3-carbonitrile (260 mg, 68% yield) as a colorless foam. 1H NMR (400 MHZ, $CDCl_3$) δ ppm 1.77 (s, 3H), 1.85 (s, 3H), 3.89 (s, 3H), 7.00 (d, J=8.3 Hz, 1H), 7.23 (d, J=8.6 Hz, 1H), 8.08 (d, J=2.4 Hz, 1H), 8.33 (d, J=2.4 Hz, 1H). MS: [M+1]: 348.0.

Step 2. To a solution/suspension of 2,5-dichloro-1-(3-methoxy-2,6-dimethylphenyl)-1H-pyrrolo[2,3-b]pyridine-3-carbonitrile (250 mg, 0.722 mmol) in ethanol (4 mL) was added $H_2O$ (1 mL) then Ghaffar-Parkins catalyst [PtH{$(PMe_2O)_2H$}($PMe_2OH$)] (7.0 mg, 0.016 mmol). The reaction mixture was stirred at 80° C. for 30 min. A solid was formed. The reaction mixture was cooled to rt, diluted with $H_2O$ (about 15 mL) and the solid was collected by filtration and oven-dried (60° C.) under reduced pressure to afford 2,5-dichloro-1-(3-methoxy-2,6-dimethylphenyl)-1Hpyrrolo[2,3-b]pyridine-3-carboxamide (225 mg, 85% yield) as a grey solid. 1H NMR (400 MHZ, DMSO-d6) δ ppm 1.64 (s, 3H), 1.76 (s, 3H), 3.86 (s, 3H), 7.14 (d, J=8.3 Hz, 1H), 7.28 (d, J=8.6 Hz, 1H), 7.45 (br. s, 1H), 7.65 (br. s, 1H), 8.28 (d, J=2.2 Hz, 1H), 8.42 (d, J=2.4 Hz, 1H). MS: [M+1]: 366.0.

Step 3. Following general procedure 2, deprotection of 2,5-dichloro-1-(3-methoxy-2,6-dimethylphenyl)-1H-pyrrolo[2,3-b]pyridine-3-carboxamide (110 mg, 0.302 mmol) led to 2,5-dichloro-1-(3-hydroxy-2,6-dimethylphenyl)-1Hpyrrolo[2,3-b]pyridine-3-carboxamide (compound 344, 18 mg, 17% yield) as a white fluffy solid after purification by reverse phase flash chromatography on $C_{18}$ (10-100% MeOH in $H_2O$). 1H NMR (400 MHZ, DMSO-d6) δ ppm 1.61 (s, 3H), 1.71 (s, 3H), 6.96 (d, J=8.3 Hz, 1H), 7.10 (d, J=8.3 Hz, 1H), 7.44 (br. s, 1H), 7.64 (br. s, 1H), 8.28 (d, J=2.4 Hz, 1H), 8.42 (d, J=2.2 Hz, 1H), 9.67 (s, 1H). MS: [M+1]: 352.0.

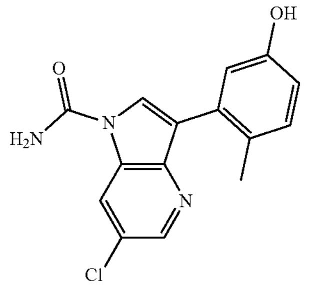 [SMILES: Cc1ccc(O)cc1-c1cn(C(N)=O)c2cc(Cl)cnc12]

Compound 345 (6-chloro-3-(5-hydroxy-2-methyl-phenyl) pyrrolo[3,2-b]pyridine-1-carboxamide)

Step 1. To a suspension of 6-chloro-1H-pyrrolo[3,2-b]pyridine (1.14 g, 7.47 mmol) in DMF (20 mL) was added N-iodosuccinimide (1.85 g, 8.22 mmol). The resulting solution was stirred at RT for 20 min, then $H_2O$ was added dropwise. The precipitate was collected by filtration on Buchner, washed with $H_2O$ and air-dried, affording 6-chloro-3-iodo-1H-pyrrolo[3,2-b]pyridine (2.02 g, 97% yield) as a white solid.

Step 2. A MW vial was charged with 6-chloro-3-iodo-1H-pyrrolo[3,2-b]pyridine (514 mg, 1.85 mmol) and [5-(methoxymethoxy)-2-methyl-phenyl]boronic acid (469 mg, 2.39 mmol) in dioxane (12 mL), and aqueous potassium carbonate (2 M, 2.77 mL). The mixture was flushed with $N_2$ (3×), $Pd(dppf)Cl_2$.DCM (228 mg, 0.28 mmol) was added, the mixture was flushed with $N_2$ again (3×), the vial was capped and transferred to a preheated (80° C.) heat block overnight. The reaction mixture was diluted with $H_2O$ and DCM, filtered on celite and the layers were separated. The aqueous layer was extracted with DCM (2×). The combined organic extracts were dried over $Na_2SO_4$, filtered and concentrated. The residue was purified by silica gel chromatography eluting with a gradient of EtOAc (0 to 100%) in heptanes. The appropriate fractions were combined and concentrated in vacuo to afford 6-chloro-3-[5-(methoxymethoxy)-2-methyl-phenyl]-1H-pyrrolo[3,2-b]pyridine (218 mg, 39% yield) as a yellowish white solid.

Step 3. To a solution of 6-chloro-3-[5-(methoxymethoxy)-2-methyl-phenyl]-1H-pyrrolo[3,2-b]pyridine (48 mg, 0.16 mmol) in THF (2 mL) was added triethylamine (36 mg, 0.36 mmol, 50 μL) then (4-nitrophenyl) carbonochloridate (64 mg, 0.32 mmol) and the mixture was stirred at RT overnight. Saturated aqueous $NH_4Cl$ was added and the mixture was extracted with EtOAc (3×). The combined organic extracts were washed with brine, dried over $Na_2SO_4$, filtered and concentrated, affording 102 mg crude product, as a yellow gum which was used as such in the next step, assuming quantitative yield of (4-nitrophenyl) 6-chloro-3-[5-(methoxymethoxy)-2-methyl-phenyl]pyrrolo[3,2-b]pyridine-1-carboxylate.

Step 4. To a sample of crude (4-nitrophenyl) 6-chloro-3-[5-(methoxymethoxy)-2-methyl-phenyl]pyrrolo[3,2-b]pyridine-1-carboxylate (52 mg, assuming 0.096 mmol) in DMF (1 mL) was added ammonium carbonate (40 mg, 0.42 mmol). The vial was sealed, warmed to about 40° C. and stirred for 20 min allowing to cool to RT. The crude mixture was concentrated to dryness and the residue was purified by silica gel chromatography eluting with a gradient of EtOAc (0 to 100%) in heptanes. The appropriate fractions were combined and concentrated in vacuo to afford 6-chloro-3-[5-(methoxymethoxy)-2-methyl-phenyl]pyrrolo[3,2-b]pyridine-1-carboxamide (15 mg, 45% yield) as a white solid.

Step 5. To a solution of 6-chloro-3-[5-(methoxymethoxy)-2-methyl-phenyl]pyrrolo[3,2-b]pyridine-1-carboxamide (15 mg, 0.43 mmol) in DCM (0.5 mL) was added TFA (745 mg, 6.53 mmol, 0.5 mL) and the resulting mixture was stirred at RT for 20 min then concentrated to dryness, taken in DCM, made basic with $Et_3N$ and concentrated again. The residue was purified by preparative HPLC (Phenomenex Gemini) eluting with a gradient of $CH_3CN$ (30 to 60%) in water both containing 0.1% formic acid. The appropriate fractions were combined and lyophilized to afford 6-chloro-3-(5-hydroxy-2-methyl-phenyl) pyrrolo[3,2-b]pyridine-1-carboxamide (compound 345, 2.47 mg, 19% yield) as a white fluffy solid. 1H NMR (400 MHZ, DMSO-d6) δ 9.23 (s, 1H), 8.63 (d, J=2.3 Hz, 1H), 8.50 (d, J=2.3 Hz, 1H), 8.23 (s, 1H), 7.87 (br s, 2H), 7.10 (d, J=8.3 Hz, 1H), 6.96 (d, J=2.6 Hz, 1H), 6.70 (dd, J=8.2, 2.6 Hz, 1H), 2.19 (s, 3H). MS: [M+1]: 302.0.

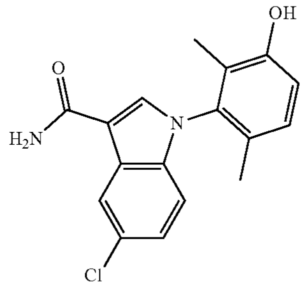 [SMILES: Cc1ccc(O)c(C)c1-n1cc(C(N)=O)c2cc(Cl)ccc21]

Compound 346 (5-chloro-1-(3-hydroxy-2,6-dimethylphenyl)-1H-indole-3-carboxamide)

Step 1. In a screw cap vial were added 2-bromo-4-chloro-1-iodobenzene (1.049 g, 3.307 mmol), arylamine A2 (500 mg, 3.31 mmol), Xantphos (143.5 mg, 0.2480 mmol), toluene (10 mL) and sodium tert-butoxide (635.5 mg, 6.613 mmol). The reaction mixture was sparged with nitrogen over the sonic bath and tris(dibenzylideneacetone)dipalladium (0) (227.1 mg, 0.2480 mmol) was added. After stirring for 3 hours at 80° C., the reaction mixture was filtered through a pad of silica gel and the filter cake was rinsed with EtOAc. The filtrate was washed with brine, dried over $Na_2SO_4$ and evaporated. The crude residue was purified by silica gel chromatography) using a gradient of 0 to 20% EtOAc in heptanes to yield N-(2-bromo-4-chlorophenyl)-3-methoxy-2,6-dimethylaniline (890 mg, 79%) as a yellowish solid.

Step 2. To a solution of malononitrile (340.5 mg, 5.154 mmol) in 1,2-dimethoxyethane (12.5 mL) was added sodium tert-butoxide (471.7 mg, 4.908 mmol) portion wise at room temperature under nitrogen. After 30 minutes of stirring, N-(2-bromo-4-chlorophenyl)-3-methoxy-2,6-dimethylaniline (836.0 mg, 2.454 mmol) and $Pd(dppf)Cl_2$.DCM (150.3 mg, 0.1841 mmol) were added. The reaction mixture was heated to reflux for 7 hours and was then cooled at 60° C. and diluted with ethyl acetate (~20 mL) and water (~10 mL). N-acetyl-cysteine (250 mg) was added and after 30 minutes of stirring the reaction mixture was cooled at room temperature and stirred overnight. The two layers were separated and the organic phase was washed with 1M aqueous solution of sodium carbonate, water (2×) and brine, dried over sodium sulfate and evaporated. The crude oily residue was purified by silica gel chromatography using a gradient of 5 to 50% EtOAc in heptanes to afford 2-amino-5-chloro-1-(3-methoxy-2,6-dimethylphenyl)-1H-indole-3-carbonitrile (735 mg, 91%) as a yellow solid.

Step 3. To a solution of 2-amino-5-chloro-1-(3-methoxy-2,6-dimethylphenyl)-1H-indole-3-carbonitrile (730 mg, 2.24 mmol) in THF (10 mL) was added tert-butyl nitrite (600 μL, 4.54 mmol). After 20 minutes of stirring at RT, the reaction mixture was heated to reflux for 1 hour. The solvent was evaporated to dryness and the crude residue was purified by silica gel chromatography using a gradient of 0 to 50% EtOAc in heptanes to yield 5-chloro-1-(3-methoxy-2,6-dimethylphenyl)-1H-indole-3-carbonitrile (450 mg, 64%) as an orange foam.

Step 4. 5-chloro-1-(3-methoxy-2,6-dimethylphenyl)-1H-indole-3-carbonitrile (445 mg, 1.43 mmol) was dissolved in 98% sulfuric acid (3.00 mL) and water (50 μL, 2.8 mmol) was added. After 90 minutes of stirring at room temperature, the reaction mixture was cooled to 0-5° C. and water was added to get a precipitate. The solid was collected and the filter cake was washed with water. The crude residue was dissolved into 5% methanol in dichloromethane and washed with water and brine, dried over $Na_2SO_4$ and evaporated. The crude product was purified by reverse phase column chromatography (C18) using a gradient of 10 to 100% methanol in water. Pure fractions were concentrated to remove volatiles and lyophilized to get 5-chloro-1-(3-methoxy-2,6-dimethylphenyl)-1H-indole-3-carboxamide (152 mg, 32%) as a beige fluffy solid.

Step 5. Following general procedure 2, deprotection of 5-chloro-1-(3-methoxy-2,6-dimethylphenyl)-1H-indole-3-carboxamide (146 mg, 0.444 mmol) led to 5-chloro-1-(3-hydroxy-2,6-dimethylphenyl)-1H-indole-3-carboxamide (compound 346, 121 mg, 86%) as a white fluffy solid after purification by reverse phase flash chromatography on C18 (10-100% MeCN in $H_2O$). 1H NMR (400 MHZ, DMSO-d6) δ ppm 1.65 (s, 3H), 1.75 (s, 3H), 6.83 (d, J=8.6 Hz, 1H), 6.94 (d, J=8.1 Hz, 1H), 6.97-7.12 (m, 2H), 7.18 (dd, J=8.8, 2.2 Hz, 1H), 7.51 (br. s, 1H), 8.06 (s, 1H), 8.26 (d, J=2.0 Hz, 1H), 9.67 (s, 1H). MS: [M+1]: 315.0.

TABLE 2

| Cpd. | Structure | FW | m/z | NMR | Preparation Method |
|---|---|---|---|---|---|
| 169 | 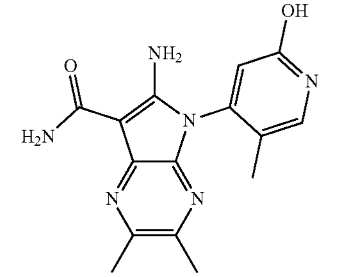 [SMILES: Cc1cnc(O)cc1-n1c(N)c(C(N)=O)c2nc(C)c(C)nc21] | 312.333 | 313.1 | 1H NMR (400 MHz, DMSO-d6) δ 7.48 (br s, 1H), 7.43 (br s, 3H), 7.17 (br s, 1H), 6.44 (s, 1H), 2.47 (s, 3H), 2.36 (s, 3H), 1.64 (s, 3H). | E |
| 262 | 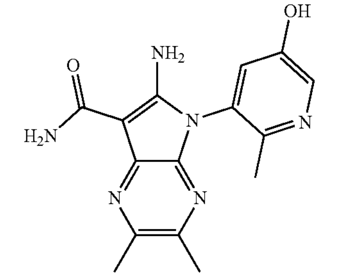 [SMILES: Cc1ncc(O)cc1-n1c(N)c(C(N)=O)c2nc(C)c(C)nc21] | 312.333 | 313.1 | 1H NMR (400 MHz, DMSO-d6) δ 10.21 (br s, 1H), 8.22 (d, J = 2.7 Hz, 1H), 7.45 (br d, J = 3.3 Hz, 1H), 7.34 (br s, 2H), 7.16 (d + br s, J = 2.6 Hz, 2H), 2.47 (s, 3H), 2.33 (s, 3H), 2.02 (s, 3H). | E |
| 277 | 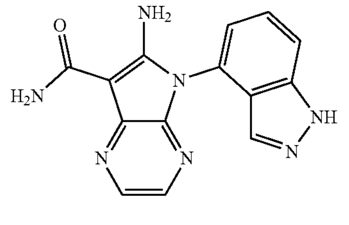 [SMILES: NC(=O)c1c(N)n(-c2cccc3[nH]ncc23)c2nccnc12] | 293.290 | 294.1 | 1H NMR (400 MHz, DMSO-d6) δ 13.43 (s, 1H), 8.15 (d, J = 3.0 Hz, 1H), 7.78-7.76 (m, 1H), 7.75 (d, J = 3.0 Hz, 2H), 7.56 (dd, J = 8.6, 7.3 Hz, 1H), 7.52 (br s, 2H), 7.49 (br s, 1H), 7.26 (dd + br s, J = 7.3, 0.5 Hz, 2H). | E |
| 329 | 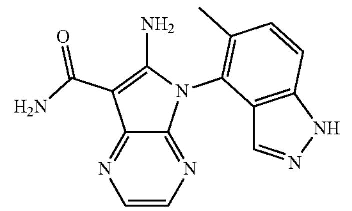 [SMILES: Cc1ccc2[nH]ncc2c1-n1c(N)c(C(N)=O)c2nccnc21] | 307.317 | 308.1 | 1H NMR (400 MHz, DMSO-d6) δ 13.28 (s, 1H), 8.10 (d, J = 3.1 Hz, 1H), 7.68 (d, J = 3.1 Hz, 1H), 7.65 (dd, J = 8.5, 1.1 Hz, 1H), 7.56 (s, 1H), 7.50-7.36 (m, 4H), 7.21 (s, 1H), 2.03 (d, J = 6.5 Hz, 3H). | E |

TABLE 2-continued
| Cpd. | Structure | FW | m/z | NMR | Preparation Method |
|---|---|---|---|---|---|
| 330 | 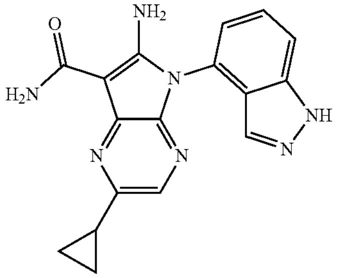 [SMILES: NC(=O)c1c(N)n(-c2cccc3[nH]ncc23)c2ncc(C3CC3)nc12] | 333.355 | 334.2 | 1H NMR (400 MHz, Methanol-d4) δ 7.77-7.69 (m, 2H), 7.67 (s, 1H), 7.59 (m, 1H), 7.27 (d, J = 7.2 Hz, 1H), 2.10 (m, 1H), 1.26-0.70 (m, 4H). | A |
| 331 | 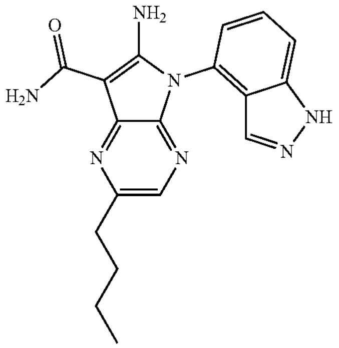 [SMILES: CCCCc1cnc2c(n1)c(C(N)=O)c(N)n2-c1cccc2[nH]ncc12] | 349.398 | 350.2 | 1H NMR (400 MHz, DMSO-d6) δ 13.37 (s, 1H), 7.73-7.66 (m, 2H), 7.59 (s, 1H), 7.57-7.47 (m, 2H), 7.39 (s, 2H), 7.25-7.17 (m, 2H), 2.70 (t, J = 7.6 Hz, 2H), 1.83-1.51 (m, 2H), 1.32 (h, J = 7.4 Hz, 2H), 0.88 (t, J = 7.3 Hz, 3H). | A |
| 332 | 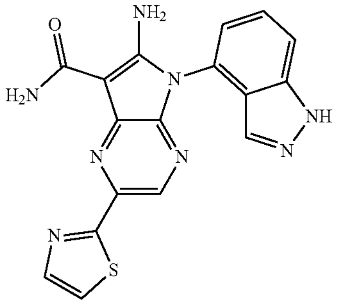 [SMILES: NC(=O)c1c(N)n(-c2cccc3[nH]ncc23)c2ncc(-c3nccs3)nc12] | 376.400 | 377.2 | 1H NMR (400 MHz, DMSO-d6) δ 13.41 (s, 1H), 7.91 (d, J = 3.2 Hz, 1H), 7.80 (d, J = 3.2 Hz, 2H), 7.77-7.65 (m, 3H), 7.53 (m, 1H), 7.43 (d, J = 6.3 Hz, 1H), 7.36 (s, 1H), 7.27 (d, J = 7.3 Hz, 1H). | A |
| 333 | 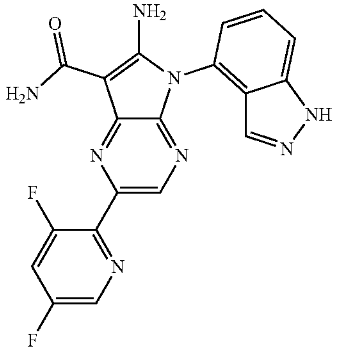 [SMILES: NC(=O)c1c(N)n(-c2cccc3[nH]ncc23)c2ncc(-c3ncc(F)cc3F)nc12] | 406.357 | 407.2 | 1H NMR (400 MHz, DMSO-d6) δ 13.41 (s, 1H), 8.61 (d, J = 2.4 Hz, 1H), 8.31 (s, 1H), 8.06 (m, 1H), 7.80 (s, 1H), 7.74 (d, J = 8.5 Hz, 1H), 7.64-7.49 (m, 4H), 7.32 (s, 1H), 7.27 (d, J = 7.2 Hz, 1H). | A |
| 334 | 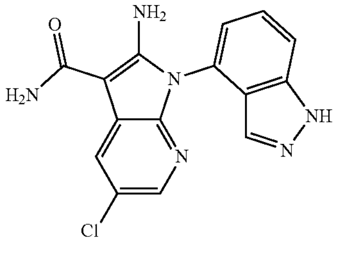 [SMILES: NC(=O)c1c(N)n(-c2cccc3[nH]ncc23)c2ncc(Cl)cc12] | 326.740 | 327.1 | 1H NMR (400 MHz, DMSO-d6) δ 13.41 (s, 1H), 8.18 (d, J = 2.2 Hz, 1H), 7.76-7.72 (m, 2H), 7.65 (d, J = 1.2 Hz, 1H), 7.54 (dd, J = 8.4, 7.3 Hz, 1H), 7.29 (s, 2H), 7.21 (dd, J = 7.3, 0.7 Hz, 1H), 6.92 (s, 2H). | K |

TABLE 2-continued
| Cpd. | Structure | FW | m/z | NMR | Preparation Method |
|---|---|---|---|---|---|
| 335 | 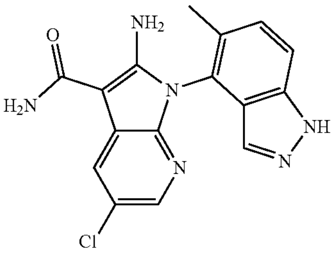 [SMILES: Cc1ccc2[nH]ncc2c1-n1c(N)c(C(N)=O)c2cc(Cl)cnc21] | 340.770 | 341.1 | 1H NMR (400 MHz, DMSO-d6) δ 13.29 (s, 1H), 8.18 (d, J = 2.1 Hz, 1H), 7.71 (d, J = 2.1 Hz, 1H), 7.66 (dd, J = 8.5, 1.0 Hz, 1H), 7.51 (s, 1H), 7.44 (d, J = 8.5 Hz, 1H), 7.23 (br s, 2H), 6.91 (br s, 2H), 2.02 (s, 3H). | K |
| 336 | 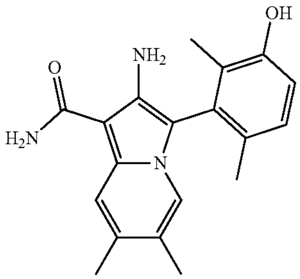 [SMILES: Cc1cc2c(C(N)=O)c(N)c(-c3c(C)ccc(O)c3C)n2cc1C] | 323.396 | 324.2 | 1H NMR (400 MHz, $CDCl_3$): δ 7.65 (s; 1H); 7.10 (d; J = 8.20 Hz; 1H); 7.03 (s; 1H); 6.89 (d; J = 8.18 Hz; 1H); 5.70 (s; 2H); 5.05 (s; 1H); 4.00 (s; 2H); 2.30 (s; 3H); 2.10 (s; 3H); 1.95 (s; 3H); 1.93 (s; 3H). | P |
| 337 | 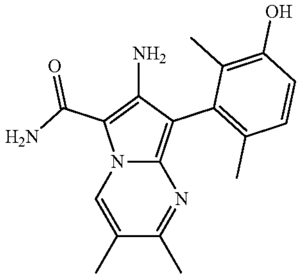 | 324.384 | 325.1 | 1H NMR (400 MHz, DMSO-d6): δ 9.21 (s; 1H); 8.97 (s; 1H); 6.90 (d; J = 8.16 Hz; 1H); 6.86 (s; 2H); 6.72 (d; J = 8.11 Hz; 1H); 4.73 (s; 2H); 2.27 (s; 3H); 2.16 (s; 3H); 1.86 (s; 3H); 1.79 (s; 3H). | Q |
| 338 | 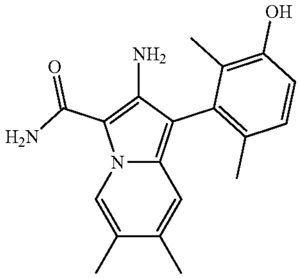 [SMILES: Cc1cc2c(-c3c(C)ccc(O)c3C)c(N)c(C(N)=O)n2cc1C] | 323.396 | 324.1 | 1H NMR (400 MHz, $CDCl_3$): δ 9.35 (s; 1H); 7.06 (d; J = 8.13 Hz; 1H); 6.81 (d; J = 8.13 Hz; 1H); 6.58 (s; 1H); 5.80 (s; 2H); 3.47 (s; 2H); 2.23 (s; 3H); 2.19 (s; 3H); 1.97 (s; 6H). | Q |
| 339 | 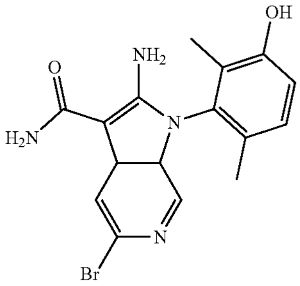 [SMILES: Cc1ccc(O)c(C)c1N1C(N)=C(C(N)=O)C2C=C(Br)N=CC21] | 375.226 | 374.2 $[M - H]^-$ | 1H NMR (400 MHz, DMSO d6) δ 9.68 (s, 1H), 7.88 (s, 1H), 7.39 (s, 1H), 7.29 (s, 1H), 7.14 (s, 2H), 6.98-6.94 (m, 2H), 1.78 (s, 3H), 1.69 (s, 3H). | R |

TABLE 2-continued

| Cpd. | Structure | FW | m/z | NMR | Preparation Method |
|---|---|---|---|---|---|
| 340 | 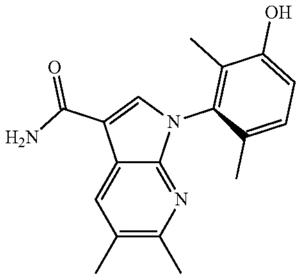 | 309.369 | 310.2 | 1H NMR (400 MHz, DMSO-d6) δ ppm 1.64 (s, 3H), 1.75 (s, 3H), 2.34 (s, 3H), 2.37 (s, 3H), 3.32 (s, 2H), 6.90 (d, J = 7.3 Hz, 1H), 6.97-7.14 (m, 2H), 7.42 (br. s, 1H), 7.94 (s, 1H), 8.28 (s, 1H), 9.53 (s, 1H). | O then N |
| 341 | 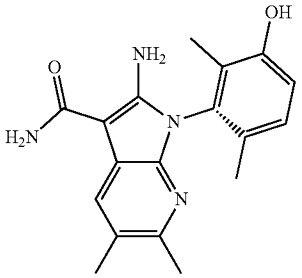 | 309.369 | 310.1 | 1H NMR (400 MHz, DMSO-d6) δ ppm 1.64 (s, 3H), 1.75 (s, 3H), 2.34 (s, 3H), 2.37 (s, 3H), 3.32 (s, 3H), 6.90 (d, J = 8.1 Hz, 1H), 6.94-7.11 (m, 2H), 7.44 (br. s, 1H), 7.94 (s, 1H), 8.28 (s, 1H), 9.53 (s, 1H). | O then N |
| 342 | 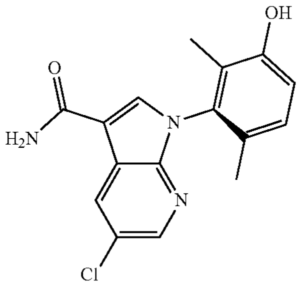 | 315.76 | 316.1 | 1H NMR (400 MHz, DMSO-d6) δ ppm 1.65 (s, 3H), 1.76 (s, 3H), 6.92 (d, J = 8.3 Hz, 1H), 7.06 (d, J = 8.3 Hz, 1H), 7.18 (br. s, 1H), 7.61 (br. s, 1H), 8.22 (s, 1H), 8.26 (d, J = 2.4 Hz, 1H), 8.55 (d, J = 2.4 Hz, 1H), 9.58 (s, 1H). | K then N |
| 343 | 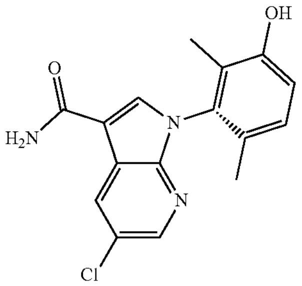 | 315.76 | 316.1 | 1H NMR (400 MHz, DMSO-d6) δ ppm 1.65 (s, 3H), 1.75 (s, 3H), 6.92 (d, J = 8.3 Hz, 1H), 7.06 (d, J = 8.3 Hz, 1H), 7.19 (br. s, 1H), 7.61 (br. s, 1H), 8.22 (s, 1H), 8.26 (d, J = 2.2 Hz, 1H), 8.55 (d, J = 2.4 Hz, 1H), 9.59 (s, 1H). | K then N |
| 344 | 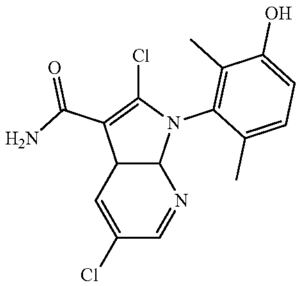 [SMILES: Cc1ccc(O)c(C)c1N1C(Cl)=C(C(N)=O)C2C=C(Cl)C=NC21] | 350.20 | 352.0 | 1H NMR (400 MHz, DMSO-d6) δ ppm 1.61 (s, 3H), 1.71 (s, 3H), 6.96 (d, J = 8.3 Hz, 1H), 7.10 (d, J = 8.3 Hz, 1H), 7.44 (br. s, 1H), 7.64 (br. s, 1H), 8.28 (d, J = 2.4 Hz, 1H), 8.42 (d, J = 2.2 Hz, 1H), 9.67 (s, 1H). | K then N |

TABLE 2-continued

| Cpd. | Structure | FW | m/z | NMR | Preparation Method |
|---|---|---|---|---|---|
| 345 | 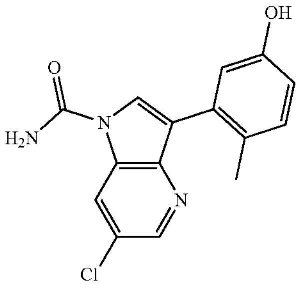 [SMILES: Cc1ccc(O)cc1-c1cn(C(N)=O)c2cc(Cl)cnc12] | 301.73 | 302.0 | 1H NMR (400 MHz, DMSO-d6) δ 9.23 (s, 1H), 8.63 (d, J = 2.3 Hz, 1H), 8.50 (d, J = 2.3 Hz, 1H), 8.23 (s, 1H), 7.87 (br s, 2H), 7.10 (d, J = 8.3 Hz, 1H), 6.96 (d, J = 2.6 Hz, 1H), 6.70 (dd, J = 8.2, 2.6 Hz, 1H), 2.19 (s, 3H). | S |
| 346 | 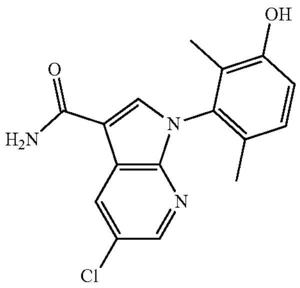 [SMILES: Cc1ccc(O)c(C)c1-n1cc(C(N)=O)c2cc(Cl)cnc21] | 314.77 | 315.0 | $^1$H NMR (400 MHz, DMSO-d6) δ ppm 1.65 (s, 3H), 1.75 (s, 3H), 6.83 (d, J = 8.6 Hz, 1H), 6.94 (d, J = 8.1 Hz, 1H), 6.97-7.12 (m, 2H), 7.18 (dd, J = 8.8, 2.2 Hz, 1H), 7.51 (br. s, 1H), 8.06 (s, 1H), 8.26 (d, J = 2.0 Hz, 1H), 9.67 (s, 1H). | R2 then N |

Examples of Arylamines Preparation

A variety of arylamines were used to prepare compounds of the present invention. Some of these arylamines were commercially available and some were prepared. Table 3 list some examples of such arylamines for which the preparation is described herein.

TABLE 3

| | |
|---|---|
| 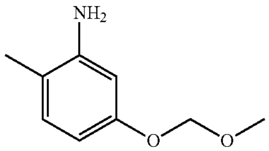 | Arylamine A1 |
| 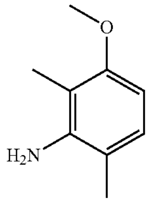 | Arylamine A2 |
| 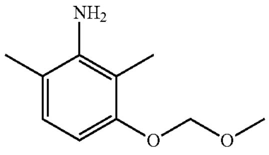 | Arylamine A3 |
| 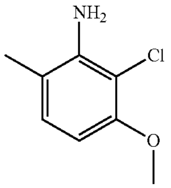 | Arylamine A4 |

TABLE 3-continued

| | |
|---|---|
| 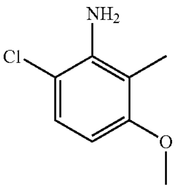 | Arylamine A5 |
| 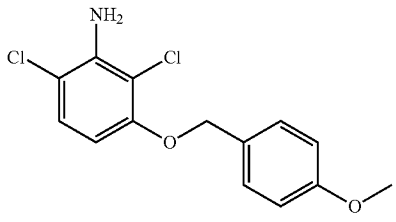 [SMILES: COc1ccc(COc2ccc(Cl)c(N)c2Cl)cc1] | Arylamine A6 |
| 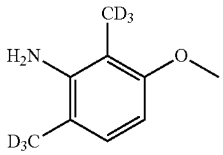 [SMILES: [2H]C([2H])([2H])c1ccc(OC)c(C([2H])([2H])[2H])c1N] | Arylamine A7 |
| 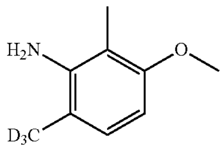 | Arylamine A8 |

TABLE 3-continued

| | |
|---|---|
| 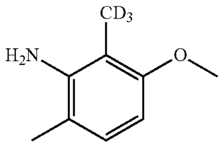 | Arylamine A9 |
| 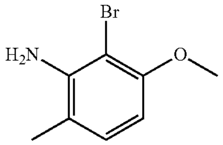 | Arylamine A10 |
| 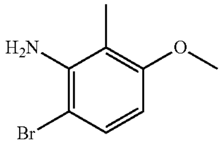 | Arylamine A11 |
| 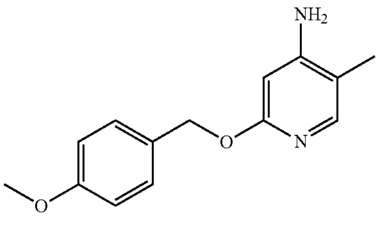 | Arylamine A13 |
| 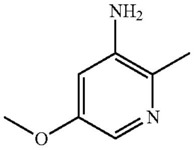 | Arylamine A14 |
| 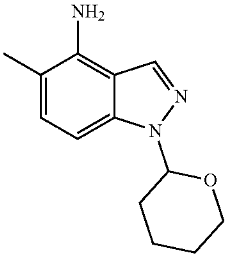 [SMILES: Cc1ccc2c(cnn2C2CCCCO2)c1N] | Arylamine A15 |

Preparation of Arylamine A1

Compounds of the present invention can be prepared from arylamine A1 which can be prepared as shown in Scheme A1 and described herein. The commercially available 4-methyl-3-nitro-phenol can be O-protected with a suitable protecting group such as O-MOM. The nitro can be reduced to generate arylamine A1.

Scheme A1

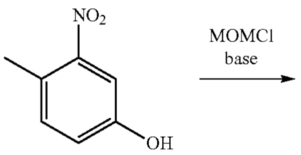

-continued

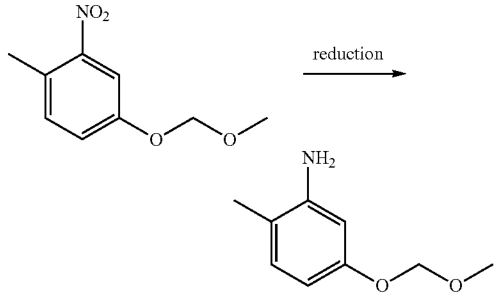

A1

Step 1. To a suspension of 4-methyl-3-nitro-phenol (25 g, 163 mmol) in DCM (250 mL) was added DIPEA (34 mL, 195 mmol) followed by chloro(methoxy)methane (26.0 g, 323 mmol, 24.5 mL) added dropwise. After stirring 18 h, the reaction mixture was washed with water. The layers were separated. The organic layer was washed with 0.2N HCl (2×), brine, dried over $MgSO_4$, filtered and concentrated, then dried in vacuo affording 4-(methoxymethoxy)-1-methyl-2-nitro-benzene (31.4 g, 98% yield) as a dark red oil.

Step 2. To a suspension of 4-(methoxymethoxy)-1-methyl-2-nitro-benzene (31.4 g, 159 mmol) in EtOH (200 mL) and water (75 mL) was added ammonium chloride (43.3 g, 809 mmol) then iron powder (44.5 g, 796 mmol). The reaction mixture was heated to 80° C. for 3.5 h, then temperature was increased to 90° C., stirring for 4 days. The reaction mixture was cooled to rt, filtered and rinsed with EtOAc. The filtrate was concentrated and diluted with EtOAc and saturated aqueous $NaHCO_3$. The layers were separated, and the aqueous layer was back extracted with EtOAc (2×). The combined organic extracts were washed with brine, dried over $MgSO_4$, filtered and concentrated, affording 26.3 g crude product as a dark brown oil which was purified on a silica gel pad, eluting with 20-30% EtOAc in hexanes. The pure fractions were combined, concentrated, then dried in vacuo, affording 5-(methoxymethoxy)-2-methyl-aniline (25.4 g, 95% yield) as a purple oil. 1H NMR (400 MHZ, Chloroform-d) δ 6.94 (dd, J=8.0, 1.7 Hz, 1H), 6.45-6.30 (m, 2H), 5.12 (s, 2H), 3.47 (s, 3H), 2.10 (s, 3H). MS: [M+1]: 168.3.

Preparation of Arylamine A2

Compounds of the present invention can be prepared from arylamine A2 which can be prepared as shown in Scheme A2 and described herein (adapted from Can J Chem 2012, 90, 75-84). Commercially available 1,3-dimethyl-2-nitrobenzene can be brominated under suitable bromination conditions. The resulting bromo can be converted to a methoxy upon treatment with sodium methoxide and copper (I) bromide. The nitro can be reduced to generate arylamine A2.

Scheme A2

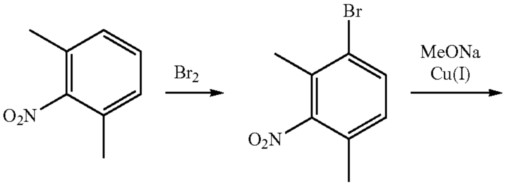

-continued

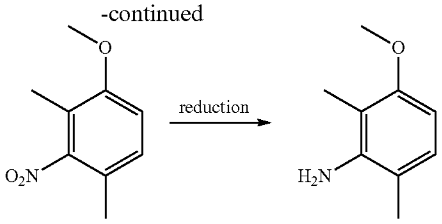

A2

Step 1. A 3 necked 3 L round-bottom flask was equipped with a mechanical stirrer, reflux condenser and addition funnel and loaded with 1,3-dimethyl-2-nitro-benzene (300 g, 1.98 mol), DCM (900 mL), iron powder (28.0 g, 501 mmol) and iron (III) bromide (11.9 g, 40.3 mmol). Bromine (112 mL, 2.19 mol) was added dropwise via an addition funnel over 45-60 min. Internal monitoring of the temperature showed an exotherm to 30° C. 90 min after the addition of bromine was complete, more bromine (5 mL, 97.6 mmol) was added and the reaction mixture was stirred for another 45 min to complete conversion. The reaction mixture was diluted with ice water (1.5 L) and $Et_2O$ (1.5 L). The layers were separated. The aqueous layer was back extracted with $Et_2O$ (0.5 L). The combined organic layers were washed with aqueous 20% $Na_2S_{203}$ (1 L), brine (500 mL), dried over $Na_2SO_4$, filtered over a silica gel pad (300 cc), concentrated then dried in vacuo to provide 1-bromo-2,4-dimethyl-3-nitro-benzene (451.5 g, 99% yield) as an off-white solid.

Step 2. A 5 L 4 neck round bottom flask equipped with a mechanical stirrer and a reflux condenser was charged with 1-bromo-2,4-dimethyl-3-nitro-benzene (451.5 g, 1.96 mol) in DMF (1.6 L). CuBr (28.0 g, 195 mmol) was added followed by MeONa (1.31 L, 5.89 mol, 25% in MeOH). The reaction mixture was slowly heated to 95° C., achieving a mild reflux. After 6 h, the reaction mixture was left to cool to rt overnight. The reaction mixture was diluted with $Et_2O$ and saturated aqueous $NH_4Cl$ (1.5 L each). The layers were separated, and the aqueous layer was back extracted with $Et_2O$ (750 mL). The combined organic extracts were washed with brine (750 mL), dried over $Na_2SO_4$ and filtered over a silica pad, rinsed with $Et_2O$ and concentrated, dried in vacuo to provide 1-methoxy-2,4-dimethyl-3-nitro-benzene (352 g, 99% yield) as an ochre solid.

Step 3. To a solution of 1-methoxy-2,4-dimethyl-3-nitro-benzene (115 g, 635 mmol) in EtOH (1.5 L) in a 3 neck 3 L flask equipped with a mechanical stirrer was added iron powder (213 g, 3.81 mol), then a solution of ammonium chloride (204 g, 3.81 mol) in water (500 mL) was added portion wise. The mixture was heated to 85° C. for 8 h. The mixture was cooled down to rt and filtered on Celite. The volume of the filtrate was reduced (most of the EtOH was evaporated) and the resulting mixture was diluted with $Et_2O$ (800 mL) and water (150 mL). The layers were separated, and the aqueous layer was back extracted with $Et_2O$ (500 mL). The combined organic extracts were washed with brine, dried over $Na_2SO_4$, filtered, concentrated and dried in vacuo to provide 3-methoxy-2,6-dimethyl-aniline (89.1 g, 93% yield) as a brown oil. $^1H$ NMR (400 MHZ, Chloroform-d) δ 6.88 (dq, J=8.3, 0.7 Hz, 1H), 6.31 (d, J=8.2 Hz, 1H), 3.79 (s, 3H), 3.61 (br s, 2H), 2.14 (d, J=0.7 Hz, 3H), 2.07 (s, 3H). MS: [M+1]: 152.3.

Preparation of Arylamine A3

Compounds of the present invention can be prepared from arylamine A3 which can be prepared as shown in Scheme A3 and described herein. The methoxy of 1-methoxy-2,4-dimethyl-3-nitro-benzene described in the preparation of Intermediate A2 can be cleaved using $BBr_3$ and the resulting phenol can be O-protected with a suitable protecting group such as O-MOM. The nitro can be reduced to generate arylamine A3.

Scheme A3

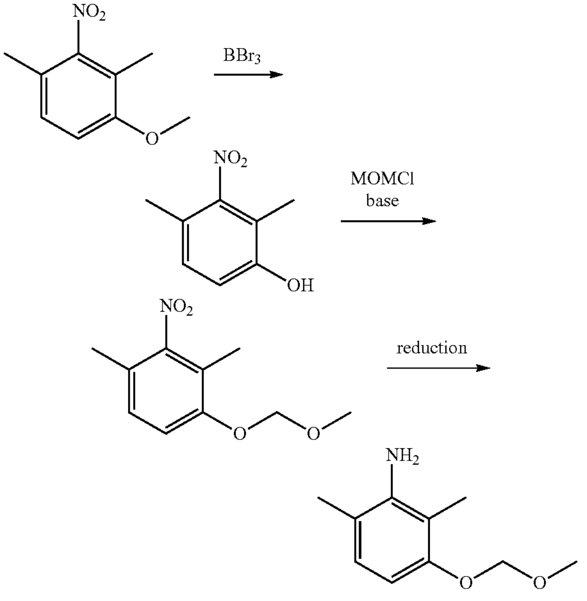

A3

Step 1. To a solution of 1-methoxy-2,4-dimethyl-3-nitro-benzene (20 g, 110 mmol) in DCM (200 mL), cooled in a dry ice/acetonitrile bath, was added $BBr_3$ solution in DCM (1 M, 168 mL) dropwise via an addition funnel. The mixture was left to slowly warm to rt overnight. The reaction mixture was then poured slowly in a stirred mixture of ice, water (1 L) and $KH_2PO_4$ (75 g). The layers were separated, and the aqueous layer was extracted with DCM (2×500 mL). The combined organic extracts were washed with brine (500 mL), dried over $MgSO_4$, filtered over a silica pad (375 g), eluting with DCM, concentrated and dried in vacuo to provide 2,4-dimethyl-3-nitro-phenol (18.0 g, 98% yield) as a yellow solid.

Step 2. To a suspension of 2,4-dimethyl-3-nitro-phenol (18.96 g, 113 mmol) in DCM (200 mL) was added DIPEA (23.7 mL, 136 mmol) then chloro(methoxy)methane (9.5 mL, 125 mmol) dropwise. After stirring for 3.5 h, more chloro(methoxy)methane (2.0 mL, 26 mmol) was added and the reaction mixture was stirred overnight. The reaction mixture was quenched with aqueous saturated $NH_4Cl$ (100 mL) and diluted with water (100 mL). The layers were separated, and the aqueous layer was back extracted with DCM (100 mL). The combined organic extracts were washed with 0.2N HCl (2×100 mL), 1M NaOH (100 mL), brine (100 mL), dried over $MgSO_4$, filtered on silica (ca 100 cc), eluting with DCM, concentrated, and dried in vacuo to provide 1-(methoxymethoxy)-2,4-dimethyl-3-nitro-benzene (22.1 g, 92% yield) as a pale yellow waxy solid.

Step 3. To a flask containing palladium on carbon (5.06 g, 4.76 mmol, 10% w/w) under nitrogen was added MeOH (300 mL) followed by 1-(methoxymethoxy)-2,4-dimethyl-3-nitro-benzene (20.1 g, 95.1 mmol). The flask was flushed with hydrogen and stirred under a hydrogen atmosphere for 2 days. The reaction mixture was flushed with nitrogen for 2 h, and Celite was added. The mixture was filtered on a Celite pad using MeOH and DCM. The filtrate was concentrated and dried in vacuo to provide 3-(methoxymethoxy)-2,6-dimethyl-aniline (17.1 g, 99% yield) as a pale orange turbid oil. 1H NMR (400 MHZ, Chloroform-d) δ 6.86 (d, J=8.3 Hz, 1H), 6.49 (d, J=8.3 Hz, 1H), 5.15 (s, 2H), 3.48 (s, 3H), 2.14 (s, 3H), 2.11 (s, 3H). MS: [M+1]: 182.2.

Preparation of Arylamine A4

Compounds of the present invention can be prepared from arylamine A4 which can be prepared as shown in Scheme A4 and described herein. Commercially available 2-chloro-3-methoxy-benzoic acid can be brominated with a suitable bromination reagent and the carboxylic acid can be converted to a NHBoc under Curtius conditions. The bromo can be converted to a methyl and the NHBoc can be cleaved under acidic conditions to generate arylamine A4.

Scheme A4

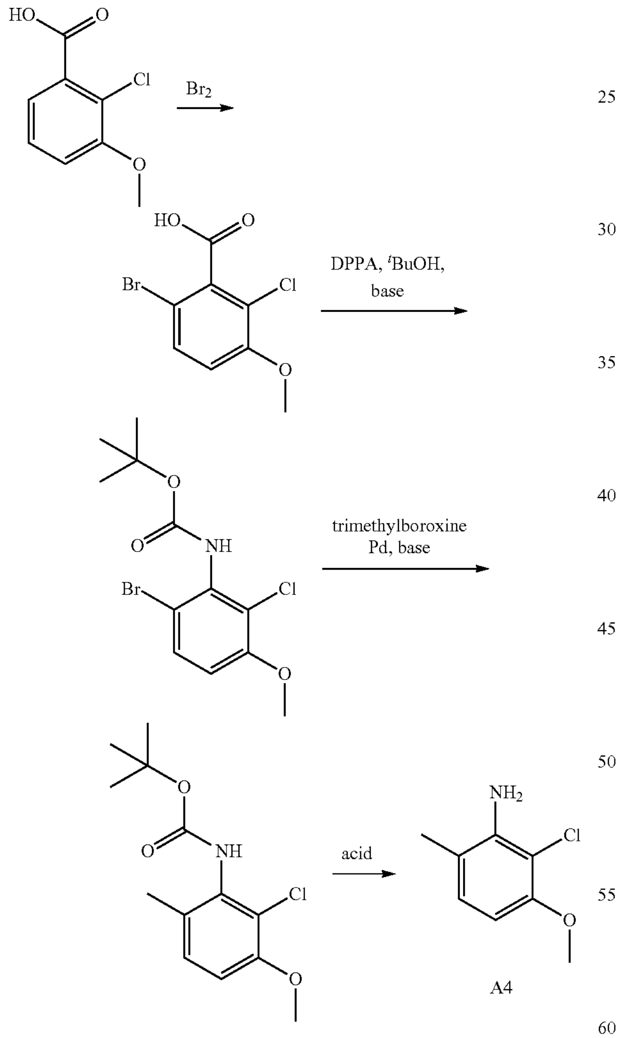

A4

Step 1. To a solution of 2-chloro-3-methoxy-benzoic acid (50 g, 268 mmol) in AcOH (250 mL) and water (250 mL) was added bromine (27.5 mL, 537 mmol) dropwise. The mixture was stirred at 60° C. for 18 h, cooled to rt, brine was added, and the mixture was extracted twice with DCM. The combined organic extracts were dried over $Na_2SO_4$, filtered and concentrated in vacuo to provide 6-bromo-2-chloro-3-methoxy-benzoic acid (71 g, quantitative yield) as a brown oil which solidified upon standing under vacuum over the weekend.

Step 2. To a solution of 6-bromo-2-chloro-3-methoxy-benzoic acid (23.6 g, 88.9 mmol). $Et_3N$ (38 mL, 271 mmol) and tert-butanol (42.5 mL, 450 mmol) in toluene (500 mL) was added [azido(phenoxy)phosphoryl]oxybenzene (29.5 mL, 136 mmol). The mixture was heated at 100° C. for 16 h, cooled down to rt then the volatiles were removed in vacuo. The residue was diluted with EtOAc (100 mL), and the organic layer was washed with 5% citric acid, water, saturated aqueous $NaHCO_3$, brine, dried over $Na_2SO_4$, filtered and concentrated to dryness. The residue was purified by silica gel chromatography eluting with a gradient of 0 to 20% EtOAc in hexanes to provide tert-butyl N-(6-bromo-2-chloro-3-methoxy-phenyl) carbamate (16.2 g, 54% yield) as a yellowish solid.

Step 3. To a solution of tert-butyl N-(6-bromo-2-chloro-3-methoxy-phenyl) carbamate (25 g, 74.3 mmol) in dioxane (500 mL) was added trimethylboroxine (50% w/w in THF, 20.51 g, 81.7 mmol). $PdCl_2(dppf)\cdot CH_2Cl_2$ (5.22 g, 7.43 mmol) and aqueous $Na_2CO_3$ (2 M, 111 mL, 223 mmol). The mixture was heated at 100° C. for 16 h, cooled down to rt then volatiles were removed in vacuo. EtOAc and water were added. The organic layer was separated and washed with brine, dried over $Na_2SO_4$, filtered and concentrated to dryness. The residue was purified by silica gel chromatography eluting with a gradient of 0 to 30% EtOAc in heptane to provide tert-butyl N-(2-chloro-3-methoxy-6-methyl-phenyl) carbamate (13.8 g, 68% yield) as a yellowish solid.

Step 4. HCl in dioxane (4 M, 100 mL) was added to a solution of tert-butyl N-(2-chloro-3-methoxy-6-methyl-phenyl) carbamate (13.8 g, 50.8 mmol) in MeOH (100 mL). After 3 h, the volatiles were evaporated to dryness under vacuum to provide a white solid to which was added under vigorous stirring 250 ml of EtOAc and 250 ml of aqueous saturated $NaHCO_3$. The organic layer was separated. The aqueous layer was back extracted with EtOAc. The combined organic layers were washed with brine, dried over $Na_2SO_4$, filtered and concentrated in vacuo. The residue was purified by silica gel chromatography eluting with a gradient of 0 to 30% EtOAc in heptane to provide 2-chloro-3-methoxy-6-methyl-aniline (7.9 g, 91% yield) as a clear oil which solidified upon standing. 1H NMR (400 MHZ, Chloroform-d) δ 6.95-6.79 (m, 1H), 6.27 (dd, J=8.3, 1.5 Hz, 1H), 4.06 (br s, 2H), 3.83 (d, J=1.6 Hz, 3H), 2.12 (d, J=0.8 Hz, 3H). MS: [M+1]: 172.2.

Preparation of Arylamine A5

Compounds of the present invention can be prepared from arylamine A5 which can be prepared as shown in Scheme A5 and described herein. Commercially available 3-methoxy-2-methyl-aniline can be chlorinated with a chlorination reagent to generate arylamine A5.

Scheme A5

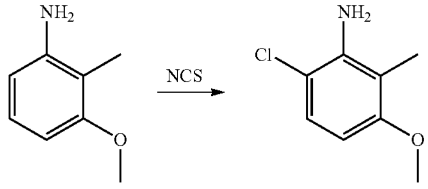

A5

Step 1. NCS (98 g, 734 mmol) was added in 4 portions (15 minutes between each addition) to a solution of 3-methoxy-2-methyl-aniline (100 g, 729 mmol) in DCM (500 mL) at 0° C. 30 min after the last addition, 100 g of silica gel was added, the mixture was evaporated under vacuum and the black residue was purified by silica gel chromatography (dry load) in eluting with a gradient of 0 to 10% EtOAc in hexanes to provide 6-chloro-3-methoxy-2-methyl-aniline (55.6 g, 44% yield) as an orange solid. 1H NMR (400 MHZ, Chloroform-d) δ 7.08 (d, J=8.8 Hz, 1H), 6.28 (d, J=8.8 Hz, 1H), 4.02 (br s, 2H), 3.78 (s, 3H), 2.07 (s, 3H). MS: [M+1]: 172.3.

Preparation of Arylamine A6

Compounds of the present invention can be prepared from arylamine A6 which can be prepared as shown in Scheme A6 and described herein. Commercially available 3-amino-2,4-dichloro-phenol can be O-protected with a suitable protecting group such as O-PMB to generate arylamine A6.

Scheme A6

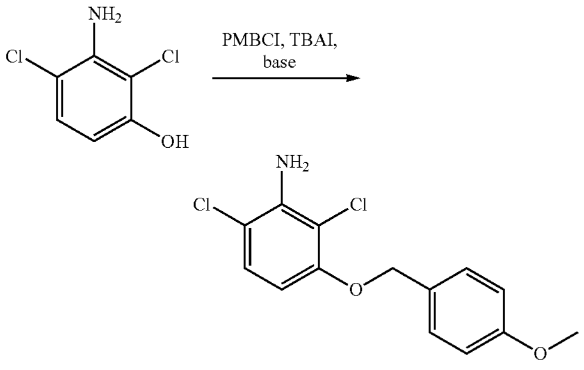

A6

To a suspension of 3-amino-2,4-dichloro-phenol·HCl salt (20 g, 93.3 mmol) in DMF (150 mL) was added 1-(chloromethyl)-4-methoxy-benzene (14.0 mL, 103 mmol), tetrabutylammonium iodide (1 g, 3.00 mmol) and $Cs_2CO_3$ (64.0 g, 196 mmol). The mixture was stirred at 40° C. overnight, then it was diluted with water, stirred for 20 min, and filtered. The precipitate was washed with water and dried in vacuo. The resulting crude product was purified by silica gel chromatography eluting with a gradient of 0 to 100% DCM in hexanes to provide 2,6-dichloro-3-[(4-methoxyphenyl)methoxy]aniline (20 g, 72% yield) as an off-white solid. $^1$H NMR (400 MHZ, Chloroform-d) δ 7.38-7.30 (m, 2H), 7.05 (d, J=8.9 Hz, 1H), 6.92-6.77 (m, 2H), 6.32 (s, 1H), 5.01 (s, 2H), 4.46 (s, 2H), 3.79 (s, 3H). MS: [M+1]: 298.0.

Preparation of Arylamine A7

Compounds of the present invention can be prepared from key Intermediate A7, A8 or A9 which can be prepared as shown in Scheme A7 and described herein. The commercially available 3-methoxyaniline can be N-protected with a suitable protecting group such as NH—PIV. A directed ortho metalation approach can be used to introduce a suitable $R^1$ such as $CH_3$ or $CD_3$. The NH—PIV protecting group can be cleaved under acidic conditions and the remaining ortho-to-nitrogen can be brominated with a suitable bromination reagent such as NBS. At this point, the bromine can be substituted by a boronate ester under metal-mediated conditions and further derivatized by a suitable $R^2$ such as $CH_3$ or $CD_3$ to generate key Intermediate A7, A8 or A9. Alternatively, the bromoaniline can be N-protected with a suitable protecting group such as NH-Boc prior to the bromo substitution. In this case, the NH-Boc can be cleaved under acidic conditions to generate key Intermediate A7, A8 or A9.

Scheme A7

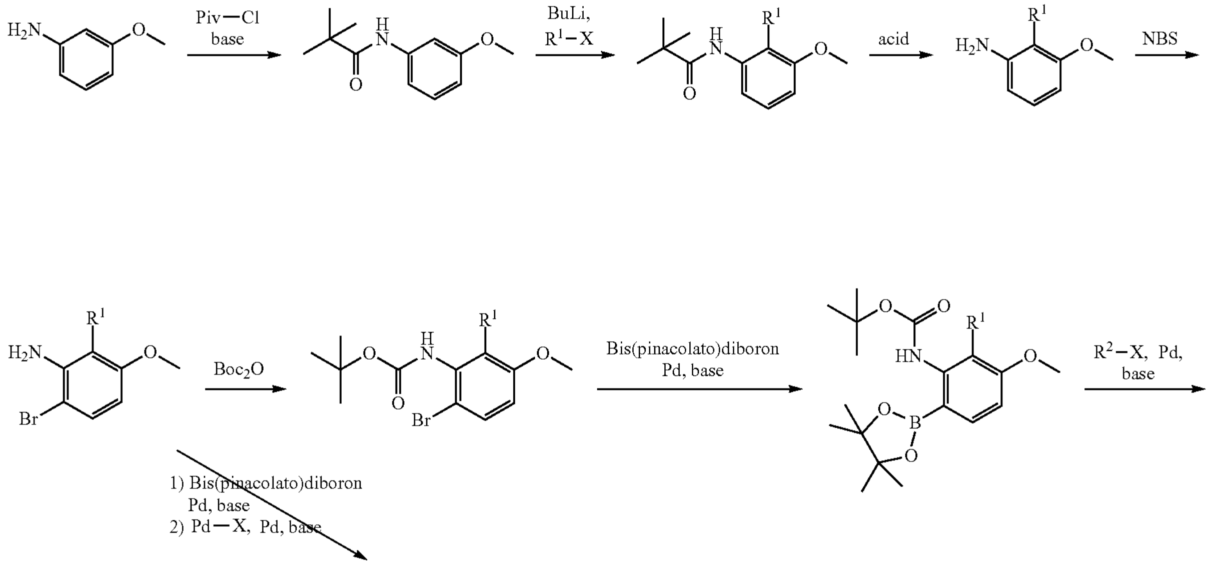

-continued

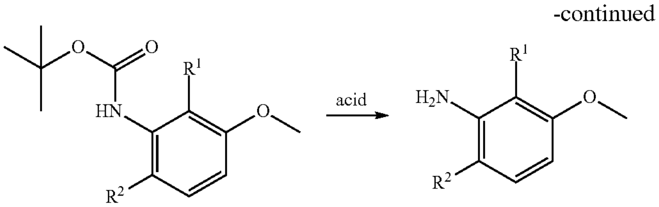

A7, $R^1 = R^2 = CD_3$
A8, $R^1 = CH_3$, $R^2 = CD_3$
A9, $R^1 = CD_3$, $R^2 = CH_3$

Arylamine A7

Step 1. 2,2-dimethylpropanoyl chloride (51 mL, 416 mmol) was slowly added to a solution of 3-methoxyaniline (50 g, 406 mmol, 45.5 mL), pyridine (66 mL, 816 mmol) and DMAP (500 mg, 4.1 mmol) in DCM (500 mL). After 1 h, aqueous 1 N HCl was added and the layers were separated. The aqueous layer was back extracted with $CH_2Cl_2$. The organic layers were combined, washed with aqueous 1 N HCl, brine, then dried over $Na_2SO_4$, filtered and evaporated to dryness to provide N-(3-methoxyphenyl)-2,2-dimethyl-propanamide (84 g, quantitative yield).

Step 2. To a solution of N-(3-methoxyphenyl)-2,2-dimethyl-propanamide (82 g, 396 mmol) in THF (820 mL) at 0° C. was added nBuLi (2.5 M, 325 mL, 813 mmol) dropwise. After 2 h at 0° C., the solution was cooled to −78° C. and $CD_3I$ (27 mL, 434 mmol) was added dropwise. The mixture was stirred for 16 h at rt. The mixture was poured into aqueous 1 N HCl and extracted with EtOAc twice. The combined organic layers were dried over $Na_2SO_4$, filtered and concentrated to dryness to provide N-[3-methoxy-2-(trideuteriomethyl)phenyl]-2,2-dimethylpropanamide (82 g, 92% yield) as a white solid.

Step 3. N-[3-methoxy-2-(trideuteriomethyl)phenyl]-2,2-dimethyl-propanamide (81.5 g, 363 mmol) in dioxane (300 mL) and HCl conc (12 M, 300 mL) was heated to reflux for 24 h. The dark mixture was cooled to 0° C. in an ice bath, neutralized with aqueous 2N NaOH, extracted with EtOAc twice. The combined organic extracts were washed with brine, dried over $Na_2SO_4$, filtered and concentrated to dryness to provide a dark residue that was purified by silica gel chromatography eluting with a gradient of 0 to 50% EtOAc in heptane to provide 3-methoxy-2-(trideuteriomethyl) aniline (36 g, 71% yield) as a clear oil.

Step 4. To a solution of 3-methoxy-2-(trideuteriomethyl) aniline (35 g, 250 mmol) in DCM (500 mL) at 0° C. was added NBS (45 g, 253 mmol). The mixture was stirred at 0° C. for 3 h and concentrated to approximately 75 mL and filtered. The filtrate was evaporated to dryness and the residue was purified by silica gel chromatography eluting with a gradient of 0% to 50% EtOAc in heptane to provide 6-bromo-3-methoxy-2-(trideuteriomethyl) aniline (35 g, 64% yield).

Step 5. tert-butoxycarbonyl tert-butyl carbonate (87.2 g, 400 mmol) was added to a solution of 6-bromo-3-methoxy-2-(trideuteriomethyl) aniline (35 g, 160 mmol), DMAP (3.90 g, 32 mmol) and DIPEA (415 mmol, 72.3 mL) in THF (500 mL). The mixture was heated to reflux for 18 h. The volatiles were removed under vacuum and the residue was filtered trough silica gel eluting with 50% EtOAc in heptane to provide a mixture of tert-butyl N-[6-bromo-3-methoxy-2-(trideuteriomethyl)phenyl]carbamate and tert-butyl N-[6-bromo-3-methoxy-2-(trideuteriomethyl)phenyl]-N-tert-butoxycarbonyl-carbamate (64 g) as a clear oil that was dissolved in methanol (500 mL). $K_2CO_3$ (110 g, 796 mmol) was added and the mixture was stirred at 60° C. for 48 h. The volatiles were removed under vacuum. EtOAc and water were added to the residue. The organic layer was separated, washed with brine, dried over $Na_2SO_4$, filtered and concentrated. The residue was purified by silica gel chromatography eluting with a gradient of 0 to 40% EtOAc to provide tert-butyl N-[6-bromo-3-methoxy-2-trideuteriomethyl)phenyl]carbamate (50 g, quantitative yield) as a clear oil.

Step 6. To a solution of tert-butyl N-[6-bromo-3-methoxy-2-(trideuteriomethyl)phenyl]carbamate (33 g, 103 mmol) in dioxane (700 mL) were added Bis(pinacolato)diboron (51 g, 201 mmol), KOAc (35.5 g, 362 mmol) and $PdCl_2$(dppf)·$CH_2Cl_2$ (7.6 g, 10.4 mmol). The mixture was degassed in vacuo, back filled with nitrogen and stirred at reflux for 18 h. The mixture was cooled to rt and concentrated to a smaller volume. The black residue was diluted with EtOAc and filtered trough a silica gel pad (250 g) eluting with 2 L of 50% EtOAc in heptane. The filtrate was evaporated, and the residue was purified by silica gel chromatography eluting with a gradient of 0 to 20% EtOAc in heptane to provide tert-butyl N-[3-methoxy-6-(4,4,5,5-tetramethyl-1,3,2-dioxaborolan-2-yl)-2-(trideuteriomethyl)phenyl]carbamate (22.5 g, 59% yield), which solidified upon standing under vacuum.

Step 7. To a solution of $PdCl_2$(dppf)·$CH_2Cl_2$ (5.3 g, 7.24 mmol) in DMF (500 mL) was quickly added consecutively $CD_3I$ (60.6 g, 418 mmol, 26 mL), tert-butyl N-[3-methoxy-6-(4,4,5,5-tetramethyl-1,3,2-dioxaborolan-2-yl)-2-(trideuteriomethyl)phenyl]carbamate (52 g, 142 mmol) and aqueous potassium phosphate tribasic (2 M, 350 mL). Nitrogen was bubbled in the solution for 2 min, then the mixture was stirred at 80° C. for 30 min under a nitrogen atmosphere then cooled to rt, and EtOAc was added. The organic layer was washed with water, brine, dried over $Na_2SO_4$, filtered and concentrated to dryness. The residue was purified by silica gel chromatography eluting with a gradient of 0 to 20% EtOAc in heptane to provide tert-butyl N-[3-methoxy-2,6-bis(trideuteriomethyl)phenyl]carbamate (15 g, 41% yield) as a thick clear oil.

Step 8. HCl in dioxane (4 M, 100 mL) was added to a solution of tert-butyl N-[3-methoxy-2,6-bis(trideuteriomethyl)phenyl]carbamate (22.5 g, 87.4 mmol) in MeOH (100 mL). After 3 h the volatiles were removed under vacuum to provide a white solid. EtOAc and water were added followed by a saturated $NaHCO_3$ aqueous solution until basic pH. The organic layer was washed with brine, dried over $Na_2SO_4$, filtered and evaporated to dryness. The residue was purified by silica gel chromatography eluting with a gradient of 0 to 40% EtOAc in heptane to provide 3-methoxy-2,6-bis(trideuteriomethyl) aniline (7.5 g, 55% yield) as a clear oil. 1H NMR (400 MHZ, Chloroform-d) δ 6.96 (dd, J=8.3, 2.6 Hz, 1H), 6.38 (dd, J=8.3, 2.5 Hz, 1H), 3.86 (d, J=2.4 Hz, 3H), 3.64 (s, 2H). MS: [M+1]: 158.3.

Alternative Route Used for Preparation Arylamine A8 (without Boc)

Step 1. In a sealed tube, 6-bromo-3-methoxy-2-methylaniline (3.4 g, 15.7 mmol), Bis(pinacolato)diboron (5.58 g, 21.98 mmol) and $Cs_2CO_3$ (15.4 g, 47.1 mmol) was taken in anhydrous 1,4-dioxane (68 mL) and nitrogen gas was purged into the reaction mixture for 15 min. Then, $PdCl_2$(dppf) (1.92 g, 2.36 mmol) was added into the reaction mixture and heated at 100° C. for 2 h. After completion, the reaction mixture was quenched with ice water and extracted using EtOAc (3×100 mL). The combined organic layer was dried over $Na_2SO_4$, filtered and concentrated to give the crude product which was purified by silica gel chromatography eluting with a gradient of 10 to 12% EtOAc in hexanes) to provide 3-methoxy-2-methyl-6-(4,4,5,5-tetramethyl-1,3,2-dioxaborolan-2-yl) aniline (2.50 g, 60% yield).

Step 2. In a sealed tube, 3-methoxy-2-methyl-6-(4,4,5,5-tetramethyl-1,3,2-dioxaborolan-2-yl) aniline (2.5 g, 9.39 mmol), iodomethane-$d_3$ (4.08 g, 28.19 mmol) and potassium phosphate tribasic (9.95 g, 46.9 mmol) was taken in anhydrous DMF (50 mL) and nitrogen gas was purged into the reaction mixture for 15 min. Then, $PdCl_2$(dppf) (0.766 g, 0.939 mmol) was added and the reaction mixture was heated at 80° C. for 2 h. After completion, the reaction mixture was quenched using ice water and extracted using EtOAc (3×50 mL). The combined organic layer was dried over $Na_2SO_4$, filtered and concentrated to give the crude product which was purified by silica gel chromatography eluting with a gradient of 6 to 8% EtOAc in hexanes) to get pure 3-methoxy-2-methyl-6-(methyl-$d_3$) aniline as colorless liquid (0.75 g, 51% yield). $^1H$ NMR (400 MHZ, DMSO-$d_6$) δ 6.68 (d, J=7.2 Hz, 1H), 6.31 (d, J=7.4 Hz, 1H), 4.63 (s, 2H), 3.55 (s, 3H), 1.94 (s, 3H). MS: [M+1]: 155.3.

Preparation of Arylamine A10

Compounds of the present invention can be prepared from key Intermediate A10 which can be prepared as shown in Scheme A8 and described herein. The commercially available 3-methoxy-2-nitrobenzoic acid can be brominated. The acid can then be esterified, the bromo converted to a methyl and the nitro reduced to the amino. The resulting amino can be converted to a bromo under Sandmeyer conditions and the ester may then be saponified. The resulting acid can then be converted to the NHBoc under Curtius conditions. In this case, the NH-Boc can be cleaved under acidic conditions to generate key Intermediate A10.

Scheme A8

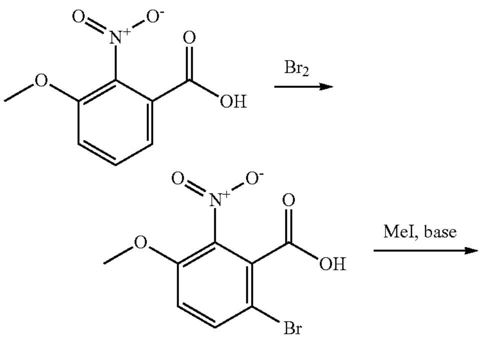

-continued

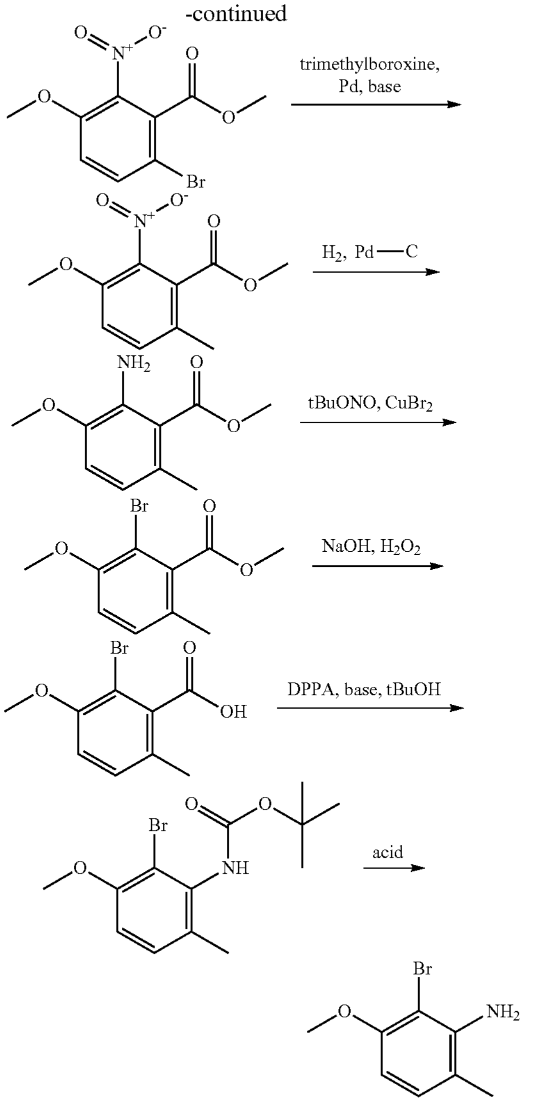

A10

Step 1. To 3-methoxy-2-nitro-benzoic acid (10.04 g, 50.93 mmol) and $Ag_2SO_4$ (8.10 g, 26.0 mmol) in the dark was added conc. sulfuric acid (200 mL) and molecular bromine (9.4 g, 58.6 mmol, 3.0 mL) dropwise. The mixture was stirred in the dark for 3.5 h, then quenched by adding crushed ice, cooled in an ice bath and stirred. The solids were collected by filtration, washed with $H_2O$ and air-dried. The resulting solid was taken in acetone (300 mL), filtered, residue (silver salts) washed with acetone. The filtrate was dried over $MgSO_4$, filtered and concentrated, affording 6-bromo-3-methoxy-2-nitro-benzoic acid (14.64 g, 100% yield) as a purple solid.

Step 2. To a solution of 6-bromo-3-methoxy-2-nitro-benzoic acid (14.64 g, 53.0 mmol) in DMF (140 mL) was added anhydrous potassium carbonate (14.66 g, 106.1 mmol) followed by methyl iodide (11.4 g, 80.3 mmol, 5.0 mL). After stirring the reaction mixture for 2 h, $H_2O$ was added dropwise (420 mL). The solid was collected by filtration and washed with $H_2O$, air-dried then dried in vacuo, affording methyl 6-bromo-3-methoxy-2-nitro-benzoate (12.89 g, 84% yield) as a light beige solid.

Step 3. In a pressure vessel, a solution of methyl 6-bromo-3-methoxy-2-nitro-benzoate (6.0 g, 20.7 mmol) in dioxane (100 mL) and aqueous $Na_2CO_3$ solution (2 M, 31 mL, 62.3 mmol) was bubbled through with $N_2$ then Pd(dppf)$Cl_2$ (1.64 g, 2.01 mmol) and trimethylboroxine (6.74 g, 26.8 mmol, 7.5 mL) were added. The solution was bubbled through with $N_2$. The vessel was capped stirred at 100° C. overnight. The reaction mixture was cooled to rt, poured in $H_2O$ and extracted with EtOAc (3×). The combined organic layers were washed with brine, dried over $Na_2SO_4$, filtered over a silica plug and concentrated in vacuo. The residue was purified by silica gel chromatography eluting with a gradient of EtOAc (0 to 100%) in Hep. Appropriate fractions were combined and concentrated in vacuo to afford methyl 3-methoxy-6-methyl-2-nitro-benzoate (3.06 g, 66% yield) as a light beige waxy solid. Step 4. To a solution of methyl 3-methoxy-6-methyl-2-nitro-benzoate (3.06 g, 13.6 mmol) in MeOH (225 mL) was added palladium on carbon (10% w/w, 1.42 g, 1.33 mmol) slurried in some of the MeOH. The mixture was flushed with $H_2$ and stirred under a hydrogen atmosphere for 2 h. The suspension was filtered through Celite and the filtrate was concentrated then dried in vacuo, affording methyl 2-amino-3-methoxy-6-methyl-benzoate (2.56 g, 97% yield) as a light amber oil.

Step 5. To a solution of methyl 2-amino-3-methoxy-6-methyl-benzoate (2.13 g, 10.9 mmol) in DMF (12 mL) and MeCN (18 mL) was added tert-butyl nitrite (2.0 mL, 17 mmol) followed by copper (II) bromide (2.86 g, 12.8 mmol). The reaction mixture was stirred at 55° C. for 9 min, then cooled to RT, diluted with $H_2O$ and extracted with EtOAc (3×). The combined organic extracts washed with saturated aqueous $NH_4Cl$, brine, dried over $Na_2SO_4$, filtered and concentrated. The residue was purified by silica gel chromatography (dry-load) eluting with a gradient of EtOAc (0 to 70%) in Hep. Appropriate fractions were combined and concentrated in vacuo to afford methyl 2-bromo-3-methoxy-6-methyl-benzoate (1.52 g, 54% yield) as a yellow oil. 1H NMR (400 MHZ, Chloroform-d) δ 7.15-7.05 (m, 1H), 6.84 (d, J=8.4 Hz, 1H), 3.95 (s, 3H), 3.88 (s, 3H), 2.26 (d, J=0.7 Hz, 3H).

Step 6. To a solution of methyl 2-bromo-3-methoxy-6-methyl-benzoate (1.52 g, 5.87 mmol) in MeOH (15 mL) and THF (15 mL) was added NaOH aqueous (4 M, 15 mL, 60.0 mmol) and hydrogen peroxide solution 30% (1.5 mL). The reaction mixture was stirred at 70° C. overnight, then at 90° C. for 4 days. The reaction mixture was cooled to RT and the volatiles were removed in vacuo. The residue was diluted with 3N HCl (20 mL) and extracted with $CHCl_3$/iPrOH (4:1, 4×). The combined organic extracts were concentrated then dried in vacuo and the crude product was purified by silica gel chromatography (dry load) eluting with a gradient of MeOH (0 to 10%) in $CH_2Cl_2$ with 1% AcOH modifier. Appropriate fractions were combined and concentrated in vacuo to afford 2-bromo-3-methoxy-6-methyl-benzoic acid (896 mg, 62% yield) as a white solid.

Step 7. To a solution of 2-bromo-3-methoxy-6-methyl-benzoic acid (1.15 g, 4.68 mmol), triethylamine (1.42 g, 14.1 mmol, 2.0 mL), and tert-butanol (1.73 g, 23.4 mmol, 2.25 mL) in toluene (8 mL) was added DPPA (1.93 g, 7.01 mmol, 1.52 mL) and the mixture was heated to reflux for 1 h and cooled to rt. The volatiles were removed in vacuo. The residue was diluted with aq. citric acid 15% and extracted with EtOAc (3×). The combined organic layers were washed with aqueous 1N NaOH, brine, dried over $Na_2SO_4$, filtered and concentrated in vacuo. The crude product was purified by silica gel chromatography (dry load) eluting with a gradient of EtOAc (0 to 30%) in Hep. Appropriate fractions were combined and concentrated in vacuo to afford tert-butyl N-(2-bromo-3-methoxy-6-methyl-phenyl) carbamate (1.34 g, 91% yield) as a colorless oil.

Step 8. To a solution of tert-butyl N-(2-bromo-3-methoxy-6-methyl-phenyl) carbamate (1.34 g, 4.24 mmol) in MeOH (10 mL) was added HCl in dioxane (4 M, 10.5 mL, 42.0 mmol). The reaction mixture was stirred at RT for 75 min. The solution was evaporated to dryness in vacuo then suspended in saturated aqueous $NaHCO_3$ and extracted with DCM (3×, phase separator). The combined organic extracts were concentrated and the crude product was purified by silica gel chromatography eluting with a gradient of EtOAc (0 to 50%) in Hep. Appropriate fractions were combined and concentrated in vacuo to afford 2-bromo-3-methoxy-6-methyl-aniline (807 mg, 88% yield) as an off-white waxy solid. MS: [M+1]: 218.0.

Preparation of Arylamine A11

Compounds of the present invention can be prepared from key Intermediate A11 which can be prepared as shown in Scheme A9 and described herein. The commercially available 6-bromo-3-methoxy-2-methylbenzoic acid can be converted to the N-Boc under Curtius rearrangement conditions. The NH-Boc can be cleaved under acidic conditions to generate key Intermediate A11.

Scheme A9

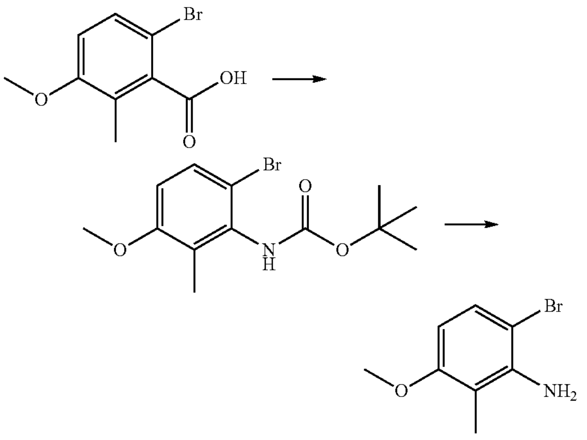

A11

Step 1. To a solution of 6-bromo-3-methoxy-2-methylbenzoic acid (1 g, 4.08 mmol), triethylamine (1.23 g, 12.2 mmol, 1.70 mL), and tert-butanol (1.55 g, 20.9 mmol) in toluene (7 mL) was added [azido(phenoxy)phosphoryl]oxybenzene (1.72 g, 6.25 mmol, 1.35 mL). The mixture was heated to reflux for 5 h and cooled to rt. The volatiles were removed in vacuo. The residue was diluted with aq. citric acid 15% and extracted with EtOAc (3×). The combined organic layers were washed with brine, dried over $Na_2SO_4$, filtered, and concentrated in vacuo. The residue was purified by silica gel chromatography (dry load) eluting with a gradient of EtOAc (0 to 30%) in Hep. Appropriate fractions were combined and concentrated in vacuo to afford tert-butyl N-(6-bromo-3-methoxy-2-methyl-phenyl) carbamate (1.41 g, quantitative yield) as a colorless oil, which was not pure but used as is in the next step.

Step 2. To a solution of tert-butyl N-(6-bromo-3-methoxy-2-methyl-phenyl) carbamate (1.41 g, 4.46 mmol) in MeOH (22 mL) was added HCl in dioxane (4 M, 22 mL). The reaction mixture was stirred at RT for 80 min. The solution was evaporated to dryness in vacuo, then suspended in saturated aqueous $NaHCO_3$ and extracted with DCM (3×). The combined organic extracts were dried over $Na_2SO_4$, filtered and concentrated. The residue was purified by silica gel chromatography (dry load) eluting with a gradient of EtOAc (0 to 50%) in Hep. Appropriate fractions were combined and concentrated in vacuo to afford 6-bromo-3-methoxy-2-methyl-aniline (586 mg, 61% yield) as a white solid. 1H NMR (400 MHZ, Chloroform-d) δ 7.23 (dd, J=8.8, 0.6 Hz, 1H), 6.26 (d, J=8.8 Hz, 1H), 4.06 (br s, 2H), 3.78 (s, 3H), 2.09 (t, J=0.5 Hz, 3H). MS: [M+1]: 218.0.

Preparation of Arylamine A13

Compounds of the present invention can be prepared from arylamine A13 which can be prepared as shown in Scheme A11 and described herein. The fluorine of commercially available 2-fluoro-4-iodo-5-methylpyridine can displaced with the anion 4-methoxybenzyl alcohol. The remaining iodo can be displaced with copper mediated reaction with sodium azide. The resulting azido can be reduced to generate arylamine A13.

Scheme A11

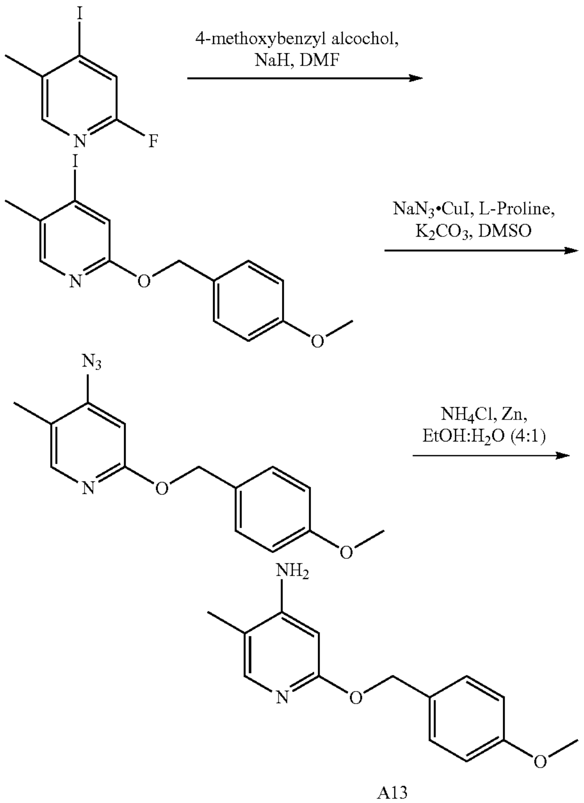

A13

Step 1. To a solution of 4-methoxybenzyl alcohol (0.561 g, 4.06 mmol) in DMF (5 mL) was added NaH (60% dispersion in mineral oil, 0.135 g, 3.375 mmol) at 0° C. The reaction mixture was stirred for 30 min at the same temperature, 2-fluoro-4-iodo-5-methylpyridine (0.8 g, 3.4 mmol) was added and the reaction mixture was stirred at rt for 2 h. After completion of the reaction (TLC, 10% EtOAc/hexanes), the reaction mixture was poured into water and extracted with ethyl acetate (3×). The combined organic layers were dried over sodium sulfate and concentrated under vacuum to get the crude product, which was purified by silica gel flash chromatography (0-1% EtOAc in hexanes). The appropriate fractions were combined, concentrated and dried in vacuo to afford 4-iodo-2-((4-methoxybenzyl)oxy)-5-methylpyridine (0.35 g, 29% yield). LC-MS (ESI) m/z: 356.2 $[M+H]^+$.

Step 2. To a solution of 4-iodo-2-((4-methoxybenzyl)oxy)-5-methylpyridine (0.5 g, 1.407 mmol) in DMSO (5 mL) was added $NaN_3$ (0.183 g, 2.82 mmol) and the resulting mixture was stirred at rt for 10 min. CuI (0.53 g, 2.82 mmol), $K_2CO_3$ (0.388 g, 2.82 mmol) and L-proline (0.323 g, 2.82 mmol) were added and the resulting mixture was submitted to microwave irradiation for 1 h at 80° C. for 1 h. After completion of the reaction (TLC, 10% EtOAc/hexanes), the reaction mixture was poured into water and extracted with ethyl acetate (3×). The combined organic layers were dried over sodium sulfate and concentrated under vacuum to get the crude product, which was purified by silica gel flash chromatography (0-5% EtOAc in hexanes). The appropriate fractions were combined, concentrated and dried in vacuo to afford 4-azido-2-((4-methoxybenzyl)oxy)-5-methylpyridine (0.29 g, 76% yield). LC-MS (ESI) m/z: 271.2 $[M+H]^+$.

Step 3. To a mixture of 4-azido-2-((4-methoxybenzyl)oxy)-5-methylpyridine (0.8 g, 3.0 mmol) in EtOH:water (4:1, 10 mL) was added $NH_4Cl$ (0.365 g, 6.81 mmol) and Zn powder (0.25 g, 3.85 mmol). The resulting mixture was stirred at 80° C. for 1.5 hour. After completion of reaction (TLC, 30% EtOAc/hexanes), the reaction mixture was filtered through a celite plug and the filtrate was concentrated under vacuum to get crude product, which was purified by silica gel flash chromatography (0-25% EtOAc in hexanes). The appropriate fractions were combined, concentrated and dried in vacuo to afford 2-((4-methoxybenzyl)oxy)-5-methylpyridin-4-amine (Arylamine A13, 0.146 g, 20% yield). 1H NMR (400 MHZ, DMSO-d6) δ 7.50 (s, 1H), 7.30 (d, J=8.8 Hz, 2H), 6.90 (d, J=8.8 Hz, 2H), 5.87 (s, 1H), 5.72 (s, 2H), 5.11 (s, 2H), 3.74 (s, 3H), 1.92 (s, 3H). LC-MS (ESI) m/z: 245.2 $[M+H]^+$.

Preparation of Arylamine A14

Compounds of the present invention can be prepared from arylamine A14 which can be prepared as shown in Scheme A12 and described herein (see, e.g., WO 2009/10794). Commercially available 2-chloro-5-methoxypyridin-3-amine can be coupled with trimethyl boroxine under palladium catalysis to generate arylamine A14.

Scheme A12

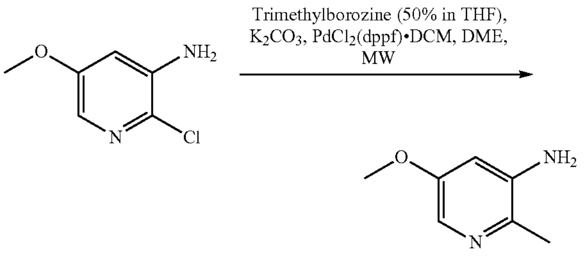

A14

Three microwave sealed tubes were each loaded with 2-chloro-5-methoxypyridin-3-amine (0.5 g, 3.2 mmol) and DME (5 mL), followed by $K_2CO_3$ (1.3 g, 9.45 mmol). The reaction mixtures were purged with $N_2$ gas for 5 min followed by addition of trimethylboroxine (50% in THF, 0.87 g, 3.46 mmol) and $PdCl_2$(dppf).DCM (0.128 g, 0.157 mmol) in each tube. The reaction mixtures were submitted to microwave irradiation for 45 min at 120° C. After completion of reaction (TLC, 5% MeOH in DCM), the reaction mixtures were combined, diluted with EtOAc and filtered on a celite plug, washed with EtOAc. The collected filtrate was concentrated under vacuum. The residue was purified by silica gel flash chromatography (0-25% EtOAc in hexanes). The appropriate fractions were combined, concentrated and dried in vacuo to afford 5-methoxy-2-methylpyridin-3-amine (Arylamine A14, 0.948 g, 73% yield). 1H NMR (400 MHZ, $CDCl_3$) δ 7.67 (d, J=2.4 Hz, 1H), 6.51 (d, J=2.4 Hz, 1H), 3.79 (s, 3H), 3.64 (bs, 2H), 2.34 (s, 3H). LC-MS (ESI) m/z: 139.2 $[M+H]^+$.

Preparation of Arylamine A15

Compounds of the present invention can be prepared from arylamine A15 which can be prepared as shown in Scheme A13 and described herein. Commercially available 4-bromo-5-methyl-1H-indazole can be protected with a THP group. Reaction of the bromo with 4-methoxybenzylamine under palladium mediated conditions can provide a PMB intermediate which can be removed by hydrogenolysis over palladium on carbon.

Scheme A13

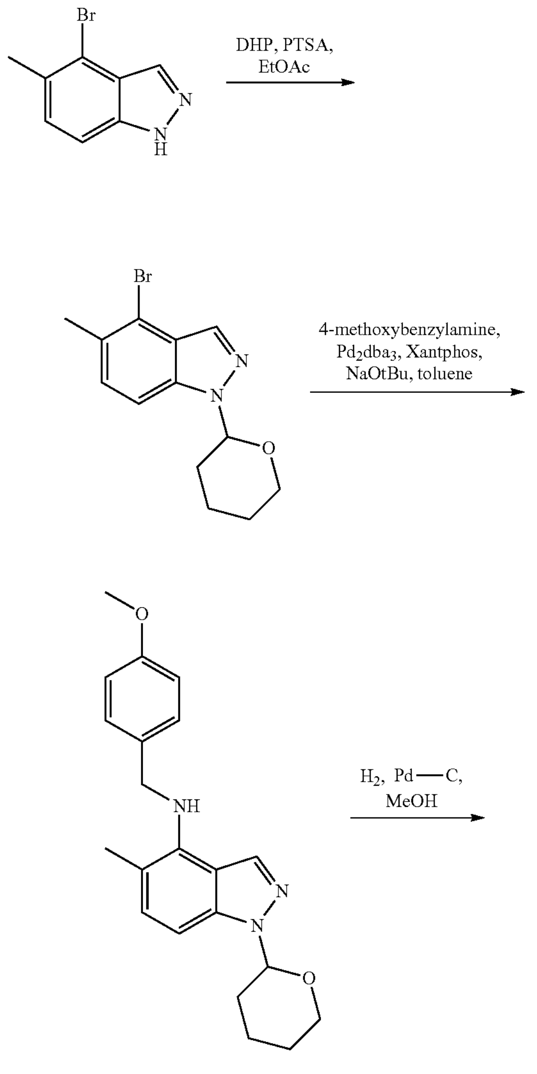

-continued

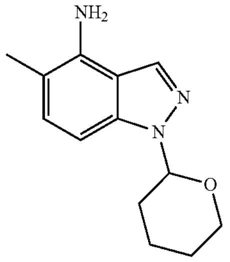

A15

Step 1. Based on WO 2017/182495. 3,4-dihydro-2H-pyran (4.44 g, 52.8 mmol, 4.8 mL) was added to a suspension of 4-bromo-5-methyl-1H-indazole (5.00 g, 23.7 mmol) and PTSA (212 mg, 1.23 mmol) in EtOAc (100 mL) and the mixture was heated at 70° C. for 1 h 20 min. The mixture was cooled to RT, added to saturated aqueous sodium bicarbonate (100 mL) and the layers were separated. The aqueous layer was extracted once with EtOAc and the combined organic layers were washed with brine before being dried over $Na_2SO_4$, filtered and concentrated in vacuo. The residue was adsorbed on silica using DCM and purified by flash chromatography on silica gel (0-20% EtOAc in heptanes). The appropriate fractions were combined, concentrated, coevaporated with DCM/heptane and dried in vacuo to provide 4-bromo-5-methyl-1-tetrahydropyran-2-yl-indazole (7.06 g, quantitative yield) as a white solid. $^1H$ NMR (400 MHZ, Chloroform-d) δ 7.98 (d, J=0.9 Hz, 1H), 7.44 (dd, J=8.4, 0.9 Hz, 1H), 7.24 (d, J=8.5 Hz, 1H), 5.67 (dd, J=9.2, 2.8 Hz, 1H), 4.00 (dtd, J=11.5, 3.6, 1.5 Hz, 1H), 3.78-3.63 (m, 1H), 2.63-2.51 (m, 1H), 2.49 (s, 3H), 2.26-1.96 (m, 2H), 1.94-1.43 (m, 3H). LC-MS (ESI) m/z: 297.0 $[M+H]^+$.

Step 2. A RBF equipped with a condenser was charged with 4-bromo-5-methyl-1-tetrahydropyran-2-yl-indazole (3.45 g, 11.7 mmol), $Pd_2dba_3$ (640 mg, 0.699 mmol), Xantphos (640 mg, 1.11 mmol) and sodium tert-butoxide (1.70 g, 17.7 mmol). Toluene (75 mL) was added, followed by 4-methoxybenzylamine (1.73 g, 12.63 mmol, 1.65 mL), $N_2$ was bubbled through the solution and the mixture was stirred at 110° C.) heat block for 2.25 h. After cooling down to rt, the reaction mixture was diluted with equal amounts of $H_2O$ and aqueous saturated $NH_4Cl$ solution and extracted with EtOAc (3×). The combined organic extracts were washed with brine, dried over $Na_2SO_4$, filtered on a silica plug and concentrated. The crude residue was adsorbed on silica using DCM purified by flash chromatography on silica gel (0-60% EtOAc in heptanes). The appropriate fractions were combined, concentrated and dried in vacuo to provide N-[(4-methoxyphenyl)methyl]-5-methyl-1-tetrahydropyran-2-yl-indazol-4-amine (3.91 g, 95% yield) as a sticky yellow gum. LC-MS (ESI) m/z: 352.2 $[M+H]^+$.

Step 3. To a solution of N-[(4-methoxyphenyl)methyl]-5-methyl-1-tetrahydropyran-2-yl-indazol-4-amine (3.91 g, 11.1 mmol) in MeOH (40 mL) under $N_2$ was added palladium on carbon (10% w/w, 1.18 g, 1.11 mmol) slurried in MeOH. The flask was flushed with $H_2$ and stirred under $H_2$ atmosphere (balloon) over 4 days, replacing balloon as needed. The reaction mixture was filtered on celite, rinsed with MeOH and DCM. The filtrate was adsorbed on silica and purified by flash chromatography on silica gel (0.70% EtOAc in heptanes). The appropriate fractions were combined, concentrated and dried in vacuo to provide 5-methyl- 1-tetrahydropyran-2-yl-indazol-4-amine (arylamine A15, 1.94 g, 75% yield) as a peach solid. LC-MS (ESI) m/z: 232.2 $[M+H]^+$.

Chiral Separation of Selected Compounds

Racemic mixtures of atropisomers were separated using chiral SFC methods on a Mettler Toledo Minigram SFC (MTM), a Waters Prep 15 SFC-MS (WP15), a Waters Prep 100 SFC-MS (WP100) or a Pic Solution Hybrid 10-150 (PSH) (Table 4). An appropriate column was selected to achieve a satisfactory resolution of the peaks. The appropriate fractions for each peak were combined, concentrated and usually taken in a mixture of water and a suitable water miscible organic solvent such as EtOH, IPA, $CH_3CN$ or a mixture thereof and freeze-dried. The separated products were reanalyzed by chiral SFC or chiral HPLC to assess chiral purity.

C1A is Phenomenex Lux Cellulose-2, 10×250 mm, 5 μm; C1B is Phenomenex Lux Cellulose-2, 30×250 mm, 5 μm; C2 is Chiral Technologies IA, 10×250 mm, 5 μm; C3 is Chiral Technologies IC, 10×250 mm, 5 μm; C4 is Chiral Technologies ID, 10×250 mm, 5 μm; C5 is Chiral Technologies IG, 10×250 mm, 5 μm; C6 is Chiral Technologies AS, 10×250 mm, 5 μm; C7 is Phenomenex Lux Cellulose-4, 10×250 mm, 5 μm; C8 is Phenomenex Lux Cellulose-1, 21.2×250 mm, 5 μm.

Structural assignments of the separated atropisomers were confirmed by biological activity where the biologically active enantiomer was assigned to have the(S) configuration, which was confirmed by X-ray crystallography of key compounds.

TABLE 4

| Mixture Cmpd # | Peak 1 Cmpd # | Peak 2 Cmpd # | Instrument | Column | Eluent (%, Flow Rate (mL/min)) |
|---|---|---|---|---|---|
| 28 | 29 | 30 | WP15 | C4 | IPA + 10 mM Ammonium Formate (40%,10) |
| 38 | 39 | 40 | MTM | C2 | IPA + 10 mM Ammonium Formate (40%,10) |
| 43 | 44 | 45 | MTM | C4 | IPA + 10 mM Ammonium Formate (40%,10) |
| 46 | 47 | 48 | MTM | C1A | 1:1 ACN/EtOH + 0.1% Formic Acid (55%,10) |
| 49 | 50 | 51 | MTM | C4 | MeOH + 10 mM Ammonium Formate (25%,10) |
| 54 | 55 | 56 | MTM | C1A | MeOH + 10 mM Ammonium Formate (55%,10) |
| 61 | 62 | 63 | MTM | C4 | IPA + 10 mM Ammonium Formate (40%,10) |
| 69 | 70 | 71 | MTM | C4 | MeOH (20%, 10) |
| 83 | 84 | 82 | MTM | C1A | 1:1 ACN/EtOH (55%, 10) |
| 97 | 98 | 99 | MTM | C5 | IPA (30%, 10) |
| 104 | 105 | 106 | MTM | C1A | MeOH + 10 mM Ammonium Formate (35%,10) |
| 110 | 111 | 112 | WP15 | C1A | MeOH (55%, 10) |
| 113 | 114 | 115 | MTM | C3 | MeOH (20%, 10) |
| 116 | 117 | 118 | WP100 | C1B | 1:1 ACN/EtOH (50%, 70) |
| 119 | 120 | 121 | WP100 | C1B | 1:1 ACN/EtOH (45%, 70) |
| 125 | 126 | 127 | WP100 | C1B | 1:1 ACN/EtOH (50%, 70) |
| 132 | 133 | 134 | WP100 | C1B | 1:1 ACN/EtOH (45%, 70) |
| 135 | 136 | 137 | MTM | C1A | 1:1 ACN/EtOH (45%, 10) |
| 138 | 139 | 140 | MTM | C1A | 1:1 ACN/EtOH (40%, 10) |
| 141 | 142 | nd | WP100 | C1B | 1:1 ACN/EtOH (50%, 70) |
| 143 | 144 | 145 | MTM | C5 | IPA (30%, 10) |
| 147 | 148 | 149 | MTM | C1A | 1:1 ACN/EtOH (55%, 10) |
| 164 | 165 | 166 | WP100 | C1B | 1:1 ACN/EtOH (55%, 70) |
| 170 | 171 | 172 | MTM | C3 | MeOH (45%, 10) |
| 173 | 174 | 175 | MTM | C1A | 1:1 ACN/EtOH (55%, 10) |
| 285 | 176 | 177 | MTM | C1A | IPA (50%, 10) |
| 178 | 179 | 180 | MTM | C1A | ACN/EtOH (45%, 10) |
| 181 | 182 | 183 | WP-100 | C1B | IPA + 10 mM Ammonium Formate (55%, 70) |
| 184 | 185 | 186 | MTM | C1A | IPA + 10 mM Ammonium Formate (40%, 10) |
| 187 | 188 | 189 | MTM | C1A | IPA + 10 mM Ammonium Formate (40%, 10) |
| 190 | 191 | 192 | MTM | C1A | IPA + 10 mM Ammonium Formate (40%, 10) |
| 193 | 194 | 195 | MTM | C5 | 1:1 ACN/EtOH + 0.1% Formic Acid (30%, 10) |
| 201 | 203 | 205 | WP100 | C1B | ACN/EtOH (45%, 70) |
| 286 | 196 | 197 | MTM | C1A | IPA (50%, 10) |
| 198 | 199 | 200 | MTM | C1A | 1:1 ACN/EtOH (40%, 10) |
| 266 | 264 | 265 | WP100 | C1B | ACN/EtOH (55%,70) |
| 271 | 272 | 273 | MTM | C1A | IPA + 10 mM Ammonium Formate (45%, 10) |
| 275 | 274 | 276 | MTM | C1A | IPA + 10 mM Ammonium Formate (50%, 10) |
| Int. D | Int. D1 | Int. D2 | WP100 | C1B | MeOH (25%,70) |
| 270 | 288 | 269 | MTM | C1A | IPA + 10 mM Ammonium Formate (55%, 10) |
| 267 | 287 | 268 | MTM | C1A | IPA + 10 mM Ammonium Formate (55%, 10) |
| 289 | 290 | 291 | MTM | C3 | MeOH + 10 mM Ammonium Formate (30%, 10) |
| 292 | 293 | 294 | WP15 | C7 | MeOH + 10 mM Ammonium Formate (55%, 10) |
| 295 | 296 | 297 | MTM | C1A | MeOH (55%, 10) |
| 298 | 299 | 300 | MTM | C1A | MeOH (55%, 10) |
| 301 | 302 | 303 | MTM | C1A | MeOH (35%, 10) |
| 304 | 305 | 306 | MTM | C1A | 1:1 ACN/EtOH (55%, 10) |
| 308 | 309 | 310 | WP15 | C1A | MeOH (55%, 10) |
| 313 | 314 | 315 | MTM | C1A | 1:1 ACN/EtOH (40%, 10) |
| 316 | 317 | 318 | MTM | C1A | 1:1 ACN/EtOH (40%, 10) |
| 319 | 320 | 321 | MTM | C1A | 1:1 ACN/EtOH (50%, 10) |
| 131 | 322 | 323 | MTM | C1A | 1:1 ACN/EtOH (35%, 10) |
| 324 | 325 | 326 | MTM | C1A | 1:1 ACN/EtOH (45%, 10) |
| | 340 | 341 | PSH | C8 | MeOH (35%, 75) |
| | 342 | 343 | PSH | C8 | MeOH (35%, 75) |

Example 2. Enzymatic Assay

Detection of Myt1 kinase activity utilized a recombinant human Myt1 kinase assay measuring the hydrolysis of ATP using a commercially available ADP-Glo Assay (ADP-Glo™ Kinase Assay from Promega, 10 000 assays, #V9102). Briefly, 5 μL recombinant human Myt1 (full length PKMYT1 recombinant human protein expressed in insect cells from Thermo Fisher #A33387; ~ 80% purity) was prepared in reaction buffer (70 mM HEPES, 3 mM $MgCl_2$, 3 mM $MnCl_2$, 50 μg/ml PEG 20000, 3 μM Na-orthovanadate, 1.2 mM DTT) and added to 384 well white polystyrene, flat bottom well, non-treated, microplate (Corning #3572). After this, 5 μL of compounds (diluted in reaction buffer to 0.5% DMSO) was added to the microplate and the plate was spun briefly and incubated at 22° C. for 15 minutes. Ultra-Pure Adenosine Triphosphate (ATP) solution (ADP-Glo kit from Promega) was diluted in reaction buffer and 5 μL was added to the microplate, spun down briefly and incubated for 60 minutes at 30° C. The final Myt1 enzyme concentration was 18 nM and the final ATP concentration was 10 UM. After the 60-minute incubation, 15 UL of ADP-Glo reagent was added and the plate was spun briefly and sealed and incubated in the dark for 40 minutes at 22° C. Following this, 30 UL of kinase detection reagent was added per well and the plate was spun briefly, sealed and incubated for 45-60 minutes at 22° C. in the dark. Luminescence was read using the Envision (250 ms integration). The $IC_{50}$ and the % max inhibition were calculated for each inhibitor compound tested.

Exemplary prepared compounds and their activities were shown in Table 5 below.

TABLE 5

| Compound | Method | Myt1 $IC_{50}$ (nM) | MS (+ESI) [M + 1] |
|---|---|---|---|
| 1 | A | 50 | m/z 412.4 |
| 2 | A | 231 | m/z 395.5 |
| 3 | A | 462 | m/z 391.5 |
| 4 | C | 922 | m/z 317.2 |
| 5 | C | 277 | m/z 349.4 |
| 6 | C | 1240 | m/z 349.2 |
| 7 | C | 605 | m/z 445.2 |
| 8 | C | 164 | m/z 375.4 |
| 9 | C | 363 | m/z 403.2 |
| 10 | C | 187 | m/z 403.4 |
| 11 | C | 252 | m/z 349.2 |
| 12 | C | 988 | m/z 363.2 |
| 13 | C | 190 | m/z 487.5 |
| 14 | C | 480 | m/z 384.2 |
| 15 | C | 1090 | m/z 411.9 |
| 16 | C | 9630 | m/z 505.6 |
| 17 | C | 9060 | m/z 379.2 |
| 18 | C | 1940 | m/z 410.4 |
| 19 | C | 527 | m/z 383.2 |
| 20 | C | 182 | m/z 417.2 |
| 21 | C | 283 | m/z 417.2 |
| 22 | C | 79 | m/z 375.4 |
| 23 | C | 2470 | m/z 361.2 |
| 24 | C | 29 | m/z 366.2 |
| 25 | C | 399 | m/z 378.2 |
| 26 | C | 2000 | m/z 464.4 |
| 27 | C | 604 | m/z 365.3 |
| 28 | A | <10 | m/z 381.2 |
| 29 | A | <10 | m/z 381.2 |
| 30 | A | 1830 | m/z 381.2 |
| 31 | J | <10 | m/z 395.2 |
| 32 | A | <10 | m/z 409.4 |
| 33 | L | <10 | m/z 460.2 |
| 34 | A | <10 | m/z 375.4 |
| 35 | A | <10 | m/z 443.4 |
| 36 | A | 14 | m/z 443.4 |

TABLE 5-continued

| Compound | Method | Myt1 $IC_{50}$ (nM) | MS (+ESI) [M + 1] |
|---|---|---|---|
| 37 | A | <10 | m/z 381.2 |
| 38 | A | <10 | m/z 376.2 |
| 39 | A | >5000 | m/z 376.2 |
| 40 | A | <10 | m/z 376.2 |
| 41 | A | <10 | m/z 381.2 |
| 42 | A | <10 | m/z 401.4 |
| 43 | A | <10 | m/z 4112 |
| 44 | A | 3020 | m/z 411.2 |
| 45 | A | <10 | m/z 411.2 |
| 46 | A | <10 | m/z 437.4 |
| 47 | A | <10 | m/z 437.4 |
| 48 | A | >5000 | m/z 437.4 |
| 49 | A | <10 | m/z 409.7 |
| 50 | A | <10 | m/z 409.7 |
| 51 | A | 87 | m/z 409.7 |
| 52 | A | 10 | m/z 411.2 |
| 53 | A | 16 | m/z 396.2 |
| 54 | A | <10 | m/z 383.2 |
| 55 | A | <10 | m/z 383.2 |
| 56 | A | 549 | m/z 383.2 |
| 57 | A | <10 | m/z 376.2 |
| 58 | A | <10 | m/z 449.2 |
| 59 | A | 12 | m/z 397.4 |
| 60 | A | 10 | m/z 365.3 |
| 61 | A | <10 | m/z 389.2 |
| 62 | A | >5000 | m/z 389.2 |
| 63 | A | <10 | m/z 389.2 |
| 64 | A | <10 | m/z 393.2 |
| 65 | A | <10 | m/z 364.2 |
| 66 | A | 10 | m/z 396.2 |
| 67 | A | 14 | m/z 382.2 |
| 68 | A | 10 | m/z 416.2 |
| 69 | A | <10 | m/z 398.4 |
| 70 | A | 2920 | m/z 398.4 |
| 71 | A | <10 | m/z 399.3 |
| 72 | A | 11 | m/z 378.2 |
| 73 | A | 10 | m/z 396.2 |
| 74 | A | 14 | m/z 466.5 |
| 75 | A | 11 | m/z 431.5 |
| 76 | A | <10 | m/z 378.2 |
| 77 | A | <10 | m/z 363.2 |
| 78 | A | 18 | m/z 437.4 |
| 79 | A | <10 | m/z 437.4 |
| 80 | A | <10 | m/z 452.5 |
| 81 | A | <10 | m/z 381.2 |
| 82 | A | >5000 | m/z 380.2 |
| 83 | A | <10 | m/z 380.2 |
| 84 | A | <10 | m/z 380.2 |
| 85 | A | <10 | m/z 367.2 |
| 86 | A | <10 | m/z 378.2 |
| 87 | A | <10 | m/z 424.5 |
| 88 | A | <10 | m/z 369.2 |
| 89 | A | <10 | m/z 369.2 |
| 90 | A | 2800 | m/z 369.2 |
| 91 | A | <10 | m/z 369.2 |
| 92 | A | <10 | m/z 409.2 |
| 93 | A (from int D2) | <10 | m/z 409.2 |
| 94 | A | <10 | m/z 338.2 |
| 95 | A (from int D2) | <10 | m/z 338.2 |
| 96 | A | 10 | m/z 354.2 |
| 97 | M | 12 | m/z 375.2 |
| 98 | M | >5000 | m/z 375.2 |
| 99 | M | <10 | m/z 375.2 |
| 100 | J | <10 | m/z 352.2 |
| 101 | J | <10 | m/z 367.2 |
| 102 | J | 13 | m/z 392.2 |
| 104 | A | <10 | m/z 358.5 |
| 105 | A | 3060 | m/z 358.5 |
| 106 | A | <10 | m/z 358.5 |
| 107 | A | 12 | m/z 373.8 |
| 110 | J | Nd | m/z 355.2 |
| 111 | J | <10 | m/z 355.2 |
| 112 | J | 1380 | m/z 355.2 |
| 113 | A | <10 | m/z 344.2 |
| 114 | A | 4680 | m/z 344.2 |
| 115 | A | <10 | m/z 344.2 |
| 116 | D | <10 | m/z 337.2 |

TABLE 5-continued

| Compound | Method | Myt1 $IC_{50}$ (nM) | MS (+ESI) [M + 1] |
|---|---|---|---|
| 117 | D | <10 | m/z 337.3 |
| 118 | D | 611 | m/z 337.3 |
| 119 | D | <10 | m/z 311.2 |
| 120 | D | <10 | m/z 311.2 |
| 121 | D | 1020 | m/z 311.2 |
| 125 | D | 16 | m/z 325.2 |
| 126 | D | <10 | m/z 325.2 |
| 127 | D | 271 | m/z 325.2 |
| 131 | D | <10 | m/z 355.2 |
| 132 | D or K | <10 | m/z 331.2 |
| 133 | D or K | <10 | m/z 331.2 |
| 134 | D or K | 653 | m/z 331.2 |
| 135 | D | <10 | m/z 314.2 |
| 136 | D | <10 | m/z 314.2 |
| 137 | D | 476 | m/z 314.2 |
| 138 | D | <10 | m/z 339.2 |
| 139 | D | <10 | m/z 339.2 |
| 140 | D | 526 | m/z 339.2 |
| 141 | D | <10 | m/z 375.2 |
| 142 | D | <10 | m/z 375.2 |
| 143 | D or K/N | <10 | m/z 322.2 |
| 144 | D or K/N | <10 | m/z 322.2 |
| 145 | D or K/N | >2000 | m/z 322.2 |
| 146 | E | 1420 | m/z 284.2 |
| 147 | E | 55 | m/z 299.3 |
| 148 | E | 32 | m/z 299.3 |
| 149 | E | >5000 | m/z 299.3 |
| 150 | B | 1350 | m/z 360.2 |
| 151 | B | 2750 | m/z 390.2 |
| 152 | E | 84 | m/z 312.1 |
| 153 | B | 3550 | m/z 391.2 |
| 154 | B | 6350 | m/z 413.2 |
| 155 | B | 1020 | m/z 350.2 |
| 156 | B | 465 | m/z 403.3 |
| 157 | B | 1240 | m/z 417.2 |
| 158 | B | 953 | m/z 385.2 |
| 159 | B | 1720 | m/z 389.2 |
| 160 | B | 554 | m/z 385.3 |
| 161 | B | 671 | m/z 411.3 |
| 162 | B | 596 | m/z 389.2 |
| 163 | B | 334 | m/z 407.2 |
| 164 | E | <10 | m/z 326.1 |
| 165 | E | <10 | m/z 326.1 |
| 166 | E | 3140 | m/z 326.1 |
| 167 | B | 361 | m/z 298.2 |
| 168 | E | <10 | m/z 346.4 |
| 169 | E | 1730 | m/z 313.1 |
| 170 | E | Nd | m/z 346.3 |
| 171 | E | 6140 | m/z 346.3 |
| 172 | E | <10 | m/z 346.3 |
| 173 | A | <10 | m/z 352.4 |
| 174 | A | <10 | m/z 352.4 |
| 175 | A | >5000 | m/z 352.4 |
| 176 | A | <10 | m/z 312.1 |
| 177 | A | >2000 | m/z 312.2 |
| 178 | A | <10 | m/z 358.2 |
| 179 | A | <10 | m/z 358.2 |
| 180 | A | 89 | m/z 358.2 |
| 181 | D or O | <10 | m/z 325.1 |
| 182 | D or O | <10 | m/z 325.2 |
| 183 | D or O | 1360 | m/z 325.2 |
| 184 | A | 10 | m/z 340.1 |
| 185 | A | <10 | m/z 340.2 |
| 186 | A | 1750 | m/z 340.1 |
| 187 | D | <10 | m/z 391.1 |
| 188 | D | <10 | m/z 391.1 |
| 189 | D | 1010 | m/z 391.1 |
| 190 | A | 12 | m/z 356.2 |
| 191 | A | <10 | m/z 356.2 |
| 192 | A | >2000 | m/z 356.2 |
| 193 | D | <10 | m/z 311.1 |
| 194 | D | >2000 | m/z 311.1 |
| 195 | D | <10 | m/z 311.1 |
| 196 | F | <10 | m/z 312.1 |
| 197 | F | 1700 | m/z 312.1 |
| 198 | A | <10 | m/z 406.1 |
| 199 | A | <10 | m/z 406.2 |

TABLE 5-continued

| Compound | Method | Myt1 $IC_{50}$ (nM) | MS (+ESI) [M + 1] |
|---|---|---|---|
| 200 | A | >2000 | m/z 406.2 |
| 201 | D | <10 | m/z 345.1 |
| 202 | A | <10 | m/z 338.1 |
| 203 | D | <10 | m/z 345.1 |
| 204 | A (from int D2) | <10 | m/z 340.1 |
| 205 | D | 168 | m/z 345.1 |
| 206 | A (from int D2) | <10 | m/z 326.1 |
| 208 | A (from int D2) | <10 | m/z 322.1 |
| 209 | N | 28 | m/z 311.1 |
| 212 | G | 3440 | m/z 351.3 |
| 213 | G | 195 | m/z 351.3 |
| 214 | H | 136 | m/z 445.3 |
| 215 | H | 24 | m/z 544.5 |
| 216 | H | 76 | m/z 504.5 |
| 217 | A | 168 | m/z 421.4 |
| 218 | F | 22 | m/z 421.4 |
| 219 | A | 46 | m/z 324.2 |
| 220 | A | <10 | m/z 341.4 |
| 221 | I | 81 | m/z 365.3 |
| 222 | F | <10 | m/z 420.4 |
| 223 | F | 15 | m/z 457.4 |
| 224 | F | 13 | m/z 406.4 |
| 225 | F | 34 | m/z 406.4 |
| 226 | F | 12 | m/z 379.4 |
| 227 | F | 50 | m/z 399.3 |
| 228 | F | 21 | m/z 362.4 |
| 229 | F | 52 | m/z 366.4 |
| 230 | F | 368 | m/z 398.4 |
| 231 | F | <10 | m/z 422.4 |
| 232 | F | 11 | m/z 392.4 |
| 233 | F | 10 | m/z 426.3 |
| 234 | F | 14 | m/z 408.3 |
| 235 | F | 13 | m/z 406.4 |
| 236 | F | 16 | m/z 408.4 |
| 237 | F | 19 | m/z 436.4 |
| 238 | F | 10 | m/z 394.3 |
| 239 | F | 15 | m/z 380.4 |
| 240 | F | 191 | m/z 410.4 |
| 241 | F | 24 | m/z 366.4 |
| 242 | F | <10 | m/z 456.4 |
| 243 | A | 69 | m/z 418.3 |
| 244 | A | 16 | m/z 369.4 |
| 245 | A | 11 | m/z 431.4 |
| 246 | A | 84 | m/z 397.4 |
| 247 | A | 17 | m/z 427.4 |
| 248 | A | <10 | m/z 431.3 |
| 249 | A | 20 | m/z 415.4 |
| 250 | A | <10 | m/z 376.3 |
| 251 | A | 1420 | m/z 376.3 |
| 252 | A | <10 | m/z 376.3 |
| 253 | A | 24 | m/z 395.4 |
| 254 | A | 10 | m/z 428.4 |
| 255 | A | 109 | m/z 393.4 |
| 256 | H | 50 | m/z 378.4 |
| 257 | F | 43 | m/z 324.3 |
| 258 | A | 3130 | m/z 475.5 |
| 259 | A | <10 | m/z 324.3 |
| 260 | A | 27 | m/z 354.4 |
| 261 | A | 45 | m/z 376.3 |
| 262 | E | 3230 | m/z 313.1 |
| 263 | A | 16 | m/z 348.2 |
| 264 | L | <10 | m/z 332.2 |
| 265 | L | >2000 | m/z 332.2 |
| 266 | L | nd | m/z 332.2 |
| 267 | L | nd | m/z 329.2 |
| 268 | L | >2000 | m/z 329.2 |
| 269 | L | >2000 | m/z 329.3 |
| 270 | L | nd | m/z 329.2 |
| 271 | L | nd | m/z 395.1 |
| 272 | L | <10 | m/z 395.1 |

TABLE 5-continued

| Compound | Method | Myt1 $IC_{50}$ (nM) | MS (+ESI) [M + 1] |
|---|---|---|---|
| 273 | L | 585 | m/z 395.1 |
| 274 | A | <10 | m/z 315.3 |
| 275 | A | nd | m/z 315.3 |
| 276 | A | >2000 | m/z 315.3 |
| 277 | E | 1380 | m/z 294.1 |
| 278 | A with 2-(methylsulfonyl)acetonitrile instead of malononitirle | >5000 | m/z 411.3 |
| 279 | A | 250 | m/z 391.4 |
| 280 | A | 80 | m/z 395.4 |
| 281 | A | 784 | m/z 390.5 |
| 282 | A | 625 | m/z 389.4 |
| 283 | A | 32 | m/z 459.2 |
| 284 | A | 238 | m/z 391.5 |
| 285 | A | 11 | m/z 312.0 |
| 286 | F | nd | m/z 312.1 |
| 287 | L | <10 | m/z 329.2 |
| 288 | L | <10 | m/z 329.2 |
| 289 | K | <10 | m/z 397.0 |
| 290 | K | <10 | m/z 397.0 |
| 291 | K | >2000 | m/z 397.0 |
| 292 | D or O | <10 | m/z 331.3 |
| 293 | D or O | <10 | m/z 331.3 |
| 294 | D or O | >2000 | m/z 331.3 |
| 295 | D | <10 | m/z 374.2 |
| 296 | D | <10 | m/z 374.2 |
| 297 | D | >2000 | m/z 374.2 |
| 298 | D | <10 | m/z 380.2 |
| 299 | D | <10 | m/z 380.2 |
| 300 | D | >2000 | m/z 380.2 |
| 301 | K | 13 | m/z 397.0 |
| 302 | K | <10 | m/z 397.0 |
| 303 | K | >2000 | m/z 397.0 |
| 304 | D | <10 | m/z 379.2 |
| 305 | D | <10 | m/z 379.2 |
| 306 | D | >2000 | m/z 379.2 |
| 307 | D | <10 | m/z 381.2 |
| 308 | D | <10 | m/z 380.2 |
| 309 | D | <10 | m/z 380.2 |
| 310 | D | >2000 | m/z 380.2 |
| 311 | D | <10 | m/z 401.2 |
| 312 | D | <10 | m/z 322.2 |
| 313 | K | <10 | m/z 345.1 |
| 314 | K | <10 | m/z 345.1 |
| 315 | K | >2000 | m/z 345.1 |
| 316 | K | <10 | m/z 365.2 |
| 317 | K | <10 | m/z 365.2 |
| 318 | K | >2000 | m/z 365.2 |
| 319 | D | <10 | m/z 423.2 |
| 320 | D | <10 | m/z 423.2 |
| 321 | D | >2000 | m/z 423.2 |
| 322 | D | <10 | m/z 355.2 |
| 323 | D | >2000 | m/z 355.2 |
| 324 | D | <10 | m/z 337.2 |
| 325 | D | <10 | m/z 337.2 |
| 326 | D | >2000 | m/z 337.2 |
| 327 | D | <10 | m/z 351.1 |
| 328 | Hydrogenolysis of 142 | <10 | m/z 297.3 |
| 329 | E | 1320 | m/z 308.1 |
| 330 | A | 106 | m/z 334.2 |
| 331 | A | 1320 | m/z 350.2 |
| 332 | A | 142 | m/z 377.2 |
| 333 | A | 52 | m/z 407.2 |
| 334 | K | 50 | m/z 327.1 |
| 335 | K | 40 | m/z 341.1 |
| 336 | P | 38 | m/z 324.2 |
| 337 | Q | <10 | m/z 325.1 |
| 338 | Q | 108 | m/z 324.1 |
| 339 | R | 23 | m/z 374.2 [M − H]$^-$ |
| 340 | O/N | <10 | m/z 310.2 |
| 341 | O/N | >10000 | m/z 310.1 |
| 342 | K/N | 41 | m/z 316.1 |
| 343 | K/N | >10000 | m/z 316.1 |
| 344 | K/N | 4700 | m/z 352.0 |
| 345 | S | 323 | m/z 302.0 |
| 346 | R2/N | 234 | m/z 315.0 |

In Table 5, the Method column indicates a preparatory method described above used in the preparation of the compounds.

Example 3. Genetic Validation

Figure 3B:
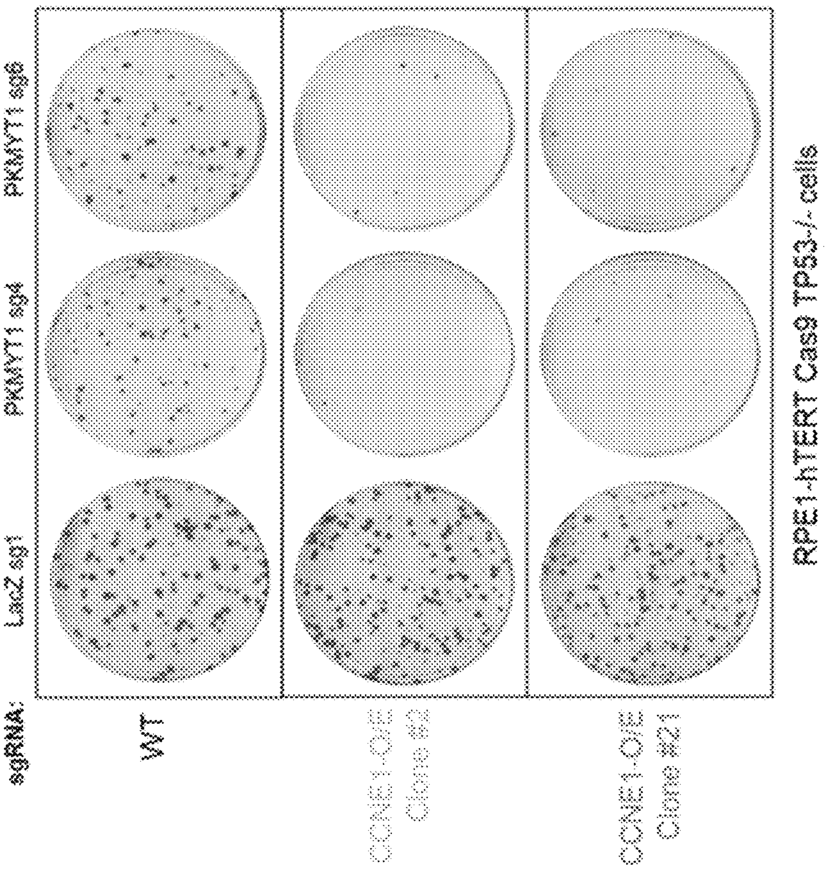
FIG. 3B is a series of images depicting the results of a clonogenic survival assay using RPE1-hTERT Cas9 TP53−/− and CCNE1-overexpressing clones transduced with PKMYT1 sgRNAs. Infected cells were plated at low density to measure their ability to form colonies of >50 cells. After 10 days of growth, the colonies were stained, imaged, and quantified. The results are normalized to the survival of RPE1-hTERT Cas9 TP53−/− parental and CCNE1-overexpressing clones transduced with a non-targeting LacZ control sgRNA.
Figure 3A:
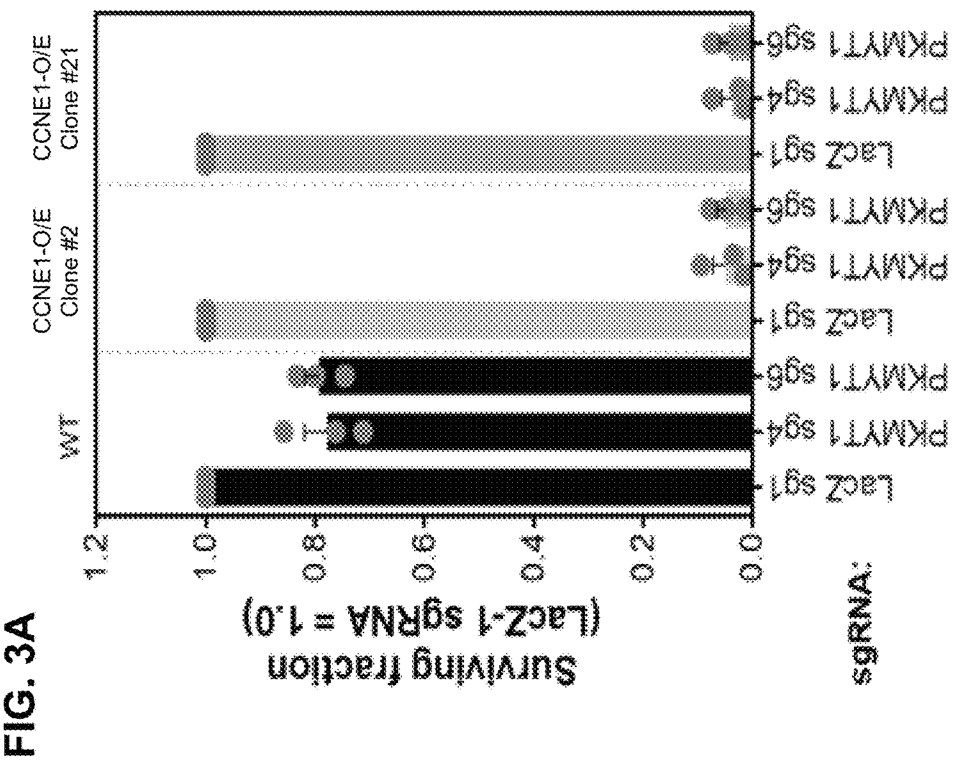
FIG. 3A is a bar graph showing the results of a proliferation assay using RPE1-hTERT Cas9 TP53−/− and CCNE1-overexpressing clones treated with different doses of compound 133.
Figure 4B:
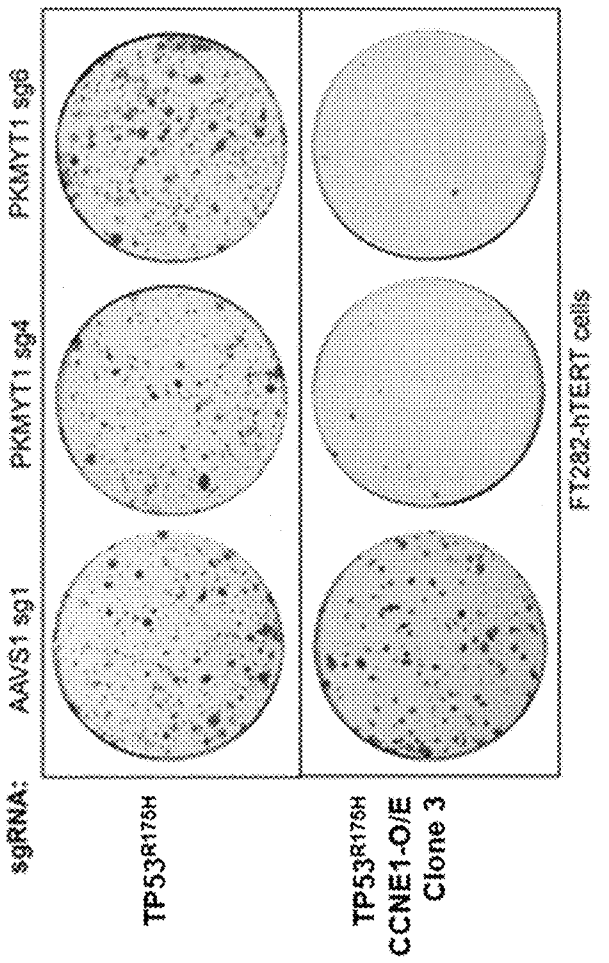
FIG. 4B is a series of images showing of stained colonies described in FIG. 4A.
Figure 4A:
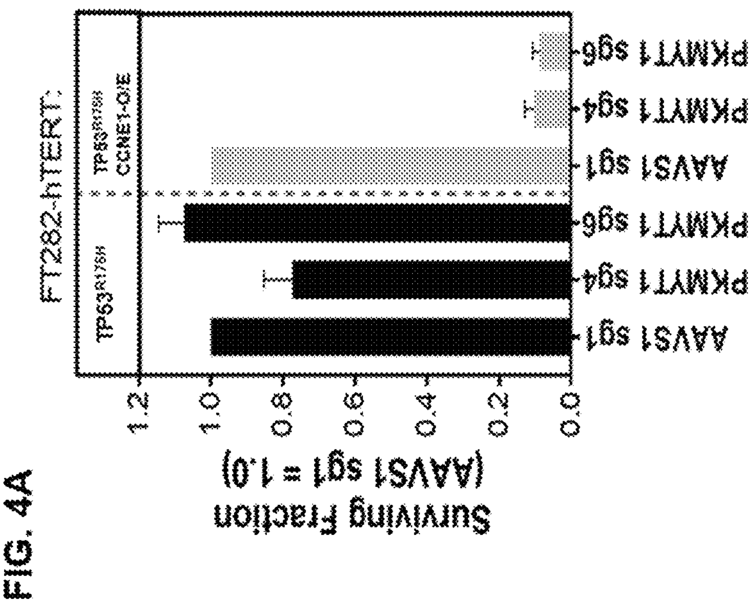
FIG. 4A is a bar graph showing the results of a clonogenic survival assay using FT282-hTERT $TP53^{R175H}$ and CCNE1-overexpressing cells transduced with PKMYT1 sgRNAs. Infected cells were plated at low density to measure their ability to form colonies of >50 cells. After 10 days of growth, the colonies were stained, imaged, and quantified. The results are normalized to the survival of FT282-hTERT $TP53^{R175H}$ and CCNE1-overexpressing cells transduced with an AAVS1 control sgRNA.

Two sgRNAs for PKMYT1 and one sgRNA for LacZ (control) were transduced into the RPE1-hTERT Cas9 TP53−/− parental (WT) and CCNE1-overexpressing clones. Infected cells were plated at low density to measure their ability to form colonies of <50 cells. After 10 days of growth, the colonies were stained, imaged, and quantified. Using clonogenic survival assays, we observed a profound cellular fitness defect in CCNE1-overexpressing cells compared to parental cells transduced with PKMYT1 sgRNAs (FIGS. 3A and 3B). This experiment was repeated using FT282-hTERT TP53−/− parental (WT) and CCNE1-overexpressing clones and similar results were observed (FIGS. 4A and 4B).

Figure 5A:
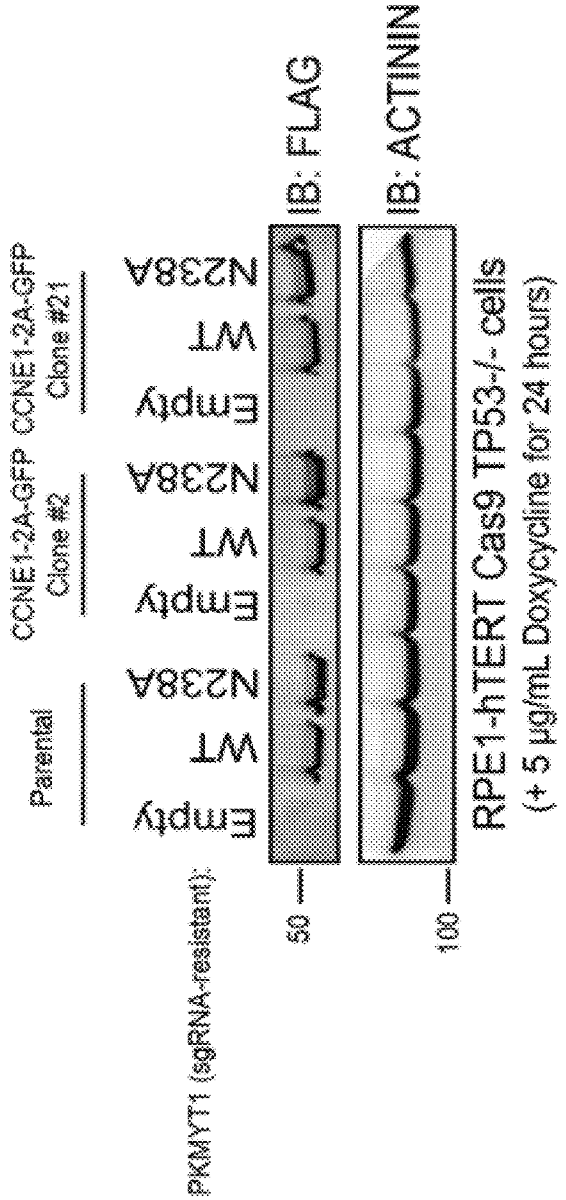
FIGS. 5A, 5B, and 5C show the results of clonogenic survival assays for stable RPE1-hTERT Cas9 TP53−/− parental and CCNE1-overexpressing clones expressing either a wild type or catalytic-dead FLAG-tagged PKMYT1 sgRNA-resistant ORF. These stable cell lines were transduced with either a LacZ non-targeting sgRNA or PKMYT1 sgRNA #4 and plated at low density to measure their ability to form colonies of >50 cells. After 10 days of growth, the colonies were stained, imaged, and quantified. The results are normalized to the survival of RPE1-hTERT Cas9 TP53−/− CCNE1-overexpressing clones transduced with a non-targeting LacZ control sgRNA and represented as a bar graph in FIG. 5C. Both clones 2 and 21 behave similarly in this study.
Figure 5B:
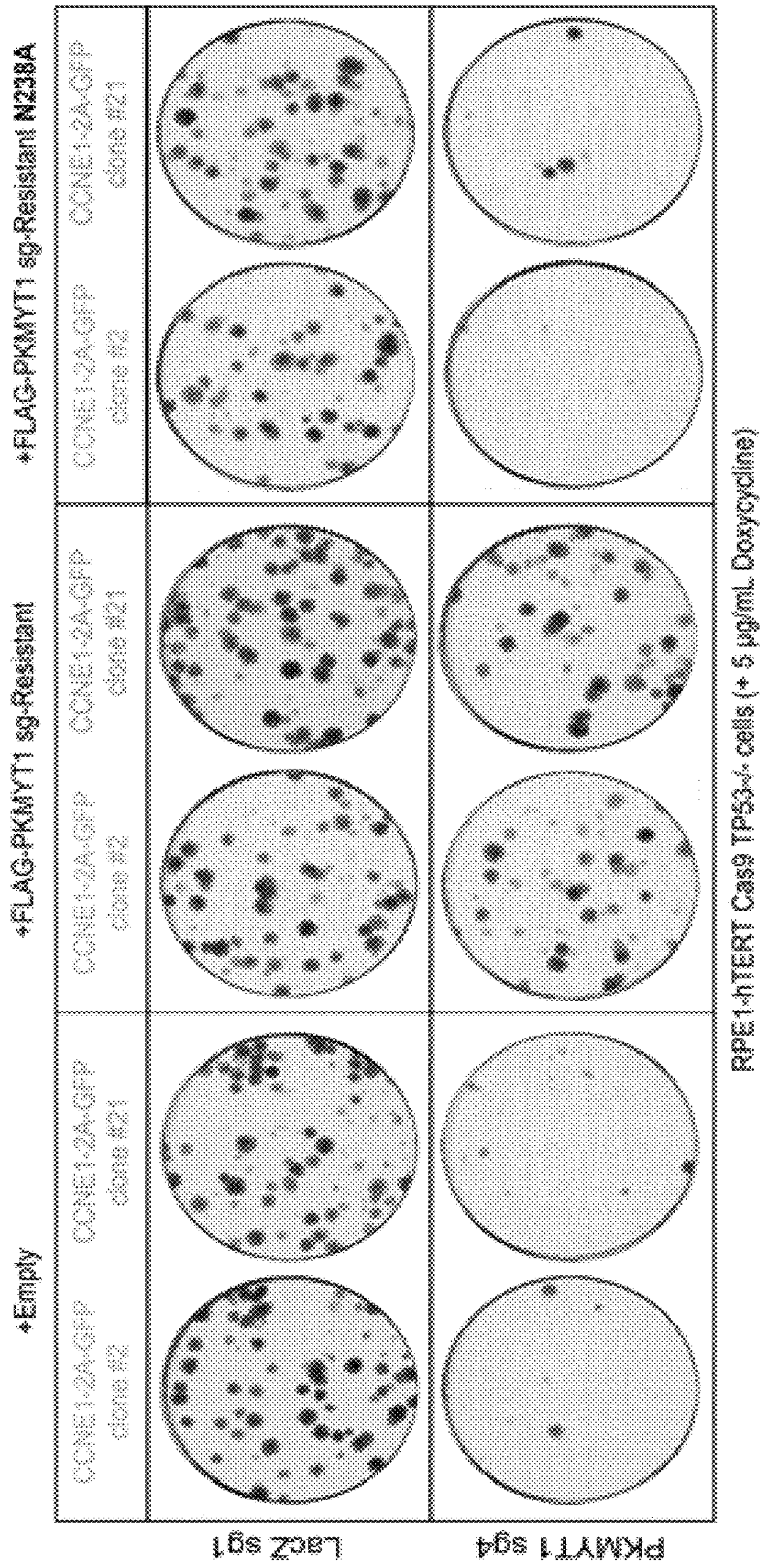
Figure 5C:
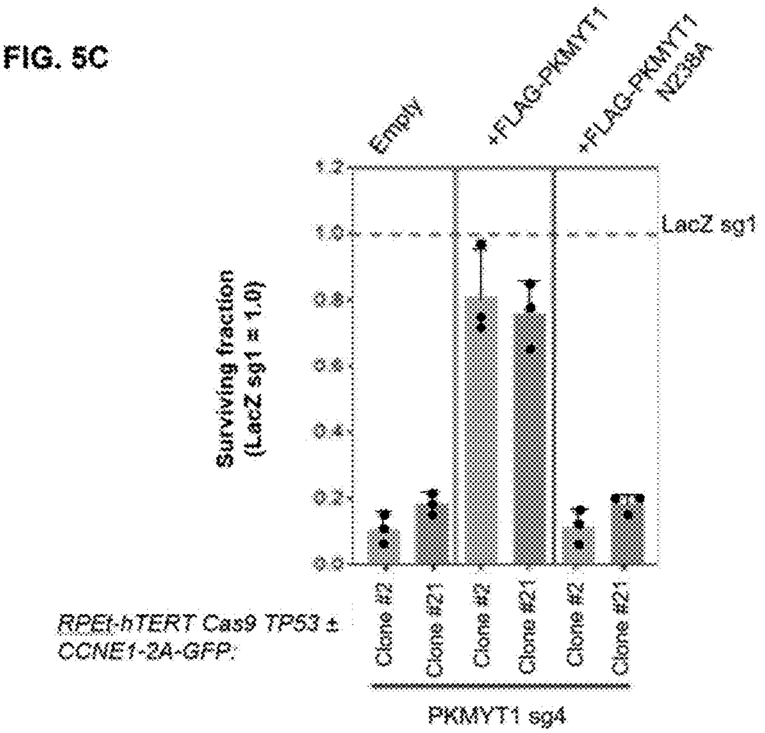

To determine if the kinase activity of PKMYT1 was responsible for maintaining the viability of CCNE1-overexpressing RPE1-hTERT Cas9 TP53−/− cells, the PKMYT1 open reading frame (ORF) was cloned into an inducible mammalian expression vector. sgRNA-resistant silent mutations in the PKMYT1 ORF sequence were then created by PCR mutagenesis. A single point mutation was generated that resulted in an asparagine (N) to alanine (A) amino acid change at residue 238. The N238A amino acid change in the kinase domain resulted in a catalytically inactive PKMYT1 mutant. Stable cell lines in the RPE1-hTERT Cas9 TP53−/− parental and CCNE1-overexpressing clones were generated that either expressed the wild type PKMYT1 ORF or the kinase-dead N238A mutant (FIG. 5A). These stable cell lines were transduced with either a LacZ non-targeting sgRNA or PKMYT1 sgRNA #4. The cells were then plated at low density to measure their ability to form colonies of >50 cells. After 10 days of growth, the colonies were stained, imaged, and quantified. Expression of an sgRNA-resistant PKMYT1 ORF but not the catalytic-dead version rescued the fitness defect induced by transduction of sgRNA #4 into both CCNE1-overexpressing clones (FIGS. 5B and 5C). This result demonstrated that targeting the kinase activity of PKMYT1 selectively kills CCNE1-overexpressing cells.

Example 4. Pharmacological Validation

Figure 3C:
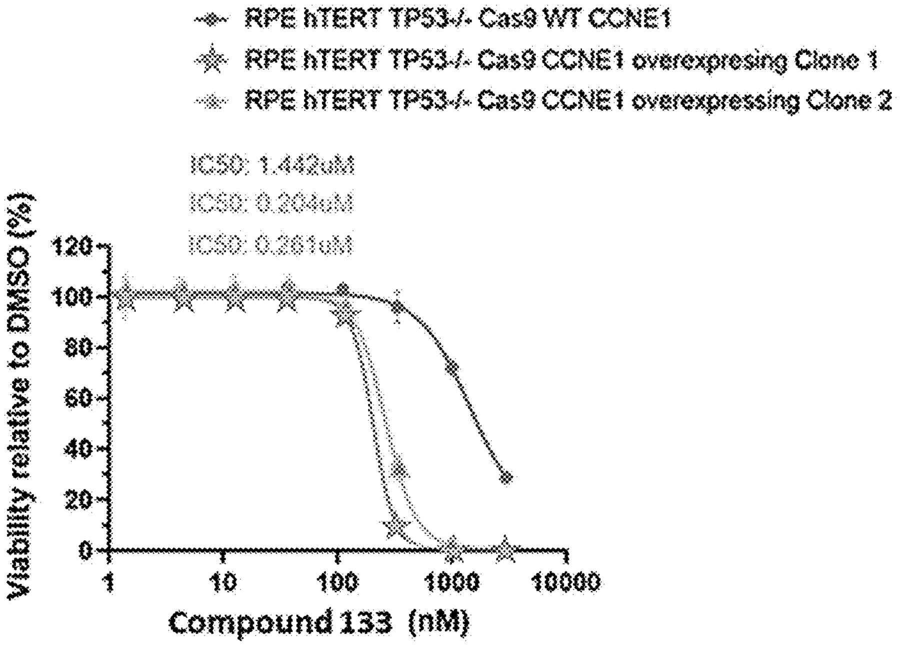
FIG. 3C is a line graph showing the results of a proliferation assay using RPE1-hTERT Cas9 TP54−/− and CCNE1-overexpressing clones treated with different doses of compound 133.
Figure 4C:
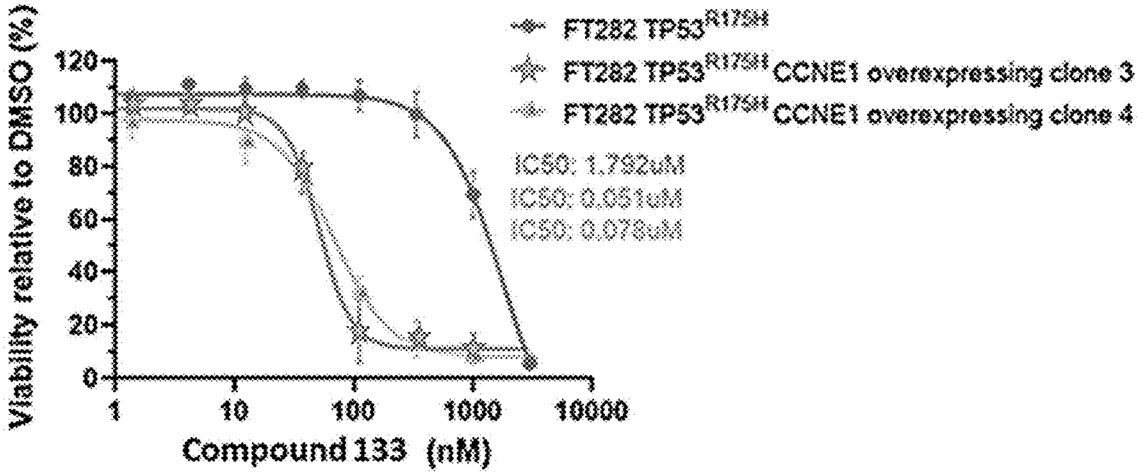
FIG. 4C is a line graph showing the results of a proliferation assay using FT282-hTERT $TP53^{R175H}$ and CCNE1-overexpressing clones treated with different doses of compound 133.

RPE1-hTERT Cas9 TP53−/− parental (WT) and CCNE1-overexpressing clones were treated with compound 133 in a dose titration and cell viability was determined. The CCNE1-overexpressing cells were found to be more sensitive to compound 133 than the corresponding WT cells (FIG. 3C). A similar effect was seen in FT282-hTERT $TP53^{R175H}$ WT and CCNE1-overexpressing clones (FIG. 4C). For dose-response proliferation assays using RPE1-hTERT and FT282-hTERT cell lines, cells were seeded in 96-well plates and dosed with serially diluted Myt1 inhibitor. Cells were imaged once per day using the IncuCyte S3 microscope and percent well confluency was calculated over time. Once cells reached four population doublings the experiment was ended and $IC_{50}$ curves were plotted for the final time point. Percentage confluency was calculated relative to the cell confluency in the untreated wells.

Figure 6:
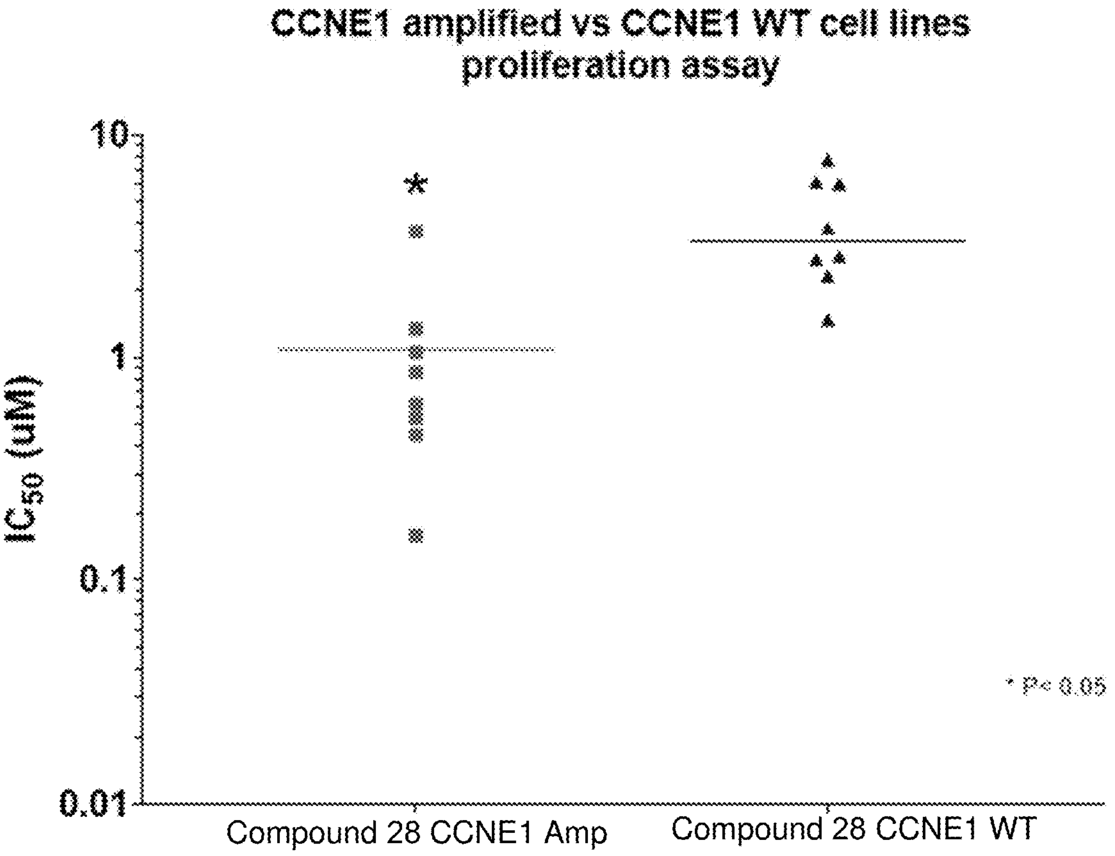
FIG. 6 is a chart showing the results of proliferation assays for a panel of CCNE1 wild type and CCNE1-amplified/overexpressing cancer cell lines treated with different doses of compound 28. The $IC_{50}$ values are plotted for each cell line and demonstrate that CCNE1-overexpressing cell lines show enhanced sensitivity to a Myt1 inhibitor compared to CCNE1 WT cell lines.

A panel of 16 cancer cell lines with either normal (n=8) or elevated levels of CCNE1 (n=8) was evaluated for their sensitivity to compound 28 in a cell proliferation assay (FIG. 6). Dose-response curves in these cancer cell line proliferation assays were generated as follows. Cells were seeded in 96-well plates and dosed with serially diluted compound 28. After 7 days, Cell Titer Glo (CTG) was used to assess the proliferation status of these cells and the $IC_{50}$ values were plotted.

Figure 7:
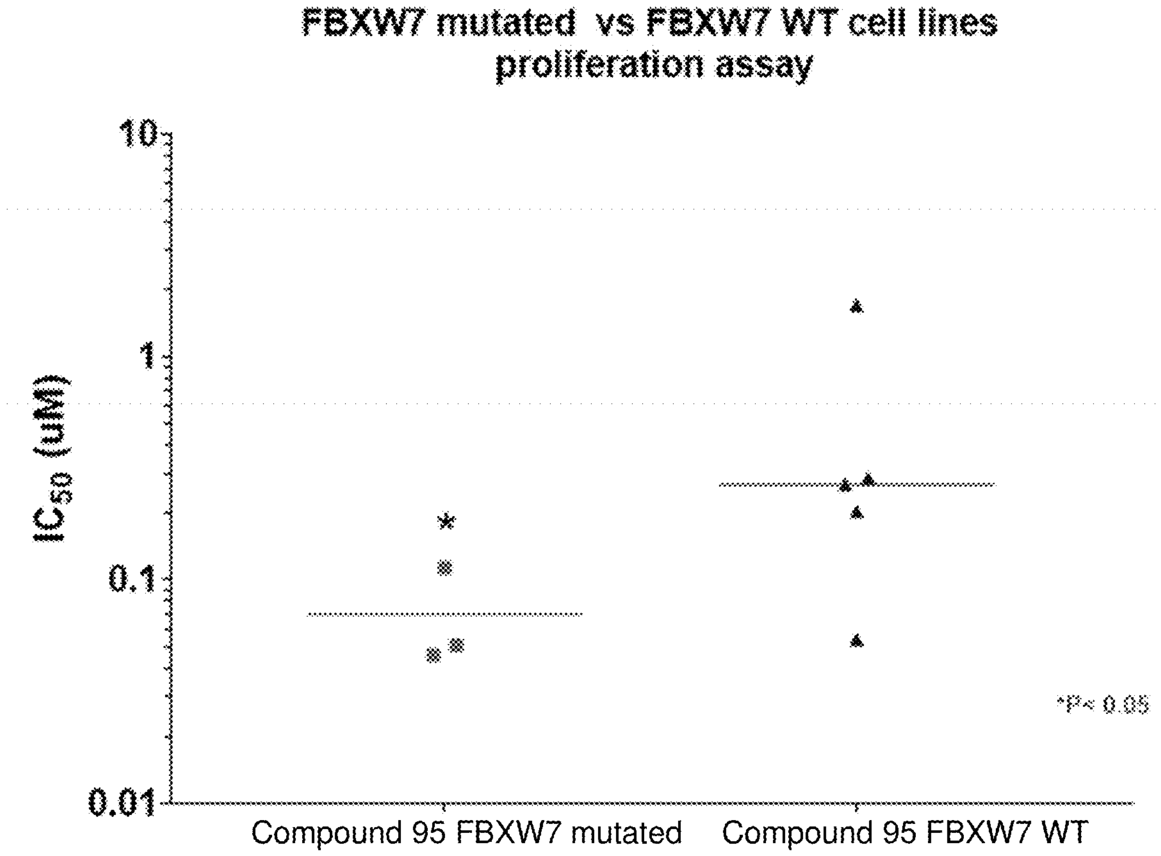
FIG. 7 is a chart showing the results of proliferation assays for a panel of FBXW7 wild type and FBXW7-mutated cancer cell lines treated with different doses of compound 95. The IC50 values are plotted for each cell line and demonstrate that FBXW7-mutated cell lines show enhanced sensitivity to a Myt1 inhibitor compared to FBXW7 WT cell lines.

A similar experiment was conducted in a panel of 8 cancer cell lines with either wild-type FBXW7 (n=5) or FBXW7-mutations (n=3) in which these cells were evaluated for their sensitivity to compound 95 in a cell proliferation assay (FIG. 7). Dose-response curves in these cancer cell line proliferation assays were generated as follows. Cells were seeded in 96-well plates and dosed with serially diluted Myt1 inhibitor. Cells were imaged once per day using the IncuCyte $S_3$ microscope and percent well confluency was calculated over time. Once cells reached four population doublings the experiment was ended and $IC_{50}$ curves were plotted for the final time point. Percentage confluency was calculated relative to the cell confluency in the untreated wells.

OTHER EMBODIMENTS

Various modifications and variations of the described invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

The invention claimed is:

1. A compound of formula (I):

(I)

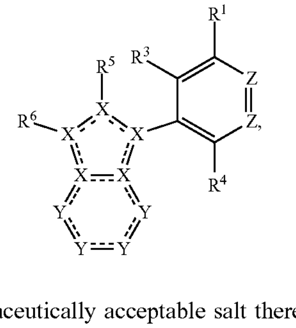

or a pharmaceutically acceptable salt thereof, wherein each ------ is a single or double bond;

one, two, or three X groups are N, and the remaining X groups are C;

each Y is independently N or $CR^2$;

each Z is independently N or CH;

$R^1$ is OH, and $R^3$ is optionally substituted $C_{3-8}$ cycloalkyl;

or $R^1$ and $R^3$ combine to form —$CR^9$=N—NH—;

each $R^2$ is independently hydrogen, optionally substituted $C_{1-6}$ alkyl, optionally substituted $C_{2-6}$ alkenyl, optionally substituted $C_{2-6}$ alkynyl, optionally substituted $C_{3-8}$ cycloalkyl, optionally substituted $C_{3-8}$ cycloalkenyl, optionally substituted $C_{2-9}$ heterocyclyl, optionally substituted $C_{2-9}$ heterocyclyl $C_{1-6}$ alkyl, optionally substituted $C_{6-10}$ aryl, optionally substituted $C_{1-9}$ heteroaryl, optionally substituted $C_{1-9}$ heteroaryl $C_{1-6}$ alkyl, halogen, cyano, —$N(R^7)_2$, —$OR^7$, —$C(O)N(R^8)_2$, —$SO_2N(R^8)_2$, —$SO_2R^{7A}$, or -Q-$R^{7B}$;

$R^4$ is independently hydrogen, optionally substituted $C_{1-6}$ alkyl, or halogen;

$R^5$ is hydrogen, halogen, or —$N(R^7)_2$;

$R^6$ is —$C(O)NH(R^8)$ or —$C(O)R^{7A}$;

each $R^7$ is independently hydrogen, optionally substituted $C_{1-6}$ alkyl, optionally substituted $C_{6-10}$ aryl $C_{1-6}$ alkyl, optionally substituted $C_{3-8}$ cycloalkyl, optionally substituted $C_{6-10}$ aryl, optionally substituted $C_{2-9}$ heterocyclyl, optionally substituted $C_{1-9}$ heteroaryl, optionally substituted $C_{1-9}$ heteroaryl $C_{1-6}$ alkyl, or —$SO_2R^{7A}$; or two $R^7$ groups, together with the atom to which both are attached, combine to form an optionally substituted $C_{2-9}$ heterocyclyl;

each $R^{7A}$ is independently optionally substituted $C_{1-6}$ alkyl or optionally substituted $C_{3-8}$ cycloalkyl;

each $R^{7B}$ is independently hydroxyl, optionally substituted $C_{1-6}$ alkyl, optionally substituted $C_{6-10}$ aryl, optionally substituted $C_{2-9}$ heterocyclyl, optionally substituted $C_{1-9}$ heteroaryl, —$N(R^7)_2$, —$C(O)N(R^8)_2$, —$SO_2N(R^8)_2$, —$SO_2R^{7A}$, or optionally substituted alkoxy;

each $R^8$ is independently hydrogen, optionally substituted $C_{1-6}$ alkyl, optionally substituted $C_{2-6}$ alkoxyalkyl, optionally substituted $C_{6-10}$ aryl $C_{1-6}$ alkyl, optionally substituted $C_{6-10}$ aryl, optionally substituted $C_{3-8}$ cycloalkyl, or optionally substituted $C_{1-9}$ heteroaryl; or two $R^8$, together with the atom to which they are attached, combine to form an optionally substituted $C_{2-9}$ heterocyclyl;

$R^9$ is hydrogen or halogen; and

Q is optionally substituted $C_{1-6}$ alkylene, optionally substituted $C_{2-6}$ alkenylene, optionally substituted $C_{2-6}$ alkynylene, optionally substituted $C_{3-8}$ cycloalkylene, optionally substituted $C_{3-8}$ cycloalkenylene optionally substituted $C_{6-10}$ arylene, optionally substituted $C_{2-9}$ heterocyclylene, or optionally substituted $C_{1-9}$ heteroarylene.

2. The compound of claim 1, or a pharmaceutically acceptable salt thereof, wherein one X group is N, and the remaining X groups are C.

3. The compound of claim 1, or a pharmaceutically acceptable salt thereof, wherein zero, one, or two Y groups are N, and the remaining Y groups are $CR^2$.

4. The compound of claim 1, or a pharmaceutically acceptable salt thereof, wherein $R^1$ is OH or $R^1$ and $R^3$ combine to form —CH=N—NH—.

5. The compound of claim 1, or a pharmaceutically acceptable salt thereof, wherein $R^6$ is —$C(O)NH(R^8)$ or —$C(O)NH_2$.

6. A pharmaceutical composition comprising the compound of claim 1, or a pharmaceutically acceptable salt thereof, and a pharmaceutically acceptable excipient.

7. A compound of formula (II):

(II)

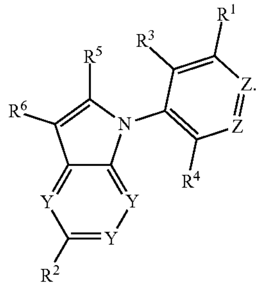

or a pharmaceutically acceptable salt thereof, wherein each ═══ is a single or double bond;

each Y is independently N or $CR^2$;

each Z is independently N or CH;

$R^1$ is OH, and $R^3$ is optionally substituted $C_{3-8}$ cycloalkyl;

or $R^1$ and $R^3$ combine to form —$CR^9$═N—NH—;

each $R^2$ is independently hydrogen, optionally substituted $C_{1-6}$ alkyl, optionally substituted $C_{2-6}$ alkenyl, optionally substituted $C_{2-6}$ alkynyl, optionally substituted $C_{3-8}$ cycloalkyl, optionally substituted $C_{3-8}$ cycloalkenyl, optionally substituted $C_{2-9}$ heterocyclyl, optionally substituted $C_{2-9}$ heterocyclyl $C_{1-6}$ alkyl, optionally substituted $C_{6-10}$ aryl, optionally substituted $C_{1-9}$ heteroaryl, optionally substituted $C_{1-9}$ heteroaryl $C_{1-6}$ alkyl, halogen, cyano, —$N(R^7)_2$, —$OR^7$, —$C(O)N(R^8)_2$, —$SO_2N(R^8)_2$, —$SO_2R^{7A}$, or -Q-$R^{7B}$;

$R^4$ is independently hydrogen, optionally substituted $C_{1-6}$ alkyl, or halogen;

$R^5$ is hydrogen, halogen, or —$N(R^7)_2$;

$R^6$ is —$C(O)NH(R^8)$, —$C(O)R^{7A}$, or —$SO_2R^{7A}$;

each $R^7$ is independently hydrogen, optionally substituted $C_{1-6}$ alkyl, optionally substituted $C_{6-10}$ aryl $C_{1-6}$ alkyl, optionally substituted $C_{3-8}$ cycloalkyl, optionally substituted $C_{6-10}$ aryl, optionally substituted $C_{2-9}$ heterocyclyl, optionally substituted $C_{1-9}$ heteroaryl, optionally substituted $C_{1-9}$ heteroaryl $C_{1-6}$ alkyl, or —$SO_2R^{7A}$; or two $R^7$ groups, together with the atom to which both are attached, combine to form an optionally substituted $C_{2-9}$ heterocyclyl;

each $R^{7A}$ is independently optionally substituted $C_{1-6}$ alkyl or optionally substituted $C_{3-8}$ cycloalkyl;

each $R^{7B}$ is independently hydroxyl, optionally substituted $C_{1-6}$ alkyl, optionally substituted $C_{6-10}$ aryl, optionally substituted $C_{2-9}$ heterocyclyl, optionally substituted $C_{1-9}$ heteroaryl, —$N(R^7)_2$, —$C(O)N(R^8)_2$, —$SO_2N(R^8)_2$, —$SO_2R^{7A}$, or optionally substituted alkoxy;

each $R^8$ is independently hydrogen, optionally substituted $C_{1-6}$ alkyl, optionally substituted $C_{2-6}$ alkoxyalkyl, optionally substituted $C_{6-10}$ aryl $C_{1-6}$ alkyl, optionally substituted $C_{6-10}$ aryl, optionally substituted $C_{3-8}$ cycloalkyl, or optionally substituted $C_{1-9}$ heteroaryl; or two $R^8$, together with the atom to which they are attached, combine to form an optionally substituted $C_{2-9}$ heterocyclyl;

$R^9$ is hydrogen or halogen; and

Q is optionally substituted $C_{1-6}$ alkylene, optionally substituted $C_{2-6}$ alkenylene, optionally substituted $C_{2-6}$ alkynylene, optionally substituted $C_{3-8}$ cycloalkylene, optionally substituted $C_{3-8}$ cycloalkenylene optionally substituted $C_{6-10}$ arylene, optionally substituted $C_{2-9}$ heterocyclylene, or optionally substituted $C_{1-9}$ heteroarylene.

8. The compound of claim 7, or a pharmaceutically acceptable salt thereof, wherein the compound is enriched for the atropisomer of formula (II-i):

(II-i)

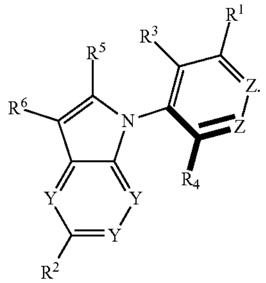

9. The compound of claim 7, or a pharmaceutically acceptable salt thereof, wherein the compound is of formula (IIB):

(IIB)

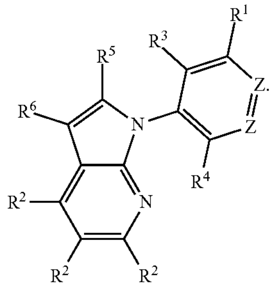

10. The compound of claim 9, or a pharmaceutically acceptable salt thereof, wherein the compound is enriched for the atropisomer of (IIB-i):

(IIB-i)

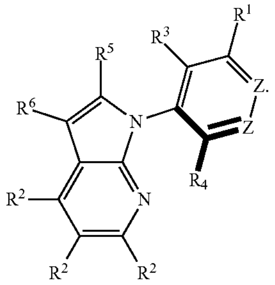

* * * * *